(12) United States Patent
Greka et al.

(10) Patent No.: US 11,207,278 B2
(45) Date of Patent: Dec. 28, 2021

(54) AGENTS FOR REVERSING TOXIC PROTEINOPATHIES

(71) Applicants: THE BROAD INSTITUTE, INC., Cambridge, MA (US); THE BRIGHAM & WOMEN'S HOSPITAL, INC., Boston, MA (US); DANA-FARBER CANCER INSTITUTE, INC., Boston, MA (US); Instituto Carlos Slim de la Salud, A.C., Mexico City (MX)

(72) Inventors: Anna Greka, Boston, MA (US); Moran Dvela-Levitt, Cambridge, MA (US); Maria Alimova, Cambridge, MA (US); Eric Lander, Cambridge, MA (US); Todd R. Golub, Cambridge, MA (US); Florence Wagner, Cambridge, MA (US); Brian Chamberlain, Cambridge, MA (US); Valeria Padovano, Cambridge, MA (US); Joseph Growney, Cambridge, MA (US)

(73) Assignees: The Broad Institute, Inc., Cambridge, MA (US); Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/161,431

(22) Filed: Jan. 28, 2021

(65) Prior Publication Data

US 2021/0169827 A1 Jun. 10, 2021

Related U.S. Application Data

(63) Continuation of application No. PCT/US2020/038847, filed on Jun. 20, 2020.
(Continued)

(51) Int. Cl.
*A61K 31/13* (2006.01)
*A61P 27/02* (2006.01)
(Continued)

(52) U.S. Cl.
CPC ............. *A61K 31/13* (2013.01); *A61P 13/12* (2018.01); *A61P 27/02* (2018.01); *C12Q 1/6883* (2013.01)

(58) Field of Classification Search
CPC .................................................... A61K 31/13
(Continued)

(56) References Cited

U.S. PATENT DOCUMENTS

| | | | |
|---|---|---|---|
| 5,914,330 A * | 6/1999 | Ritz ........................ | A61P 13/02 514/269 |
| 9,845,327 B2 | 12/2017 | Krainc et al. | |

(Continued)

FOREIGN PATENT DOCUMENTS

| | | |
|---|---|---|
| WO | 2000046189 | 8/2000 |
| WO | 2016105449 A1 | 6/2016 |

OTHER PUBLICATIONS

Bleyer et al. "Autosomal Dominant Tubulointerstitial kidney Disease, MUC1-related," 2016, U.S. National Library of Medicine. https://www.ncbi.nlm.nih.gov/books/NBK153723/pdf/Bookshelf_NBK153723.pdf (Year: 2016).*
(Continued)

*Primary Examiner* — Shengjun Wang
(74) *Attorney, Agent, or Firm* — Withers Bergman, LLP; Christopher R. Cowles; Gina A. Ciolek

(57) ABSTRACT

The present disclosure relates to compositions and methods for the diagnosis and treatment or prevention of proteinopathies, particularly MUC1-associated kidney disease (ADTKD-MUC1 or MKD), Retinitis Pigmentosa (e.g., due to rhodopsin mutations), autosomal dominant tubulo-inter-
(Continued)

stitial kidney disease due to UMOD mutation(s) (ADTKD-UMOD), and other forms of toxic proteinopathies resulting from mutant protein accumulation in the ER or other secretory pathway compartments and/or vesicles, among others. The disclosure also identifies and provides TMED9-binding agents as capable of treating or preventing proteinopathies of the secretory pathway, and further provides methods for identifying additional TMED9-binding agents.

20 Claims, 66 Drawing Sheets

Specification includes a Sequence Listing.

Related U.S. Application Data

(60) Provisional application No. 62/878,304, filed on Jul. 24, 2019, provisional application No. 62/865,096, filed on Jun. 21, 2019.

(51) Int. Cl.
*A61P 13/12* (2006.01)
*C12Q 1/6883* (2018.01)

(58) Field of Classification Search
USPC .......................................................... 514/579
See application file for complete search history.

(56) References Cited

U.S. PATENT DOCUMENTS

2011/0229571 A1* 9/2011 Baum .................... A61P 13/02
424/475
2015/0284472 A1 10/2015 Sardi et al.

OTHER PUBLICATIONS

Munk et al. "Synthesis and Pharmacologic Evaluation of 2-endo-Amino-3-exo-isopropylbicyclo[2.2.1Theptane: A Potent Imidazolinel Receptor Specific Agent" Journal of Medicinal Chemistry. Mar. 15, 1996 (Mar. 15, 1996) vol. 39, p. 1193-1195; p. 1193, title.
Dvela-Levitt et al. "Small Molecule Targets TMED9 and Promotes Lysosomal Degradation to Reverse Proteinopathy" Cell. Jul. 25, 2019 (Jul. 25, 2019) vol. 178, p. 521-535; entire document.
International Search Report dated Nov. 13, 2020 for related Application No. PCT/US2020/038847.

* cited by examiner

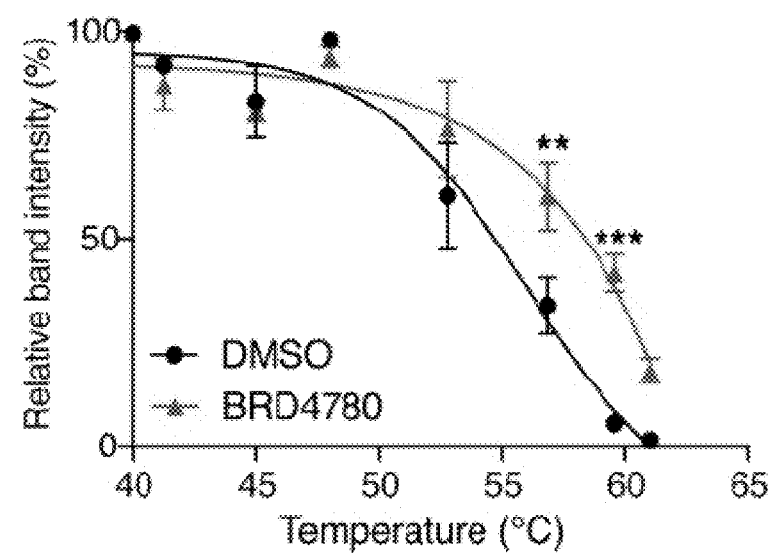
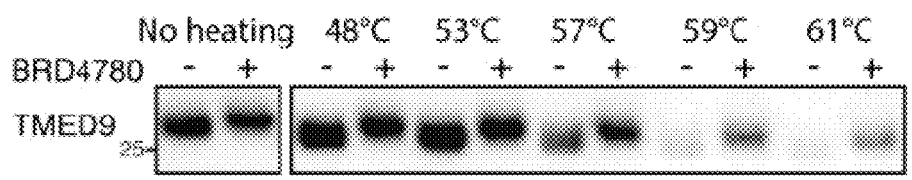
FIG. 6E

| PK Parameters | BRD-4780 in Plasma | | BRD-4780 in Kidney | |
|---|---|---|---|---|
| | I.V. | P.O | IV | PO |
| Rsq_adj | 0.989 | 0.955 | 0.891 | 0.989 |
| No. points used for $T_{1/2}$ | 7.00 | 5.00 | 7.00 | 4.00 |
| $C_0$ (ng/mL) | 921 | – | – | – |
| $C_{max}$ (ng/mL) | – | 2433 | – | – |
| $C_{max}$ (ng/g) | – | – | 17733 | 30333 |
| $T_{max}$ (h) | – | 1.00 | 0.250 | 2.00 |
| $T_{1/2}$ (h) | 1.35 | 2.35 | 2.51 | 2.38 |
| $Vd_{ss}$ (L/kg) | 2.70 | – | – | – |
| Cl (mL/min/kg) | 22.7 | – | – | – |
| $T_{last}$ (h) | 8.00 | 24.0 | 24.0 | 24.0 |
| $AUC_{0-last}$ (ng.h/mL) | 2162 | 8700 | – | – |
| $AUC_{0-inf}$ (ng.h/mL) | 2199 | 8708 | – | – |
| $AUC_{0-last}$ (ng.h/g) | – | – | 48121 | 164514 |
| $AUC_{0-inf}$ (ng.h/g) | – | – | 48211 | 164666 |
| $AUC_{Extra}$ (%) | 1.72 | 0.0904 | 0.187 | 0.0921 |
| $AUMC_{Extra}$ (%) | 8.62 | 0.852 | 1.87 | 0.681 |
| Bioavailability (%) | – | 119 | – | – |
| $AUC_{0-last}$ Ratio (K/P) | – | – | 22.3 | 18.9 |

FIG. 11B

| PK Parameters (males) | BRD-4780 in Plasma | | | BRD-4780 in Kidney | | |
|---|---|---|---|---|---|---|
| | 10 mg/kg | 20 mg/kg | 60 mg/kg | 10 mg/kg | 20 mg/kg | 60 mg/kg |
| Rsq_adj | 0.961 | 0.944 | 1.00 | 0.999 | 0.932 | 1.00 |
| No. points used for $T_{1/2}$ | 5.00 | 7.00 | 3.00 | 3.00 | 3.00 | 3.00 |
| $C_{max}$ (ng/mL) | 1780 | 2203 | 4127 | – | – | – |
| $C_{max}$ (ng/g) | – | – | – | 22930 | 33867 | 48487 |
| $T_{max}$ (h) | 0.500 | 0.250 | 0.250 | 0.250 | 2.00 | 2.00 |
| $T_{1/2}$ (h) | 2.18 | 3.07 | 5.33 | 2.46 | 2.43 | 4.71 |
| $T_{last}$ (h) | 12.0 | 24.0 | 24.0 | 24.0 | 24.0 | 24.0 |
| $AUC_{0-last}$ (ng.h/mL) | 7186 | 14681 | 33780 | – | – | – |
| $AUC_{0-last}$ (ng.h/g) | – | – | – | 154782 | 314997 | 616128 |
| $AUC_{0-inf}$ (ng.h/mL) | 7296 | 14725 | 35733 | – | – | – |
| $AUC_{0-inf}$ (ng.h/g) | – | – | – | 155189 | 314997 | 644148 |
| $AUC_{Extrap}$ (%) | 1.78 | 0.439 | 5.47 | 0.234 | 0.283 | 4.35 |
| $AUMC_{Extrap}$ (%) | 7.54 | 2.57 | 19.5 | 1.28 | 1.38 | 15.0 |
| $C_{max}$ (μM) | 11.11 | 14.49 | 27.0 | – | – | – |
| $C_{max}$ (μmol/kg) | – | – | – | 159 | 221 | 323 |
| $AUC_{0-last}$ (μM.h) | 46.8 | 95.8 | 221 | – | – | – |
| $AUC_{0-last}$ (μmol/kg.h) | – | – | – | 1012 | 2053 | 4027 |
| $AUC_{0-inf}$ (μM.h) | 47.7 | 96.2 | 234 | – | – | – |
| $AUC_{0-inf}$ (μmol/kg.h) | – | – | – | 1014 | 2059 | 4210 |
| $AUC_{0-inf}$ Ratio (K/P) | – | – | – | 21.6 | 21.4 | 18.2 |

FIG. 11E

| PK Parameters (females) | BRD-4780 in Plasma | | | BRD-4780 in Kidney | | |
|---|---|---|---|---|---|---|
| | 10 mg/kg | 20 mg/kg | 50 mg/kg | 10 mg/kg | 20 mg/kg | 50 mg/kg |
| Rsq_adj | 0.969 | 0.934 | 1.00 | 0.968 | 0.947 | 1.00 |
| No. points used for $T_{1/2}$ | 6.00 | 7.00 | 3.00 | 4.00 | 6.00 | 3.00 |
| $C_{max}$ (ng/mL) | 1913 | 2833 | 4103 | — | — | — |
| $C_{max}$ (ng/g) | — | — | — | 11493 | 22833 | 27433 |
| $T_{max}$ (h) | 0.250 | 0.250 | 0.250 | 1.000 | 0.50 | 1.00 |
| $T_{1/2}$ (h) | 1.16 | 1.97 | 1.69 | 1.18 | 2.04 | 1.99 |
| $T_{last}$ (h) | 12.0 | 24.0 | 24.0 | 12.0 | 24.0 | 24.0 |
| $AUC_{0-last}$ (ng·h/mL) | 2738 | 8155 | 32384 | — | — | — |
| $AUC_{0-last}$ (ng·h/g) | — | — | — | 31759 | 75488 | 232357 |
| $AUC_{0-inf}$ (ng·h/mL) | 2741 | 8159 | 32272 | — | — | — |
| $AUC_{0-inf}$ (ng·h/g) | — | — | — | 31897 | 75448 | 232539 |
| $AUC_{Extrap}$ (%) | 0.12 | 0.041 | 0.02 | 0.149 | 0.041 | 0.08 |
| $AUMC_{Extrap}$ (%) | 1.08 | 0.48 | 0.1 | 0.99 | 0.36 | 0.4 |
| $C_{max}$ (µM) | 12.50 | 17.21 | 26.8 | — | — | — |
| $C_{max}$ (µmol/kg) | — | — | — | 75 | 144 | 179 |
| $AUC_{0-last}$ (µM·h) | 17.9 | 53.3 | 211 | — | — | — |
| $AUC_{0-last}$ (µmol/kg·h) | — | — | — | 208 | 493 | 1518 |
| $AUC_{0-inf}$ (µM·h) | 17.9 | 53.3 | 211 | — | — | — |
| $AUC_{0-inf}$ (µmol/kg·h) | — | — | — | 208 | 493 | 1520 |
| $AUC_{0-inf}$ Ratio (K/P) | — | — | — | 11.6 | 9.2 | 7.2 |

FIG. 11F

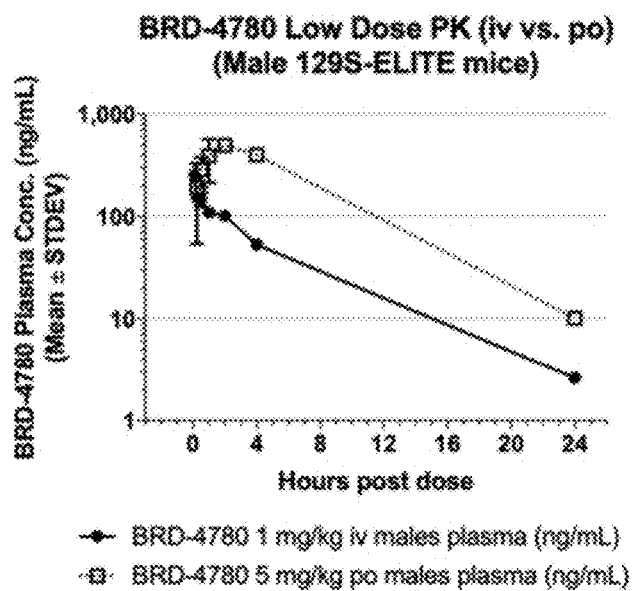

FIG. 11G

| Compound | BRD4780 | | BRD1368 | | BRD7709 | |
|---|---|---|---|---|---|---|
| Dose | 1 mg/kg | 5 mg/kg | 1 mg/kg | 5 mg/kg | 1 mg/kg | 5 mg/kg |
| Route | IV | PO | IV | PO | IV | PO |
| PK parameters | Mean | Mean | Mean | Mean | Mean | Mean |
| $C_{max}$ (ng/mL) | 256 | 522 | 612 | 467 | 476 | 303 |
| $T_{max}$ (hr) | 0.083 | 1.67 | 0.083 | 1.42 | 0.083 | 1.67 |
| $C_{24h}$ (ng/mL) | 36 | 19.2 | 4.25 | 7.04 | 34.4 | 107 |
| $T_{last}$ (hr) | 10.7 | 24 | 24 | 24 | 4 | 10.7 |
| $AUC_{all}$ (hr*ng/mL) | 740 | 5747 | 1470 | 4580 | 547 | 2336 |
| $AUC_{0-4h}$ (hr*ng/mL) | 420 | 1595 | 607 | 1441 | 467 | 892 |
| $C_{max}/D$ (ng/mL/μg) | 10.3 | 4.17 | 20.5 | 3.74 | 19 | 2.43 |
| $AUC_{all}/D$ (hr*ng/mL) | 29.6 | 46 | 58.9 | 36.6 | 21.9 | 18.7 |
| $T_{1/2}$ (hr) | 3.11 | 3.87 | 4.47 | 3.7 | 1.55 | 4.26 |
| Vz (mL) | 151 | 122 | 110 | 147 | 102 | 349 |
| CL (mL/hr) | 33.8 | 21.8 | 17.1 | 27.4 | 46.4 | 59.8 |
| Bioavailability (%) | --- | 75.96 | --- | 47.52 | --- | 36.2 |

| Molecule | BRD4780 | | BRD7709 | | BRD1365 | |
|---|---|---|---|---|---|---|
| Dose (mg/kg) | 1 | 5 | 1 | 5 | 1 | 5 |
| Route | IV | PO | IV | PO | IV | PO |
| PK parameters | Mean | Mean | Mean | Mean | Mean | Mean |
| Cmax (ng/mL) | 259 | 168 | 230 | 220 | 182 | 116 |
| Tmax (hr) | 0.083 | 1 | 0.083 | 1 | 0.083 | 0.5 |
| Clast (ng/mL) | 4.44 | 21.5 | 1.33 | 13.7 | 1.65 | 3.17 |
| Tlast (hr) | 6 | 10 | 10 | 10 | 6 | 10 |
| AUCINF (hr*ng/mL) | 356 | 805.3 | 348 | 1010 | 231 | 385 |
| AUC0-4hr (hr*ng/mL) | 327 | 486 | 304 | 670 | 216 | 368 |
| Cmax/D (ng/mL/mg) | 706 | 91.9 | 653 | 131 | 678 | 73.5 |
| AUClast (hr*ng/mL) | 349 | 712 | 345 | 966 | 229 | 376 |
| AUClast/D (hr*ng/mL/mg) | 955 | 388 | 1028 | 577 | 727.9 | 238 |
| AUC% Extrap | 1.86 | 11.6 | 0.758 | 4.29 | 0.905 | 2.12 |
| Vz (mL) | 1732 | 10589 | 1531 | 9894 | 1922 | 5262 |
| t1/2 (hr) | 1.93 | 3.01 | 1.38 | 2.2 | 0.882 | 1.79 |
| CL (mL/hr) | 1028 | 2276 | 965.3 | 1658 | 1361 | 4104 |
| Bioavailability (%) | -- | 40.6 | -- | 56.1 | -- | 32.7 |

| Dose | (mg/kg) | BRD7789 PK parameters in CD(SD) rats |||||||
|---|---|---|---|---|---|---|---|---|
| | | 10 mg/kg || 30 mg/kg || 50 mg/kg || 100 mg/kg ||
| Gender | | Male | Female | Male | Female | Male | Female | Male | Female |
| Cmax | (ng/mL) | 488 | 1880 | 1974 | 2556 | 2192 | 3915 | 3680 | 4505 |
| Tmax | (hr) | 1 | 1 | 0.833 | 0.667 | 1.5 | 0.833 | 2.33 | 3.17 |
| Clast | (ng/mL) | 11.7 | 1.62 | 6.25 | 3.4 | 4.83 | 13.2 | 42 | 316 |
| Tlast | (hr) | 32 | 48 | 48 | 48 | 48 | 48 | 48 | 48 |
| t1/2 | (hr) | 7.2 | 9.38 | 5.97 | 4.57 | 4.68 | 9.42 | 9.83 | 11.9 |
| AUC0-24h | (hr*ng/mL) | 2555 | 5604 | 11878 | 24618 | 25858 | 37770 | 45879 | 61746 |
| AUClast | (hr*ng/mL) | 2752 | 5696 | 12156 | 25538 | 26988 | 39558 | 53886 | 79516 |
| AUCinf | (hr*ng/mL) | 2983 | 5708 | 12216 | 25558 | 26938 | 43668 | 54118 | 85486 |
| AUC% Extrap | % | 5.27 | 0.218 | 0.569 | 0.0883 | 0.121 | 9.243 | 0.867 | 6.77 |
| Cmax/D | (ng/mL/mg) | 195 | 455 | 295 | 389 | 163 | 341 | 161 | 207 |
| AUC0-24h/D (hr*ng/ | (hr*ng/mL/mg) | 1027 | 2361 | 1548 | 3445 | 2018 | 3271 | 1964 | 2827 |
| AUClast/D (hr*ng/ | (hr*ng/mL/mg) | 1105 | 2400 | 1585 | 3575 | 2083 | 3936 | 2338 | 3635 |
| CL | (mL/hr) | 346 | 423 | 642 | 280 | 484 | 257 | 428 | 287 |
| Vz | (mL) | 7864 | 3584 | 8879 | 1842 | 3350 | 2880 | 4111 | 4383 |

|  |  | BRD7768 PK parameters in CB(SD) rats | | | | | | | |
|---|---|---|---|---|---|---|---|---|---|
| Dose | (mg/kg) | 10 mg/kg | | 30 mg/kg | | 50 mg/kg | | 100 mg/kg | |
| Gender |  | Male | Female | Male | Female | Male | Female | Male | Female |
| Cmax | (ng/mL) | 572 | 1058 | 1646 | 2499 | 2082 | 5363 | 4634 | 6472 |
| Tmax | (hr) | 1 | 1 | 2.67 | 3 | 4.33 | 1.42 | 0.667 | 1.42 |
| Clast | (ng/mL) | 1.46 | 9.36 | 2.2 | 6.17 | 8.8 | 16.1 | 108 | 428 |
| Tlast | (hr) | 48 | 24 | 48 | 48 | 48 | 48 | 48 | 48 |
| t1/2 | (hr) | 6.86 | 3.39 | 4.74 | 4.74 | 4.89 | 5.64 | 8.33 | 13.9 |
| AUC0-24h | (hr*ng/mL) | 2722 | 8295 | 13970 | 29430 | 26290 | 51560 | 49780 | 82130 |
| AUClast | (hr*ng/mL) | 2775 | 8295 | 14680 | 31030 | 27880 | 65840 | 64040 | 118600 |
| AUCinf | (hr*ng/mL) | 2790 | 8252 | 14690 | 31070 | 27930 | 65980 | 65440 | 125000 |
| AUC% Extrap | % | 0.517 | 0.71 | 0.111 | 0.136 | 0.178 | 0.292 | 2.22 | 9.74 |
| Cmax/D | (ng/mL/mg) | 333 | 458 | 319 | 356 | 168 | 481 | 173 | 366 |
| AUC0-24h/D (hr*ng/ | (hr*ng/mL/mg) | 1109 | 2882 | 1837 | 4121 | 2126 | 4581 | 2138 | 3879 |
| AUClast/D (hr*ng/ | (hr*ng/mL/mg) | 1136 | 2882 | 1865 | 4345 | 2255 | 5845 | 2746 | 5218 |
| CL | (mL/hr) | 881 | 374 | 541 | 238 | 443 | 171 | 358 | 174 |
| Vz | (mL) | 8734 | 1760 | 3712 | 1616 | 3117 | 1388 | 4380 | 3173 |

FIG. 11AC

|  |  | BRD1365 PK parameters in CB(SD) rats | | | | | | | |
|---|---|---|---|---|---|---|---|---|---|
| Dose | (mg/kg) | 10 mg/kg | | 30 mg/kg | | 50 mg/kg | | 100 mg/kg | |
| Gender |  | Male | Female | Male | Female | Male | Female | Male | Female |
| Cmax | (ng/mL) | 482 | 738 | 1636 | 1945 | 2146 | 2865 | 4387 | 7833 |
| Tmax | (hr) | 0.667 | 1.67 | 2.33 | 1.5 | 1.42 | 3.08 | 1.5 | 3.33 |
| Clast | (ng/mL) | 112 | 3.2 | 1.88 | 1.68 | 4.63 | 4.44 | 43.7 | 355 |
| Tlast | (hr) | 48 | 24 | 48 | 48 | 48 | 48 | 48 | 48 |
| t1/2 | (hr) | 6.94 | 2.69 | 4.98 | 4.19 | 4.82 | 4.44 | 6.61 | 13.2 |
| AUC0-24h | (hr*ng/mL) | 3324 | 4654 | 10870 | 18370 | 21970 | 32600 | 46710 | 74610 |
| AUClast | (hr*ng/mL) | 4562 | 4654 | 11386 | 18660 | 22670 | 36490 | 68770 | 98110 |
| AUCinf | (hr*ng/mL) | 5562 | 4667 | 11976 | 18660 | 22700 | 36490 | 81240 | 102700 |
| AUC% Extrap | % | 6.09 | 0.266 | 0.128 | 0.0534 | 0.14 | 0.0783 | 0.782 | 6.19 |
| Cmax/D | (ng/mL/mg) | 180 | 330 | 219 | 275 | 155 | 242 | 166 | 308 |
| AUC0-24h/D (hr*ng/ | (hr*ng/mL/mg) | 983 | 1888 | 1418 | 2567 | 1696 | 2893 | 1753 | 3289 |
| AUClast/D (hr*ng/ | (hr*ng/mL/mg) | 1787 | 1888 | 1421 | 2630 | 1848 | 3062 | 2281 | 4183 |
| CL | (mL/hr) | 1828 | 817 | 707 | 383 | 623 | 327 | 436 | 228 |
| Vz | (mL) | 16210 | 1969 | 5089 | 2324 | 4362 | 2092 | 4205 | 3934 |

FIG. 11AD

| Compound Name | MoA | EC50 [M] |
|---|---|---|
| BRD4780 | ? | 1.43E-07 |
| Guanfacine | IRL | N/A |
| Harmine hydrochloride | IRL | N/A |
| 6-Methoxyharmalan | IRL | N/A |
| Efaroxan hydrochloride | IRL | N/A |
| Idazoxan | IRL | N/A |
| tetrahydro-Harmin | IRL | N/A |
| p-Iodoclonidine hydrochloride | IRL | N/A |
| Oxymetazoline hydrochloride | IRL | N/A |
| Agmatine | IRL | N/A |
| Cirazoline | IRL | N/A |
| BU 224 Hydrochloride | IRL | N/A |
| TVP1022 | IRL | N/A |
| Guanabenz acetate | IRL | N/A |
| Naphazoline hydrochloride | IRL | N/A |
| Moxonidine hydrochloride | IRL | N/A |
| Harmaline hydrochloride dihydrate | IRL | N/A |
| Clonidine | IRL | N/A |
| Rilmenidine | IRL | N/A |

FIG. 14D

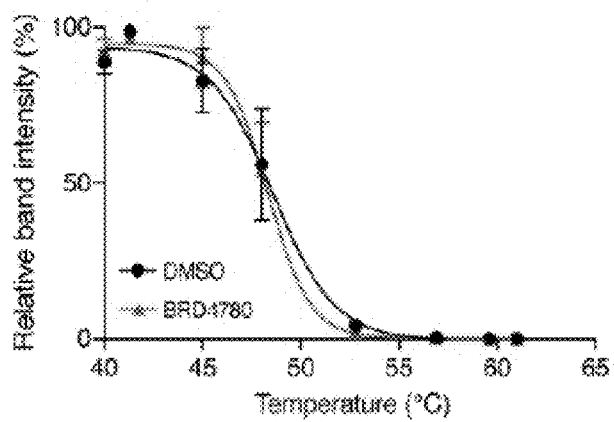

FIG. 14E

| Parameter | Target Profile Criteria | BRD4780 |
|---|---|---|
| Functional activity EC50 (MUC1-fs, whole cell) | <200 nM | 143 nM (Emax: -88.6%) |
| PBS solubility | > 10 μM | > 500 μM |
| LE / LLE | >0.3 / >3.5 | LE: 0.9<br>LLE: 3.8 |
| Metabolic stability in mouse liver microsomes (% remaining at 30 min) | >50% | 96.3% |
| Plasma stability (% remaining at 3hr) | > 90% | mouse: 96.7%<br>human: 118.4% |
| Plasma protein binding (% bound) | < 99% | mouse: 25.5%<br>human: 30.6% |
| Oral bioavailability (mouse) | > 20 % | > 100 % (male, 129S2) |
| Half-life (mouse) | > 1 h | 10 mpk PO: male 2.4 h; female 1.2 h |

FIG. 16

| Animal age (weeks) | Mean | SEM | N | Mean | SEM | N | Mean | SEM | N | Mean | SEM | N |
|---|---|---|---|---|---|---|---|---|---|---|---|---|
| 12 | 0.119 | 0.008 | 20 | 0.110 | 0.005 | 28 | 0.117 | 0.006 | 24 | 0.114 | 0.011 | 19 |
| 16 | 0.110 | 0.004 | 26 | 0.094 | 0.004 | 41 | 0.108 | 0.004 | 30 | 0.108 | 0.005 | 25 |
| 20 | 0.124 | 0.005 | 45 | 0.120 | 0.010 | 49 | 0.128 | 0.006 | 40 | 0.117 | 0.004 | 36 |
| 24 | 0.126 | 0.004 | 33 | 0.109 | 0.003 | 39 | 0.135 | 0.004 | 28 | 0.111 | 0.003 | 34 |
| 28 | 0.118 | 0.004 | 29 | 0.097 | 0.003 | 32 | 0.122 | 0.004 | 28 | 0.100 | 0.003 | 29 |
| 32 | 0.135 | 0.007 | 32 | 0.119 | 0.004 | 33 | 0.125 | 0.006 | 21 | 0.109 | 0.005 | 20 |
| 36 | 0.110 | 0.005 | 27 | 0.093 | 0.004 | 33 | 0.102 | 0.004 | 27 | 0.087 | 0.006 | 29 |
| 40 | 0.123 | 0.010 | 21 | 0.101 | 0.006 | 27 | 0.148 | 0.014 | 30 | 0.103 | 0.004 | 20 |
| 44 | 0.102 | 0.005 | 25 | 0.109 | 0.005 | 27 | 0.113 | 0.006 | 27 | 0.087 | 0.004 | 26 |
| 48 | 0.111 | 0.006 | 23 | 0.084 | 0.005 | 25 | 0.113 | 0.005 | 24 | 0.087 | 0.007 | 22 |
| 52 | 0.112 | 0.004 | 25 | 0.099 | 0.006 | 36 | 0.127 | 0.007 | 23 | 0.098 | 0.006 | 23 |
| 56 | 0.117 | 0.007 | 23 | 0.101 | 0.004 | 28 | 0.128 | 0.007 | 21 | 0.091 | 0.005 | 20 |
| 60 | 0.140 | 0.006 | 24 | 0.105 | 0.010 | 23 | 0.147 | 0.009 | 20 | 0.102 | 0.006 | 25 |
| 64 | 0.120 | 0.006 | 22 | 0.105 | 0.004 | 22 | 0.142 | 0.008 | 21 | 0.099 | 0.004 | 21 |
| 68 | 0.117 | 0.006 | 24 | 0.084 | 0.004 | 22 | 0.152 | 0.020 | 26 | 0.087 | 0.006 | 19 |
| 72 | 0.122 | 0.007 | 20 | 0.096 | 0.005 | 22 | 0.150 | 0.011 | 31 | 0.071 | 0.003 | 17 |
| 76 | 0.101 | 0.005 | 23 | 0.092 | 0.006 | 24 | 0.161 | 0.016 | 24 | 0.081 | 0.006 | 26 |
| 80 | 0.102 | 0.008 | 17 | 0.090 | 0.004 | 22 | 0.192 | 0.036 | 25 | 0.102 | 0.012 | 18 |
| 84 | 0.135 | 0.017 | 16 | 0.119 | 0.015 | 17 | 0.174 | 0.016 | 17 | 0.096 | 0.007 | 11 |
| 88 | 0.131 | 0.008 | 18 | 0.124 | 0.026 | 17 | 0.206 | 0.025 | 12 | 0.115 | 0.013 | 13 |
| 92 | 0.123 | 0.006 | 20 | 0.090 | 0.006 | 13 | 0.253 | 0.035 | 17 | 0.156 | 0.053 | 12 |
| 96 | 0.143 | 0.018 | 15 | 0.130 | 0.018 | 15 | 0.286 | 0.064 | 16 | 0.120 | 0.011 | 11 |
| 100 | 0.137 | 0.020 | 18 | 0.100 | 0.005 | 17 | 0.399 | 0.078 | 13 | 0.100 | 0.012 | 10 |

SEQUENCE LISTING

```
<160> NUMBER OF SEQ ID NOS: 13

<210> SEQ ID NO 1
<211> LENGTH: 3607
<212> TYPE: DNA
<213> ORGANISM: Homo sapiens

<400> SEQUENCE: 1
atgacaccgg gcacccagtc tcctttcttc ctgctgctgc tcctcacagt gcttacagtt      60
gttacgggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagccccgg ttcaggctcc tccaccactc agggacagga tgtcactctg     240
gccccggcca cggaaccagc ttcaggttca gctgccacct ggggacagga tgtcacctcg     300
gtcccagtca ccaggccagc cctgggctcc accacccccac cagcccacga tgtcacctca     360
gccccggaca acaagccagc cccgggctcc accgcccccc ccagcccacg gtgtcacctc     420
```

```
ggccccggac accaggccgg ccccgggctc caccgccccc caagcccacg gtgtcacctc      480
ggccccggac accaggccgg ccccgggctc caccgccccc ccagcccacg gtgtcacctc      540
ggccccggac accaggcccg ccccgggctc caccgccccc ccagcccacg gtgtcacctc      600
ggccccggac accaggccgg ccccgggctc caccgccccc ccagcccacg gtgtcacctc      660
ggccccggag agcaggccgg ccccgggctc caccgcgccc gcagcccacg gtgtcacctc      720
ggccccggag agcaggccgg ccccgggctc caccgcgccc gcagcccacg gtgtcacctc      780
ggccccggag agcaggccgg ccccgggctc caccgcgccc gcagcccacg gtgtcacctc      840
ggccccggag agcaggccgg ccccgggctc caccgcgccc gcagcccacg gtgtcacctc      900
ggccccggag agcaggccgg ccccgggctc caccgccccc ccagcccacg gtgtcacctc      960
ggccccggac accaggccgg ccccgggctc caccgccccc ccagcccacg gtgtcacctc     1020
ggccccggac accaggccgg ccccgggctc caccgccccc ccagcccacg gtgtcacctc     1080
ggccccggac accaggccgg ccccgggctc caccgccccc ccagcccacg gtgtcacctc     1140
ggccccggac accaggccgg ccccgggctc caccgccccc ccagcccacg gtgtcacctc     1200
ggccccggag agcaggccgg ccccgggctc caccgccccc ccagcccacg gtgtcacctc     1260
ggccccggag agcaggccgg ccccgggctc caccgcgccc gcagcccacg gtgtcacctc     1320
ggccccggag agcaggccgg ccccgggctc caccgcgccc gcagcccacg gtgtcacctc     1380
ggccccggag agcaggccgg ccccgggctc caccgccccc ccagcccacg gtgtcacctc     1440
ggccccggac accaggccgg ccccgggctc caccgccccc ccagcccacg gtgtcacctc     1500
ggccccggac accaggccgg ccccgggctc caccgccccc ccagcccacg gtgtcacctc     1560
ggccccggac accaggccgg ccccgggctc caccgccccc ccagcccacg gtgtcacctc     1620
ggccccggac accaggccgg ccccgggctc caccgccccc ccagcccacg gtgtcacctc     1680
ggccccggac accaggccgg ccccgggctc caccgccccc ccagcccacg gtgtcacctc     1740
ggccccggac accaggccgg ccccgggctc caccgccccc ccagcccacg gtgtcacctc     1800
ggccccggac accaggccgg ccccgggctc caccgccccc ccagcccacg gtgtcacctc     1860
ggccccggac accaggccgg ccccgggctc caccgcgccc gcagcccacg gtgtcacctc     1920
ggccccggag agcaggccgg ccccgggctc caccgcgccc gcagcccacg gtgtcacctc     1980
ggccccggag agcaggccgg ccccgggctc caccgccccc ccagcccacg gtgtcacctc     2040
ggccccggac accaggccgg ccccgggctc caccgccccc ccagcccacg gtgtcacctc     2100
ggccccggac accaggccgg ccccgggctc caccgccccc ccagcccacg gtgtcacctc     2160
ggccccggac accaggccgg ccccgggctc caccgccccc ccagcccacg gtgtcacctc     2220
ggccccggac accaggccgg ccccgggctc caccgccccc ccagcccacg gtgtcacctc     2280
ggccccggac accaggccgg ccccgggctc caccgccccc ccagcccacg gtgtcacctc     2340
ggccccggac accaggccgg ccccgggctc caccgccccc ccagcccacg gtgtcacctc     2400
ggccccggac accaggccgg ccccgggctc caccgccccc ccagcccacg gtgtcacctc     2460
ggccccggac accaggccgg ccccgggctc caccgccccc ccagcccacg gtgtcacctc     2520
ggccccggac accaggcggg ccccgggctc cacccggcc ccgggctcca ccgcccccc       2580 agcccacggt gtcaccttgg ccccggacac caggccggcc ccgggctcca ccgccccccc     2640
agcccatggt gtcacctcgg ccccggacaa caggcccgcc ttgggctcca ccgccctcc     2700 agtccacaat gtcacctcgg cctcaggctc tgcatcaggc tcagcttcta ctctggtgca     2760
caacggcacc tctgccaggg ctaccacaac cccagccagc aagagcactc cattctcaat     2820
```

| | |
|---|---|
| tcccagccac cactctgata ctcctaccac ccttgccagc catagcacca agactgatgc | 2880 |
| cagtagcact caccatagct cggtacctcc tctcacctcc tccaatcaca gcacttctcc | 2940 |
| ccagttgtct actggggtct cttctttttt cctgtctttt cacatttcaa acctccagtt | 3000 |
| taattcctct ctggaagatc ccagcaccga ctactaccaa gagctgcaga gagacatttc | 3060 |
| tgaaatgttt ttgcagattt ataaacaagg gggttttctg ggcctctcca atattaagtt | 3120 |
| caggccagga tctgtggtgg tacaattgac tctggccttc cgagaaggta ccatcaatgt | 3180 |
| gcacgacgtg agacacagt tcaatcagta taaaacggaa gcagcctctc gatataacct | 3240 |
| gacgatctca gacgtcagcg tgagtgatgt gccatttcct ttctctgccc agtctggggc | 3300 |
| tggggtgcca ggctggggca tcgcgctgct ggtgctggtc tgtgttctgg ttgcgctggc | 3360 |
| cattgtctat ctcattgcct tggctgtctg tcagtgccgc cgaaagaact acgggcagct | 3420 |
| ggacatcttt ccagcccggg atacctacca tcctatgagc gagtacccca cctaccacac | 3480 |
| ccatgggcgc tatgtgcccc ctagcagtac cgatcgtagc ccctatgaga aggtttctgc | 3540 |
| aggtaacggt ggcagcagcc tctcttacac aaacccagca gtggcagcca cttctgccaa | 3600 |
| cttgtag | 3607 |

<210> SEQ ID NO 2
<211> LENGTH: 1923
<212> TYPE: DNA
<213> ORGANISM: Homo sapiens

<400> SEQUENCE: 2

| | |
|---|---|
| atggggcagc catctctgac ttggatgctg atggtggtgg tggcctcttg gttcatcaca | 60 |
| actgcagcca ctgacacctc agaagcaaga tggtgctctg aatgtcacag caatgccacc | 120 |
| tgcacggagg atgaggccgt tacgacgtgc acctgtcagg agggcttcac cggcgatggc | 180 |
| ctgacctgcg tggacctgga tgagtgcgcc attcctggag ctcacaactg ctccgccaac | 240 |
| agcagctgcg taaacacgcc aggctccttc tcctgcgtct gccccgaagg cttccgcctg | 300 |
| tcgcccggtc tcggctgcac agacgtggat gagtgcgctg agcctgggct tagccactgc | 360 |
| cacgccctgg ccacacgtgt caatgtggtg gcagctact tgtgcgtatg ccccgcgggc | 420 |
| taccgggggg atggatggca ctgtgagtgc tccccgggct cctgcgggcc ggggttggac | 480 |
| tgcgtgcccg agggcgacgc gctcgtgtgc gcggatccgt gccaggcgca ccgcaccctg | 540 |
| gacgagtact ggcgcagcac cgagtacggg gagggctacg cctgcgacac ggacctgcgc | 600 |
| ggctggtacc gcttcgtggg ccagggcggt gcgcgcatgg ccgagacctg cgtgccagtc | 660 |
| ctgcgctgca acacggccgc ccccatgtgg ctcaatggca cgcatccgtc cagcgacgag | 720 |
| ggcatcgtga ccgcaaggc ctgcgcgcac tggagcggcc actgctgcct gtgggatgcg | 780 |
| tccgtccagg tgaaggcctg tgccggcggc tactacgtct acaacctgac agcgcccccc | 840 |
| gagtgtcacc tggcgtactg cacagacccc gctccgtgg aggggacgtg tgaggagtgc | 900 |
| agtatagacg aggactgcaa atcgaataat ggcagatggc actgccagtg caaacaggac | 960 |
| ttcaacatca ctgatatctc cctcctggag cacaggctgg aatgtgggc caatgacatg | 1020 |
| aaggtgtcgc tggcaagtg ccagctgaag agtctgggct cgacaaggt cttcatgtac | 1080 |
| ctgagtgaca gccggtgctc gggcttcaat gacagagaca accgggactg ggtgtctgta | 1140 |
| gtgacccag cccgggatgg cccctgtggg acagtgttga cgaggaatga aacccatgcc | 1200 |
| acttacagca acacctctca cctggcagat gagatcatca tccgtgacct caacatcaaa | 1260 |

-continued

| | |
|---|---|
| atcaactttg catgctccta cccctggac atgaaagtca gcctgaagac cgccctacag | 1320 |
| ccaatggtca gtgctctaaa catcagagtg ggcgggaccg gcatgttcac cgtgcggatg | 1380 |
| gcgctcttcc agacccttc ctacacgcag ccctaccaag gctcctccgt gacactgtcc | 1440 |
| actgaggctt ttctctacgt gggcaccatg ttggatgggg gcgacctgtc ccgatttgca | 1500 |
| ctgctcatga ccaactgcta tgccacaccc agtagcaatg ccacggaccc cctgaagtac | 1560 |
| ttcatcatcc aggacagatg cccacacact agagactcaa ctatccaagt ggtgagaat | 1620 |
| ggggagtcct cccagggccg atttccgtc cagatgttcc ggtttgctgg aaactatgac | 1680 |
| ctagtctacc tgcactgtga agtctatctc tgtgacacca tgaatgaaaa gtgcaagcct | 1740 |
| acctgctctg ggaccagatt ccgaagtggg agtgtcatag atcaatcccg tgtcctgaac | 1800 |
| ttgggtccca tcacacggaa aggtgtccag gccacagtct caagggcttt tagcagcttg | 1860 |
| gggctcctga aagtctggct gcctctgctt ctctcggcca ccttgaccct gacttttcag | 1920 |
| tga | 1923 |

<210> SEQ ID NO 3
<211> LENGTH: 2768
<212> TYPE: DNA
<213> ORGANISM: Homo sapiens

<400> SEQUENCE: 3

| | |
|---|---|
| agagtcatcc agctggagcc ctgagtggct gagctcaggc cttcgcagca ttcttgggtg | 60 |
| ggagcagcca cgggtcagcc acaagggcca cagccatgaa tggcacagaa ggccctaact | 120 |
| tctacgtgcc cttctccaat gcgacgggtg tggtacgcag ccacttcgag tacccacagt | 180 |
| actacctggc tgagccatgg cagttctcca tgctggccgc ctacatgttt ctgctgatcg | 240 |
| tgctgggctt cccatcaac ttcctcacgc tctacgtcac cgtccagcac aagaagctgc | 300 |
| gcacgcctct caactacatc ctgctcaacc tagccgtggc tgacctcttc atggtcctag | 360 |
| gtggcttcac cagcaccctc tacacctctc tgcatggata cttcgtcttc gggcccacag | 420 |
| gatgcaattt ggagggcttc tttgccaccc tgggcggtga aattgccctg tggtccttgg | 480 |
| tggtcctggc catcgagcgg tacgtggtgg tgtgtaagcc catgagcaac ttccgcttcg | 540 |
| gggagaacca tgccatcatg ggcgttgcct tcacctgggt catggcgctg gcctgcgccg | 600 |
| cacccccact cgccggctgg tccaggtaca tccccgaggg cctgcagtgc tcgtgtggaa | 660 |
| tcgactacta cacgctcaag ccggaggtca caacgagtc ttttgtcatc tacatgttcg | 720 |
| tggtccactt caccatcccc atgattatca tctttttctg ctatgggcag ctcgtcttca | 780 |
| ccgtcaagga ggccgctgcc cagcagcagg agtcagccac cacacagaag gcagagaagg | 840 |
| aggtcacccg catggtcatc atcatggtca tcgcttttcc tgatctgctgg gtgccctacg | 900 |
| ccagcgtggc attctacatc ttcacccacc agggctccaa cttcggtccc atcttcatga | 960 |
| ccatcccagc gttctttgcc aagagcgcc ccatctacaa ccctgtcatc tatatcatga | 1020 |
| tgaacaagca gttccggaac tgcatgctca ccaccatctg ctgcggcaag aacccactgg | 1080 |
| gtgacgatga ggcctctgct accgtgtcca agacggagac gagccaggtg gccccggcct | 1140 |
| aagacctgcc taggactctg tggccgacta taggcgtctc ccatccccta cccttcccc | 1200 |
| cagccacagc catcccacca ggagcagcgc ctgtgcagaa tgaacgaagt cacataggct | 1260 |
| ccttaatttt ttttttttt ttaagaaata attaatgagg ctcctcactc acctgggaca | 1320 |
| gcctgagaag ggacatccac caagacctac tgatctggaa tccacgttc cccaaggcca | 1380 |
| gcgggatgtg tgcccctcct cctcccaact catctttcag gaacacgagg attcttgctt | 1440 |

```
tctggaaaag tgtcccagct tagggataag tgtctagcac agaatggggc acacagtagg    1500
tgcttaataa atgctggatg gatgcaggaa ggaatggagg aatgaatggg aagggagaac    1560
atatctatcc tctcagaccc tcgcagcagc agcaactcat acttggctaa tgatatggag    1620
cagttgtttt tccctcsctg ggcctcactt tcttctccta taaaatggaa atcccagatc    1680
cctggtcctg ccgacacgca gctactgaga agaccaaaag aggtgtgtgt gtgtctatgt    1740
gtgtgtttca gcactttgta aatagcaaga agctgtacag attctagtta atgttgtgaa    1800
taacatcaat taatgtaact agttaattac tatgattatc acctcctgat agtgaacatt    1860
ttgagattgg gcattcagat gatgggsttt cacccaacct tggggcaggt ttttaaaaat    1920
tagctaggca tcaaggccag accagggctg ggggttgggc tgtaggcagg gacagtcaca    1980
ggaatgcaga atgcagtcat cagacctgaa aaaacaacac tggggagggg ggacggtgaa    2040
ggccaagttc ccaatgaggg tgagattggg cctggggtct cacccctagt gtggggcccc    2100
aggtcccgtg cctcccttc ccaatgtggc ctatggagag acaggccttt ctctcagcct     2160
ctggaagcca cctgctcttt tgctctagca cctgggtccc agcatctaga gcatggagcc    2220
tctagaagcc atgctcaccc gcccacattt aattaacagc tgagtccctg atgtcatcct    2280
tatctcgaag agcttagaaa caaagagtgg gaaattccac tgggcctacc ttccttgggg    2340
atgttcatgg gccccagttt ccagtttccc ttgccagaca agcccatctt cagcagttgc    2400
tagtccattc tccattctgg agaatctgct ccaaaaagct ggccacatct ctgaggtgtc    2460
agaattaagc tgcctcagta actgctcccc cttctccata taagcaaagc cagaagctct    2520
agctttaccc agctctgcct ggagactaag gcaaattggg ccattaaaag ctcagctcct    2580
atgttggtat taacggtggt gggttttgtt gctttcacac tctatccaca ggatagattg    2640
aaactgccag cttccacctg atccctgacc ctgggatggc tggattgagc aatgagcaga    2700
gccaagcagc acagagtccc ctggggctag aggtggagga ggcagtcctg ggaatgggaa    2760
aaaccccca                                                            2768

<210> SEQ ID NO 4
<211> LENGTH: 2546
<212> TYPE: DNA
<213> ORGANISM: Homo sapiens

<400> SEQUENCE: 4
aggtggagca agatggctgt ggagctgggc gtgctgctcg tccggccccg gcccggaacc      60
gggctgggta gagtgatgcg gaccctcctg ctggtgctgt ggctggcgac gcgcggaagc     120
gcgctctact ttcacatcgg agagacggag aagaagtgct ttattgagga gatcccggac     180
gagaccatgg tcataggaaa ctaccggacg cagctgtatg acaagcagcg ggaggagtac     240
cagccggcca ccccgggggct tggcatgttt gtggaggtga aggacccaga ggacaaggtc     300
atcctggccc ggcagtatgg ctccgagggc aggttcactt tcacttccca tacccctggt     360
gagcaccaga tctgtcttca ctccaattcc accaagttct ccctctttgc tggaggcatg     420
ctgagagttc acctggacat ccaggtaggt gaacatgcca atgactatgc agaaattgct     480
gctaaagaca agttgagtga gttgcagcta cgagtgcgac agctggtgga acaagtggag     540
cagatccaga aagagcagaa ctaccagcgg tggcgagagg agcgcttccg gcagaccagt     600
gagagcacca accagcgggt gctgtggtgg tccattctgc agaccctcat cctcgtggcc     660
atcggtgtct ggcagatgcg gcacctcaag agcttctttg aagccaagaa gcttgtgtag    720
```

-continued

```
ctgtcccagg cgtcacaacc catcctccca ggctggggga gaaaggacct cctggaactg    780
acttcttctg tcaggaggac tggtttccag ccatacctgt tctggaaggg agaggggctg    840
gaggcaccca caggcacaag ctgaaggcag cagcttggct aatactgagc aggtagtggg    900
gcaaattcct gccctctctc tctggcctct gggccgtttg gtagtaatca cccaagggct    960
ggtaaagccc ctcctcttgg cacctcagaa tcacagtgtt actgatcagg gatgtgaggc   1020
tgctgttggg ggtgggggga ggggaatggg caggcaagcc agtcttctgt cttcctttgc   1080
taacttaggg ttttgagcag gttggggtat ggtgcctgtc atacccacct gccaccctgg   1140
gaacctcact gttctctctt tcagcctaga cctgctgatc cagggtgtgt gtgagttgag   1200
ggtgggtgga ggggtttgca gtgtgggaat gtggccctgc agttgacctg agctgcttca   1260
catggttgtc cattctgggg cttaaagaac tgggaccaga ccaagtagag gccttggtgc   1320
tggttggggt ggggcctgca gagtcttagt tactgatttc attttcaata aatgtaggtt   1380
tgttacatga gtttcccaat aaaaaaaaaa atgacttctt gtccagtgca agtgactcag   1440
tcatcagtgg gcacacactg cagggtgcct cagggaatgc cagttcttcc aaagagcaaa   1500
gcacttcaca ttccaaagtg aattcccacc agtcagcttc attctttcct tcttctccag   1560
gccttcctgt ggcagggaat agtgggtttg tccaagatta taacaagt aaattgggct    1620
ggggctcaaa tttacaccct ttcctctgtg ccagctccct ggtgaagttc cctctttcta   1680
gagtcagtaa gcaggattgt catggatgct gccaggaagt gcctggtaag gaggtgcatt   1740
gagcagggga gtgctacagg acagccaccc tgggctggca gggacaagga tgttgatggg   1800
ctaaaccaac agcaagtgat ttcaaccagg accatgaagg agaggaagga ttctgctgga   1860
aggagatggc aggacagggg tggttggaga agtggaggca aacagctgga atggaggtgg   1920
gtgggtgttt aatttcagct gcagagggtg ttgtgaggaa gctggaaagg aaggttggat   1980
tagagaagcc tcgagctcca ggtaagcgat ttggacatgc ccacctttca agaggggctg   2040
caggcaccca caggcacaag ctgaaggcag cagcttggct ggcttaatac tgagcaggtg   2100
gtggggtaaa tgcctgcccc cctccctctg gcctctgggc cctttgcagt aatcacccag   2160
ggtctggtaa agccactgag agccctactg gcacctcaga atcacagtgt tattgatcag   2220
ggatgtgagg ctgctgttgg gggttggggg aggcaaatgg gcaggcagtt ttgagaagaa   2280
ccttctaata agaaatgtga gggaggttac agcagtgtgt gagaaagacc aggaagaagg   2340
agacaagttt gggggctgct tccctaatg ggatgatgca atctgggctc atgctgccaa   2400
ctaattcttc cacatgaaaa aaaaaagttt tttggcgggc acggtggttc acacctgtaa   2460
tcccagcact ttgggaggct gaggtaggtg gatggcctga ggccaggagt ttgagaccag   2520
cctggccaac atggtgaaac ctcatc                                          2546
```

<210> SEQ ID NO 5
<211> LENGTH: 235
<212> TYPE: PRT
<213> ORGANISM: Homo sapiens

<400> SEQUENCE: 5

```
Met Ala Val Glu Leu Gly Val Leu Leu Val Arg Pro Arg Pro Gly Thr
1               5                   10                  15

Gly Leu Gly Arg Val Met Arg Thr Leu Leu Val Leu Trp Leu Ala
                20                  25                  30

Thr Arg Gly Ser Ala Leu Tyr Phe His Ile Gly Glu Thr Glu Lys Lys
            35                  40                  45
```

```
Cys Phe Ile Glu Glu Ile Pro Asp Glu Thr Met Val Ile Gly Asn Tyr
 50                  55                  60

Arg Thr Gln Leu Tyr Asp Lys Gln Arg Glu Tyr Gln Pro Ala Thr
 65                  70                  75                  80

Pro Gly Leu Gly Met Phe Val Glu Val Lys Asp Pro Glu Asp Lys Val
                 85                  90                  95

Ile Leu Ala Arg Gln Tyr Gly Ser Glu Gly Arg Phe Thr Phe Thr Ser
            100                 105                 110

His Thr Pro Gly Glu His Gln Ile Cys Leu His Ser Asn Ser Thr Lys
        115                 120                 125

Phe Ser Leu Phe Ala Gly Gly Met Leu Arg Val His Leu Asp Ile Gln
130                 135                 140

Val Gly Glu His Ala Asn Asp Tyr Ala Glu Ile Ala Ala Lys Asp Lys
145                 150                 155                 160

Leu Ser Glu Leu Gln Leu Arg Val Arg Gln Leu Val Glu Gln Val Glu
                165                 170                 175

Gln Ile Gln Lys Glu Gly Asn Tyr Gln Arg Trp Arg Glu Glu Arg Phe
            180                 185                 190

Arg Gln Thr Ser Glu Ser Thr Asn Gln Arg Val Leu Trp Trp Ser Ile
        195                 200                 205

Leu Gln Thr Leu Ile Leu Val Ala Ile Gly Val Trp Gln Met Arg His
210                 215                 220

Leu Lys Ser Phe Phe Glu Ala Lys Lys Leu Val
225                 230                 235

<210> SEQ ID NO 6
<211> LENGTH: 27
<212> TYPE: DNA
<213> ORGANISM: Artificial
<220> FEATURE:
<223> OTHER INFORMATION: synthetic

<400> SEQUENCE: 6
ggcagagaaa ggaaatggca catcact                                         27

<210> SEQ ID NO 7
<211> LENGTH: 27
<212> TYPE: DNA
<213> ORGANISM: Artificial
<220> FEATURE:
<223> OTHER INFORMATION: synthetic

<400> SEQUENCE: 7
ctgctgctcc tcacagtgct tacaggt                                         27

<210> SEQ ID NO 8
<211> LENGTH: 20
<212> TYPE: DNA
<213> ORGANISM: Artificial
<220> FEATURE:
<223> OTHER INFORMATION: synthetic

<400> SEQUENCE: 8
gctaccacag cccctaaacc                                                 20

<210> SEQ ID NO 9
<211> LENGTH: 19
<212> TYPE: DNA
<213> ORGANISM: Artificial
<220> FEATURE:
<223> OTHER INFORMATION: synthetic
```

```
<400> SEQUENCE: 9
gctgtggctg gagagtacg                                                  19

<210> SEQ ID NO 10
<211> LENGTH: 20
<212> TYPE: DNA
<213> ORGANISM: Artificial
<220> FEATURE:
<223> OTHER INFORMATION: synthetic

<400> SEQUENCE: 10
ccagccatag caccaagact                                                 20

<210> SEQ ID NO 11
<211> LENGTH: 20
<212> TYPE: DNA
<213> ORGANISM: Artificial
<220> FEATURE:
<223> OTHER INFORMATION: synthetic

<400> SEQUENCE: 11
ggaaggaaag gccgatactc                                                 20

<210> SEQ ID NO 12
<211> LENGTH: 22
<212> TYPE: DNA
<213> ORGANISM: Artificial
<220> FEATURE:
<223> OTHER INFORMATION: synthetic

<400> SEQUENCE: 12
ttacgagaga aaactcatgg cc                                              22

<210> SEQ ID NO 13
<211> LENGTH: 22
<212> TYPE: DNA
<213> ORGANISM: Artificial
<220> FEATURE:
<223> OTHER INFORMATION: synthetic

<400> SEQUENCE: 13
gggtccaagt tgtccagaat gc                                              22
```

US 11,207,278 B2

AGENTS FOR REVERSING TOXIC PROTEINOPATHIES

CROSS-REFERENCE TO RELATED APPLICATION

This application is a continuation of PCT application No. PCT/US2020/038847, filed Jun. 20, 2020, which claims the benefit of U.S. Provisional Application No. 62/865,096, filed Jun. 21, 2019, entitled "Agents for Reversing Toxic Proteinopathies," and of U.S. Provisional Application No. 62/878,304, filed Jul. 24, 2019, entitled "Agents for Reversing Toxic Proteinopathies." The entire contents of the aforementioned applications are incorporated herein by reference.

FIELD OF THE INVENTION

The invention relates generally to compositions, methods and kits for the treatment of toxic proteinopathies.

BACKGROUND OF THE INVENTION

Proteinopathies are a class of disease caused by genetic mutations that result in protein misfolding, truncation or mutation and the accumulation of the resulting protein aggregates inside the cell. There are no known, effective treatments for toxic proteinopathies. A need therefore exists for compounds capable of treating toxic proteinopathies, as well as therapeutic methods associated with such compounds.

BRIEF SUMMARY OF THE INVENTION

The current disclosure relates, at least in part, to the identification of a compound, (±)-2-endo-amino-3-exo-isopropylbicyclo[2.2.1]heptane (identified as "BRD-4780" herein and also previously known as AGN 192403), which was discovered herein to be an effective treatment for MUC1-associated kidney disease (MKD) and other toxic proteinopathies associated with extended endoplasmic reticulum (ER) residence of certain polypeptides (e.g., ADTKD-MUC1 or MKD (e.g., due to a frameshift or other mutation in MUC1), Retinitis Pigmentosa (e.g., due to rhodopsin mutations), autosomal dominant tubulo-interstitial kidney disease due to UMOD mutations (ADTKD-UMOD), and other forms of toxic proteinopathies resulting from mutant protein accumulation in the early secretory pathway, between the ER and cis-Golgi compartments. Such identification of (±)-2-endo-amino-3-exo-isopropylbicyclo [2.2.1]heptane as an agent capable of treating or preventing toxic proteinopathies derives from the instant disclosure's specific identification of MKD as a toxic proteinopathy caused by a frameshift in MUC1 ("MUC1-fs") that results in accumulation of MUC1-fs protein in the early secretory pathway (between the ER and cis-Golgi compartments, in TMED9-enriched vesicles), where it induces ER stress and activates the unfolded protein response (UPR).

One aspect of the instant disclosure provides a method of treating or preventing a toxic proteinopathy with (±)-2-endo-amino-3-exo-isopropylbicyclo[2.2.1]heptane or a pharmaceutically acceptable salt thereof.

In one embodiment, the 2-endo-amino-3-exo-isopropylbicyclo[2.2.1]heptane is racemic (±) 2-endo-amino-3-exo-isopropylbicyclo[2.2.1]heptane.

In certain embodiments, the 2-endo-amino-3-exo-isopropylbicyclo[2.2.1]heptane is (+) 2-endo-amino-3-exo-isopropylbicyclo[2.2.1]heptane.

In some embodiments, the 2-endo-amino-3-exo-isopropylbicyclo[2.2.1]heptane is (−) 2-endo-amino-3-exo-isopropylbicyclo[2.2.1]heptane.

Optionally, the 2-endo-amino-3-exo-isopropylbicyclo [2.2.1]heptane is a hydrochloride salt of 2-endo-amino-3-exo-isopropylbicyclo[2.2.1]heptane.

Another aspect of the instant disclosure provides a method for treating or preventing a proteinopathy resulting from mutant protein accumulation in the early secretory pathway in a subject, the method involving identifying a subject as having or at risk of developing a proteinopathy resulting from mutant protein accumulation in the early secretory pathway in a subject; and administering 2-endo-amino-3-exo-isopropylbicyclo[2.2.1]heptane or a pharmaceutically acceptable salt thereof, to the subject in an amount sufficient to cause reduction or improvement of a symptom of the proteinopathy resulting from mutant protein accumulation in the early secretory pathway in the subject, thereby treating or preventing the proteinopathy resulting from mutant protein accumulation in the early secretory pathway in the subject.

In certain embodiments, the compound causes release of MUC1, UMOD and/or rhodopsin from the early secretory compartment.

In one embodiment, the symptom of the proteinopathy is one or more of: end-stage renal disease, urinalysis revealing minimal protein and no blood, slowly progressive kidney failure, hyperglycemia, gout, a need for dialysis or kidney transplantation, night blindness; tunnel vision (optionally due to loss of peripheral vision); latticework vision; photopsia (blinking/shimmering lights); photophobia (aversion to bright lights); development of bone spicules in the fundus; slow adjustment from dark to light environments and vice versa; blurring of vision; poor color separation; loss of central vision; and/or blindness.

In some embodiments, the subject has a mutation in MUC1, UMOD and/or rhodopsin. Optionally, the MUC1 mutation is a MUC1 frameshift mutation, the UMOD mutation is a C126R UMOD mutation and/or the rhodopsin mutation is a P23H rhodopsin mutation.

In certain embodiments, the pharmaceutical composition that includes 2-endo-amino-3-exo-isopropylbicyclo[2.2.1] heptane is administered to the subject via the oral route ("per os" or "P.O.").

In one embodiment, the 2-endo-amino-3-exo-isopropylbicyclo[2.2.1]heptane or pharmaceutically acceptable salt thereof further includes a pharmaceutically-acceptable carrier/excipient.

Another aspect of the instant disclosure provides a method for reducing or eliminating accumulation of a mutant protein in the ER lumen of a cell, in COPI and/or COPII vesicles of a cell, in the cis-Golgi lumen of a cell, in the medial cisternae of the Golgi of a cell, and/or in the trans-Golgi network (TGN) of a cell, the method involving administering 2-endo-amino-3-exo-isopropylbicyclo[2.2.1] heptane to the environment of a cell in an amount sufficient to reduce or eliminate accumulation of the mutant protein in the ER lumen of the cell, in COPI and/or COPII vesicles of a cell, in the cis-Golgi lumen of the cell, in the medial cisternae of the Golgi of the cell, and/or in the trans-Golgi network (TGN) of the cell, thereby reducing or eliminating accumulation of the mutant protein in the ER lumen of the cell, in COPI and/or COPII vesicles of a cell, in the cis-Golgi lumen of the cell, in the medial cisternae of the Golgi of the cell, and/or in the trans-Golgi network (TGN) of the cell.

In one embodiment, the mutant protein is a MUC1 frameshift mutant protein, a UMOD pathogenic variant or a rhodopsin mutant. Optionally, the MUC1 mutation is a MUC1 frameshift mutation, the UMOD mutation is a C126R UMOD mutation and/or the rhodopsin mutation is a P23H rhodopsin mutation.

An additional aspect of the instant disclosure provides a kit for identifying a proteinopathy resulting from mutant protein accumulation in the early secretory pathway in a sample, where the kit includes: (a) an oligonucleotide for detection of a MUC1 frameshift mutant, a UMOD pathogenic variant and/or a rhodopsin mutant or (b) an antibody (optionally a labeled primary antibody, or the kit may include a labeled secondary antibody that binds the primary antibody) capable of binding a MUC1 frameshift mutant protein, a UMOD pathogenic variant protein and/or a rhodopsin mutant protein, and instructions for its use.

In certain embodiments, the sample is a sample of a subject having or at risk of developing a proteinopathy. Optionally, the proteinopathy is a neurodegenerative disease, MUC1-associated kidney disease, autosomal dominant kidney disease caused by uromodulin mutation(s) or a form of retinitis pigmentosa (RP) caused by a rhodopsin mutation. In certain embodiments, the proteinopathy is MUC1 kidney disease, Uromodulin kidney disease, Retinitis Pigmentosa, Parkinson's disease and other synucleinopathies, Familial Danish dementia, CADASIL (cerebral autosomal dominant arteriopathy with subcortical infarcts and leukoencephalopathy), Seipinopathies, Serpinopathies, Type II diabetes, Lysozyme amyloidosis, Dialysis amyloidosis, Cystic Fibrosis, Cataracts, Odontogenic tumor amyloid, Familial British dementia, Hereditary cerebral hemorrhage with amyloidosis (Icelandic), Familial amyloidotic neuropathy or Senile systemic/cardiomyopathy, ApoAII amyloidosis, Familial amyloidosis of the Finnish type (FAF), Fibrinogen amyloidosis, Inclusion body myositis/myopathy, Hereditary lattice corneal dystrophy, Pulmonary alveolar proteinosis or ApoL1-positive kidney disease.

A further aspect of the instant disclosure provides a pharmaceutical composition for treating a subject having or at risk of developing a proteinopathy that includes a therapeutically effective amount of 2-endo-amino-3-exo-isopropylbicyclo[2.2.1]heptane and a pharmaceutically acceptable carrier.

An additional aspect of the instant disclosure provides a method for preparing a 3-isopropylbicyclo[2.2.1]heptan-2-amine salt as a single enantiomer, the method involving protecting the amino group of a 3-isopropylbicyclo[2.2.1] heptan-2-amine salt to form an amide; performing a solvent separation step; and deprotecting the amino group, thereby preparing a 3-isopropylbicyclo[2.2.1]heptan-2-amine salt as a single enantiomer.

In one embodiment, the protecting group is pNO$_2$—Cbz. In another embodiment, the solvent separation step involves supercritical fluid chromatography, optionally performed on an AD-H column.

Another aspect of the instant disclosure provides a method for preparing 2-endo-amino-3-exo-isopropylbicyclo [2.2.1]heptane as a single enantiomer, the method involving:

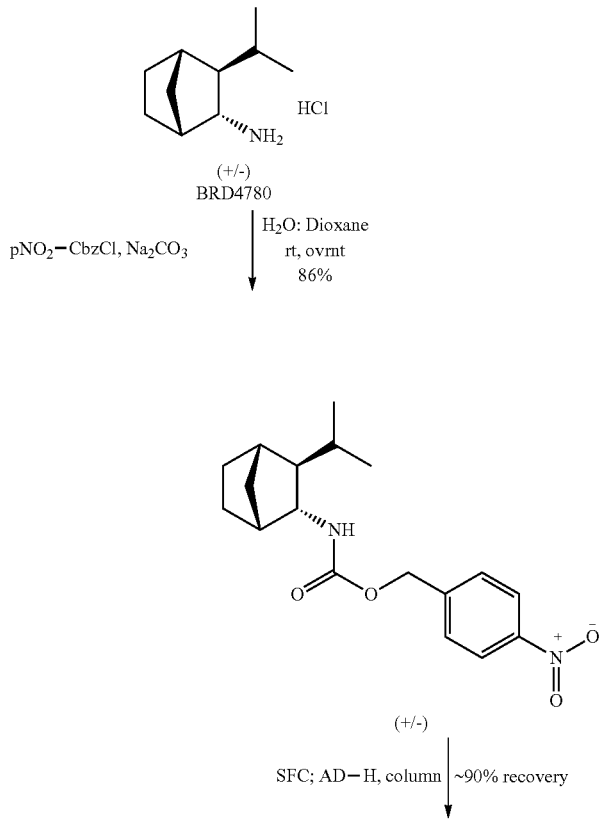

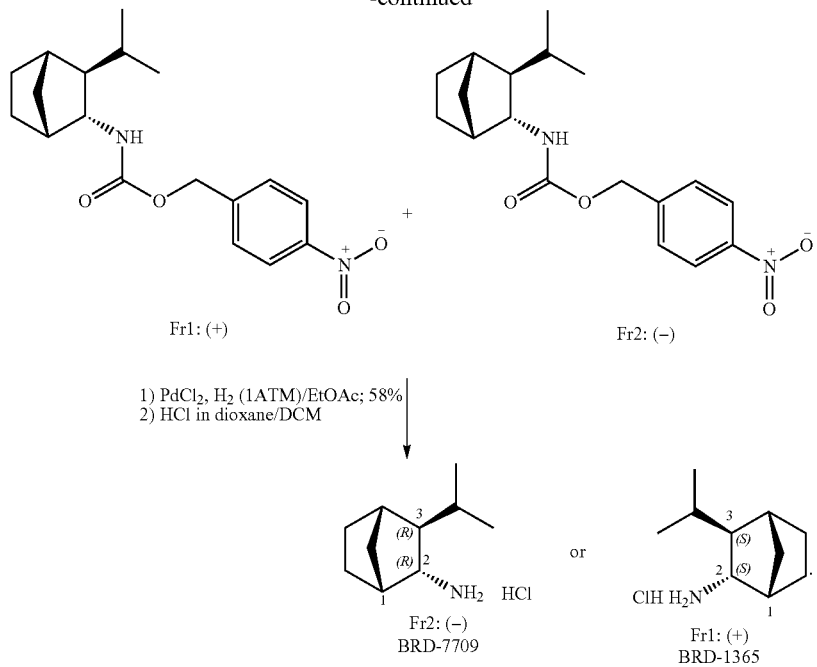

Another aspect of the instant disclosure provides a method of treating or preventing MUC1-associated kidney disease (MKD) in a subject in need thereof, the method involving administering to the subject 2-endo-amino-3-exo-isopropylbicyclo[2.2.1]heptane or a pharmaceutically acceptable salt thereof as a first agent and a second agent that is vitamin D, a phosphate binder, a blood pressure medication or a diuretic, thereby treating or preventing MKD in the subject.

In a further aspect, the instant disclosure provides a method for treating or preventing a proteinopathy, the method involving contacting a TMED9 gene or gene product with an agent that binds the TMED9 gene or gene product, thereby treating or preventing the proteinopathy.

In one embodiment, the proteinopathy is MUC1-associated kidney disease, autosomal dominant kidney disease caused by uromodulin mutations, a form of retinitis pigmentosa (RP) caused by a rhodopsin mutation, or a neurodegenerative disease (e.g., Alzheimer's disease (AD) or other dementia; Parkinson's disease (PD) or a PD-related disorder; prion disease (including, e.g., Creutzfeldt-Jakob Disease, variant Creutzfeldt-Jakob Disease, Bovine Spongiform Encephalopathy, Kuru, Gerstmann-Straussler-Scheinker disease, fatal familial insomnia (FFI), scrapie, or other animal TSE); motor neuron disease (MND; including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), or Kennedy's Disease); or spinocerebellar ataxia (SCA)).

In certain embodiments, the proteinopathy is a proteinopathy of the secretory pathway.

In some embodiments, the agent that binds the TMED9 gene or gene product binds the TMED9 protein.

In one embodiment, the agent that binds the TMED9 gene or gene product is a small molecule. Optionally, the agent that binds the TMED9 gene or gene product is 2-endo-amino-3-exo-isopropylbicyclo[2.2.1]heptane.

In certain embodiments, the proteinopathy is treated in a cell.

In one embodiment, the proteinopathy is treated in a tissue or subject. Optionally, the subject is human.

In another embodiment, the agent that binds the TMED9 gene or gene product inhibits and/or downregulates the TMED9 gene or gene product.

An additional aspect of the instant disclosure provides a method for treating or preventing a proteinopathy in a cell, the method involving disrupting the TMED9 gene of the cell, thereby treating or preventing the proteinopathy in the cell.

Another aspect of the instant disclosure provides a method for treating or preventing a proteinopathy in a cell, the method involving contacting the cell with an agent that binds a TMED9 gene product in the cell, thereby treating or preventing the proteinopathy in the cell.

In one embodiment, the agent that binds the TMED9 gene product inhibits and/or downregulates the TMED9 gene product.

In certain embodiments, the TMED9 gene product is a TMED9 mRNA.

In another embodiment, the TMED9 gene product is a TMED9 protein.

A further aspect of the instant disclosure provides a method for releasing a misfolded protein from the secretory pathway of a cell, the method involving contacting the cell with an agent that binds a TMED9 gene or gene product, thereby releasing the misfolded protein from the secretory pathway of the cell.

In one embodiment, the misfolded protein is a MUC1 mutant protein (e.g., a MUC1 frameshift mutant protein), a UMOD pathogenic variant protein (e.g., a C126R UMOD mutant protein) and a rhodopsin mutant protein (e.g., a P23H rhodopsin mutant protein).

Another aspect of the instant disclosure provides a method for treating or preventing a proteinopathy in a subject, the method involving administering a pharmaceutical composition that includes an agent that binds the TMED9 gene or gene product to the subject, thereby treating or preventing the proteinopathy in the subject.

In one embodiment, the subject is human.

An additional aspect of the instant disclosure provides a method for identifying a candidate TMED9 gene- or gene product-binding agent, the method involving (a) providing a cell harboring a misfolded protein of the secretory pathway; (b) contacting the cell with a test compound; and (c) identifying removal of the misfolded protein from the cell in the presence of the test compound, as compared to an appropriate control, thereby identifying the test compound as a candidate TMED9 gene- or gene product-binding agent.

In certain embodiments, the test compound is a small molecule.

In other embodiments, the test compound is a macromolecule. Optionally, the test compound is a nucleic acid.

In one embodiment, step (c) includes identifying preferential removal of the misfolded protein from the cell, as compared to the corresponding wild-type form of the misfolded protein.

In certain embodiments, the removal of the misfolded protein from the cell is detected as a change in fluorescence. Optionally, the removal of the misfolded protein from the cell is detected as a reduction in immunofluorescence.

In some embodiments, the misfolded protein is labeled.

A further aspect of the instant disclosure provides a method for treating or preventing a proteinopathy, the method involving contacting a TMED9 gene or gene product with an agent that binds the TMED9 gene or gene product, where the agent that binds the TMED9 gene or gene product is identified by: (a) providing a cell harboring a misfolded protein of the secretory pathway; (b) contacting the cell with a test compound; and (c) identifying the test compound as an agent that binds the TMED9 gene or gene product by detecting removal of the misfolded protein from the cell in the presence of the test compound, as compared to an appropriate control, thereby treating or preventing the proteinopathy.

Another aspect of the instant disclosure provides a pharmaceutical composition for treating a subject having or at risk of developing a proteinopathy of the secretory pathway, the pharmaceutical composition including a therapeutically effective amount of a TMED9 gene- or gene product-binding agent and a pharmaceutically acceptable carrier.

In certain embodiments, the proteinopathy of the secretory pathway is MUC1-associated kidney disease, autosomal dominant kidney disease caused by uromodulin mutations, a form of retinitis pigmentosa (RP) caused by a rhodopsin mutation, or a neurodegenerative disease (e.g., Alzheimer's disease (AD) or other dementia; Parkinson's disease (PD) or a PD-related disorder; prion disease (including, e.g., Creutzfeldt-Jakob Disease, variant Creutzfeldt-Jakob Disease, Bovine Spongiform Encephalopathy, Kuru, Gerstmann-Straussler-Scheinker disease, fatal familial insomnia (FFI), scrapie, or other animal TSE); motor neuron disease (MND; including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), or Kennedy's Disease); or spinocerebellar ataxia (SCA)).

In some embodiments, the TMED9 gene- or gene product-binding agent disrupts, inhibits and/or downregulates the TMED9 gene or gene product.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

A proteinopathy is a disease, disorder, or dysfunction in which abnormal protein metabolism or accumulation has been implicated. Some proteinopathies may include neurodegenerative diseases, cognitive impairment, lysosomal storage diseases, immunologic diseases, mitochondrial diseases, ocular diseases, inflammatory diseases, cardiovascular diseases, and proliferative diseases, etc. Further, included under the umbrella definition of proteinopathies are such specific pathologies as synucleinopathies, tauopathies, amyloidopathies, TDP-43 proteinopathies and others.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medic judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethylamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.).

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows periodic acid-schiff (PAS) staining of kidney biopsies from a normal individual (left panel) and an MKD patient (right panel), with the latter showing prominent dilated tubules. FIG. 1B shows immunoperoxidase staining for MUC1-wt protein (apical tubular cell staining, left) and MUC1-fs protein (diffuse intracellular tubular cell staining, right) in an MKD patient kidney biopsy. FIG. 1C shows PAS-stained kidney sections from 24 month old +/+ and wt/+ female knock-in mice, serving as a negative control. (n=67+/+ mice; 23 wt/+ mice). FIG. 1D shows immunoperoxidase staining for MUC1-wt protein (apical tubular cell staining, left) and MUC1-fs protein (diffuse intracellular tubular cell staining, right) from a fs/+ knock-in mouse showed similar localization as in human MKD kidney tissue (FIG. 1B). FIG. 1E shows PAS stained kidney sections from female fs/+ knock-in mice at ages 4, 8, 12 and 24 months old, illustrating progressively prominent dilated tubules as the disease advances. Kidney regions (cortex, medulla) are marked with dashed lines. (n=23 fs/+ mice). FIG. 1F shows immunofluorescence (IF) co-staining of distal tubule in MKD patient kidney organoid for MUC1-wt (red), MUC1-fs (green), E-cadherin (blue) and Na+/K+ ATPase (yellow), which showed that MUC1-fs was localized intracellularly (middle) compared to MUC1-wt, which was apical (left). FIG. 1G depicts IF co-staining in P cells for MUC1-fs (green), MUC1-wt (red) and Hoechst (grey), which showed that MUC1-fs was localized intracellularly (middle) compared to MUC1-wt, which was found on the plasma membrane (left).

FIG. 2A shows UPR branch activation analysis in N and P cells. Generalized (Complex), or specific branch activation (ATF6, PERK and IRE1) was evaluated using a previously described UPR branch transcriptome (Adamson et al., 2016). Z-scores of normalized expression values obtained from RNA-Seq were used to generate scaled mean expression profiles. A single boxplot represents the genes in the indicated UPR arm (n=3 replicates). FIG. 2B shows that inhibition of the three UPR branches demonstrates a specific involvement of ATF6 in P cell cytoprotection. Cell apoptosis was calculated using the protocol summarized in FIG. 9G below, after 72 hour treatment of N and P cells with either PERK inhibitor (PERKi, GSK2656157, 10 µM), IRE inhibitor (IREi, 4µ8c, 10 µM) or ATF6 inhibitor (ATF6i, PF-429242, 10 µM). Caspase 3/7 activation was calculated as the fraction of caspase 3/7 positive cells. Values are means+SD. (n=4 replicates). FIG. 2C depicts immunoblot and RT-PCR analysis of downstream effectors of the three UPR branches in N and P cells. Protein abundance of BiP (Complex), GRP94 and ERp72 (ATF6), ATF4 and CHOP (PERK) and mRNA levels of spliced XBP1 (sXBP1; IRE) were consistent with trends in transcriptomic data in FIG. 2A and cell protection data in FIG. 2B. (n>3 replicates). FIG. 2D shows activation of downstream effectors (as described in FIG. 2C) of all UPR branches, including PERK, in P compared to N cells after treatment with THP (100 nM) for 12 hours. (n>3 replicates). FIG. 2E shows low magnification IF images of kidney section stained for MUC1-wt (blue), MUC1-fs (green) and ERp72 (red) in 4 month old female fs/+ mice (before disease onset). Images demonstrate co-staining of MUC1-fs with the ATF6 effector ERp72 in the tubules of the outer medulla. FIG. 2F shows results of immunoblot analysis of MUC1-fs as well as downstream effectors of ATF6 and PERK branches in 12 month old female+/+ and fs/+ mice (advanced disease). Increased abundance of calreticulin, ERp72 and GRP94 (ATF6 branch), and CHOP (PERK branch) was observed in fs/+ mice. (n=3 mice/genotype). FIG. 2G is a digital illustration of representative kidney sections stained with TUNEL to detect apoptotic cells in 12 month old female+/+ and fs/+ mice (advanced disease). All cells detected in the tissue section have been plotted according to their slide position (grey dots). Increased number of TUNEL positive cells (red dots) is shown in fs/+ kidney section mainly in the area of tubular damage (dashed line). FIG. 2H presents a graph depicting increased apoptosis in 12 month old female fs/+ mice versus female+/+ mice, as indicated by TUNEL staining quantification. Values are means+SD (n=3 mice/genotype). See also FIGS. 9A-9J below.

FIG. 3A shows a schematic illustration demonstrating the high content screen (HCS) strategy that resulted in the identification of BRD-4780. FIG. 3B shows primary screen results showing IF quantification of MUC1-fs versus MUC1 fs/wt ratio in P cells treated for 48 hours with each of 3713 compounds of the Repurposing Library at 5 dose points. DMSO (light yellow) was the negative control. JQ1 (orange) was used as a positive control. All compounds are marked in gray and progressively higher concentrations of BRD-4780 are highlighted with a pink to red dot color gradient (also in FIGS. 13A-13H). FIG. 3C shows secondary screen results demonstrating IF quantification of MUC1-fs versus MUC1 fs/wt ratio in P cells treated for 48 hours with each of 203 compounds (identified as hits from the primary screen) at 10 dose points. DMSO (light yellow) was the negative control. JQ1 (orange) was used as a positive control. FIG. 3D depicts results of the MUC1-fs profiling assay showing IF quantification of MUC1-fs versus MUC1-wt in P cells treated for 48 hours at 10 dose points with each of 71 compounds derived from the secondary screen. FIG. 3E depicts results of the MUC1 transcription assay showing measurement of total MUC1 mRNA versus IF quantification of MUC1 fs/wt ratio in P cells treated for 24 hours and 48 hours, respectively, with 71 compounds from the secondary screen. Only doses active in removing MUC1-fs are shown. FIG. 3F depicts results of a cell viability assay showing quantification for P cells treated for 5 days with 71 compounds from the secondary screen in the absence versus presence of THP (100 nM). Only doses active in removing MUC1-fs are shown. Cell viability was measured using live imaging, followed by measuring the fraction of live cells (cells negative to caspase 3/7 and DRAQ7). FIG. 3G presents IF images of P cells treated for 48 hours with DMSO or BRD-4780 (5 µM). MUC1-wt (yellow), MUC1-fs (green), Hoechst (grey). FIG. 3H shows BRD-4780 dose-response curves for IF-detected MUC1-fs, MUC1-wt and cell number in P cells treated as in FIG. 3G. Solid lines represent the best fits of the data to the four-parameter dose-response curve (GraphPad Prism software). EC50=143 nM. Values are means±SD. FIG. 3I comprises bright field images of representative P cells pre-treated for 48 hours with BRD-4780 (5 µM) or DMSO followed by 5 days co-treatment with BRD-4780 (5 µM) (or DMSO) plus THP (100 nM). Dead cells were identified based on far red autofluorescence. FIG. 3J shows dose response curves of P cell viability upon THP treatment as in FIG. 3I. Cell viability was measured as live cell number (See Example 1 below). Solid lines represent the best fits of the data to the four-parameter dose-response curve (GraphPad Prism software). $EC_{50}$ [THP]=17 nM; $EC_{50}$ [THP+BRD-4780]=75 nM. Values are means±SD. (n=3 replicates). See also FIGS. 10A and 10B below.

FIG. 4A shows IF images of MUC1-fs (green), MUC1-wt (red) and NCC (blue) in fs/+ mice treated for 7 days with vehicle (left) or BRD-4780 (50 mg/kg, middle) compared with vehicle treated+/+ mice (right). FIG. 4B presents results of mean MUC1-fs IF intensity in NCC-positive cells in kidney sections from fs/+ and +/+ mice treated with vehicle or BRD-4780 (1, 10 and 50 mg/kg) for 7 days. Mean intensity values were normalized to vehicle treated+1+ mice (0%) and to vehicle treated fs/+ mice (100%). Values are means f SD. (n=4 mice/genotype/dose; see Example 1 below for details). FIG. 4C shows immunoblot analysis of MUC1-fs in kidney lysates from fs/+ mice treated with vehicle or BRD-4780 (1, 10 and 50 mg/kg) for 7 days. (n=4 mice/genotype/dose). FIG. 4D shows results of RNA-Seq analysis of mouse kidney lysates from fs/+ mice treated with BRD-4780 (50 mg/kg/day) or vehicle for 7 days revealed GO pathways downregulated by BRD-4780. (n=3 mice/genotype). FIG. 4E shows IF images of MUC1-wt (red), MUC1-fs (green) and laminin (blue) in representative iPSC-derived kidney organoids from a normal individual (N1) and from three MKD patients (P1, P2 and P3), each treated for 72 hours with DMSO or BRD-4780 (10 µM). FIG. 4F depicts reduction in MUC1-fs protein abundance in human iPSC-derived kidney organoids generated from three MKD patients after treatment with BRD-4780 for 72 hours. Mean fluorescence intensity of tubular MUC1-fs was calculated using the protocol summarized in FIG. 12B below. Mean intensity values were normalized to DMSO treated normal organoids (0%) and to DMSO treated patient organoids (100%). Values are means±SD. (n=3 replicates). FIG. 4G shows results that depict that there was no effect of BRD-4780 treatment on MUC1-wt abundance in human iPSC-derived kidney organoids generated as in FIG. 4F. Mean intensity values were normalized to DMSO treated normal organoids (100%). Values are means±SD (n=3). See also FIGS. 12A and 12B below.

FIG. 5A is a schematic of the mammalian cell secretory pathway including relevant cellular compartments involved in vesicular transport, color code as labeled. FIG. 5B shows a subcellular distribution of MUC1-fs in P cells as detected by MUC1-fs co-localization with organelle-specific markers calnexin (Canx, ER), SEC31A (COPII), ERGIC-53 (ERGIC), TMED9 (COPI), GM130 (cis-Golgi), TGN46, (trans-Golgi), EEA1 (early endosomes), Rab7 (late endosomes) and LAMP1 (lysosomes). Co-localization was calculated using the protocol summarized in FIG. 13A below. Representative images of MUC1-fs colocalization with the organelle-specific markers are shown in FIG. 13B below. Values are means±SD. (n=3 replicates). FIG. 5C presents representative IF images showing co-localization of MUC1-fs (green) with TMED9 (red) in four systems: P cells, fs/+ mouse kidney sections, MKD patient iPSC-derived kidney organoids and kidney section of MKD patient. DAPI (grey). FIG. 5D depicts changes observed in the subcellular distribution of MUC1-fs in P cells after 3 and 5 hours of BRD-4780 treatment (5 µM). Changes are shown as the percentages of DMSO control (as in FIG. 5B). (n=3 replicates). FIG. 5E shows immunoblot analysis of MUC1-fs in P cells following 24 hour inhibition of anterograde ER-Golgi transport by BFA (200 ng/mL) or inhibition of lysosomal degradation by Bafilomycin A (100 nM) in the absence or presence of BRD-4780 (5 µM). Both perturbations abolished the BRD-4780 effect (n=3 replicates). See also FIGS. 13A-13D below.

FIGS. 6A to 6F show the mechanism of action of BRD-4780 by engagement of its target, TMED9. FIG. 6A presents IF images of MUC1-fs (green), TMED9 (red) and MUC1-wt (blue) showing increased abundance of TMED9 in MUC1-fs-positive tubules in patient iPSC-derived kidney organoids (middle) compared to normal control (top). TMED9 increased abundance was directly correlated with the increase of MUC1-fs and was reversed by BRD-4780 treatment (10 µM; 72 hours). FIG. 6B shows immunoblot analysis of P cells in which TMED9 was knocked out using CRISPR-Cas9 with two different sgRNAs (KO1 and KO2). Non-targeting sgRNAs were used as controls (NTC1 and NTC2). BRD-4780 (5 µM) treatment was applied for 72 hours and the abundance of TMED9, MUC1-fs and the coatomer protein 13-COP was tested. Knock out of TMED9 phenocopied the BRD-4780 effect. FIG. 6C presents IF images of MUC1-fs (green) and Hoechst (grey) in P cells after TMED9 or Nischarin deletion compared to cells treated with non-targeting sgRNA control (NTC) before and after treatment with BRD-4780 (5 µM) for 72 hours. FIG. 6D shows mean MUC1-fs IF intensity in P cells treated as in FIG. 6C. TMED9 deletion (red) phenocopied the BRD-4780 effect. Values are means±SD. (n>3 replicates). FIG. 6E depicts increased thermal stability assessed by CETSA suggestive of direct binding of BRD-4780 to TMED9. Representative immunoblot (top) and densitometric analysis (bottom) of TMED9 abundance in P cells at escalating temperatures (as indicated) with or without treatment with BRD-4780 (5 µM; 1 hour). Higher abundance of TMED9 was noted at temperatures>47° C. in the presence of BRD-4780. Solid lines represent the best fit of the data to the Boltzmann sigmoid. Values are means±SEM. (n=3 replicates). FIG. 6F depicts a schematic of a proposed BRD-4780 mechanism of action illustrating the untreated tubular epithelial cell (top) with MUC1-fs trapped in the early secretory pathway (in TMED9-enriched compartments). Without wishing to be bound by theory, following either engagement of TMED9 by BRD-4780 or TMED9 deletion (bottom), MUC1-fs is released from COPI/cis-Golgi/COPII compartments, thus allowing its anterograde transport through the secretory pathway, ultimately resulting in lysosomal degradation.

FIG. 7A is a schematic of hMUC1-wt and hMUC1-fs genomic constructs (the latter differing only by a single +C (cytosine) insertion (red asterisk) in exon 2) used to generate the wt/+ and fs/+ knock-in mouse models. Box (grey dotted line) shows extent of knock-in fs human gene sequence. FIG. 7B presents schematics of hMUC1-wt (left) and hMUC1-fs (right) proteins encoded by the mouse knock-in transgene transcripts. SP, signal peptide. VNTR, variable number of tandem repeats. SEA, sperm protein enterokinase and agrin domain. TMD, trans membrane domain; fs-VNTR, mutant neosequence VNTR; Neopeptide, unique neosequence C-terminal to the FS-VNTR. FIG. 7C shows immunoblot analysis of MUC1-wt and MUC1-fs expression in whole kidney lysates from +1+ and fs/+KI mice. (n=4 replicates). FIG. 7D shows immunoperoxidase staining for MUC1-wt (top) and MUC1-fs (bottom) in kidney sections from +/+ and fs/+KI mice. FIG. 7E depicts serum creatinine levels in +/+, wt/+ and fs/+ mice as function of age and gender. Values are means±SEM. * annotates statistically significant difference between fs/+ females +/+ females (for number of animals tested, please refer to FIG. 17 below). FIG. 7F shows PAS-stained kidney sections from male fs/+ mice at ages 4, 8, 12 and 24 months, illustrating disease progression (n=20 mice).

FIG. 8A presents IF images that demonstrate the distribution of MUC1-wt (red) and MUC1-fs (green) in kidneys of 4 month old female fs/+ mice. Top, low magnification of an entire kidney section, showing the location of the subsequent high magnification images presented in the bottom rows. First column, co-staining with NCC (blue) in cortex showing distal convoluted tubules positive for both, MUC1-fs and -wt. Second column, co-staining with AQP2 (blue) in cortex and outer stripe of the outer medulla showing collecting ducts positive for both, MUC1-fs and -wt. Third column, co-staining with LTL (blue) in cortex and outer stripe of the outer medulla showing lack of MUC1 staining with LTL-positive proximal tubules in the cortex (8/9) and positive MUC1-fs staining in proximal 10 tubules in the outer medulla (no MUC1-wt is detected). Fourth column, co-staining with AQP2 (blue) in inner medulla showing collecting ducts positive for both, MUC1-fs and -wt. FIG. 8B shows the characterization of fs/+ mouse model, specifically presenting an IF image of a coronal section from a 24 month old female fs/+ mouse, showing distributions of MUC1-wt (red), MUC1-fs (green) and AQP2 (blue). Note severely dilated tubules, particularly in the outer medulla were associated with high expression of MUC1-fs (green).

FIG. 9A presents IF images of human kidney organoids derived from iPSC cells from a normal sibling or an affected MKD patient. Distribution of MUC1-wt (red) and MUC1-fs (green) is shown in proximal and distal tubular structures, marked by LTL (yellow) and by E-cadherin (blue), respectively. FIG. 9B presents IF images of normal kidney-derived epithelial cells (N) and MKD patient kidney-derived epithelial cells (P). Co-staining for MUC1-fs (green), MUC1-wt (red) and Hoechst (blue) showed that MUC1-fs is exclusively expressed in P cells and localized intracellularly compared to MUC1-wt, which is expressed in both cell lines and is localized to the plasma membrane. FIG. 9C shows immunoblot analysis of MUC1-wt and MUC1-fs proteins in N and P cells, which showed MUC1-wt expression in both cell lines while MUC1-fs is expressed only in P cells. (n=5 replicates). FIG. 9D shows the results of RT-PCR analysis of P cells treated with THP (100 nM), which show that IRE inhibitor (IREi, 4μ8c) inhibited IRE activation, as detected by dose-dependent inhibition of XBP1 splicing (sXBP1). FIG. 9E shows immunoblot analysis of eIF2a in P cells, which showed that PERK inhibitor (PERM, GSK2656157) inhibited PERK activation, as detected by dose-dependent reduction of eIF2a phosphorylation (p-eIF2a). FIG. 9F shows immunoblot analysis of BiP in P cells treated with THP (100 nM), which showed that ATF6 inhibitor (ATF6i, PF-429242) inhibited ATF6 activation, as detected by dose-dependent reduction of BiP abundance. FIG. 9G shows results from the quantitative live imaging analysis sequence of caspase 3/7 activation. Following image acquisition (left panel), single cells were first identified using the digital phase contrast channel and cell number was calculated. Green fluorescence intensity was then measured using 488 channel (middle panel) and the threshold for Caspase 3/7-positive staining was determined. As an output, the fraction of caspase 3/7-positive apoptotic cells (right panel, green) or caspase 3/7-negative live cells (right panel, blue) was calculated in each well at each time point. FIG. 9H shows immunoblot analysis of MUC1-fs in P cells, which showed MUC1-fs accumulation following ATF6 inhibition (ATF6i, 10 μM) for 24 hours. (n=3 replicates). FIG. 9I is a set of bright field images of representative N and P cells treated with DMSO or THP (33 nM) overlaid with images of caspase 3/7 activation (apoptosis, green) show reduced cell number and increased proportion of caspase positive P cells (quantification is shown in FIG. 9J). FIG. 9J shows higher susceptibility of P cells to THP-induced apoptosis after 72 hour treatment with indicated concentrations of THP. Cell apoptosis was calculated using the protocol summarized in FIG. 9G. Values are means+SD (n=4 replicates).

FIG. 10A presents results from a primary screen. Primary screen statistics present the median and ±3 median absolute deviations for MUC1-fs IF quantification. Broad Repurposing Library 3713 compounds (grey), DMSO negative control (orange) and JQ1 positive control (yellow). The Z' score statistic for this high content assay was 0.35. FIG. JOB shows results from the RNA-Seq analysis of UPR branch activation (as in FIG. 2A) in P cells pretreated with DMSO or BRD-4780 (1 μM) for 12 hours, followed by 12 hour co-treatment with THP (100 nM) (n=3 replicates).

FIG. 11A shows a plot of the plasma and kidney BRD-4780 concentration vs. time curves in male 129S2 mice following a single i.v. or p.o. dose of BRD-4780 from a low dose PK study. FIG. 11B is a table of the calculated PK parameters from the data plotted in FIG. 11A following a single i.v. or p.o. dose of BRD-4780 in male 129S2 mice. "Rsq_adj" indicates the R-squared adjustment. "No." indicates number. "$C_o$" indicates the initial extrapolated concentration. "$C_{max}$" indicates the maximum concentration. "$T_{max}$" indicates the time of maximum concentration. "$T_{1/2}$" indicates the half-life. "$V_{dss}$" indicates the volume of distribution. "Cl" indicates clearance. "Inf" indicates infinity. Exrtrap" indicates extrapolated. "AUC" indicates the area under the curve. "$AUC_{0-last}$ Ratio (K/P)" indicates the ratio of $AUC_{0-last}$ in kidney/$AUC_{0-last}$ in plasma. FIG. 11E is a table of the calculated PK parameters from the data plotted in FIG. 11C following a single i.v. or p.o. dose of BRD-4780 at the indicated doses in male 129S2 mice. "Rsq_adj" indicates the R-squared adjustment. "No." indicates number. "$C_o$" indicates the initial extrapolated concentration. "$C_{max}$" indicates the maximum concentration. "$T_{max}$" indicates the time of maximum concentration. "$T_{1/2}$" indicates the half-life. "$V_{dss}$" indicates the volume of distribution. "Cl" indicates clearance. "Inf" indicates infinity. Exrtrap" indicates extrapolated. "AUC" indicates the area under the curve. "$AUC_{0-last}$ Ratio (K/P)" indicates the ratio of $AUC_{0-last}$ in kidney/$AUC_{0-last}$ in plasma. FIG. 11F is a table of the calculated PK parameters from the data plotted in FIG. 11D following a single i.v. or p.o. dose of BRD-4780 at the indicated doses in female 129S2 mice. "Rsq_adj" indicates the R-squared adjustment. "No." indicates number. "$C_o$" indicates the initial extrapolated concentration. "$C_{max}$" indicates the maximum concentration. "$T_{max}$" indicates the time of maximum concentration. "$T_{1/2}$" indicates the half-life. "$V_{dss}$" indicates the volume of distribution. "Cl" indicates clearance. "Inf" indicates infinity. Exrtrap" indicates extrapolated. "AUC" indicates the area under the curve. "$AUC_{0-last}$ Ratio (K/P)" indicates the ratio of $AUC_{0-last}$ in kidney/$AUC_{0-last}$ in plasma. FIG. 11G shows a plot of the plasma BRD-4780 concentration vs. time curves in male 129S-ELITE mice following a single i.v. or p.o. dose of BRD-4780 from a low dose PK study. FIG. 11O is a table of the calculated PK parameters from the data plotted in FIG. 11L following a single p.o. dose of BRD-1365 at the indicated doses in male 129S-ELITE mice. "$C_{max}$" indicates the maximum concentration. "$T_{max}$" indicates the time of maximum concentration. "AUC" indicates the area under the curve. "Inf" indicates infinity. "$C_{max}D$" indicates the dose normalized maximum concentration. "$T_{1/2}$" indicates the half-life. "Cl" indicates clearance. "$C_{max}$" indicates the maximum concentration. "h" indicates hour. "$C_{max}$" indicates the maximum concentration. "Vz" indicates the volume of distribution. "$AUC_{0-last}$ Ratio (K/P)" indicates the ratio of $AUC_{0-last}$ in kidney/$AUC_{0-last}$ in plasma. FIG. 11P is a table of the calculated PK parameters from the data plotted in FIG. 11L following a single p.o. dose of BRD-7709 at the indicated doses in male 129S-ELITE mice. "$C_{max}$" indicates the maximum concentration. "$T_{max}$" indicates the time of maximum concentration. "AUC" indicates the area under the curve. "Inf" indicates infinity. "$C_{max}D$" indicates the dose normalized maximum concentration. "$T_{1/2}$" indicates the half-life. "Cl" indicates clearance. $C_{max}$" indicates the maximum concentration. "h" indicates hour. "$C_{max}$" indicates the maximum concentration. "Vz" indicates the volume of distribution. "$AUC_{0-last}$ Ratio (K/P)" indicates the ratio of $AUG_{0-last}$ in kidney/$AUC_{0-last}$ in plasma. FIG. 11U shows a plot of the percent oral bioavailability of BRD-4780, BRD-1365 or BRD-7709 at the indicated doses in male Sprague Dawley rats from a low dose PK study. FIG. 11AA shows a plot of the mean and standard deviation plasma BRD-1365 concentration vs. time curves in female CD(SD) rats following a single p.o. dose of BRD-1365 at 10 mg/kg p.o., 30 mg/kg p.o., 50 mg/kg p.o. or 100 mg/kg p.o. FIG. 11AB is a table of calculated PK parameters from the data plotted in FIG. 11V and FIG. 11W following a single p.o. dose of BRD-4780 at the indicated doses in male and female CD(SD) rats. "$C_{max}$" indicates the maximum concentration. "$T_{max}$" indicates the time of maximum concentration. "$C_{last}$" indicates the last measured concentration. "$T_{last}$" indicates the time of last detected plasma concentration. "$T_{1/2}$" indicates the half-life. "$AUC_{0-24}$" indicates the area under curve up to 24 hours. "$AUC_{last}$" indicates the area under the curve up to last measured time point. "$AUC_{0-inf}$" indicates the extrapolated area under the curve. "$AUC_{\% Extrap}$" indicates the percentage of the area of the curve that is extrapolated. "CD" indicates the dose normalized $C_{max}$. "$AUC_{0-24/D}$" indicates the dose normalized area of the curve to 24 hours. "$AUC_{last/D}$" indicates the dose normalized area of the curve to last time point. "CL" indicates clearance. "$V_z$" indicates the volume of distribution. FIG. 11AC is a table of calculated PK parameters from the data plotted in FIG. 11X and FIG. 11Y following a single p.o. dose of BRD-7709 at the indicated doses in male and female CD(SD) rats. "$C_{max}$" indicates the maximum concentration. "$T_{max}$" indicates the time of maximum concentration. "$C_{last}$" indicates the last measured concentration. "$T_{last}$" indicates the time of last detected plasma concentration. "$T_{1/2}$" indicates the half-life. "$AUC_{0-24}$" indicates the area under curve up to 24 hours. "$AUC_{last}$" indicates the area under the curve up to last measured time point. "$AUC_{0-inf}$" indicates the extrapolated area under the curve. "$AUC_{\% Extrap}$" indicates the percentage of the area of the curve that is extrapolated. "$C_D$" indicates the dose normalized Cmax. "$AUC_{0-24/D}$" indicates the dose normalized area of the curve to 24 hours. "$AUC_{last/D}$" indicates the dose normalized area of the curve to last time point. "CL" indicates clearance. "$V_z$" indicates the volume of distribution. FIG. 11AD is a table of calculated PK parameters from the data plotted in FIG. 11Z and FIG. 11AA following a single p.o. dose of BRD-1365 at the indicated doses in male and female CD(SD) rats. "$C_{max}$" indicates the maximum concentration. "$T_{max}$" indicates the time of maximum concentration. "$C_{last}$" indicates last measured concentration. "$T_{last}$" indicates the time of last detected plasma concentration, where no data (ND) is listed if $T_{last}$ is not equal for the 3 rats. "$T_{1/2}$" indicates the half-life. "$AUC_{0-24}$" indicates the area under the curve for up to 24 hours. "$AUC_{0-inf}$" indicates the extrapolated area under the curve. "$AUC_{\% Extrap}$" indicates the percentage of the area of the curve that is extrapolated. "$C_D$" indicates the dose normalized Cmax. "$AUC_{0-24/D}$" indicates the dose normalized area of the curve up to 24 hours. "$AUC_{last/D}$" indicates the dose normalized area of the curve to last time point. "CL" indicates clearance. "$V_z$" indicates volume of distribution.

FIG. 12A depicts mean MUC1-wt IF intensity in NCC-positive cells in kidney sections from fs/+ mice treated with vehicle or BRD-4780 (1, 10 and 50 mg/kg) for 7 days. Values are means+SD (see Example 1 below for details; n=4 mice/genotype/dose). FIG. 12B shows results of the quantitative region-of-interest IF analysis sequence performed in FIGS. 4F and 4G. Image acquisition of an entire organoid section (original image of a single field), was performed for MUC1-fs (green), MUC1-wt (red) and laminin (blue) staining. MUC1-wt positive regions were identified using MUC1-wt staining (red) using a threshold of >7000 intensity and >2500 µm². MUC1-wt mean intensity was subsequently calculated in these regions and averaged for the entire organoid section. MUC1-wt regions, which were <5 µm apart, were clustered together and an area of 20 µm surrounding these clusters was selected as a MUC1 positive tubule. MUC1-fs signal was then detected using a spot identifier within these tubules excluding laminin area; the mean intensity of FS signal was calculated there and averaged for the entire organoid section.

FIG. 13A shows results of the IF analysis sequence of MUC1-fs intracellular co-localization in P cells. Following image acquisition of MUC1-fs (green) and organelle (red), single cell cytoplasm was identified (white border lines)(bottom right and middle panels) and the signals of MUC1-fs and the organelle within the cytoplasm was detected and displayed as spots of different colors (bottom left and middle, respectively). Overlap between MUC1-fs signal (bottom right, green) and the organelle signal (bottom right, red) was obtained only when pixels of the two signals (green and red) overlapped (bottom left, yellow). Co-localization was then calculated as total overlap area, normalized (divided) to the total area of MUC1-fs, and then to the total area of the organelle. FIG. 13B presents representative IF images of MUC1-fs colocalization with organelle-specific markers (as calculated in FIG. 5B). Right panel shows the software reconstruction that was used for downstream measurements (MUC1-fs, green; organelle, red; overlap, yellow). FIG. 13C depicts the effects of BFA and of Bafilomycin A on MUC1-fs subcellular distribution. P cells were treated with BFA (200 ng/mL) or Bafilomycin A (100 nM) for 24 hours and MUC1-fs distribution was tested as described in FIG. 5B. Percent change of DMSO treated cells was calculated for MUC1-fs co-localization with each organelle marker (n=3 replicates). Treatment with BFA resulted in MUC1-fs accumulation in the ER (and reduction in the late secretory pathway i.e. cis- and trans-Golgi, and endosomes). Treatment with Bafilomycin A resulted in accumulation of MUC1-fs in the late secretory pathway, and especially the late endosome/lysosome). FIG. 13D shows immunoblot analysis of MUC1-fs in P cells following 5 hour inhibition of the proteosome by Bortezomib (50 nM) in the absence or presence of BRD-4780 (5 µM) (left). Proteasomal inhibition was confirmed in N cells by increased ubiquitin levels after Bortezomib treatment (50 nM) (right). Proteosomal inhibition did not affect MUC1-fs removal by BRD-4780, indicating that its degradation did not occur in the proteasome (n=3 replicates).

FIGS. 14A to 14E depict that BRD-4780 was identified to act by engagement of its target, the cargo receptor TMED9. FIG. 14A presents IF images of MUC1-fs (green), GM130 (red) and MUC1-wt (blue) in MKD patient iPSC-derived kidney organoids, which showed no change in GM130 abundance upon BRD-4780 (10 μM) treatment for 72 hour. FIG. 14B presents IF images of MUC1-wt (yellow) and Hoechst (grey) in P cells after TMED9 or Nischarin deletion, as compared to cells treated with non-targeting sgRNA control (NTC) before and after treatment with BRD-4780 (5 μM) for 72 hours. No change in either MUC1-wt abundance or its plasma membrane localization was observed. FIG. 14C shows immunoblot analysis of P cells after depletion of I1R candidate (Nischarin) using shRNAs (KD1 and KD2; top) or CRISPR-Cas9 deletion (KO1 and KO2; bottom). BRD-4780 (5 μM) treatment was applied for 72 hours. BRD-4780 remained effective despite I1R depletion. FIG. 14D shows a table of eighteen compounds annotated as imidazoline-1 receptor ligands (IRLs) and their $EC_{50}$ values for reduction in MUC1-fs levels. Each compound was applied to P cells for 48 hours and effects on MUC1-fs were analyzed by IF imaging. (N/A, non-active, EC50>2E-05 [M]). FIG. 14E shows that BRD-4780 did not bind Nischarin, as assessed by CETSA. Densitometric analysis of Nischarin abundance after treatment of P cells with BRD-4780 (5 μM, 1 hour) or DMSO, followed by exposure to escalating temperatures showed no change in nischarin abundance in the presence of BRD-4780. Solid lines represent the best fits of the data to the Boltzmann sigmoid. Values are means±SEM. (n=3 replicates).

FIG. 15A shows IF images of UMOD (green) and Hoechst (grey) in AtT-20 cells stably transfected with C126R-UMOD and treated for 72 hours with DMSO or BRD-4780 (10 μM). FIG. 15B presents results of IF quantification of C126R-UMOD in AtT-20 cells treated as in FIG. 4A. Values are means±SD (n=4 replicates). FIG. 15C shows an immunoblot analysis of UMOD and ERp72 in AtT-20 cells stably transfected with C126R-UMOD, pre-treated for 24 hours with DMSO or BRD-4780 (1 μM or 10 μM) and an additional 24 hours with THP (10 nM). FIG. 15D presents bright field (BF) images (grey), overlaid with images of mutant rhodopsin P23H-GFP (green) in N cells pre-treated for 48 hours with DMSO or BRD-4780 (5 μM) followed by transient transfection with mutant rhodopsin P23H-GFP. FIG. 15E presents results of GFP intensity in live N cells expressing P23H-GFP and treated as in FIG. 15D (see Example 1 below for details). Values are means±SD. (n=8 replicates). FIG. 15F shows the results of an experiment in which the fraction of DRAQ7-positive cells (cell death marker) was determined in live N cells transiently transfected with mutant rhodopsin P23H-GFP and treated with DMSO or BRD-4780 (5 μM) for 72 hours. Values are means±SD. (n=8 replicates). FIG. 15G shows bright field (BF) images (grey), overlaid with images of huntingtin-GFP containing 97 polyQ repeats (green) in HEK cells transiently transfected with huntingtin-GFP containing 97 polyQ repeats and treated for 72 hours with DMSO or BRD-4780 (10 μM). FIG. 15H presents results of GFP puncta fluorescence intensity of huntingtin protein in live HEK cells expressing huntingtin-GFP and treated as in FIG. 15G (see Example 1 below for details). Values are means±SD (n=3 replicates).

FIG. 16 presents a table which shows how BRD-4780 has drug-like properties, as demonstrated by target profile criteria. LE, Ligand efficiency. LLE, Ligand lipophilic efficiency. PO, per os.

FIG. 20A shows fraction 1 (Fr1) results. FIG. 20B shows fraction 2 (Fr2) results.

FIG. 21A shows representative images of retinal sections from mice (Rho/+ or +/+) treated with vehicle or 50 mg/Kg/day BRD-4780 for 28 days. Rhodopsin antibody staining is shown in green and DAPI staining of nuclei is shown in blue. The arrows indicate the outer segment (OS) of the photoreceptors; the asterisks indicate the outer nuclear layer (ONL) of the photoreceptors. Bars=100 μm. FIG. 21B shows quantification of rhodopsin staining in the ONL normalized to the number of nuclei. Rhodopsin mainly localizes to the OS of the photoreceptors, therefore changes observed in the staining in the ONL bona fide reflected changes in the accumulation of rhodopsin in intracellular compartments.

DETAILED DESCRIPTION OF THE INVENTION

Figure 1A:
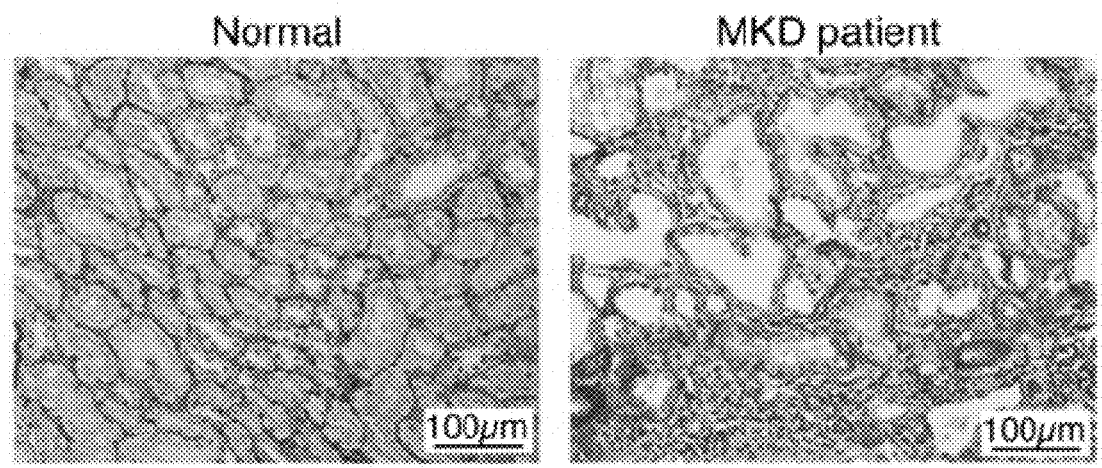
FIGS. 1A to 1G demonstrate that mutant MUC1-fs is retained intracellularly in tubular epithelial cells.

The present disclosure is directed, at least in part, to the discovery that a small molecule, 2-endo-amino-3-exo-isopropylbicyclo[2.2.1]heptane (also referred to as BRD-4780 herein and previously known as AGN 192403), was capable of reversing and therefore treating a number of toxic proteinopathies, via a mechanism involving the clearance of mutant proteins (that would otherwise provoke proteinopathies via extended residence within an affected cell, tissue, organoid and/or subject).

Compositions and methods for treatment of toxic proteinopathies (e.g., MKD (e.g., due to a frameshift or other mutation in MUC1), Retinitis Pigmentosa (e.g., due to rhodopsin mutations), autosomal dominant tubulo-interstitial kidney disease due to UMOD mutations (ADTKD-UMOD), and other forms of toxic proteinopathies resulting from mutant protein accumulation in the ER and/or other secretory pathway compartments and/or vesicles) are described in additional detail below.

Intracellular accumulation of misfolded proteins causes toxic proteinopathies, diseases which have been heretofore lacking in treatment options. MUC1 kidney disease (MKD) results from a frameshift mutation in the mucin 1 gene (MUC1-fs). The instant disclosure has identified that MKD is a toxic proteinopathy. As has been demonstrated herein, intracellular MUC1-fs accumulation activated the ATF6 unfolded protein response (UPR) branch. A small molecule, BRD-4780, was then identified via screening to be capable of clearing MUC1-fs from patient cells, from kidneys of knock-in mice and from patient kidney organoids. MUC1-fs was trapped in TMED9 cargo receptor-containing vesicles of the early secretory pathway. Without wishing to be bound by theory, BRD-4780 was identified herein to bind TMED9, releasing MUC1-fs and re-routing it for lysosomal degradation, an effect that was found to be phenocopied by TMED9 deletion. The instant disclosure has therefore identified BRD-4780 as a promising therapeutic lead compound for treatment of MKD. BRD-4780 also diminished mutant proteins associated with two additional toxic proteinopathies in in vitro studies. In certain aspects, the instant disclosure has therefore generally elucidated a novel therapeutic strategy for the release of misfolded, truncated or mutated proteins from cargo receptors and their anterograde trafficking to the lysosome.

Toxic Proteinopathies and Protein Trafficking

Diseases associated with protein misfolding and aggregation are known as proteinopathies (Bayer, 2015). More than 50 proteinopathies are caused by genetic mutations that result in protein misfolding and intracellular accumulation (Dubnikov et al., 2017; Dugger and Dickson, 2017). The accumulated proteins can cause cellular toxicity, as seen in some forms of Amyotrophic Lateral Sclerosis (ALS), Parkinson's disease, and Retinitis Pigmentosa (RP) (Dubnikov et al., 2017; Dugger and Dickson, 2017). Some proteinopathies, such as RP (Athanasiou et al., 2018), are characterized by the accumulation of misfolded proteins in the early secretory pathway (endoplasmic reticulum (ER) and Golgi apparatus), whereas others, such as Huntington's disease (Zoghbi and Orr, 2000), involve accumulation of misfolded protein aggregates in the cytoplasm or the nucleus.

The early secretory pathway of eukaryotic cells is composed of three organelles, the ER, the ER-Golgi intermediate compartment (ERGIC; also including COPI- and COPII coated transport vesicles), and the Golgi apparatus (Gomez-Navarro and Miller, 2016; including the cis-Golgi, medial cisternae of the Golgi apparatus, and the trans-Golgi network (TGN), also including Golgi transport vesicles). The ER is a multifunctional organelle that orchestrates the synthesis, folding, and structural maturation of nearly one third of all cellular proteins (Hetz et al., 2015). The Golgi apparatus occupies a central position within the secretory pathway, acting as a hub for vesicular trafficking. Distinct classes of vesicles transport diverse cargoes into and out of this organelle, as well as between the cis- and trans-Golgi sub-compartments (Gomez-Navarro and Miller, 2016; Witkos and Lowe, 2017). Maintenance of the ER and Golgi apparatus requires a balance of anterograde coat protein II (COPII)-mediated and retrograde (COPI)-mediated vesicular trafficking (Gomez-Navarro and Miller, 2016). Together, the ER and the Golgi are responsible for biogenesis and proper intracellular distribution of a wide range of proteins (Gomez-Navarro and Miller, 2016).

The Unfolded Protein Response (UPR) is activated upon increased secretory protein load to ensure maintenance of cellular homeostasis (Brandizzi and Barlowe, 2013; Plate and Wiseman, 2017; Walter and Ron, 2011). Mutant proteins disrupt the secretory pathway and trigger the UPR (Walter and Ron, 2011). The three principal branches of the UPR, IRE1 (inositol requiring enzyme), PERK (PKR-like ER kinase), and ATF6 (activating transcription factor 6) work together to maintain ER homeostasis (Walter and Ron, 2011). However, in the setting of excess or prolonged cellular stress, the protective capacity of the UPR may be insufficient to restore homeostasis, triggering the induction of cell death (Walter and Ron, 2011), a hallmark of many proteinopathies (Remondelli and Renna, 2017).

Autosomal Dominant Tubulo-interstitial Kidney Disease-Mucin1 (ADTKD-MUC1 or MUC1 kidney disease, MKD) is caused by a frameshift in the GC-rich Variable Number of Tandem Repeats (VNTR) region of the MUC1 gene (Kirby et al., 2013). MKD is characterized by slowly progressive tubulo-interstitial disease that leads to kidney failure (Bleyer et al., 2017; Yu et al., 2018). Affected individuals develop kidney failure by the second to seventh decade of life, requiring kidney replacement procedures (dialysis) complicated by high mortality rates, or kidney transplantation complicated by chronic immunosuppression and associated toxicities (Bleyer et al., 2017; Yu et al., 2018).

The MUC1 gene encodes the transmembrane glycoprotein mucin 1 (MUC1), which is expressed at the apical surface of glandular or luminal epithelial cells in the mammary gland, digestive tract, uterus, prostate, lung and kidney (Hattrup and Gendler, 2008). MUC1 has been mainly studied in epithelial cancers (Nath and Mukherjee, 2014). In the healthy adult kidney, MUC1 localizes to distal convoluted tubule and collecting duct (Leroy et al., 2002), while following ischemia, the protein may be induced in the proximal tubule (Al-bataineh et al., 2016; Gibier et al., 2017). As a plasma membrane protein, MUC1 is synthesized and core-glycosylated in the ER, followed by extensive O-glycosylation of its VNTR region in the Golgi apparatus (Hilkens and Buijs, 1988; Litvinov and Hilkens, 1993).

Figure 7A:
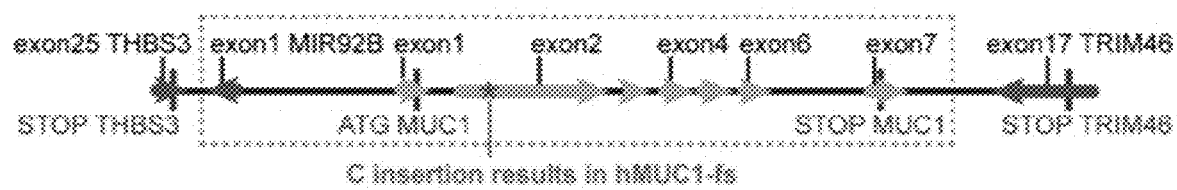
FIGS. 7A to 7F show the generation and characterization of a MUC1-fs knock-in fs/+ mouse.
Figure 7B:
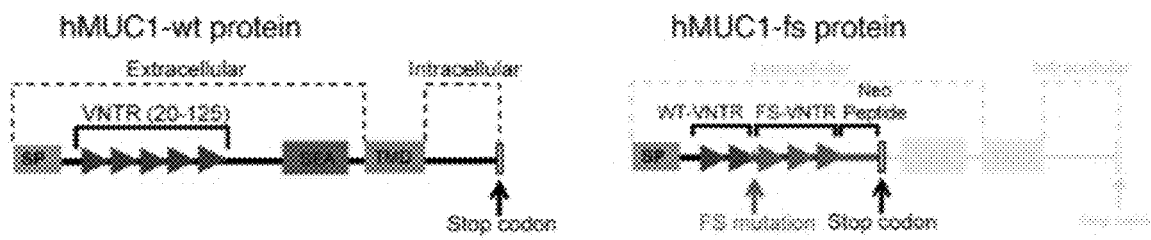

In all known cases of MKD, the causative mutations result in the same frameshift, producing a mutant MUC1 neo-protein (MUC1-fs) (Kirby et al., 2013; Wenzel et al., 2018; Yamamoto et al., 2017; ivná et al., 2018). The vast majority of these mutations involve the insertion of an extra cytosine in a string of seven cytosines within one of the VNTR subunits (Kirby et al., 2013). MUC1-fs retains the wild-type N-terminal signal sequence that drives ER translation, but beyond the insertion, it has tandem series of novel 20 amino acid imperfect repeats and a C-terminal neo-peptide with an early stop codon, resulting in the absence of the transmembrane and intracellular domains found in the wild-type MUC1 protein (Kirby et al., 2013; FIGS. 7A and 7B). The molecular mechanism responsible for MKD has been heretofore unknown and no therapy has been previously available for MKD.

The instant disclosure has established that intracellular accumulation of MUC1-fs in early secretory compartments leads to activation of the UPR. Also described herein is the identification of a small molecule, BRD-4780 (2-endo-amino-3-exo-isopropylbicyclo[2.2.1]heptane), that clears mutant MUC1-fs in patient cells, knock-in mouse kidneys and patient iPSC-derived kidney organoids. BRD-4780 (2-endo-amino-3-exo-isopropylbicyclo[2.2.1]heptane), has additionally been described herein to release mutant MUC1-fs trapped in TMED9 cargo receptor-enriched and cis-Golgi compartments of the early secretory pathway in patient cells, knock-in mouse kidneys and patient iPSC-derived kidney organoids. Without wishing to be bound by theory, BRD-4780 thus promotes MUC1-fs anterograde trafficking toward lysosomal degradation. TMED9 deletion was discovered to phenocopy the effect of BRD-4780. The instant disclosure has therefore elucidated the cellular mechanism underlying MKD and has identified BRD-4780 as a promising lead for the treatment of toxic proteinopathies.

MUC1-Associated Kidney Disease (MKD, aka Autosomal Dominant Tubulointerstitial Kidney Disease, MUC1-Related or ADTKD-MUC1)

MUC1-Associated Kidney Disease (MKD), also known as autosomal dominant tubulointerstitial kidney disease, MUC1-related (ADTKD-MUC1), was previously known as medullary cystic kidney disease type 1. It is characterized by slowly progressive tubulointerstitial disease that leads to end-stage renal disease (ESRD) and the need for dialysis or kidney transplantation. ESRD typically occurs in adulthood but is extremely variable, occurring at any age between 20 and 70 years. There are no other systemic manifestations (Bleyer and Kmoch. Gene Reviews 2016).

Autosomal Dominant Tubulointerstitial Kidney Disease Caused by UMOD Pathogenic Variants (ADTKD-UMOD)

Autosomal dominant tubulointerstitial kidney disease caused by UMOD pathogenic variants (ADTKD-UMOD) was previously known as familial juvenile hyperuricemic nephropathy type 1 (FJHN1), medullary cystic kidney disease type 2 (MCKD2), and UMOD-associated kidney disease (or uromodulin-associated kidney disease). Typical clinical findings include urinalysis revealing minimal protein and no blood; slowly progressive chronic kidney failure, usually first noted in the teen years and progressing to end-stage renal disease (ESRD) between the fourth and seventh decades (Age at ESRD varies among and within families.); and hyperuricemia and gout (resulting from reduced kidney excretion of uric acid) that occurs as early as the teenage years (Bleyer et al. Gene Reviews).

Retinitis Pigmentosa

Retinitis pigmentosa (RP) is a genetic disorder of the eyes that causes loss of vision ("Facts About Retinitis Pigmentosa". National Eye Institute. May 2014). Symptoms include trouble seeing at night and decreased peripheral vision (side vision; "Facts About Retinitis Pigmentosa". National Eye Institute. May 2014). Onset of symptoms is generally gradual (Understanding Retinitis Pigmentosa (PDF). University of Michigan Kellogg Eye Center). As peripheral vision worsens, people may experience "tunnel vision". Complete blindness is uncommon (Understanding Retinitis Pigmentosa).

Retinitis pigmentosa is generally inherited from a person's parents. Mutations in one or more than 50 genes is involved. The underlying mechanism involves the progressive loss of rod photoreceptor cells in the back of the eye. This is generally followed by loss of cone photoreceptor cells. Diagnosis is by an examination of the retina finding dark pigment deposits. Other supportive testing may include an electroretinogram, visual field testing, or genetic testing ("Facts About Retinitis Pigmentosa").

There is currently no cure for retinitis pigmentosa (Understanding Retinitis Pigmentosa). Efforts to manage the problem may include the use of low vision aids, portable lighting, or a guide dog. Vitamin A palmitate supplements may be useful to slow worsening. A visual prosthesis may be an option in certain people with severe disease. It is estimated to affect 1 in 4,000 people. Onset is often in childhood but some are not affected until adulthood ("Facts About Retinitis Pigmentosa"; Understanding Retinitis Pigmentosa).

The initial retinal degenerative symptoms of retinitis pigmentosa are characterized by decreased night vision (nyctalopia) and the loss of the mid-peripheral visual field (Shintani et al. *Optometry*. 80: 384-401). The rod photoreceptor cells, which are responsible for low-light vision and are orientated in the retinal periphery, are the retinal processes affected first during non-syndromic forms of this disease (Soucy et al. *Neuron*. 21: 481-93). Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field (Soucy et al. *Neuron*. 21: 481-93). The progression of disease symptoms occurs in a symmetrical manner, with both the left and right eyes experiencing symptoms at a similar rate (Hartong et al. The Lancet. 368: 1795-1809).

A variety of indirect symptoms characterize retinitis pigmentosa along with the direct effects of the initial rod photoreceptor degeneration and later cone photoreceptor decline. Phenomena such as photophobia, which describes the event in which light is perceived as an intense glare, and photopsia, the presence of blinking or shimmering lights within the visual field, often manifest during the later stages of RP. Findings related to RP have often been characterized in the fundus of the eye as the "ophthalamic triad". This includes the development of (1) a mottled appearance of the retinal pigment epithelium (RPE) caused by bone spicule formation, (2) a waxy appearance of the optic nerve, and (3) the attenuation of blood vessels in the retina (Shintani et al. *Optometry*. 80: 384-401).

Non-syndromic RP usually presents a variety of the following symptoms: night blindness; tunnel vision (due to loss of peripheral vision); latticework vision; photopsia (blinking/shimmering lights); photophobia (aversion to bright lights); development of bone spicules in the fundus; slow adjustment from dark to light environments and vice versa; blurring of vision; poor color separation; loss of central vision; and eventual blindness.

A variety of retinal molecular pathway defects have been matched to multiple known RP gene mutations. Mutations in the rhodopsin gene, which is responsible for the majority of autosomal-dominantly inherited RP cases, disrupts the rodopsin protein essential for translating light into decipherable electrical signals within the phototransduction cascade of the central nervous system. Defects in the activity of this G-protein-coupled receptor are classified into distinct classes that depend on the specific folding abnormality and the resulting molecular pathway defects. The Class I mutant protein's activity is compromised as specific point mutations in the protein-coding amino acid sequence affect the pigment protein's transportation into the outer segment of the eye, where the phototransduction cascade is localized. Additionally, the misfolding of Class II rhodopsin gene mutations disrupts the protein's conjunction with 11-cis-retinal to induce proper chromophore formation. Additional mutants in this pigment-encoding gene affect protein stability, disrupt mRNA integrity post-translationally, and affect the activation rates of transducin and opsin optical proteins (Mendes et al. *Trends in Molecular Medicine*. 11: 177-185).

Additionally, animal models suggest that the retinal pigment epithelium fails to phagocytose the outer rod segment discs that have been shed, leading to an accumulation of outer rod segment debris. In mice that are homozygous recessive for retinal degeneration mutation, rod photoreceptors stop developing and undergo degeneration before cellular maturation completes. A defect in cGMP-phosphodiesterase has also been documented; this leads to toxic levels of cGMP.

An accurate diagnosis of retinitis pigmentosa relies on the documentation of the progressive loss photoreceptor cell function, confirmed by a combination of visual field and visual acuity tests, fundus and optical coherence imagery, and electroretinography (ERG).

Visual field and acuity tests measure and compare the size of the patient's field of vision and the clarity of their visual perception with the standard visual measurements associated with healthy 20/20 vision. Clinical diagnostic features indicative of retinitis pigmentosa include a substantially small and progressively decreasing visual area in the visual field test, and compromised levels of clarity measured during the visual acuity test (Abigail T Fahim. "Retinitis Pigmentosa Overview"). Additionally, optical tomography such as fundus and retinal (optical coherence) imagery provide further diagnostic tools when determining an RP diagnosis. Photographing the back of the dilated eye allows the confirmation of bone spicule accumulation in the fundus, which presents during the later stages of RP retinal degeneration. Combined with cross-sectional imagery of optical coherence tomography, which provides clues into photoreceptor thickness, retinal layer morphology, and retinal pigment epithelium physiology, fundus imagery can help determine the state of RP progression (Chang et al. *Current Genomics*. 12: 267-75).

While visual field and acuity test results combined with retinal imagery support the diagnosis of retinitis pigmentosa, additional testing is necessary to confirm other pathological features of this disease. Electroretinography (ERG) confirms the RP diagnosis by evaluating functional aspects associated with photoreceptor degeneration, and can detect physiological abnormalities before the initial manifestation of symptoms. An electrode lens is applied to the eye as photoreceptor response to varying degrees of quick light pulses is measured. Patients exhibiting the retinitis pigmentosa phenotype would show decreased or delayed electrical response in the rod photoreceptors, as well as possibly compromised cone photoreceptor cell response (cdn.intechopen.com/pdfs-wm/17267.pdf).

There is currently no cure for retinitis pigmentosa, but the efficacy and safety of various prospective treatments are currently being evaluated.

It is explicitly contemplated that toxic proteinopathies amenable to treatment with a TMED9-binding agent, e.g., BRD-4780, include, without limitation, MUC1 kidney disease (Autosomal Dominant Tubulointerstitial Kidney Disease—MUC1, with frameshift MUC1 as the major aggregating protein), uromodulin kidney disease (Autosomal Dominant Tubulointerstitial Kidney Disease—UMOD, with mutant uromodulin as the major aggregating protein), retinitis pigmentosa due to rhodopsin mutations (Rhodopsin mutations as the major aggregating protein), Parkinson's disease and other synucleinopathies—mutations in alpha-synuclein (α-Synuclein mutations as the major aggregating protein), familial Danish dementia due to ADan amyloid protein, CADASIL (cerebral autosomal dominant arteriopathy with subcortical infarcts and leukoencephalopathy) due to Notch3 mutations, seipinopathies due to seipin, serpinopathies (multiple) due to serpin, type II diabetes due to islet amylin polypeptide, lysozyme amyloidosis due to lysozyme, dialysis amyloidosis due to beta2 microglobumin, cataracts due to crystallins, odontogenic tumor amyloid due to Odontogenic ameloblast-associated protein, familial British dementia due to ABri amyloid protein, hereditary cerebral hemorrhage with amyloidosis (Icelandic) due to Cystatin C, familial amyloidotic neuropathy or Senile systemic amyloidosis due to Transthyretin, ApoAII amyloidosis due to ApoAII protein, familial amyloidosis of the Finnish type (FAF) due to Gelsolin, fibrinogen amyloidosis due to Fibrinogen, inclusion body myositis/myopathy due to Amyloid β peptide (Aβ), hereditary lattice corneal dystrophy due to Keratoepithelin, pulmonary alveolar proteinosis due to Surfactant protein C (SP-C), cystic fibrosis due to CFTR mutations, and any other disease or disorder in which a misfolded protein is trapped in the ER, COPI, COPII, ERGIC and/or Golgi compartments and/or early secretory pathway transport vesicles.

Identification of Proteinopathy in a Cell, Tissue and/or Subject

Identification of a cell and/or tissue of a subject as exhibiting a proteinopathy can be performed by any method available in the art. Such methods include those for assessing kidney, eye, nervous system, etc. function and/or for diagnosing kidney disease (e.g., MKD, ADTKD-UMOD, etc.) and/or RP. Evaluation of a subject for kidney function can include, for example, urinalysis (e.g., assessment of protein or blood in the urine), any signs of kidney failure, etc. Evaluation of a subject for eye function that might be indicative of RP can be performed via art-recognized methods of assessing for RP (e.g., diagnosis by an examination of the retina finding dark pigment deposits, assessment by electroretinogram, visual field testing, or genetic testing) and/or one or more symptoms of RP (e.g., night blindness; tunnel vision (due to loss of peripheral vision); latticework vision; photopsia (blinking/shimmering lights); photophobia (aversion to bright lights); development of bone spicules in the fundus; slow adjustment from dark to light environments and vice versa; blurring of vision; poor color separation; loss of central vision; and/or eventual blindness).

In certain embodiments, detection of a mutant locus and/or encoded protein is performed, including, e.g., detection of one or more of the following: a MUC1 frameshift mutant, a UMOD mutant characterized by ER retention (e.g., C126R UMOD) and/or a rhodopsin mutant characterized by ER retention (e.g., P23H rhodopsin) and/or other gene or gene product associated with a toxic proteinopathy.

Exemplary proteinopathy-associated mutations of the instant disclosure include the above-referenced MUC1 frameshift mutation, C126R UMOD mutation and P23H rhodopsin mutation. Sequences for these mutations are provided immediately below.

```
cDNA sequence of MUC1-fs (mutation site in lower
case)
                                       (SEQ ID NO: 1)
ATGACACCGGGCACCCAGTCTCCTTTCTTCCTGCTGCTGCTCCTCACAGT GCTTACAGTTGTTACgGGGTTCTGGTCATGCAAGCTCTACCCCAGGTGGAG

AAAAGGAGACTTCGGCTACCCAGAGAAGTTCAGTGCCCAGCTCTACTGAG

AAGAATGCTGTGAGTATGACCAGCAGCGTACTCTCCAGCCACAGCCCCGG

TTCAGGCTCCTCCACCACTCAGGGACAGGATGTCACTCTGGCCCCGGCCA

CGGAACCAGCTTCAGGTTCAGCTGCCACCTGGGGACAGGATGTCACCTCG

GTCCCAGTCACCAGGCCAGCCCTGGGCTCCACCACCCCACCAGCCCACGA

TGTCACCTCAGCCCCGGACAACAAGCCAGCCCCGGGCTCCACCGCCCCCC

CCAGCCCACGGTGTCACCTCGGCCCCGGACACCAGGCCGGCCCCGGGCTC

CACCGCCCCCCAAGCCCACGGTGTCACCTCGGCCCCGGACACCAGGCCGG

CCCCGGGCTCCACCGCCCCCCCAGCCCACGGTGTCACCTCGGCCCCGGAC

ACCAGGCCCGCCCCGGGCTCCACCGCCCCCCCAGCCCACGGTGTCACCTC

GGCCCCGGACACCAGGCCGGCCCCGGGCTCCACCGCCCCCCAGCCCACG

GTGTCACCTCGGCCCCGGAGAGCAGGCCGGCCCCGGGCTCCACCGCGCCC

GCAGCCCACGGTGTCACCTCGGCCCCGGAGAGCAGGCCGGCCCCGGGCTC

CACCGCGCCCGCAGCCCACGGTGTCACCTCGGCCCCGGAGAGCAGGCCGG

CCCCGGGCTCCACCGCGCCCGCAGCCCACGGTGTCACCTCGGCCCCGGAG
```

AGCAGGCCGGCCCCGGGCTCCACCGCGCCCGCAGCCCACGGTGTCACCTC
GGCCCCGGAGAGCAGGCCGGCCCCGGGCTCCACCGCCCCCCAGCCCACG
GTGTCACCTCGGCCCCGGACACCAGGCCGGCCCCGGGCTCCACCGCCCCC
CCAGCCCACGGTGTCACCTCGGCCCCGGACACCAGGCCGGCCCCGGGCTC
CACCGCCCCCCAGCCCACGGTGTCACCTCGGCCCCGGACACCAGGCCGG
CCCCGGGCTCCACCGCCCCCCAGCCCACGGTGTCACCTCGGCCCCGGAC
ACCAGGCCGGCCCCGGGCTCCACCGCCCCCCAGCCCACGGTGTCACCTC
GGCCCCGGAGAGCAGGCCGGCCCCGGGCTCCACCGCCCCCCAGCCCACG
GTGTCACCTCGGCCCCGGAGAGCAGGCCGGCCCCGGGCTCCACCGCGCCC
GCAGCCCACGGTGTCACCTCGGCCCCGGAGAGCAGGCCGGCCCCGGGCTC
CACCGCGCCCGCAGCCCACGGTGTCACCTCGGCCCCGGAGAGCAGGCCGG
CCCCGGGCTCCACCGCCCCCCAGCCCACGGTGTCACCTCGGCCCCGGAC
ACCAGGCCGGCCCCGGGCTCCACCGCCCCCCAGCCCACGGTGTCACCTC
GGCCCCGGACACCAGGCCGGCCCCGGGCTCCACCGCCCCCCAGCCCACG
GTGTCACCTCGGCCCCGGACACCAGGCCGGCCCCGGGCTCCACCGCCCCC
CCAGCCCACGGTGTCACCTCGGCCCCGGACACCAGGCCGGCCCCGGGCTC
CACCGCCCCCCAGCCCACGGTGTCACCTCGGCCCCGGACACCAGGCCGG
CCCCGGGCTCCACCGCCCCCCAGCCCACGGTGTCACCTCGGCCCCGGAC
ACCAGGCCGGCCCCGGGCTCCACCGCCCCCCAGCCCACGGTGTCACCTC
GGCCCCGGACACCAGGCCGGCCCCGGGCTCCACCGCCCCCCAGCCCACG
GTGTCACCTCGGCCCCGGACACCAGGCCGGCCCCGGGCTCCACCGCCCCC
CCAGCCCACGGTGTCACCTCGGCCCCGGACACCAGGCCGGCCCCGGGCTC
CACCGCCCCCCAGCCCACGGTGTCACCTCGGCCCCGGACACCAGGCCGG
CCCCGGGCTCCACCGCCCCCCAGCCCACGGTGTCACCTCGGCCCCGGAC
ACCAGGCCGGCCCCGGGCTCCACCGCCCCCCAGCCCACGGTGTCACCTC
GGCCCCGGACACCAGGCCGGCCCCGGGCTCCACCGCCCCCCAGCCCACG
GTGTCACCTCGGCCCCGGACACCAGGCCGGCCCCGGGCTCCACCGCCCCC
CCAGCCCACGGTGTCACCTCGGCCCCGGACACCAGGCGGGCCCCGGGCTC
CACCCCGGCCCGGGCTCCACCGCCCCCCAGCCCACGGTGTCACCTTGG
CCCCGGACACCAGGCCGGCCCCGGGCTCCACCGCCCCCCAGCCCATGGT
GTCACCTCGGCCCCGGACAACAGGCCCGCCTTGGGCTCCACCGCCCCTCC
AGTCCACAATGTCACCTCGGCCTCAGGCTCTGCATCAGGCTCAGCTTCTA
CTCTGGTGCACAACGGCACCTCTGCCAGGGCTACCACAACCCCAGCAGC
AAGAGCACTCCATTCTCAATTCCCAGCCACCACTCTGATACTCCTACCAC
CCTTGCCAGCCATAGCACCAAGACTGATGCCAGTAGCACTCACCATAGCT

CGGTACCTCCTCTCACCTCCTCCAATCACAGCACTTCTCCCCAGTTGTCT
ACTGGGGTCTCTTTCTTTTTCCTGTCTTTTCACATTTCAAACCTCCAGTT
TAATTCCTCTCTGGAAGATCCCAGCACCGACTACTACCAAGAGCTGCAGA
GAGACATTTCTGAAATGTTTTTGCAGATTTATAAACAAGGGGGTTTTCTG
GGCCTCTCCAATATTAAGTTCAGGCCAGGATCTGTGGTGGTACAATTGAC
TCTGGCCTTCCGAGAAGGTACCATCAATGTgCACGACGTGGAGACACAGT
TCAATCAGTATAAAACGGAAGCAGCCTCTCGATATAACCTGACGATCTCA
GACGTCAGCGTGAGTGATGTGCCATTTCCTTTCTCTGCCCAGTCTGGGGC
TGGGGTGCCAGGCTGGGGCATCGCGCTGCTGGTGCTGGTCTGTGTTCTGG
TTGCGCTGGCCATTGTCTATCTCATTGCCTTGGCTGTCTGTCAGTGCCGC
CGAAAGAACTACGGGCAGCTGGACATCTTTCCAGCCCGGGATACCTACCA
TCCTATGAGCGAGTACCCCACCTACCACACCCATGGGCGCTATGTGCCCC
CTAGCAGTACCGATCGTAGCCCCTATGAGAAGGTTTCTGCAGGTAACGGT
GGCAGCAGCCTCTCTTACACAAACCCAGCAGTGGCAGCCaCTTCTGCCAA
CTTGTAG
cDNA sequence of UMOD C126R (mutant residue in
bold and underlined)
(SEQ ID NO: 2)
ATGGGGCAGCCATCTCTGACTTGGATGCTGATGGTGGTGGTGGCCTCTTG
GTTCATCACAACTGCAGCCACTGACACCTCAGAAGCAAGATGGTGCTCTG
AATGTCACAGCAATGCCACCTGCACGGAGGATGAGGCCGTTACGACGTGC
ACCTGTCAGGAGGGCTTCACCGGCGATGCCTGACCTGCGTGGACCTGGA
TGAGTGCGCCATTCCTGGAGCTCACAACTGCTCCGCCAACAGCAGCTGCG
TAAACACGCCAGGCTCCTTCTCCTGCGTCTGCCCCGAAGGCTTCCGCCTG
TCGCCCGGTCTCGGCTGCACAGACGTGGATGAGTGCGCTGAGCCTGGGCT
TAGCCACTGCCACGCCCTGGCCACACGTGTCAATGTGGTGGGCAGCTACT
TGTGCGTATGCCCCGCGGGCTACCGGGGGATGGATGGCACTGTGAGTGC
TCCCCGGGCTCCTGCGGGCCGGGGTTGGACTGCGTGCCCGAGGGCGACGC
GCTCGTGTGCGCGGATCCGTGCCAGGCGCACCGCACCCTGGACGAGTACT
GGCGCAGCACCGAGTACGGGGAGGGCTACGCCTGCGACACGGACCTGCGC
GGCTGGTACCGCTTCGTGGGCCAGGGCGGTGCGCGCATGGCCGAGACCTG
CGTGCCAGTCCTGCGCTGCAACACGGCCGCCCCCATGTGGCTCAATGGCA
CGCATCCGTCCAGCGACGAGGGCATCGTGAGCCGCAAGGCCTGCGCGCAC
TGGAGCGGCCACTGCTGCCTGTGGGATGCGTCCGTCCAGGTGAAGGCCTG
TGCCGGCGGCTACTACGTCTACAACCTGACAGCGCCCCCGAGTGTCACC
TGGCGTACTGCACAGACCCCAGCTCCGTGGAGGGACGTGTGAGGAGTGC
AGTATAGACGAGGACTGCAAATCGAATAATGGCAGATGGCACTGCCAGTG
CAAACAGGACTTCAACATCACTGATATCTCCCTCCTGGAGCACAGGCTGG
AATGTGGGGCCAATGACATGAAGGTGTCGCTGGGCAAGTGCCAGCTGAAG
AGTCTGGGCTTCGACAAGGTCTTCATGTACCTGAGTGACAGCCGGTGCTC
GGGCTTCAATGACAGAGACAACCGGGACTGGGTGTCTGTAGTGACCCCAG
CCCGGGATGGCCCCTGTGGGACAGTGTTGACGAGGAATGAAACCCATGCC

ACTTACAGCAACACCCTCTACCTGGCAGATGAGATCATCATCCGTGACCT

CAACATCAAAATCAACTTTGCATGCTCCTACCCCCTGGACATGAAAGTCA

GCCTGAAGACCGCCCTACAGCCAATGGTCAGTGCTCTAAACATCAGAGTG

GGCGGGACCGGCATGTTCACCGTGCGGATGGCGCTCTTCCAGACCCCTTC

CTACACGCAGCCCTACCAAGGCTCCTCCGTGACACTGTCCACTGAGGCTT

TTCTCTACGTGGGCACCATGTTGGATGGGGGCGACCTGTCCCGATTTGCA

CTGCTCATGACCAACTGCTATGCCACACCCAGTAGCAATGCCACGGACCC

CCTGAAGTACTTCATCATCCAGGACAGATGCCCACACACTAGAGACTCAA

CTATCCAAGTGGTGGAGAATGGGGAGTCCTCCCAGGGCCGATTTTCCGTC

CAGATGTTCCGGTTTGCTGGAAACTATGACCTAGTCTACCTGCACTGTGA

AGTCTATCTCTGTGACACCATGAATGAAAAGTGCAAGCCTACCTGCTCTG

GGACCAGATTCCGAAGTGGGAGTGTCATAGATCAATCCCGTGTCCTGAAC

TTGGGTCCCATCACACGGAAAGGTGTCCAGGCCACAGTCTCAAGGGCTTT

TAGCAGCTTGGGGCTCCTGAAAGTCTGGCTGCCTCTGCTTCTCTCGGCCA

CCTTGACCCTGACTTTTCAGTGA cDNA sequence of rhodopsin P23H (mutant residue in bold and underlined)

(SEQ ID NO: 3)

AGAGTCATCCAGCTGGAGCCCTGAGTGGCTGAGCTCAGGCCTTCGCAGCA

TTCTTGGGTGGGAGCAGCCACGGGTCAGCCACAAGGGCCACAGCCATGAA

TGGCACAGAAGGCCCTAACTTCTACGTGCCCTTCTCCAATGCGACGGGTG

TGGTACGCAGCCACTTCGAGTACCCACAGTACTACCTGGCTGAGCCATGG

CAGTTCTCCATGCTGGCCGCCTACATGTTTCTGCTGATCGTGCTGGGCTT

CCCCATCAACTTCCTCACGCTCTACGTCACCGTCCAGCACAAGAAGCTGC

GCACGCCTCTCAACTACATCCTGCTCAACCTAGCCGTGGCTGACCTCTTC

ATGGTCCTAGGTGGCTTCACCAGCACCCTCTACACCTCTCTGCATGGATA

CTTCGTCTTCGGGCCCACAGGATGCAATTTGGAGGGCTTCTTTGCCACCC

TGGGCGGTGAAATTGCCCTGTGGTCCTTGGTGGTCCTGGCCATCGAGCGG

TACGTGGTGGTGTGTAAGCCCATGAGCAACTTCCGCTTCGGGGAGAACCA

TGCCATCATGGGCGTTGCCTTCACCTGGGTCATGGCGCTGGCCTGCGCCG

CACCCCCACTCGCCGGCTGGTCCAGGTACATCCCCGAGGGCCTGCAGTGC

TCGTGTGGAATCGACTACTACACGCTCAAGCCGGAGGTCAACAACGAGTC

TTTTGTCATCTACATGTTCGTGGTCCACTTCACCATCCCCATGATTATCA

TCTTTTTCTGCTATGGGCAGCTCGTCTTCACCGTCAAGGAGGCCGCTGCC

CAGCAGCAGGAGTCAGCCACCACACAGAAGGCAGAGAAGGAGGTCACCCG

CATGGTCATCATCATGGTCATCGCTTTCCTGATCTGCTGGGTGCCCTACG

CCAGCGTGGCATTCTACATCTTCACCCACCAGGGCTCCAACTTCGGTCCC

ATCTTCATGACCATCCCAGCGTTCTTTGCCAAGAGCGCCGCCATCTACAA

CCCTGTCATCTATATCATGATGAACAAGCAGTTCCGGAACTGCATGCTCA

CCACCATCTGCTGCGGCAAGAACCCACTGGGTGACGATGAGGCCTCTGCT

ACCGTGTCCAAGACGGAGACGAGCCAGGTGGCCCCGGCCTAAGACCTGCC

TAGGACTCTGTGGCCGACTATAGGCGTCTCCCATCCCCTACACCTTCCCC

CAGCCACAGCCATCCCACCAGGAGCAGCGCCTGTGCAGAATGAACGAAGT

CACATAGGCTCCTTAATTTTTTTTTTTTTTTAAGAAATAATTAATGAGG

CTCCTCACTCACCTGGGACAGCCTGAGAAGGGACATCCACCAAGACCTAC

TGATCTGGAGTCCCACGTTCCCCAAGGCCAGCGGGATGTGTGCCCCTCCT

CCTCCCAACTCATCTTTCAGGAACACGAGGATTCTTGCTTTCTGGAAAAG

TGTCCCAGCTTAGGGATAAGTGTCTAGCACAGAATGGGGCACACAGTAGG

TGCTTAATAAATGCTGGATGGATGCAGGAAGGAATGGAGGAATGAATGGG

AAGGGAGAACATATCTATCCTCTCAGACCCTCGCAGCAGCAGCAACTCAT

ACTTGGCTAATGATATGGAGCAGTTGTTTTTCCCTCCCTGGGCCTCACTT

TCTTCTCCTATAAAATGGAAATCCCAGATCCCTGGTCCTGCCGACACGCA

GCTACTGAGAAGACCAAAAGAGGTGTGTGTGTCTATGTGTGTGTTTCA

GCACTTTGTAAATAGCAAGAAGCTGTACAGATTCTAGTTAATGTTGTGAA

TAACATCAATTAATGTAACTAGTTAATTACTATGATTATCACCTCCTGAT

AGTGAACATTTTGAGATTGGGCATTCAGATGATGGGGTTTCACCCAACCT

TGGGGCAGGTTTTTAAAAATTAGCTAGGCATCAAGGCCAGACCAGGGCTG

GGGGTTGGGCTGTAGGCAGGGACAGTCACAGGAATGCAGAATGCAGTCAT

CAGACCTGAAAAAACAACACTGGGGGAGGGGACGGTGAAGGCCAAGTTC

CCAATGAGGGTGAGATTGGGCCTGGGGTCTCACCCCTAGTGTGGGGCCCC

AGGTCCCGTGCCTCCCCTTCCCAATGTGGCCTATGGAGAGACAGGCCTTT

CTCTCAGCCTCTGGAAGCCACCTGCTCTTTTGCTCTAGCACCTGGGTCCC

AGCATCTAGAGCATGGAGCCTCTAGAAGCCATGCTCACCCGCCCACATTT

AATTAACAGCTGAGTCCCTGATGTCATCCTTATCTGAAGAGCTTAGAAA

CAAAGAGTGGGAAATTCCACTGGGCCTACCTTCCTTGGGGATGTTCATGG

GCCCCAGTTTCCAGTTTCCCTTGCCAGACAAGCCCATCTTCAGCAGTTGC

TAGTCCATTCTCCATTCTGGAGAATCTGCTCCAAAAAGCTGGCCACATCT

CTGAGGTGTCAGAATTAAGCTGCCTCAGTAACTGCTCCCCCTTCTCCATA

TAAGCAAAGCCAGAAGCTCTAGCTTTACCCAGCTCTGCCTGGAGACTAAG

GCAAATTGGGCCATTAAAAGCTCAGCTCCTATGTTGGTATTAACGGTGGT

GGGTTTTGTTGCTTTCACACTCTATCCACAGGATAGATTGAAACTGCCAG

CTTCCACCTGATCCCTGACCCTGGGATGGCTGGATTGAGCAATGAGCAGA

GCCAAGCAGCACAGAGTCCCCTGGGGCTAGAGGTGGAGGAGGCAGTCCTG

GGAATGGGAAAAACCCCA

TMED9 (Transmembrane P24 Trafficking Protein 9)

TMED9 is a member of a family of genes encoding transport proteins located in the endoplasmic reticulum and the Golgi. A representative *Homo sapiens* TMED9 mRNA sequence is that of NCBI Reference Sequence NM_017510.6 (SEQ ID NO: 4):

AGGTGGAGCAAGATGGCTGTGGAGCTGGGCGTGCTGCTCGTCCGGCCCCG

GCCCGGAACCGGGCTGGGTAGAGTGATGCGGACCCTCCTGCTGGTGCTGT

GGCTGGCGACGCGCGGAAGCGCGCTCTACTTTCACATCGGAGAGACGGAG

-continued
```
AAGAAGTGCTTTATTGAGGAGATCCCGGACGAGACCATGGTCATAGGAAA

CTACCGGACGCAGCTGTATGACAAGCAGCGGGAGGAGTACCAGCCGCCA

CCCCGGGGCTTGGCATGTTTGTGGAGGTGAAGGACCCAGAGGACAAGGTC

ATCCTGGCCCGGCAGTATGGCTCCGAGGGCAGGTTCACTTTCACTTCCCA

TACCCCTGGTGAGCACCAGATCTGTCTTCACTCCAATTCCACCAAGTTCT

CCCTCTTTGCTGGAGGCATGCTGAGAGTTCACCTGGACATCCAGGTAGGT

GAACATGCCAATGACTATGCAGAAATTGCTGCTAAAGACAAGTTGAGTGA

GTTGCAGCTACGAGTGCGACAGCTGGTGGAACAAGTGGAGCAGATCCAGA

AAGAGCAGAACTACCAGCGGTGGCGAGAGGAGCGCTTCCGGCAGACCAGT

GAGAGCACCAACCAGCGGGTGCTGTGGTGGTCCATTCTGCAGACCCTCAT

CCTCGTGGCCATCGGTGTCTGGCAGATGCGGCACCTCAAGAGCTTCTTTG

AAGCCAAGAAGCTTGTGTAGCTGTCCCAGGCGTCACAACCCATCCTCCCA

GGCTGGGGGAGAAAGGACCTCCTGGAACTGACTTCTTCTGTCAGGAGGAC

TGGTTTCCAGCCATACCTGTTCTGGAAGGGAGAGGGGCTGGAGGCACCCA

CAGGCACAAGCTGAAGGCAGCAGCTTGGCTAATACTGAGCAGGTAGTGGG

GCAAATTCCTGCCCTCTCTCTGGCCTCTGGGCCGTTTGGTAGTAATCA

CCCAAGGGCTGGTAAAGCCCCTCCTCTTGGCACCTCAGAATCACAGTGTT

ACTGATCAGGGATGTGAGGCTGCTGTTGGGGGTGGGGGAGGGAATGGG

CAGGCAAGCCAGTCTTCTGTCTTCCTTTGCTAACTTAGGGTTTTGAGCAG

GTTGGGGTATGGTGCCTGTCATACCCACCTGCCACCCTGGGAACCTCACT

GTTCTCTCTTTCAGCCTAGACCTGCTGATCCAGGGTGTGTGTGAGTTGAG

GGTGGGTGGAGGGGTTTGCAGTGTGGGAATGTGGCCCTGCAGTTGACCTG

AGCTGCTTCACATGGTTGTCCATTCTGGGGCTTAAAGAACTGGGACCAGA

CCAAGTAGAGGCCTTGGTGCTGGTTGGGGTGGGGCCTGCAGAGTCTTAGT

TACTGATTTCATTTTCAATAAATGTAGGTTTGTTACATGAGTTTCCCAAT

AAAAAAAAAAATGACTTCTTGTCCAGTGCAAGTGACTCAGTCATCAGTGG

GCACACACTGCAGGGTGCCTCAGGGAATGCCAGTTCTTCCAAAGAGCAAA

GCACTTCACATTCCAAAGTGAATTCCCACCAGTCAGCTTCATTCTTTCCT

TCTTCTCCAGGCCTTCCTGTGGCAGGGAATAGTGGGTTTGTCCAAGATTA

TACAACAAGTAAATTGGGCTGGGGCTCAAATTTACACCCTTTCCTCTGTG

CCAGCTCCCTGGTGAAGTTCCCTCTTTCTAGAGTCAGTAAGCAGGATTGT

CATGGATGCTGCCAGGAAGTGCCTGGTAAGGAGGTGCATTGAGCAGGGGA

GTGCTACAGGACAGCCACCCTGGGCTGGCAGGGACAAGGATGTTGATGGG

CTAAACCAACAGCAAGTGATTTCAACCAGGACCATGAAGGAGAGGAAGGA

TTCTGCTGGAAGGAGATGGCAGGACAGGGGTGGTTGGAGAAGTGGAGGCA

AACAGCTGGAATGGAGGTGGGTGGGTGTTTAATTTCAGCTGCAGAGGGTG

TTGTGAGGAAGCTGGAAAGGAAGGTTGGATTAGAGAAGCCTCGAGCTCCA

GGTAAGCGATTTGGACATGCCCACCTTTCAAGAGGGGCTGCAGGCACCCA

CAGGCACAAGCTGAAGGCAGCAGCTTGGCTGGCTTAATACTGAGCAGGTG

GTGGGGTAAATGCCTGCCCCCCTCCCTCTGGCCTCTGGGCCCTTTGCAGT

AATCACCCAGGGTCTGGTAAAGCCACTGAGAGCCCTACTGGCACCTCAGA

ATCACAGTGTTATTGATCAGGGATGTGAGGCTGCTGTTGGGGGTTGGGGG

AGGCAAATGGGCAGGCAGTTTTGAGAAGAACCTTCTAATAAGAAATGTGA

GGGAGGTTACAGCAGTGTGTGAGAAAGACCAGGAAGAAGGAGACAAGTTT

GGGGGCTGCTTCCCCTAATGGGATGATGCAATCTGGGCTCATGCTGCCAA

CTAATTCTTCCACATGAAAAAAAAAAGTTTTTTGGCGGGCACGGTGGTTC

ACACCTGTAATCCCAGCACTTTGGGAGGCTGAGGTAGGTGGATGGCCTGA

GGCCAGGAGTTTGAGACCAGCCTGGCCAACATGGTGAAACCTCATC
```

A corresponding representative *Homo sapiens* TMED9 protein sequence is that of (SEQ ID NO: 5):

```
MAVELGVLLVRPRPGTGLGRVMRTLLLVLWLATRGSALYFHIGETEKKCF

IEEIPDETMVIGNYRTQLYDKQREEYQPATPGLGMFVEVKDPEDKVILAR

QYGSEGRFTFTSHTPGEHQICLHSNSTKFSLFAGGMLRVHLDIQVGEHAN

DYAEIAAKDKLSELQLRVRQLVEQVEQIQKEQNYQRWREERFRQTSESTN

QRVLWWSILQTLILVAIGVWQMRHLKSFFEAKKLV
```

Treatment Selection

The compositions and methods described herein can be used for selecting, and then optionally administering, an optimal treatment (e.g., a TMED9-binding agent, e.g., BRD-4780, alone (as a mixture of enantiomers (racemic or non-racemic), or as one enantiomer) or in combination with other agents). Generally, the methods include administering a therapeutically effective amount of a treatment as described herein, to a subject who is in need of, or who has been determined to be in need of, such treatment.

As used in this context, to "treat" means to ameliorate at least one symptom of the proteinopathy. For example, a treatment can result in improved kidney function and/or amelioration in the rate of decline of kidney function that would occur in the absence of treatment, improved neurodegenerative disease and/or eye functions and/or amelioration in the rate of neurodegeneration and/or the rate of declining eye function in a subject having or at risk of a toxic proteinopathy resulting from mutant protein accumulation in the early secretory pathway, or in other organelles of the secretory pathway.

Exemplary neurodegenerative diseases of the instant disclosure include, without limitation, Alzheimer's disease (AD) and other dementias; Parkinson's disease (PD) and PD-related disorders; prion disease (including, e.g., Creutzfeldt-Jakob Disease, variant Creutzfeldt-Jakob Disease, Bovine Spongiform Encephalopathy, Kuru, Gerstmann-Straussler-Scheinker disease, fatal familial insomnia (FFI), scrapie, and other animal TSEs); motor neuron diseases (MND; including, e.g., Amyotrophic Lateral Sclerosis (ALS), Primary Lateral Sclerosis (PLS), Progressive Bulbar Palsy (PBP), Pseudobulbar Palsy, Progressive Muscular Atrophy, Spinal Muscular Atrophy (Type 1, Type 2, Type 3, Type 4), and Kennedy's Disease); and spinocerebellar ataxia (SCA).

In certain embodiments, the methods of the instant disclosure can include selecting and/or administering a treatment that includes a therapeutically effective amount of a TMED9-binding agent, e.g., BRD-4780. A TMED9-binding agent (e.g., BRD-4780) of the instant disclosure may be administered alone to a subject, or, optionally, the TMED9-binding agent (e.g., BRD-4780) may be administered in combination with an additional therapeutic agent. Without limitation, specifically contemplated combination therapies for MKD include administration of a TMED9-binding agent, e.g., BRD-4780, and any of the following: vitamin D in any or all of its forms (e.g., ergocalciferol, cholecalciferol, others), phosphate binders, blood pressure medications and diuretics. Specific examples of phosphate binders, blood pressure medications and diuretics include the following, with exemplary dosages also indicated:

Phosphate Binders:
Calcium Acetate (PhosLo, Calphron, Eliphos, PhosLo Gelcap, and Phoslyra)—667 mg or 667 mg in 5 ml (oral solution)
Sevelamer (Renagel and Renvela)—400 mg (Renagel tablet), 800 mg (Renagel tablet, Renvela tablet, and Renvela powder packet), and 2400 mg (Renvela powder packet)
Ferric Citrate (Auryxia)—210 mg (tablet)
Lanthanum Carbonate (Fosrenol)—Tablet (500 mg, 750 mg, and 1000 mg) and Oral powder (750 mg and 1000 mg).
Sucroferric Oxyhydroxide (Velphoro)—500 mg
Aluminum Hydroxide (Amphojel)—320 mg/5 ml oral suspension Diuretics:
Bumetanide (Bumex)—0.5 mg (light green), 1 mg (yellow) and 2 mg (peach) tablets for oral administration.
Chlorthalidone (Thalitone)—Oral Tablet: 15 mg, 25 mg, 50 mg
Chlorothiazide (Diuril)—Adults (500 or 1000 mg IV/Tablet)
Ethacrynate (Edecrin)—25 mg tablets for oral use
Furosemide (Lasix)—Tablets 20, 40, and 80 mg
Hydrochlorothiazide HCTZ (Esidrix, Hydrodiuril, Microzide)—25 mg; 50 mg; 100 mg; 50 mg/5 mL; 12.5 mg
Indapamide (Lozol)—2.5 mg orally once a day.
Methyclothiazide (Enduron)—2.5 to 5 mg orally once a day
Metolazone (Mykroz, Zaroxolyn)—2.5 mg orally once a day (Zaroxolyn) or
0.5 mg orally once a day (Mykrox).
Torsemide (Demadex)—5 mg orally once a day; if diuresis remains inadequate after 4 to 6 weeks, titrate up to 10 mg orally once a day; if diuresis remains inadequate with 10 mg, an additional antihypertensive is added.

Blood Pressure Medications:
Beta Blockers:
acebutolol (Sectral)—200 mg or 400 mg tablet
atenolol (Tenormin)—25 mg, 50 mg, and 100 mg tablet.
betaxolol (Kerlone)—10 mg or 20 mg.
bisoprolol (Zebeta)—5 mg or 10 mg tablet.
bisoprolol/hydrochlorothiazide (Ziac)—Bisprolol (2.5 mg)/hydrochloride (6.25 mg) tablet.
metoprolol tartrate (Lopressor)—100 mg tablet daily
metoprolol succinate (Toprol-XL)—25 mg to 100 mg daily.
nadolol (Corgard)—40 mg tablet daily.
pindolol (Visken)—5 mg tablet initial dose.
propranolol (Inderal)—40 mg twice daily.
solotol (Betapace)—80 mg-240 mg tablets in 80 mg increments.
timolol (Blocadren)—5 mg, 10 mg, and 20 mg tablet.

ACE Inhibitors:
benazepril (Lotensin)—10 mg, 20 mg, and 40 mg tablets.
captopril (Capoten)—12.5 mg, 25 mg, 50 mg, and 100 mg tablet.
enalapril (Vasotec)—5 mg initial daily dose.
fosinopril (Monopril)—10 mg once a day lisinopril (Prinivil, Zestril)—2.5 mg, 5 mg, 10 mg, 20 mg, 30 mg, 40 mg tablets 1 mg/ml oral solution.
moexipril (Univasc)—7.5 mg and 15 mg tablets.
perindopril (Aceon)—2 mg, 4 mg, and 8 mg tablets.
quinapril (Accupril)—5 mg, 10 mg, 20 mg, and 40 mg tablets.
ramipril (Altace)—1.25 mg tablet, 2.5 mg, and 5 mg tablet.
trandolapril (Mavik)—1 mg, 2 mg, and 4 mg tablet.

Calcium Channel Blockers
amlodipine (Norvasc, Lotrel)—10 mg orally
diltiazem (Cardizem CD, Cardizem SR, Dilacor XR, Tiazac)—20 mg average adult dose
felodipine (Plendil)—2.5 mg, 5 mg, and 10 mg oral tablet.
isradipine (DynaCirc, DynaCirc CR)—7.5 mg daily
nicardipine (Cardene SR)—20 mg and 30 mg capsule.
nifedipine (Adalat CC, Procardia XL)—10 mg, 20 mg, 30 mg, 60 mg, and 90 mg tablet.
nisoldipine (Sular)—17 mg orally daily.
verapamil (Calan SR, Covera HS, Isoptin SR, Verelan)—100 mg/200 mg daily.

Alpha Blockers
doxazosin (Cardura)—2 mg, 4 mg, and 8 mg daily.
prazosin (Minipress)—20 mg total daily dose.
terazosin (Hytrin)—1 mg at bedtime Alpha-Beta-Blockers
carvedilol (Coreg)—3.125 mg, 6.25 mg, 12.5 mg, and 25 mg tablet.
labetalol (Normodyne, Trandate)—100 mg, 200 mg, and 300 mg taken orally.

Central Agonists
methyldopa (Aldomet)—125 mg, 250 mg, and 500 mg tablet.
clonidine (Catapres)—0.1 mg, 0.2 mg, and 0.3 mg.
guanfacine (Tenex)—1 mg, 2 mg, 3 mg, and 4 mg.

Vasodilators
hydralazine (Apresoline)—25 mg, 50 mg, 10 mg, 100 mg, and 20 mg/ml.
minoxidil (Loniten)—2.5 mg and 10 mg tablet.

Without wishing to be bound by theory, though BRD-4780 has been primarily exemplified for its effect upon the early secretory pathway, it is contemplated that actions of BRD-4780 (or other TMED9-binding agents) upon the late secretory pathway could also exert a beneficial effect. Thus, it is contemplated that the compositions and methods of the instant disclosure could also address proteinopathy and related effects in organelles of the late secretory pathway including, without limitation, post-Golgi trafficking vesicles (whether directed to the endosome, including, e.g., ESCRT-II complex vesicles, and/or endosome-bypassing lysosomal transport vesicles and/or cell surface-directed vesicles), the endosome, and/or post-endosomal transport vesicles, including, without limitation, endosome-to-lysosome vesicles, endosome-to-cell surface transport vesicles (including, e.g., synaptic vesicles) and cell surface-to-endosome vesicles, and the lysosome.

The structure of BRD-4780 follows.
BRD-4780
2-endo-amino-3-exo-isopropylbicyclo[2.2.1]heptane (identified as BRD-4780 herein and also known as (±) AGN 192403, 2-propan-2-ylbicyclo[2.2.1]heptan-3-amine, 3-Isopropylbicyclo[2.2.1]heptan-2-amine, and trans-2-(3-Isopropyl-bicyclo-[2,2,1]-heptyl)-amine), has the following structure of formula (II):

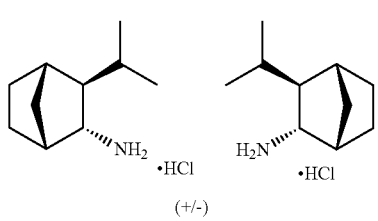

(II)

(+/−)

2-endo-amino-3-exo-isopropylbicyclo[2.2.1]heptane is commercially available as a racemic hydrochloride salt.

As exemplified herein, synthesis and separation of each of the enantiomers of racemic 2-endo-amino-3-exo-isopropylbicyclo[2.2.1]heptane has now been performed. It is explicitly contemplated that individual enantiomeric forms of 2-endo-amino-3-exo-isopropylbicyclo[2.2.1]heptane can be employed in any manner that is currently described for BRD-4780, also including, without limitation, compositions and use of pharmaceutically acceptable salts of such single enantiomer forms, e.g., including hydrochloride salt forms of individual enantiomers of 2-endo-amino-3-exo-isopropylbicyclo[2.2.1]heptane.

2-endo-amino-3-exo-isopropylbicyclo[2.2.1]heptane was disclosed in PCT/US1995/008733 (Publication No. WO 96/01813-related patents include: U.S. Pat. Nos. 5,731,337; 6,150,389; 6,319,935; and 6,706,747), as were the following structures:

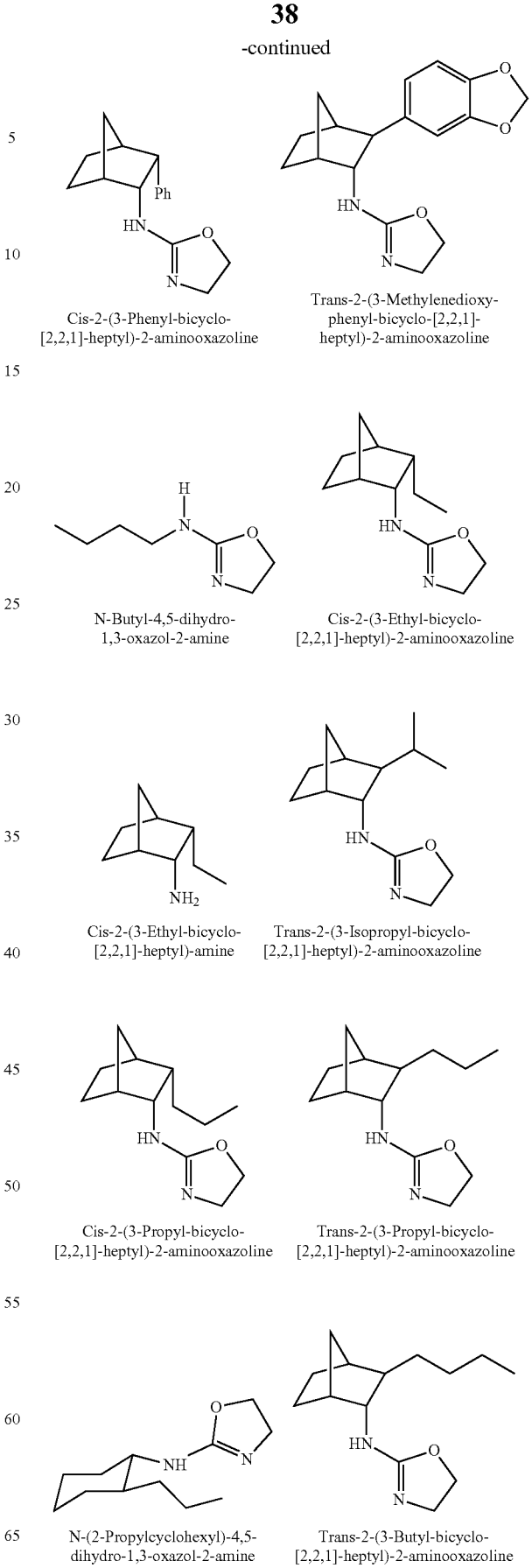

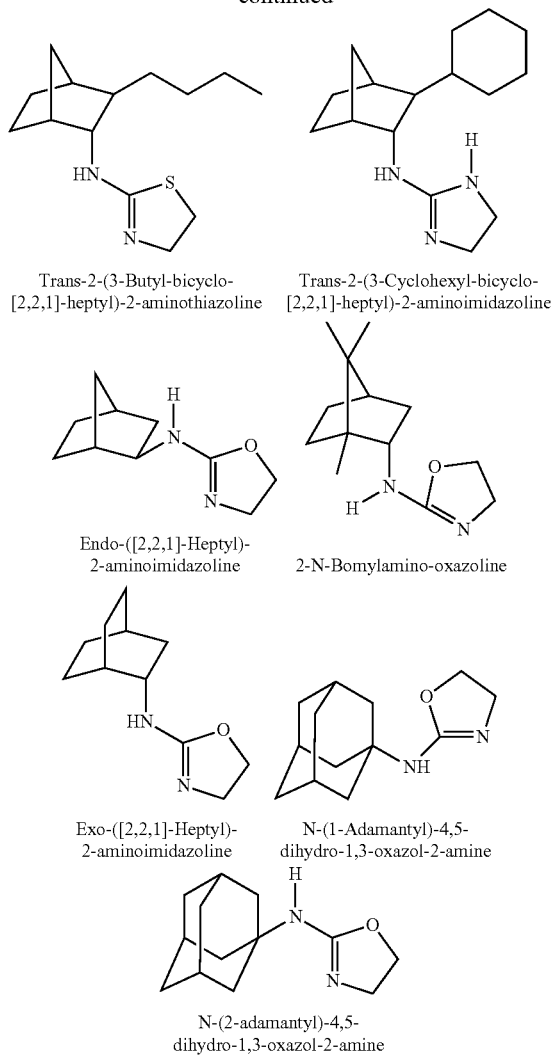

Trans-2-(3-Butyl-bicyclo-[2,2,1]-heptyl)-2-aminothiazoline

Trans-2-(3-Cyclohexyl-bicyclo-[2,2,1]-heptyl)-2-aminoimidazoline

Endo-([2,2,1]-Heptyl)-2-aminoimidazoline

2-N-Bornylamino-oxazoline

Exo-([2,2,1]-Heptyl)-2-aminoimidazoline

N-(1-Adamantyl)-4,5-dihydro-1,3-oxazol-2-amine

N-(2-adamantyl)-4,5-dihydro-1,3-oxazol-2-amine

Combination Treatments

The compositions and methods of the present disclosure may be used in the context of a number of therapeutic or prophylactic applications. In order to increase the effectiveness of a treatment with the compositions of the present disclosure, e.g., TMED9-binding agents, e.g., BRD-4780 selected and/or administered as a single agent, can be selected and/or administered with another agent or therapy, optionally to augment the efficacy of another therapy (second therapy). Thus, it may be desirable to combine these compositions and methods with one another, or with other agents and methods effective in the treatment, amelioration, or prevention of diseases and pathologic conditions, for example, toxic proteinopathies resulting from mutant protein accumulation in the early secretory pathway, such as a neurodegenerative disease, MKD, an autosomal dominant kidney disease caused by uromodulin mutation, a form of retinitis pigmentosa caused by rhodopsin mutation, etc.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing a proteinopathy) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as a TMED9-binding agent (e.g., BRD-4780), in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with a TMED9-binding agent (e.g., BRD-4780)) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxy methyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxy benzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, German® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, ° leyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., a TMED9-binding agent, e.g., BRD-4780) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for oral delivery or intravenous injection to a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., a TMED9-binding agent, e.g., BRD-4780) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., amelioration of kidney disease and/or symptoms, amelioration of neurodegenerative disease and/or neurodegenerative disease-related symptoms, reduction of retinitis pigmentosa symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., a TMED9-binding agent, e.g., BRD-4780) described herein. In certain embodiments, a dose described herein includes independently between 1 mg and 3 mg, inclusive, of an agent (e.g., a TMED9-binding agent, e.g., BRD-4780) described herein. In certain embodiments, a dose described herein includes independently between 3 mg and 10 mg, inclusive, of an agent (e.g., a TMED9-binding agent, e.g., BRD-4780) described herein. In certain embodiments, a dose described herein includes independently between 10 mg and 30 mg, inclusive, of an agent (e.g., a TMED9-binding agent, e.g., BRD-4780) described herein. In certain embodiments, a dose described herein includes independently between 30 mg and 100 mg, inclusive, of an agent (e.g., a TMED9-binding agent, e.g., BRD-4780) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., a TMED9-binding agent, e.g., BRD-4780) or composition, as described herein, can be administered in combination with one or more additional pharmaceutical agents (e.g., therapeutically and/or prophylactically active agents), which are different from the agent or composition and may be useful as, e.g., combination therapies.

The agents or compositions can be administered in combination with additional pharmaceutical agents that improve their activity (e.g., activity (e.g., potency and/or efficacy) in treating a disease (e.g., a toxic proteinopathy resulting from mutant protein accumulation in the early secretory pathway, such as a neurodegenerative disease, MKD, an autosomal dominant kidney disease caused by uromodulin mutation, a form of retinitis pigmentosa caused by rhodopsin mutation, etc.) in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., a TMED9-binding agent, e.g., BRD-4780) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy (e.g., an agent for immune checkpoint blockade such as a PD-1 inhibitor, optionally with or without one or more CTLA-4 inhibitors), an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, other kidney disease, neurodegenerative disease and/or retinitis pigmentosa therapies, anti-cancer agents, immunotherapy and/or immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with a kidney, eye or other therapy including, but not limited to, dialysis, surgery, transplantation (e.g., kidney transplantation, stem cell transplantation, etc.), immunotherapy, and/or chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. No. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., a TMED9-binding agent, e.g., BRD-4780) of this disclosure and/or may contain agents (e.g., oligonucleotide primers, probes, etc.) for identifying a kidney disease, eye disease and/or neurodegenerative disease associated with a toxic proteinopathy resulting from mutant protein accumulation in the early secretory pathway in a subject, cell, tissue and/or organoid. In some embodiments, the kits further include instructions for use in accordance with the methods of this disclosure. In some embodiments, these instructions comprise a description of administration of the agent to treat or diagnose, e.g., a toxic proteinopathy resulting from mutant protein accumulation in the early secretory pathway, according to any of the methods of this disclosure. In some embodiments, the instructions comprise a description of how to detect a toxic proteinopathy resulting from mutant protein accumulation in the early secretory pathway, for example in an individual, in a tissue sample, or in a cell. The kit may further comprise a description of selecting an individual suitable for treatment based on identifying whether that subject has a toxic proteinopathy resulting from mutant protein accumulation in the early secretory pathway and/or a biomarker (e.g., a MUC1-fs, C126R UMOD and/or P23H rhodopsin mutant) indicative of a toxic proteinopathy resulting from mutant protein accumulation in the early secretory pathway.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a toxic proteinopathy resulting from mutant protein accumulation in the early secretory pathway, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is a TMED9-binding agent, e.g., BRD-4780. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989. Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Cabs eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Human Kidney Biopsies

Kidney tissue was obtained as discarded tissue from surgical nephrectomies performed for clinical indications. Control samples were examined by a renal pathologist to select tissue for further processing. For MKD patient tissue, samples from kidney cortex and medulla were collected from a 50 year old female patient with advanced disease undergoing nephrectomy for a suspicious cyst that was proved benign.

hMUC1 knock-in replacement mice wt/+ and fs/+ knock-in (KI) 129S2 mice were generated by GenOway (Lyon, France) using embryonic stem (ES) cells genetically modified by homologous recombination, through KI of the entire human MUC1 gene into the murine MUC1 locus. Mice were maintained on a 12 hr light/dark cycle at 18-26° C. in an AAALAC accredited facility and fed ad libitum with water and PicoLab® Rodent Diet 20 pellets (0007688, LabDiet). All animal experiments were approved by the Institutional Animal Care and Use Committee (IACUC) at The Broad Institute of MIT and Harvard and were conducted in accordance with National Institutes of Health (NIH) animal research guidelines.

Normal and MKD Patient Derived iPS Cell Lines iPS cell lines from three MKD patients and their unaffected siblings were derived from erythroblasts using CTS™ CytoTune™-iPS 2.1 Sendai Reprogramming Kit (A34546, Thermo Fisher Scientific®) at the Harvard Stem Cell Institute iPS Core Facility. Cell lines were characterized for pluripotency and spontaneous differentiation to the three germ layers using qPCR based on standard protocols at the HSCI Core Facility. All iPSC cultures were maintained in mTeSR1 medium in T25 flasks coated with Matrigel. Cells were passaged using Gentle Cell Dissociation Reagent. All lines were confirmed to be karyotype normal and maintained below passage 15. Cell lines were routinely checked and were negative for mycoplasma.

HEK293T Cells

HEK293T cells (ATCC) were cultured according to standard protocol in Dulbecco's Modified Eagle's Medium (DMEM) supplemented with 10% Fetal Calf Serum (26140079, Life Technologies), 100 units/mL penicillin and 100 µg/mL streptomycin (15140-163, Life Technologies).

Kidney Epithelial Cells

N and P cells, generated herein, were cultured in Renal Life Basal Medium (102970-948, VWR) supplemented with Renal Life Factors (102970-862, VWR), with the exclusion of Gentamycin and Amphotericin B. For all experiments, P cells were maintained below passage 12.

AtT-20 Pituitary Cells Expressing UMOD

AtT-20 mouse pituitary cells (ATCC® CCL-89™) stably transfected with cDNAs encoding WT-UMOD or UMOD mutant C126R were maintained in DMEM:Nutrient Mixture F-12 (DMEM/F12) (10565042, Thermo Fisher Scientific®) supplemented with 10% Fetal Calf Serum (26140079, Life Technologies), 100 units/mL penicillin and 100 µg/mL streptomycin (15140-163, Life Technologies) and 0.8 mg/mL of G418 (04727878001, Sigma-Aldrich).

MUC1-wt and MUC1-fs Plasmid Design

Plasmid constructs for in vivo expression of MUC1-wt and MUC1-fs proteins were based on the normal and mutant MUC1 alleles of MKD patient F6:IV-3, each containing a VNTR region comprising 37 near-identical 60-mer repeat units that had been completely sequenced and assembled previously (Kirby et al., 2013). The frameshift mutation is found in the second repeat unit of this allele. The MUC1 tandem array and flanking regions were PCR-amplified in 50 µl containing 50 ng genomic DNA, 15 pmol forward (GGCAGAGAAAGGAAATGGCACATCACT; SEQ ID NO: 6) and 15 pmol reverse primer (CTGCTGCTCCT-CACAGTGCTTACAGGT; SEQ ID NO: 7), 0.2 mM of each dNTP and 1.25 U PrimeSTAR GXL DNA Polymerase in 1× PrimeSTAR GXL buffer (Takara). The thermoprofile was 1 min at 94° C., 22 cycles of 10 sec at 98° C., 10 sec at 65° C., 6 min at 68° C., with final extension for 10 min at 68° C. Bona fide full-length PCR products spanning chr1:155, 160,024-155,162,601 of the incomplete hg19 reference genome (4.15 kb in F6:IV-3) were gel-purified, cleaned up by QiaQuick gel-extraction kits (Qiagen) and TOPO-TA cloned in pCR-4-TOPO vector in TOP10 cells (Thermo Fisher Scientific®). Transformants were Sanger sequenced with vector and insert primers to determine the frameshift mutation status and to screen out clones harboring PCR induced non-synonymous mutations within reach of unique sequencing primers, i.e. flanking the 1.3 kb inaccessible core of the tandem repeat. Clones passing this test were then subjected to full-length Pacific Biosciences sequencing of a 4.7 kb fragment generated by digestion with NspI and PvuI. The clone chosen for MUC1-fs expression constructs included a synonymous PCR-induced mutation of a leucine codon located 731 codons downstream of the codon altered by the frameshift mutation.

Construction of MUC1-wt and MUC1-fs Plasmids for Generation of Knock-in Mice

To replace one copy of the endogenous mouse Muc1 gene with WT and mutant alleles of the human MUC1 gene, including its regulatory sequences (FIG. 1A), the 3.9 kb DraIII fragment was subcloned into an acceptor vector providing sequences upstream and downstream sequences of hg19 chr1:155157737-155165183 which contains the MUC1 gene body, the promoter and enhancer region up to and including micro RNA gene MIR92B (FIG. 7A), as well as flanking restriction sites required for the generation and analysis of KI transgenic mice generated by GenOway (Lyon, France). Before assembling the constructs, two synonymous single-base changes were introduced to the normal MUC1 sequence. Both artificial markers disrupt a restriction site and thus provide a simple genotyping assay for tracking and identification purposes. Marker 1 is a G to A substitution at hg19 chr1:155,161,995, which disrupts a BseY1 site in a PCR product generated with primers GCTAC-CACAGCCCCTAAACC (SEQ ID NO: 8) and GCTGTGGCTGGAGAGTACG (SEQ ID NO: 9). Marker 2 is a T to A substitution at hg19 chr1: 155,160,802, which disrupts a KpnI site in a PCR product generated with primers CCAGCCATAGCACCAAGACT (SEQ ID NO: 10) and GGAAGGAAAGGCCGATACTC (SEQ ID NO: 11). The modified VNTR-containing WT clone was verified by full-length Pacific Biosciences sequencing as before. MUC1 transgene fragments were assembled in the BigEasy v2.0 linear cloning vector pJazz-OK (Lucigen), which reduces torsional stress during replication and helps maintain otherwise unstable and difficult-to-clone sequences (Godiska et al., 2010). The final constructs underwent three independent sequence-validation checks: i) Illumina® Mi-Seq sequencing with paired-end 150 base reads and pilon analysis (Walker et al., 2014) that detected errors in the vector sequence and none in the cloned insert but has blind spots in the tandem repeat region, ii) full-length Pacific Biosciences sequencing of the 3.9-kb DraIII fragment excised from the linear pJazz clones, and iii) subcloning of the 3.9-kb DraIII in a low-copy number pSMART LC-Kan vector (Lucigen), followed by transposon hopping for deep bidirectional Sanger sequencing and tandem-repeat assembly. This sequence validation employed the same approach that was used for the original identification of the frameshift mutation in MKD patients (Kirby et al., 2013). The final constructs (22 kb including the vector) were provided to GenOway for KI transgenesis and development of a mouse model for MKD.

UMOD Plasmid

Wild-type UMOD mRNA was reverse-transcribed from human total kidney RNA, PCR amplified, and cloned into a pCR3.1 vector (Thermo Fisher Scientific®, Thermo Fisher Scientific®, California, USA). Constructs were introduced into *E. coli* TOP 10'F strain (Thermo Fisher Scientific®, California, USA), and candidate recombinant clones were confirmed by sequencing. Mutant UMOD construct c.385T>C (C126R-UMOD) was prepared by site-directed mutagenesis of the WT-UMOD/pCR3.1 construct.

Rhodopsin Plasmid

P23H mutant-GFP rhodopsin plasmid in pEGFP-N1 vector was kindly provided by Michael E. Cheetham.

Huntingtin Plasmid

Plasmid of huntingtin gene exon 1 fragments containing 97 CAG (97Q) repeats fused to GFP was kindly provided by Steven Finkbeiner.

Isolation and Immortalization of Kidney Epithelial Cells

Kidney tissues from control and MKD patient were finely minced, digested with 1 mg/mL Collagenase-type II (Worthington Corp) at 37° C. for 30 min and passed through a series of sieves (100 μm, 70 μm). Tubules that were retained on the top of 70 μm sieve were plated in RenaLife Epithelial medium on collagen coated plates for propagation. Next, cells were immortalized using lentivirus carrying human Telomerase Reverse Transcritpase (hTERT) produced in HEK293T cells. Briefly, viral supernatant was added to cells in the presence of 1 μg/mL Polybrene. Cells were then spun at 2000 rpm for 1 hr at 30° C., then washed with DMEM/F12 (10565042, Thermo Fisher Scientific®) and incubated in RenaLife Epithelial Medium for 24 hr, followed by a second identical cycle of viral transduction. Transduced cells were selected and expanded in 100 μg/mL of Hygromycin B (10687010, Thermo Fisher Scientific®), then cloned by serial dilution. Clones of control (N) cells and MKD patient (P) cells were selected for MUC1 protein abundance and cell polarization on Corning Transwell® Semipermeable support plates (07-200-560, Thermo Fisher Scientific®).

Generation of Kidney Organoids

Kidney organoids were generated as previously described (Takasato et al., 2016) with slight modifications. The iPS cells generated from MKD patients and their unaffected siblings were seeded at 375,000 cells per T25 flask in mTeSR1 media (85870, Stem Cell Technologies) supplemented with 10 μM/mL Rock Inhibitor Y-27632 (72304, Stem Cell technologies). After 24 hr, cells were treated with 8 μM CHIR 99021 (4423/10, R&D systems) in STEMdiff™ APEL™2 Medium (05270, Stem cell Technologies) for 4 days, followed by addition of 200 ng/mL Recombinant Human FGF-9 (100-23, Peprotech) and 1 μg/mL heparin (H4784, Sigma-Aldrich) for 3 more days. At day 7, cells were dissociated into single cells using ACCUTASE™ (07920, Stem Cell Technologies) at 37° C. for 5 min. Then, 500,000 cells were pelleted at 350×g for 2 min (twice with 180° flip after first spin) and transferred onto a transwell membrane (3450, Corning). Pellets were incubated with 5 μM CHIR 99021 in STEMdiff™ APEL™2 Medium for 1 hr. Afterwards, 200 ng/mL Recombinant Human FGF-9 and heparin were added for 5 days, followed by 2 days incubation with 1 μg/mL heparin. For the following 15 days, organoids were kept in STEMdiff™ APEL™2 Medium. Media were changed every other day.

MUC1 KI Replacement Mice

The wt/+ and fs/+ KI replacement mice were developed by GenOway (Lyon, France) using human MUC1-wt and MUC1-fs constructs described above. The MUC1 constructs were knocked into ES cells using homologous recombination. ES cells were injected into blastocysts, and chimeric 129S2 mice were generated. Following breeding, heterozygous mice expressing either hMUC1-wt or hMUC1-fs were obtained.

Genotyping

Mouse genotyping was performed by Transnetyx, using real-time PCR to identify mice expressing the human MUC1 versus the mouse MUC1 version.

Pharmacokinetics Studies

Figure 11A:
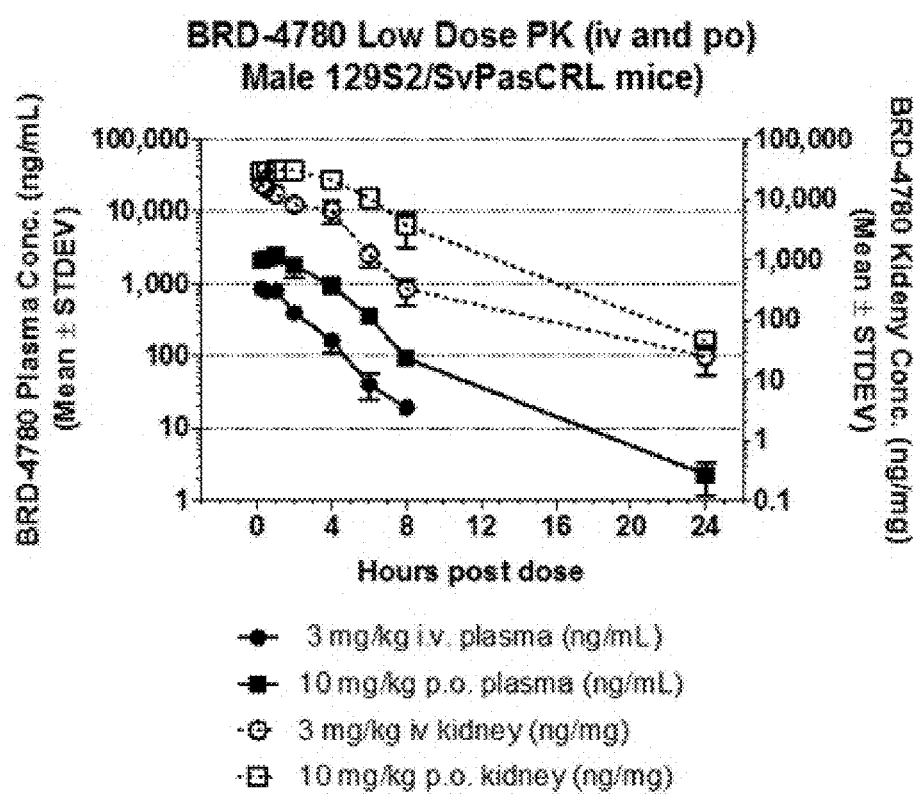
FIGS. 11A to 11U show the pharmacokinetics (PK) of candidate compounds observed in 129S2 mice, 129S-ELITE mice, and Sprague Dawley rats. Compounds were delivered either intravenously (i.v.) or orally (p.o).

1) A pharmacokinetic study was performed by WuXi AppTec (Hong Kong) in fasted male 129S2/SvPasCrl mice (study #400565-20170331-1V1PK) to determine the oral bioavailability of BRD-4780. A single dose of BRD-4780 was administered at 3.0 mg/kg intravenously (i.v.) or 10.0 mg/kg orally (p.o) in a clear solution of 10% HP-β-CD in saline. Blood was collected serially from n=3 mice per dose group at eight time points post dose administration (0.25, 0.5, 1, 2, 4, 6, 8 and 24 hours) and plasma was obtained by centrifugation. Plasma drug concentration was determined by LC-MS/MS and reported as BRD-4780 ng/mL for plasma and ng/mg for kidney tissue, and plotted as the mean±standard deviation concentration (FIG. 11A). Standard pharmacokinetic parameters were calculated (FIG. 11B). The oral bioavailability (% F) was determined to be 119%. In plasma protein binding studies, the estimated percent protein bound was 29.7%.

Figure 11C:
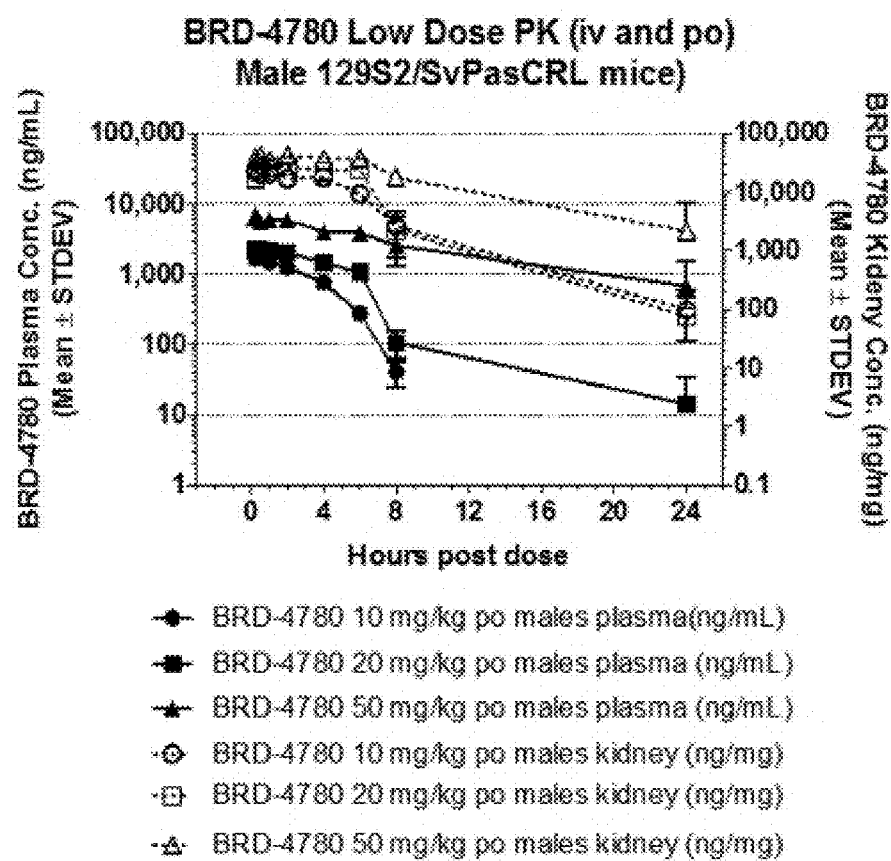
FIG. 11C shows a plot of the plasma and kidney BRD-4780 concentration vs. time curves in male mice following a single p.o. dose of BRD-4780 at the indicated doses from the dose response PK study.
Figure 11D:
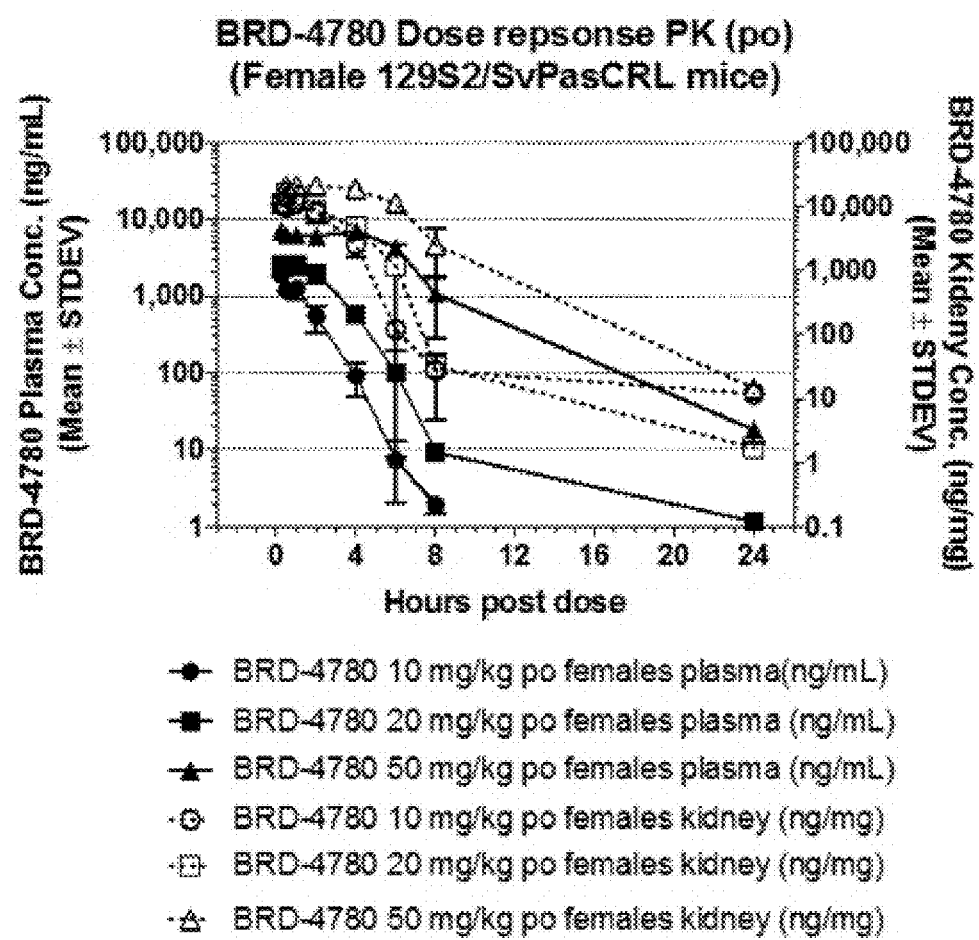
FIG. 11D shows a plot of the plasma and kidney BRD-4780 concentration vs. time curves in female mice following a single p.o. dose of BRD-4780 at the indicated doses from the dose response PK study.

2) A pharmacokinetic study for BRD-4780 was performed by WuXi AppTec (Hong Kong) in fed 129S2/SvPasCrl male (study 400565-2018051001-MPK) and female mice. A single dose of BRD-4780 was administered orally at 10.0 mg/kg, 20 mg/kg, or 50 mg/kg in a clear solution of 10% HP-β-CD in saline. "BRD-8507" was also listed in this study; BRD-8507 is the same compound as BRD-4780 but it is an alternative batch of the compound. Blood and kidney tissue were collected from n=3 mice per dose group at eight time points post dose administration (0.25, 0.5, 1, 2, 4, 6, 8 and 24 hours). Plasma was obtained by centrifugation and the kidney tissue was homogenized. Plasma and tissue drug concentrations were determined by LC-MS/MS and reported as BRD-4780 ng/mL for plasma and ng/mg for kidney tissue, and plotted as the mean f standard deviation concentration for males (FIG. 11C) and females (FIG. 11D). Standard pharmacokinetic parameters were calculated for males (FIG. 11E) and females (FIG. 11F).

3) A pharmacokinetic study was performed by Charles River Labs (CRL) (Worcester, Mass., USA) in fed male 129-ELITE mice (study EF-0022-DA-MI) to compare the oral bioavailability of BRD-1365 and BRD-7709 to BRD-4780. BRD-1365 has the following structure:

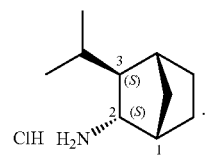

BRD-7709 has the structure:

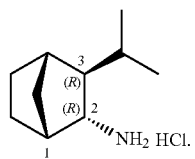

Figure 11H:
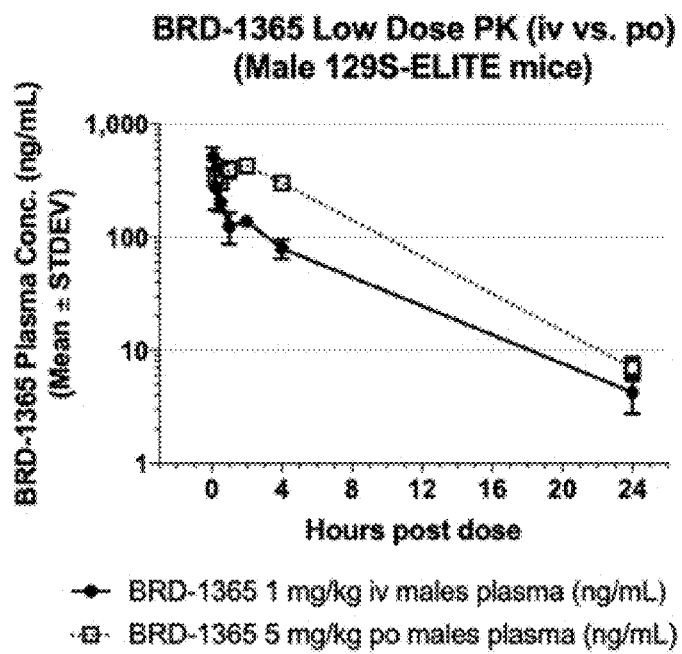
FIG. 11H shows a plot of the plasma BRD-1365 (also referred to as "Fr1 (+)" herein) concentration vs. time curves in male 129S-ELITE mice following a single i.v. or p.o. dose of BRD-4780 from a low dose PK study.
Figure 11I:
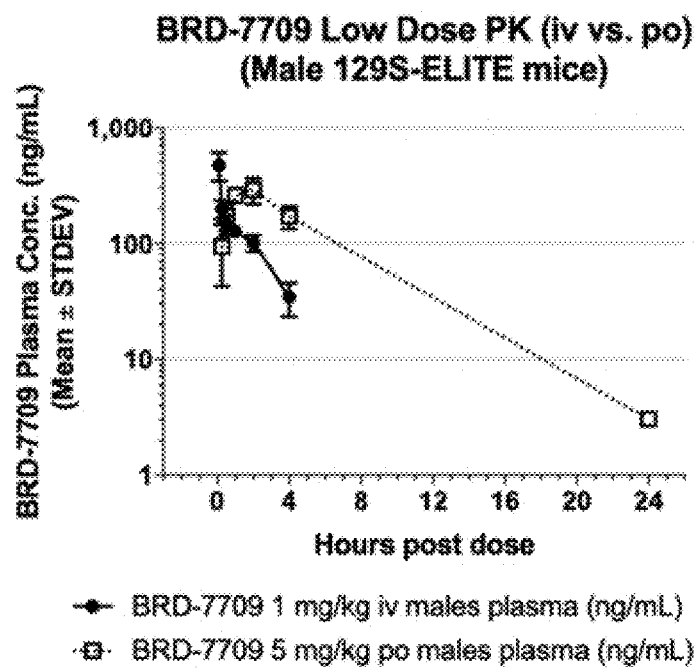
FIG. 11I shows a plot of the plasma BRD-7709 (also referred to as "Fr2 (−)" herein) concentration vs. time curves in male 129S-ELITE mice following a single i.v. or p.o. dose of BRD-4780 from a low dose PK study.
Figures 11J, 11K:
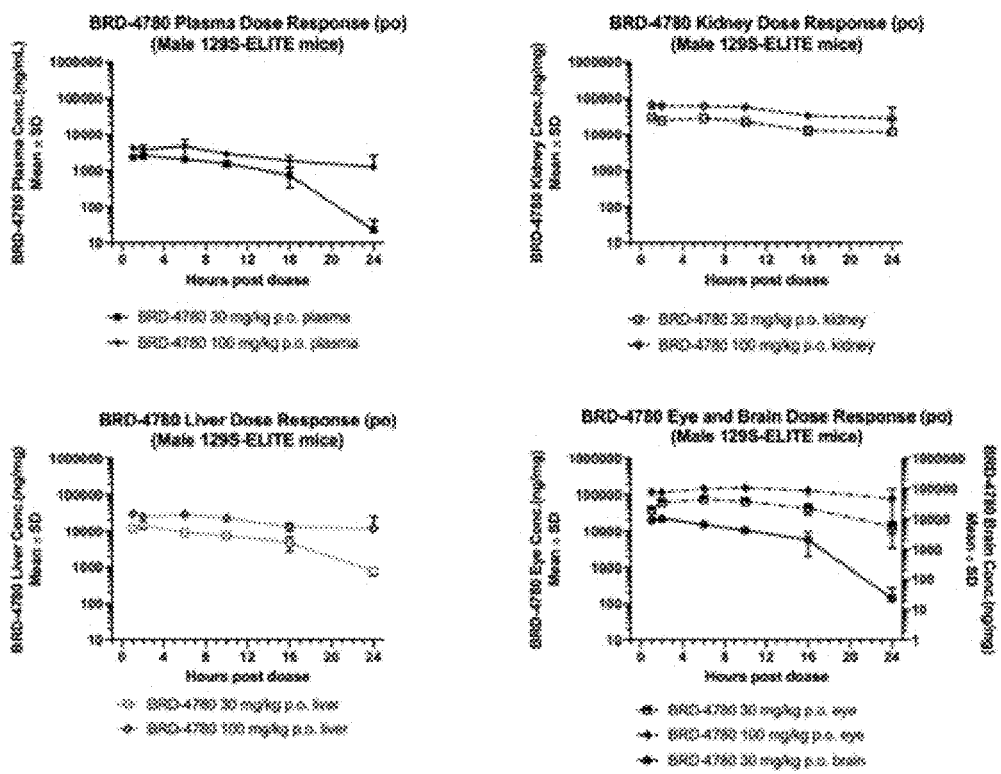
FIG. 11J is a table of the calculated PK parameters from the data plotted in FIGS. 11G to 11I following a single i.v. or p.o. dose of BRD-4780 at the indicated doses in male 129S-ELITE mice. "$C_{max}$" indicates the maximum concentration. "$T_{max}$" indicates the time of maximum concentration. "AUC" indicates the area under the curve. "Inf" indicates infinity. "$C_{max}D$" indicates the dose normalized maximum concentration. $T_{1/2}$ indicates the half-life. "Cl" indicates clearance. "$C_{max}$" indicates the maximum concentration. "h" indicates hour. "Vz" indicates the volume of distribution. "$AUC_{0-last}$ Ratio (K/P)" indicates the ratio of $AUC_{0-last}$ in kidney/$AUC_{0-last}$ in plasma.
FIG. 11K shows a plot of the plasma, kidney, liver, eye and brain BRD-4780 concentration vs. time curves in male 129S-ELITE mice following a single p.o. dose of BRD-4780 from a dose response PK study.

A single dose of BRD-4780, BRD-1365 or BRD-7709 was administered at 1.0 mg/kg intravenously (i.v.) or 5.0 mg/kg orally (p.o) in a clear solution of 5% dextrose in water (D5W). Blood was collected serially from n=3 mice per dose group at seven time points post i.v. dose administration (0.083, 0.25, 0.5, 1, 2, 4 and 24 hours) or six time points post p.o. dose administration (0.25, 0.5, 1, 2, 4 and 24 hours) and plasma obtained by centrifugation. Plasma drug concentration was determined by LC-MS/MS and reported as ng/mL in plasma plotted as the mean±standard deviation concentration for BRD-4780 (FIG. 11G), BRD-1365 (FIG. 11H) and BRD-7709 (FIG. 11I). Standard pharmacokinetic parameters were calculated (FIG. 11J).

Figure 11L:
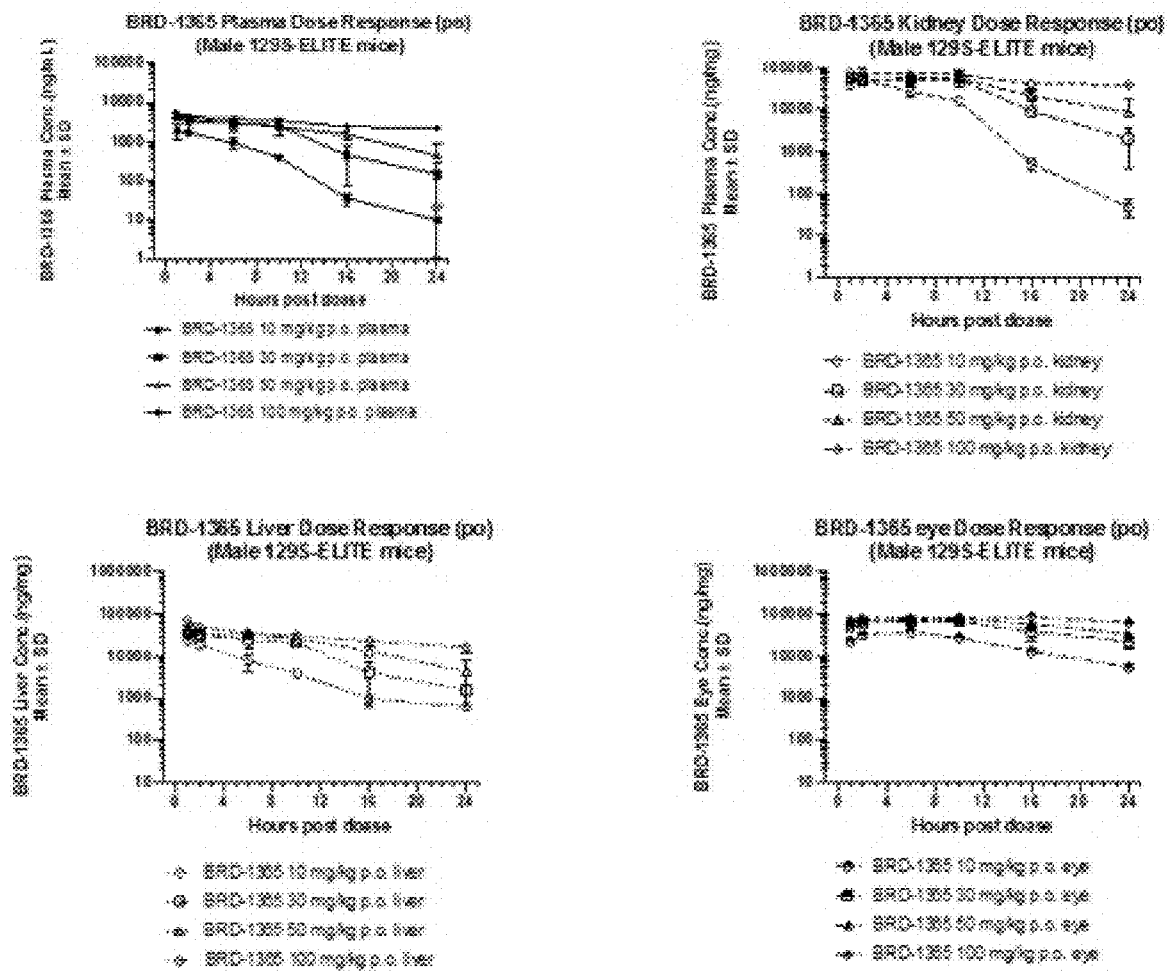
FIG. 11L shows a plot of the plasma, kidney, liver, eye and brain BRD-1365 concentration vs. time curves in male 129S-ELITE mice following a single p.o. dose of BRD-1365 from a dose response PK study.
Figures 11M, 11N:
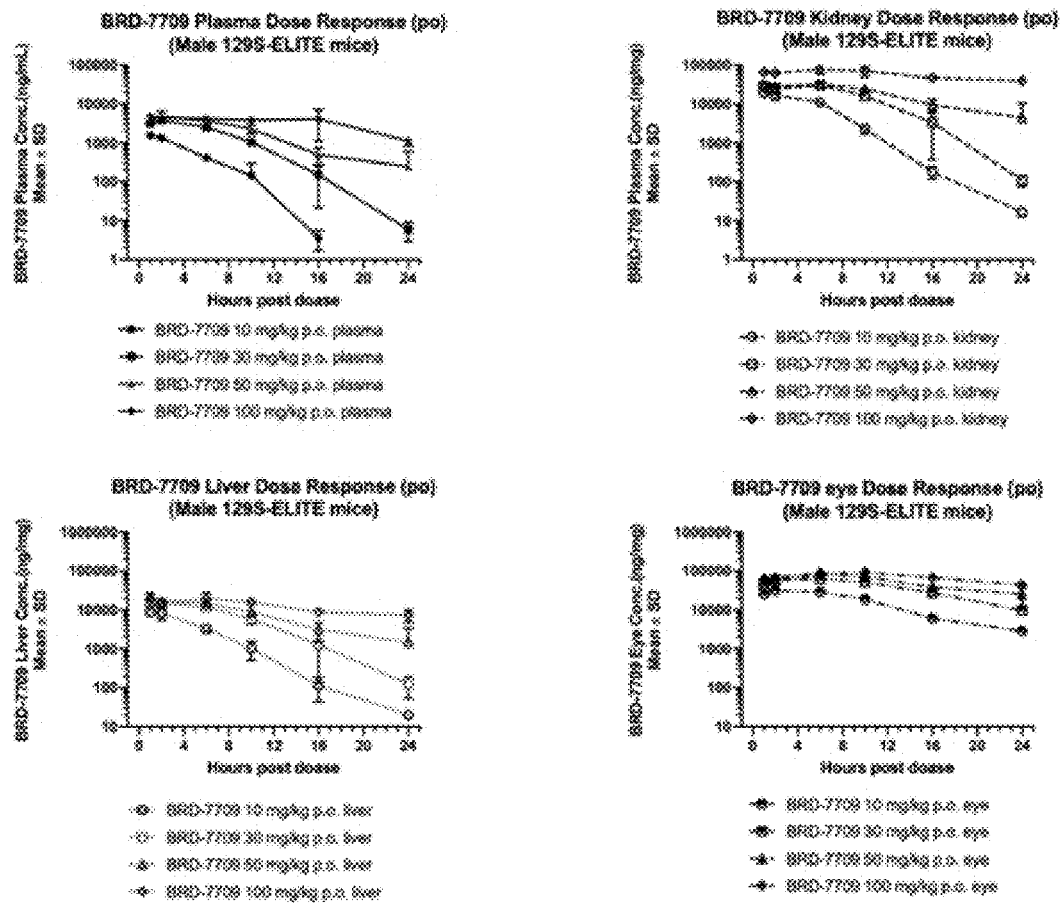
FIG. 11M shows a plot of the plasma, kidney, liver, eye and brain BRD-7709 concentration vs. time curves in male 129S-ELITE mice following a single p.o. dose of BRD-7709 from a dose response PK study.
FIG. 11N is a table of the calculated PK parameters from the data plotted in FIG. 11K following a single p.o. dose of BRD-4780 at the indicated doses in male 129S-ELITE mice. "$C_{max}$" indicates the maximum concentration. "$T_{max}$" indicates the time of maximum concentration. "AUC" indicates the area under the curve. "Inf" indicates infinity. "$C_{max}D$" indicates the dose normalized maximum concentration. "$T_{1/2}$" indicates the half-life. "Cl" indicates clearance. "$C_{max}$" indicates the maximum concentration. "h" indicates hour. "$C_{max}$" indicates the maximum concentration. "Vz" indicates the volume of distribution. "$AUC_{0-last}$ Ratio (K/P)" indicates the ratio of $AUC_{0-last}$ in kidney/$AUC_{0-last}$ in plasma
Figures 11O, 11P:
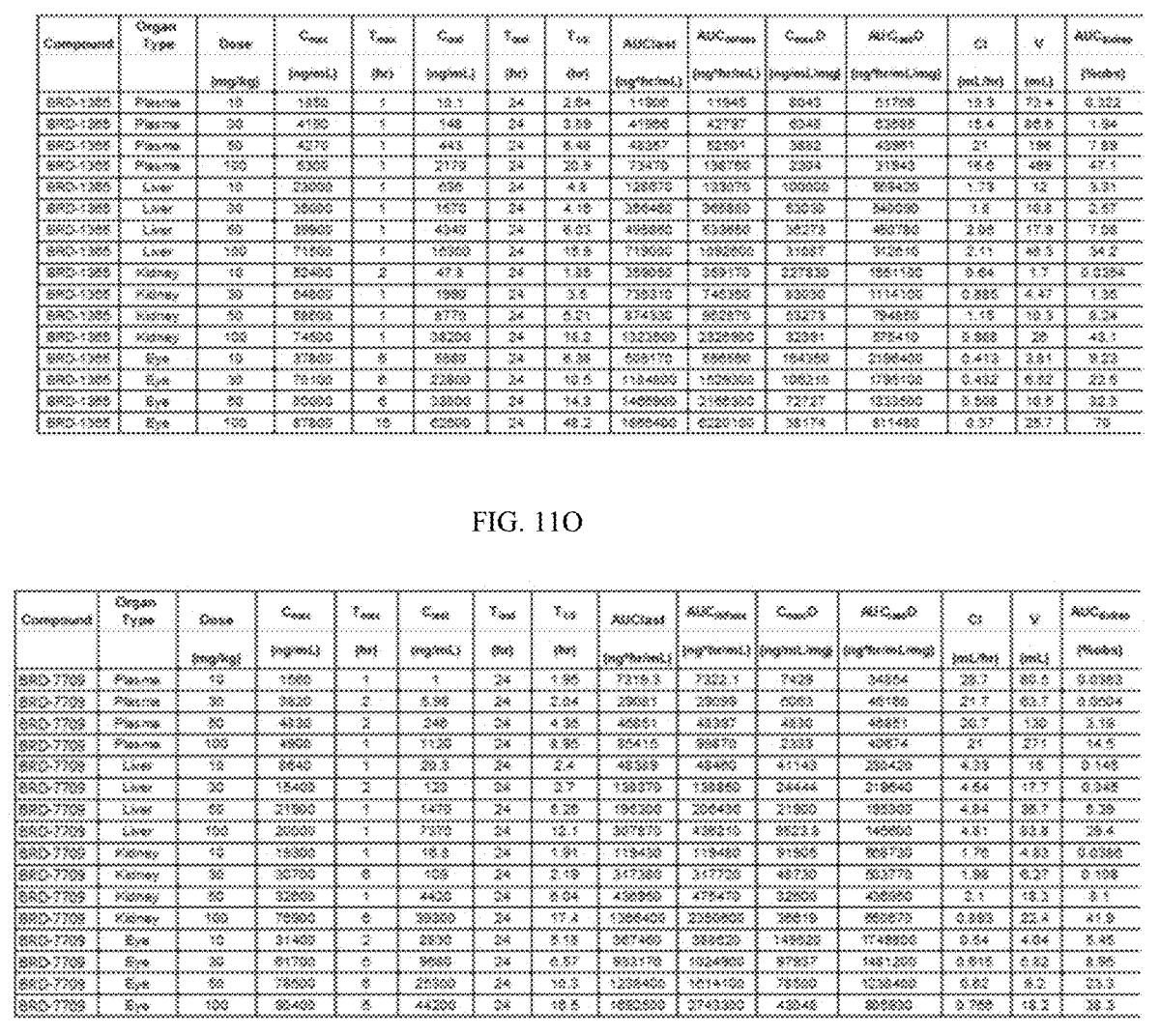

4) A pharmacokinetic study was performed by Charles River Labs (CRL) (Worcester, Mass., USA) in fed male 129-ELITE mice (study EF-0024-DA-MI) to determine the dose response exposure of BRD-4780, BRD-1365 and BRD-7709 in plasma, kidney, liver and eye. Brain exposure to BRD-4780 at 30 mg/kg was also evaluated A single dose of BRD-4780 was administered at 30.0 mg/kg or 100 mg/kg orally (p.o) in a clear solution of 5% dextrose in water (D5W). For BRD-1365 and BRD-7709, a single dose of either compound was administered at 10.0 mg/kg, 30.0 mg/kg, 50.0 mg/kg or 100 mg/kg orally (p.o) in a clear solution of 5% dextrose in water (D5W). Blood, kidney, liver and eye tissue were collected from n=3 mice per dose group at six time points post p.o. dose administration (1, 2, 6, 10, 16 and 24 hours) with all three compounds. Brain tissue was collected from n=3 mice per dose group at six time points post p.o. dose administration (1, 2, 6, 10, 16 and 24 hours) with BRD-4780 at 30 mg/kg. Plasma obtained by centrifugation and tissue fragments were homogenized. Plasma and tissue drug concentration was determined by LC-MS/MS and reported as drug concentration in ng/mL for plasma and ng/mg for kidney, liver and eye tissue, plotted as the mean±standard deviation concentration for males for BRD-4780 (FIG. 11K), BRD-1365 (FIG. 11K) and BRD-7709 (FIG. 11M). Standard pharmacokinetic parameters were calculated for males for BRD-4780 (FIG. 11B), BRD-1365 (FIG. 11O) and BRD-7709 (FIG. 11P). All three compounds had a high volume of distribution, with highest exposures in the eye. $C_{max}$ exposures for doses above 10 mg/kg were not dose proportional. AUC exposures for BRD-4780 and BRD-1365 were not dose proportional, but BRD-7709 AUC exposures were nearly dose proportional.

Figure 11Q:
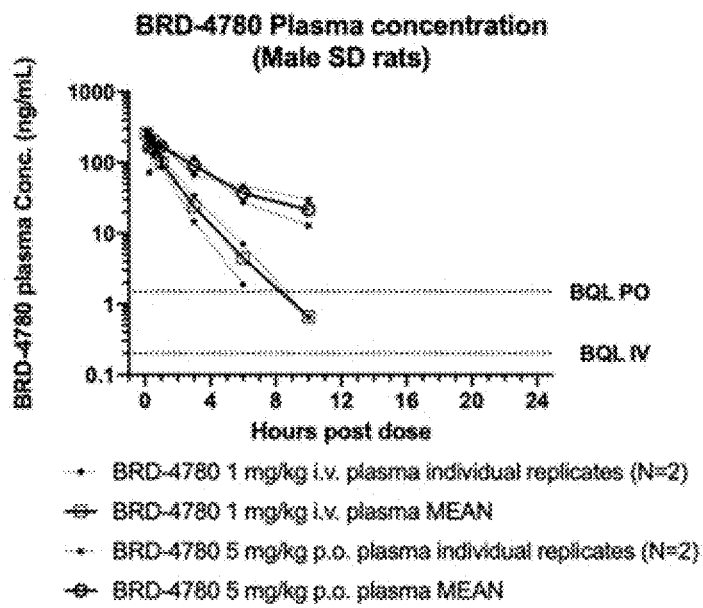
FIG. 11Q shows a plot of the plasma BRD-4780 concentration vs. time curves in male Sprague Dawley rats following a single i.v. or p.o. dose of BRD-4780 from a low dose PK study.
Figure 11R:
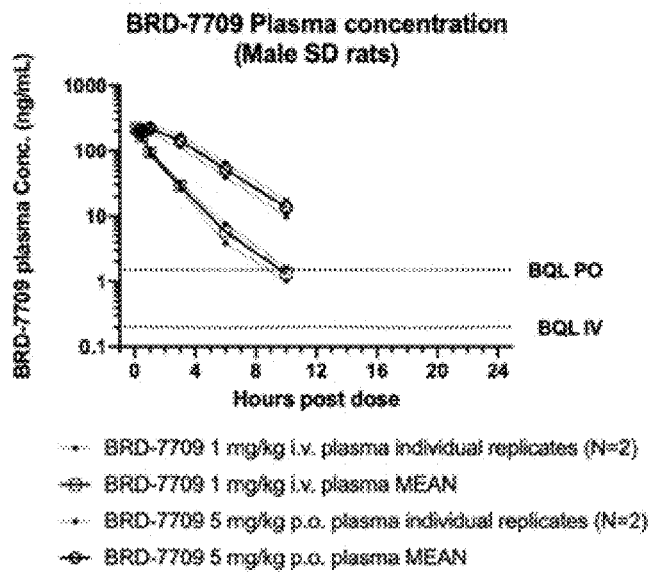
FIG. 11R shows a plot of the plasma BRD-1365 concentration vs. time curves in male Sprague Dawley rats following a single i.v. or p.o. dose of BRD-1365 from a low dose PK study.
Figures 11S, 11T:
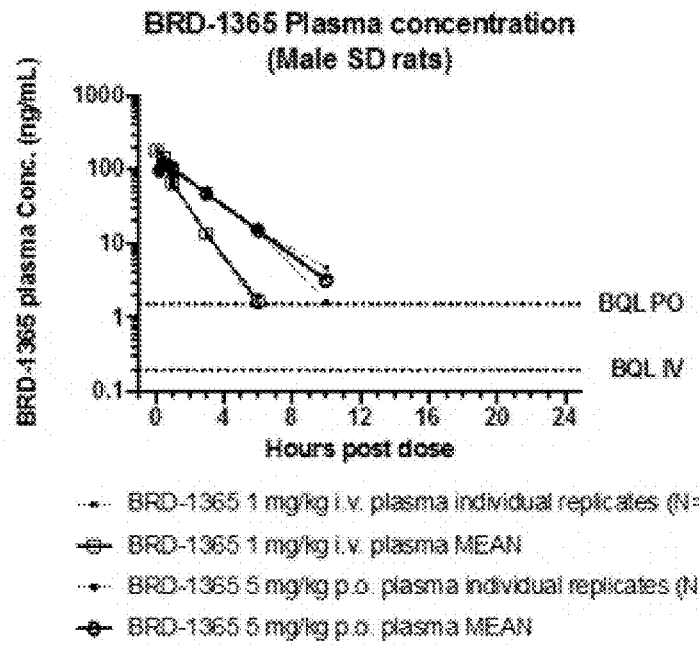
FIG. 11S shows a plot of the plasma BRD-7709 concentration vs. time curves in male Sprague Dawley rats following a single i.v. or p.o. dose of BRD-7709 from a low dose PK study.
FIG. 11T is a table of the calculated PK parameters from the data plotted in FIGS. 11Q, 11R, and 11T following a single i.v. or p.o. dose of BRD-4780, BRD-1365 or BRD-7709 at the indicated doses in male Sprague Dawley rats. "$C_{max}$" indicates the maximum concentration. "$T_{max}$" indicates the time of maximum concentration. "AUC" indicates the area under the curve. "Inf" indicates infinity. "$C_{max}D$" indicates the dose normalized maximum concentration. "$T_{1/2}$" indicates the half-life. "Cl" indicates clearance. "$C_{max}$" indicates the maximum concentration. "h" indicates hour. "$C_{max}$" indicates the maximum concentration. "Vz" indicates the volume of distribution. "$AUC_{0-last}$ Ratio (K/P)" indicates the ratio of $AUC_{0-last}$ in kidney/$AUC_{0-last}$ in plasma.
Figure 11U:
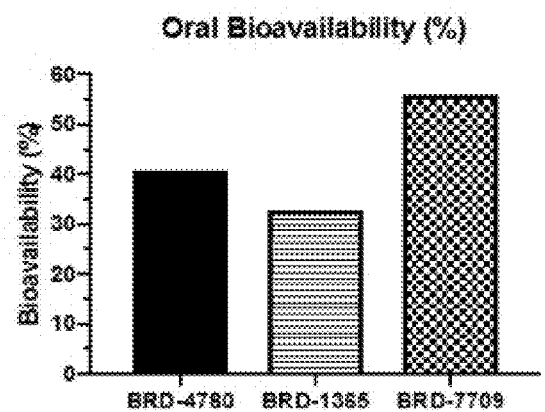

5) A pharmacokinetic study was performed by WuXi AppTec (NJ, USA) in fed male Sprague Dawley rats (study BIMH-20200211-RPK) to determine the oral bioavailability of BRD-4780, BRD-7709 and BRD-1365 in rats. A single dose of BRD-4780, BRD-1365 or BRD-7709 was administered at 1.0 mg/kg intravenously (i.v.) or 5.0 mg/kg orally (p.o) in a clear solution of 5% dextrose in water (D5W). Blood was collected serially from n=2 rats per dose group at nine time points post i.v. dose administration (0.083, 0.5, 1, 3, 6, 10, 24, 32 and 48 hours) or nine time points post p.o. dose administration (0.25, 0.5, 1, 3, 6, 10, 24, 32 and 48 hours) and plasma obtained by centrifugation. Plasma drug concentration was determined by LC-MS/MS and reported as ng/mL in plasma. Plasma concentrations vs. time for individual rats and the mean of 2 rats per group were plotted for BRD-4780 (FIG. 11Q), BRD-1365 (FIG. 11R) and BRD-7709 (FIG. 11S). Standard pharmacokinetic parameters were calculated (FIG. 11T). The oral bioavailability (% F) was determined to be 40.6%. for BRD-4780, 0.083, 0.5, 1, 3, 6, 10, 24, 32 and 48 hours 32.7% for BRD-1365 and 56.1% for BRD-7709), with BRD-7709 showing the highest oral bioavailability, plotted in FIG. 11U.

Figure 11V:
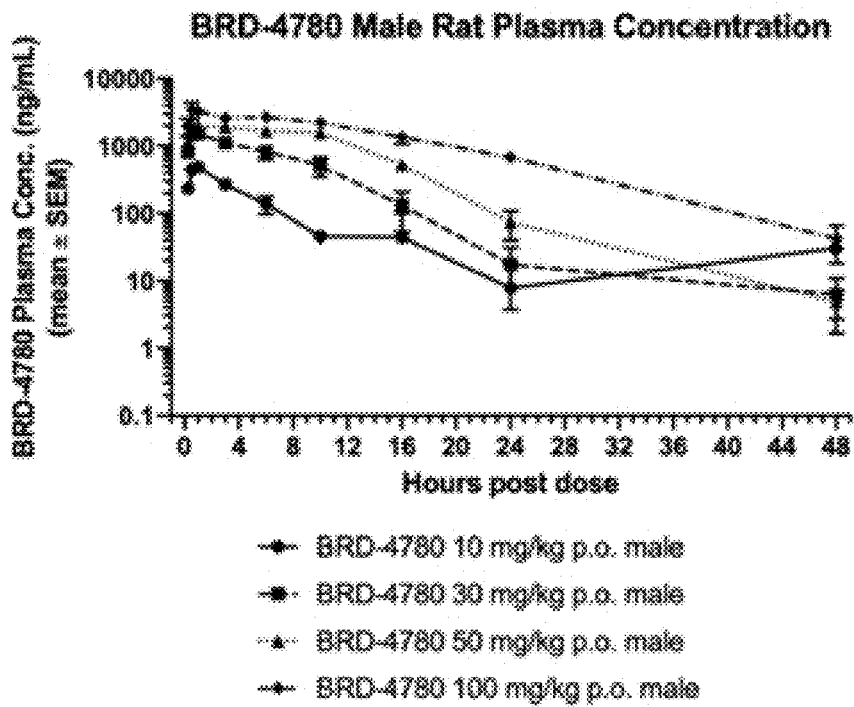
FIG. 11V shows a plot of the mean and standard deviation plasma BRD-4780 concentration vs. time curves in male CD(SD) rats following a single p.o. dose of BRD-4780 at 10 mg/kg p.o., 30 mg/kg p.o., 50 mg/kg p.o. or 100 mg/kg p.o.
Figure 11W:
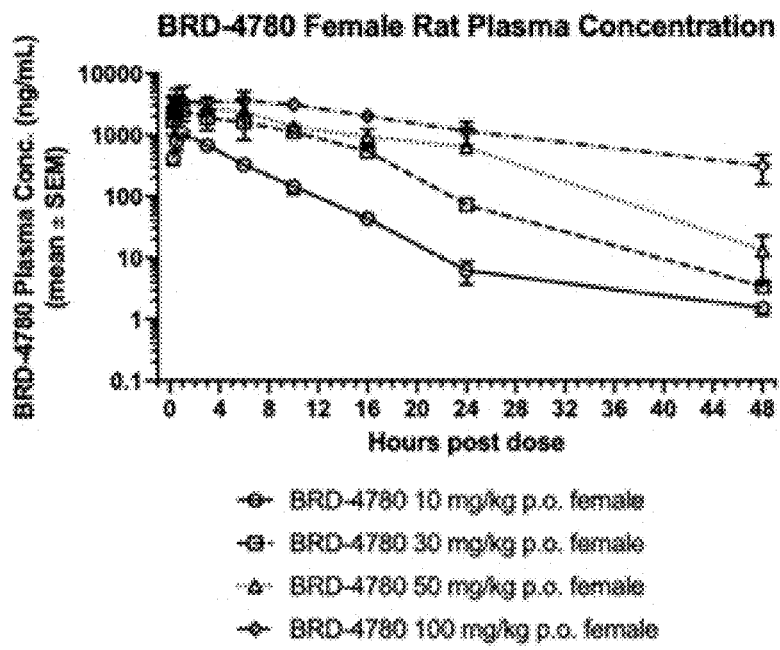
FIG. 11W shows a plot of the mean and standard deviation plasma BRD-4780 concentration vs. time curves in female CD(SD) rats following a single p.o. dose of BRD-4780 at 10 mg/kg p.o., 30 mg/kg p.o., 50 mg/kg p.o. or 100 mg/kg p.o.
Figure 11X:
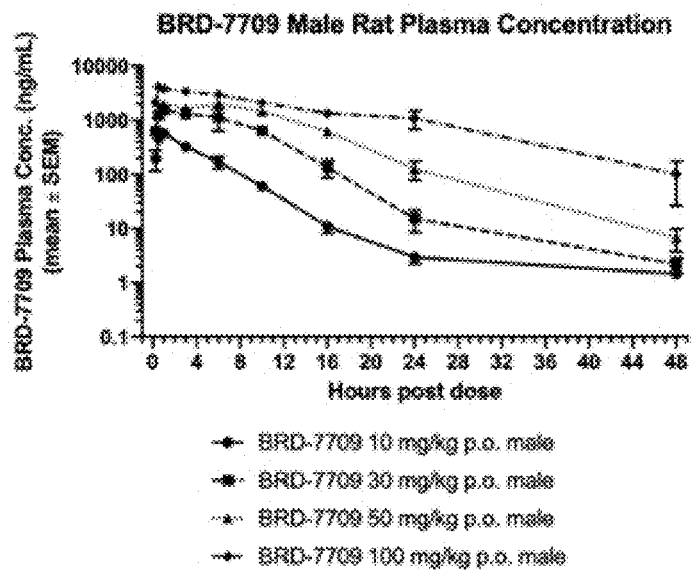
FIG. 11X shows a plot of the mean and standard deviation plasma BRD-7709 concentration vs. time curves in male CD(SD) rats following a single p.o. dose of BRD-7709 at 10 mg/kg p.o., 30 mg/kg p.o., 50 mg/kg p.o. or 100 mg/kg p.o.
Figure 11Y:
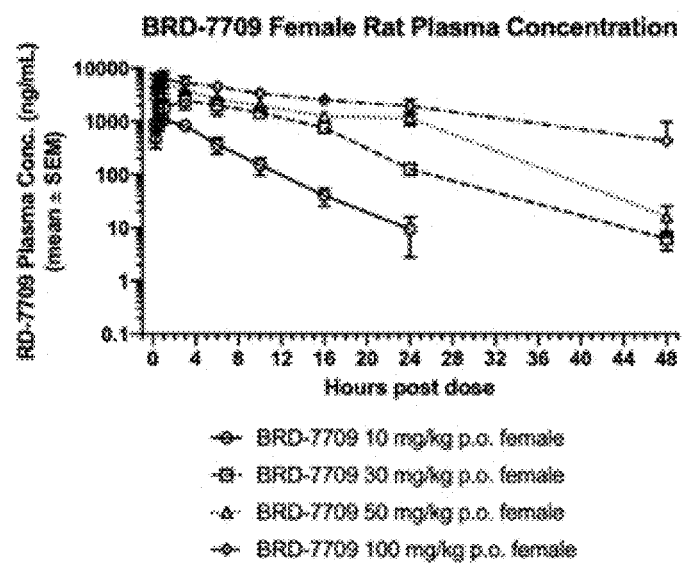
FIG. 11Y shows a plot of the mean and standard deviation plasma BRD-7709 concentration vs. time curves in female CD(SD) rats following a single p.o. dose of BRD-7709 at 10 mg/kg p.o., 30 mg/kg p.o., 50 mg/kg p.o. or 100 mg/kg p.o.
Figure 11Z:
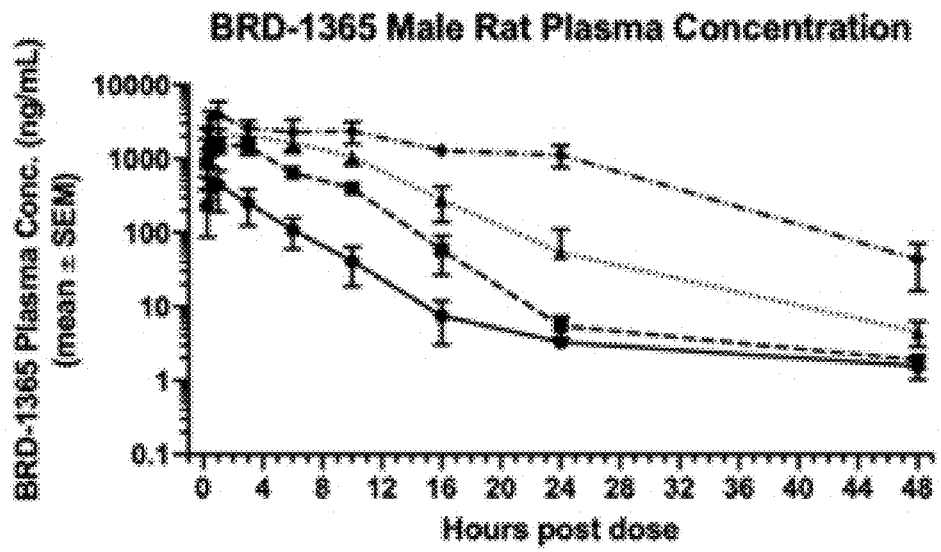
FIG. 11Z shows a plot of the mean and standard deviation plasma BRD-1365 concentration vs. time curves in male CD(SD) rats following a single p.o. dose of BRD-1365 at 10 mg/kg p.o., 30 mg/kg p.o., 50 mg/kg p.o. or 100 mg/kg p.o.
Figure 11A:
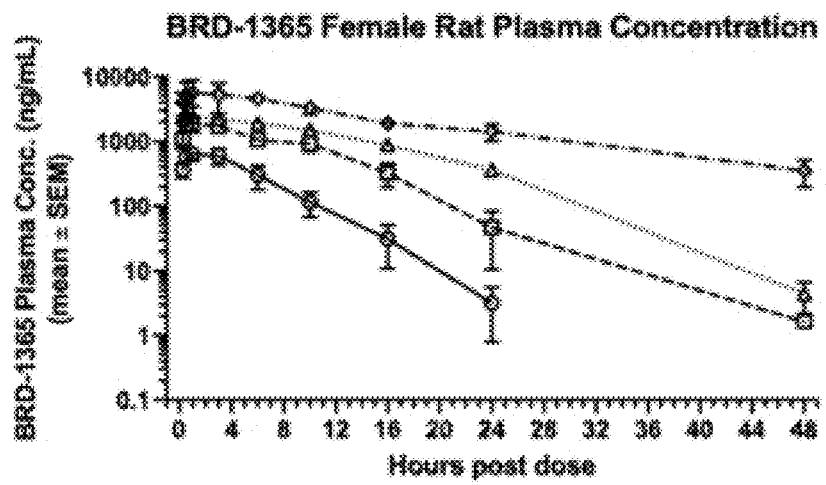

6) A pharmacokinetic study was performed by WuXi AppTec (Wuhan, China) in fed male and female CD(SD) rats (study BIMH-2020042701-RPK (BRD-4780), BIMH-2020042702-RPK (BRD-7709), and BIMH-2020042703-RPK (BRD-1365) inclusive) to determine the dose response exposure of BRD-4780, BRD-7709 and BRD-1365 following single oral administrations in male and female CD(SD) rats. A single dose of BRD-4780, BRD-1365 or BRD-7709 was orally administered at 10.0 mg/kg (p.o.), 30.0 mg/kg (p.o.), 50.0 mg/kg (p.o.) or 100.0 mg/kg (p.o.) in a clear solution of 5% dextrose in water (D5W). Blood was collected serially from n=3 rats per dose group, at nine time points post dose administration (0.25, 0.5, 1, 3, 6, 10, 16, 24, and 48 hours). Plasma was obtained by centrifugation. Plasma drug concentration was determined by LC-MS/MS and reported as ng/mL in plasma. Plasma concentrations vs. time for individual rats and the mean of 3 rats per group were plotted for BRD-4780 in male rats (FIG. 11V) and female rats (FIG. 11W). Plasma concentrations vs. time for individual rats and the mean of 3 rats per group were plotted for BRD-7709 in male rats (FIG. 11X) and female rats (FIG. 11Y). Plasma concentrations vs. time for individual rats and the mean of 3 rats per group were plotted for BRD-1365 in male rats (FIG. 11Z) and female rats (FIG. 11AA). The 24 hour and 48 hour time points for one of three male rats in the BRD-1365 10 mg/kg group were excluded as likely technical outliers. Standard pharmacokinetic parameters were calculated for BRD-4780 (FIG. 11AB), BRD-7709 (FIG. 11AC) and BRD-1365 (FIG. 11AD). In contrast to mice, in which AUC exposure values were higher in male mice than in female mice, AUC values were 1.4 to 2.3 fold higher in female rats than in male rats.

Plasma Collection and Creatinine Quantification

Monthly blood samples from conscious mice were collected into lithium heparin with plasma separator tubes (365965, BD Microtainer) by 4 mm lancet puncture of the submandibular vein (504540, World Precision Instruments), alternating right and left sides. Samples were centrifuged at 2000×g at 4° C. for 10 min, with transfer of plasma to an Eppendorf™ DNA LoBind Microcentrifuge Tube (022431021), followed by another centrifugation at 2000×g 2000 for 10 min at 4° C. Plasma samples were kept at −80° C. until sent for creatinine measurement to UAB Biochemical Genetics Laboratory, University of Alabama.

Mouse Transcardial Perfusion

Figure 5A:
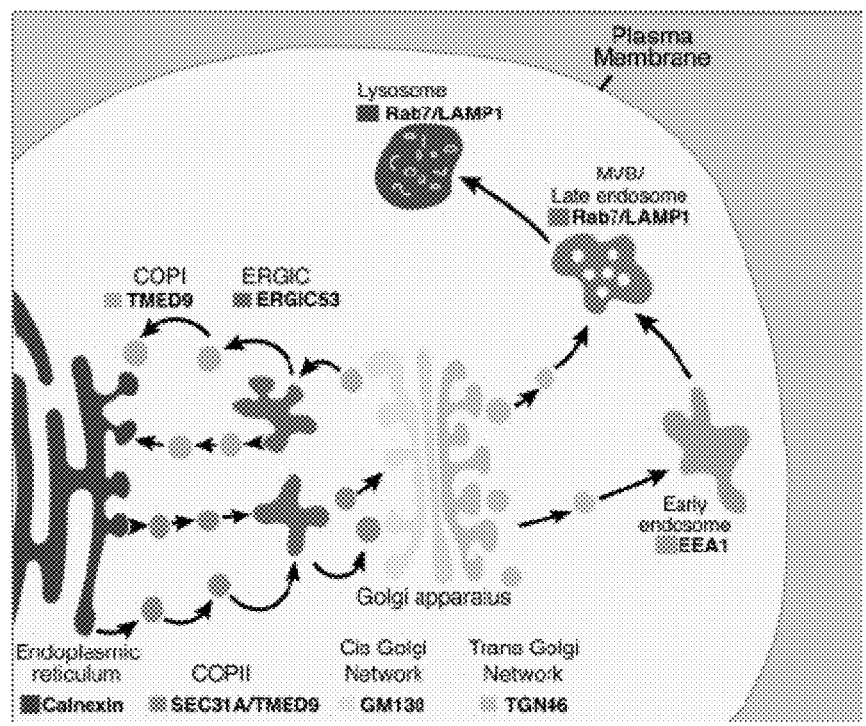
FIGS. 5A to 5E show that MUC1-fs accumulated in the early secretory pathway, in a TMED9-positive compartment.
Figure 5B:
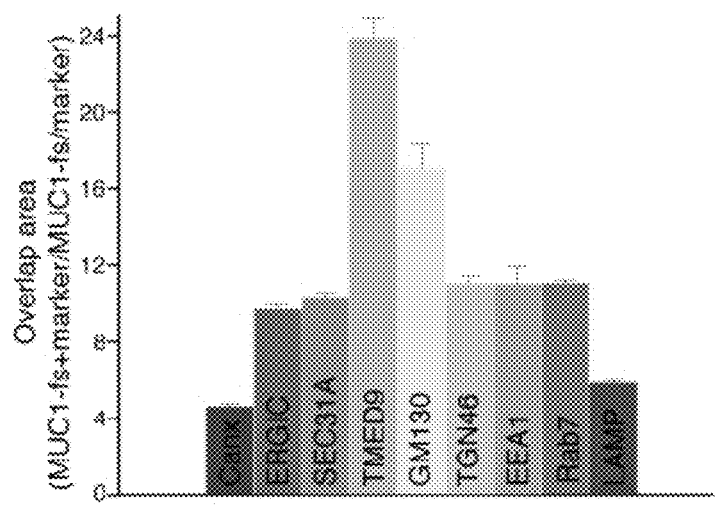
Figure 5C:
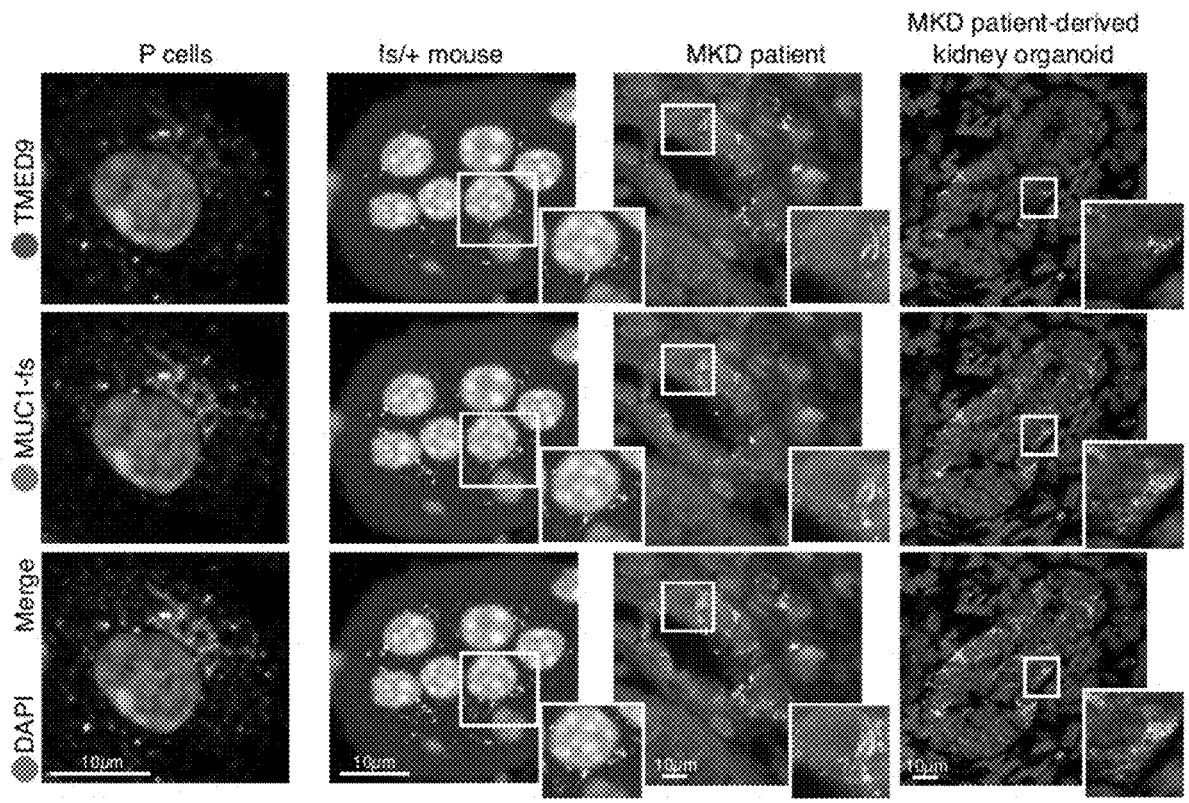

Transcardial perfusion-fixation was performed for testing MUC1-fs colocalization with TMED9-positive vesicles (FIG. 5C). Mice were anesthetized with 3 L/min of 3% isoflurane in 02 for 5 min (Combi-vet® system; Rothacher Medical, Bern, Switzerland). Anesthetized mice were transcardially perfused with 0.1 M PBS (pH 7.4) followed by 4% PFA in 0.1 M PBS. Kidneys were removed, transected into halves and postfixed in 4% PFA for 2 hr at 4° C. Fixed tissue was rinsed in 0.1 M PBS, then cryoprotected 1 hr with 10% sucrose, 5 hr with 20% sucrose, and overnight in 30% sucrose. Cryoprotected tissue was mounted in OCT in a dry ice-ethanol bath and processed for IF studies.

Lentivirus Production

Lentiviral stocks were generated by transfection of HEK293T cells. Cells were transfected with the lentiviral target vector together with a $2^{nd}$ generation packaging plasmid containing gag, pol and rev genes (e.g. pCMV-dR8.91), and a VSV-G expressing plasmid using TransIT-LT1 transfection reagent (Mirus Bio, MIR 2300/5/6) as recommended by the manufacturer. Lentiviral supernatants were collected at 48 hr and 72 hr post transfection, then were passed through a 0.45 mm filter and applied directly to cells or aliquoted and frozen.

RNA Interference

For knockdown of nischarin (putative I1R)(FIG. 14C), a short hairpin RNA (shRNA) plasmid construct (TRCN0000256843) was used to generate lentiviral stocks. For empty vector (EV) control, a similar plasmid lacking the nischarin shRNA was used (TRCN0000208001). P cells were transduced with either targeting shRNA or EV.

CRISPR Cas9 System

To generate Cas9-expressing P cells, the Cas9 expression vector pXPR_BRD111 was used. For knockout of nischarin (FIG. 14C), lentiviral stocks expressing sgRNA plasmid constructs (BRDN0001486234;KO1, BRDN0001482682; KO2) were used. For TMED9 knockout (FIG. 6B), lentiviral stocks expressing sgRNA plasmid constructs (BRDN0003481199;KO1, BRDN0003481863;KO2) were used. Non-targeting sgRNAs (BRDN0001148129;NTC1, BRDN0001146004;NTC2) were used as controls. Cas9-expressing P cells were assayed for Cas9 activity using pXPR_BRD047 plasmid which expresses eGFP and an sgRNA targeting eGFP.

Lentivirus Transduction

P cells were transduced with either lentiviral stocks of nischarin shRNA or Cas9 expressing vector. Viral supernatants were applied to cells for 24 hr in the presence of 4 µg/mL protamine sulfate (194729MP, Biomedicals). Infected cells were washed three times to remove viral particles and transduced cells were selected in either 2 µg/mL puromycin (A11138-02, Thermo Fisher Scientific®) (for nischarin shRNA transduction) or 8 µg/mL Blasticidin (A11139-03, Thermo Fisher Scientific®)(for stable Cas9 expression). For sgRNA transduction, Cas9-expressing P cells were transduced as described above and selection was made using 2 µg/mL puromycin.

Transfection of Rhodopsin Constructs

N cells plated in 96-well plates were transfected with 20 ng/well of P23H mutant rhodopsin-GFP plasmid DNA using Lipofectamine 3000 (Thermo Fisher Scientific®). Eight hr post-transfection, the cells were washed and processed as described below.

Stable Transfection of UMOD Constructs

AtT20 cells at 75% confluence were transfected with 4 µg DNA using Lipofectamine 2000 (Thermo Fisher Scientific®). After 72 hr, cells were trypsinized, diluted, and selected in 0.8 mg/mL G418 (Thermo Fisher Scientific®). UMOD-expressing clones were selected for further study using PCR, DNA sequencing, and western blot analyses.

Stable Transfection of Huntingtin Constructs

HEK293T cells were transfected with Huntingtin 97Q repeats fused to GFP and selected in 0.8 mg/mL G418 (Thermo Fisher Scientific®).

Live Fluorescence Imaging of Cell Death and Apoptosis

To study apoptosis and cell death in N and P cells, 384 well Cell Carrier Ultra plates (6057308, Perkin Elmer), pre-coated with 0.25 mg/mL Synthemax II SC Substrate (3535, Corning) were used. For UPR branch activation experiments (FIGS. 2B, 9I, 9J and 9G) N and P cells were treated as described in the corresponding figure legends. CellEvent Caspase-3/7 Green Detection Reagent (C10423, Thermo Fisher Scientific®) and DRAQ7 (DR71000, Biostatus) were used at 1:5000 to monitor apoptosis and cell death respectively. Cells were imaged daily during 4 days to monitor viability and image analysis was performed as described below. For rescue experiments, P cells were plated on 96 well Cell Carrier Ultra microplates (6055302, Perkin Elmer) at 30,000 cells/well and cultured for 24 hr. BRD-4780 (5 µM) was applied as a pretreatment for 48 hr prior to thapsigargin exposure and throughout the experiment. Thapsigargin was applied at increasing doses and the plates were imaged daily thereafter. To monitor cell death in N cells transiently expressing P23H mutant rhodopsin, DRAQ7 (1:5000) was added with DMSO or 5 µM BRD-4780 treatments. Treated plates were imaged 30 min post-dye application and daily thereafter.

Cell Immunofluorescence (IF) Staining

Cells grown on CellCarrier-96 or -384 well Ultra microplates (PerkinElmer) were fixed 10 min in PBS containing 4% PFA (Electron Microscopy Sciences), permeabilized 15 min in 0.5% Triton X100 (X100-100ML, Sigma-Aldrich), blocked for 1 hr in blocking reagent (100 mM Tris HCL pH8; 150 mM NaCL; 5 g/L Blocking Reagent [11096176001, Roche]) and treated for 1 hr with primary antibodies diluted in blocking reagent (1:500, monoclonal Fab-A-V5H anti-fsMUC1, AbD22655.2, Bio-Rad; 1:2000, monoclonal Mouse anti-MUC1 (CD227), 60137, Stemcell Technologies; 1:200, polyclonal, Mouse anti-GM130, ab169276, Abcam; 1:100, polyclonal, Rabbit anti-TMED9, 216201-AP, Proteintech; 1:800, polyclonal, Rabbit anti-SEC31A, 17913-1-AP, Proteintech; 1:400, monoclonal, Rabbit anti-EEA1 (C45B10), 3288S, Cell signaling technology; 1:100, polyclonal, Rabbit anti-ERGIC-53, E1031, Sigma-Aldrich; 1:400, monoclonal, Mouse anti-LAMP1 (D4O1S), 15665, Cell signaling technology; 1:1000, polyclonal, Rabbit anti-Calnexin, ab22595, Abcam; 1:2000, monoclonal, Rabbit anti-GM130 (D6B1) XP, 12480, Cell signaling technology; 1:200, monoclonal, Rabbit anti TNG46, ab50595, Abcam; 1:100, monoclonal, Rabbit anti-Rab7 (D95F2) XP, 9367, Cell signaling technology; 1:100, monoclonal, Rabbit anti-Rab11 (D4F5) XP, 5589, Cell signaling technology). Fixed, stained cells were washed three times in PBS and incubated for 1 hr with secondary antibodies in blocking solution (1:500, Alexa Fluor 488® Goat anti-Mouse IgG, A-11029, Thermo Fisher Scientific®; 1:500, Alexa Fluor 647® F(ab')2-Goat anti-Rabbit IgG, A21246, Thermo Fisher Scientific®; 1:2000, Hoechst 33342, H3570, Thermo Fisher Scientific®), then washed three times in PBS and imaged.

Kidney Organoid IF Staining

Kidney organoids were immersion-fixed for 15 min in 4% PFA at 4° C. and subsequently frozen in OCT using dry ice and 100% ethanol. Six pm-thick cryostat sections (CM1950, Leica) were thaw-mounted on microscope slides (Fisherbrand™ Superfrost™ Plus, Fisher Scientific) and kept in the cryostat (at −26° C.) for the duration of the sectioning process. Prior to immunostaining, organoid sections were rinsed in PBS for 5 min, incubated for 20 min at room temperature (RT) in PBS blocking solution containing 5% normal donkey serum (S30-100ML, EMD Millipore) and 1.5% Tween® 20 (P1379, Sigma-Aldrich), then incubated overnight at 4° C. with primary antibodies diluted in the same blocking solution (1:500, monoclonal Armenian hamster anti-MUC1, Ab80952, Abcam; 1:500, monoclonal Fab-A-V5H anti-fsMUC1, AbD22655.4, Bio-Rad; 1:300 monoclonal Rat anti-E Cadherin [DECMA-1], ab11512, Abcam; 1:500 polyclonal Rabbit anti-Laminin, L9393-100UL, Sigma-Aldrich; 1:500 Na/K-ATPase, ab76020, Abcam; 1:300 Fluorescein labeled Lotus Tetragonolobus Lectin (LTL), FL-1321, Vector laboratories; 1:100, polyclonal, Rabbit anti-TMED9, 21620-1-AP, Proteintech). Immunostained organoid sections were then rinsed three times for 10 min in PBS and incubated for 2 hr at RT with secondary antibodies diluted in PBS containing 1.5% Tween-20 (1:500, Alexa Fluor® 488-conjugated AffiniPure F(ab')2 Fragment Goat anti-Human IgG, Jackson Immunoresearch; 1:500, Alexa Fluor® 647-conjugated AffiniPure Goat anti-Armenian hamster IgG, Jackson Immunoresearch; 1:1000, Alexa Fluor® 568 Goat anti-Rabbit IgG, A-11036, Thermo Fisher Scientific®; 1:500, DyLight™ 405 Goat anti-Rat IgG, Jackson Immunoresearch). After a 10 min PBS wash, organoid sections were incubated for 5 min in PBS containing DAPI (1:10000, 62248, Thermo Fisher Scientific®). The stained organoid sections were then washed three times for 10 min in PBS, air dried and mounted with ProLong™ Gold Antifade Mountant (P36930, Thermo Fisher Scientific®).

Mouse Kidney IF Staining

Mice were anesthetized with 3 L/min $O_2$ mixed with 3% isoflurane using the Combi-vet® system (Rothacher Medical, Bern, Switzerland) for 5 min. Mouse kidneys were removed, sagittally cut to half and rapidly frozen in Tissue-Tek® O.C.T. Compound, Sakura® Finetek (OCT) (25608-930, VWR) using dry ice and 100% ethanol. Five pm-thick sagittal cryosections (CM1950, Leica) were thaw mounted on microscope slides (Fisherbrand™ Superfrost™ Plus, Fisher Scientific) and kept in the cryostat (at −26° C.) for the duration of the sectioning process. Sections were immersion-fixed for 10 min in 4% PFA (15710, Electron Microscopy Sciences), then washed in PBS. The slides were then subjected to antigen retrieval by immersion in 10 mM citric acid buffer (pH=6), for 10 minutes at 95° C. Following a wash in PBS, the slides were incubated for 20 min at room temperature in PBS blocking solution containing 5% normal goat serum (005-000-121, Jackson ImmunoResearch), 0.2% Triton X-100 (X100-100ML, Sigma-Aldrich) and 2% bovine serum albumin (BSA) (A9576-50ML, Sigma-Aldrich). Sections were then incubated at 4° C. overnight with primary antibodies diluted in the same blocking solution (1:500, monoclonal Armenian hamster anti-MUC1, Ab80952, Abcam; 1:500, monoclonal Fab-A-V5H anti-MUC1-fs, AbD22655.4, Bio-Rad; 1:400, polyclonal Rabbit anti-Aquaporin 2, AQP-002, Alomone labs; 1:1000, polyclonal Rabbit anti-NCC, SPC-402, StressMarq; 1:300, monoclonal Rabbit anti-ERp72, 5033, Cell signaling technology; 1:100, polyclonal, Rabbit anti-TMED9, 21620-1-AP, Proteintech). Stained sections were rinsed three times for 10 min in PBS and incubated with secondary antibodies diluted in PBS containing 0.1% Triton X-100 for 2 hr at RT (1:500, Alexa Fluor® 488-conjugated AffiniPure F(ab')2 Fragment Goat anti-Human IgG, 109-546-097, Jackson Immunoresearch; 1:500, Alexa Fluor® 647-conjugated AffiniPure Goat anti-Armenian hamster IgG, 127-605-160, Jackson Immunoresearch; 1:1000, Alexa Fluor® 568 Goat anti-Rabbit IgG, A-11036, Thermo Fisher Scientific®). Following three washes of 10 min in PBS, stained sections were treated with 1:10000 DAPI solution (62248, Thermo Fisher Scientific®) in PBS for 5 min, washed three times for 10 min in PBS, air dried and mounted using ProLong™ Gold Antifade Mountant (P36930, Thermo Fisher Scientific®).

Human Kidney Biopsies IF Staining

Paraffin sections were deparaffinated, hydrated and subjected to antigen retrieval by immersion in 10 mM citric acid buffer (pH=6). Endogenous peroxidase was blocked with 1% sodium azide and 0.3% $H_2O_2$ for 10 minutes followed by blocking with 5% fetal bovine serum (FBS) in PBS for 30 minutes. Sections were then incubated at 4° C. overnight with primary antibodies in 5% BSA in PBS (1:500, Alexa Fluor® 488-conjugated Fab fragment AbD2265454, anti-MUC1-fs, Bio-Rad; 1:100, monoclonal, Mouse anti-Epithelial Membrane Antigen (EMA), M061329-2, Dako; 1:100, polyclonal, Rabbit anti-TMED9, 21620-1-AP, Proteintech). Following washing, the sections were incubated for 1 hr at 37° C. with secondary antibodies diluted in 5% BSA in PBS (1:500, Alexa Fluor® 555 Donkey anti-Rabbit IgG, A-31572, Thermo Fisher Scientific®; 1:500, Alexa Fluor® 647 Donkey anti-Mouse IgG, A-31571, Thermo Fisher Scientific®). Slides were washed and mounted in ProLong Gold Antifade Mountant with DAPI (P36931, Thermo Fischer Scientific).

TUNEL Assay in Mouse Kidney Tissue

To detect apoptotic nuclei, tissue sections were prepared and fixed as described above, permeabilized for 20 min with 0.2% Triton X-100 (X100-100ML, Sigma-Aldrich) and stained using terminal deoxy transferase uridine triphosphate nick-end labeling (TUNEL) technique (G3250, promega), following the manufacturer's protocol. Stained sections were washed and treated with 1:10000 DAPI solution (62248, Thermo Fisher Scientific®) in PBS for 5 min. Following three washes of 10 min in PBS, the sections were air dried and mounted using ProLong™ Gold Antifade Mountant (P36930, Thermo Fisher Scientific®).

Fluorescence Image Acquisition

All fluorescence imaging performed herein was done using the Opera Phenix High-Content Screening System (HH14000000, PerkinElmer). For fluorescence imaging of cells (live cell or fixed cell imaging), CellCarrier Ultra microplates (either 96 well 6055302 or 384 well 6057308, Perkin Elmer) were used, and a minimum of nine fields were acquired per well using 20× or 63× water immersion objectives in a confocal mode. For kidney organoids and mouse kidney section imaging, microscope slides (Fisherbrand™ Superfrost™ Plus, Fisher Scientific) were used. The entire specimen was first imaged for DAPI at 5× using the PreciScan™ feature (Perkin Elmer) to identify tissue. Pre-identified tissue regions were then imaged at higher resolution (20× or 63× water immersion objectives, confocal mode).

Fluorescence Image Analysis

Image analysis for all imaging experiments was performed using the Harmony software (PerkinElmer).

Image Analysis of IF Cell Staining

Cell nuclei were first identified using Hoechst staining, and cell number was calculated. Cytoplasmic regions were then detected around each nucleus based on combined channels. The cells from the edge of the field were eliminated from the analysis. For the quantification of protein abundance, the total signal intensity value for each antibody was calculated separately in the cell cytoplasm and the average signal per cell was calculated for each well. For quantitation of MUC1-fs cellular distribution and trafficking, the analysis was performed as described in FIG. 13A using the "spot" identification feature for the detection of MUC1-fs and the different organelles.

Live Cell Image Analysis

Caspase 3/7 activation and/or DRAQ7 staining were used to calculate the fraction of cells going through apoptosis and/or cell death, respectively. Single cells were first identified using the digital phase contrast channel and cell number was calculated. Fluorescence intensities were then measured and the threshold for Caspase 3/7 and DRAQ7 positive staining was determined. As an output, the fraction of live (neither caspase3/7 nor DRAQ7 signal detected), apoptotic (caspase3/7 positive) or dead cells (DRAQ7 positive) was calculated in each well at a particular time point.

For the measurement of P cell rescue from THP-induced cell death by BRD-4780 (FIGS. 3I and 3J), no dyes were added to avoid any influence on cell growth. Digital phase contrast images were used for cell identification and count, and autofluorescence in the far-red channel was used for detection of dead cells. Cells with no autofluorescence were identified and calculated as live cell.

For the GFP-rhodopsin experiments (FIGS. 15D and 15E), cells were identified by digital phase contrast. GFP signal was calculated only in cells expressing GFP signal above a minimal background (to identify successfully transfected cells) and the mean intensity was averaged for each well.

For GFP-Huntingtin experiments (FIGS. 15G and 15H), GFP signal in each cell was calculated using the "spot" identification feature, and total spot intensity for single cells was calculated and averaged for each well.

Image Analysis for Mouse Kidney Sections

Figure 4A:
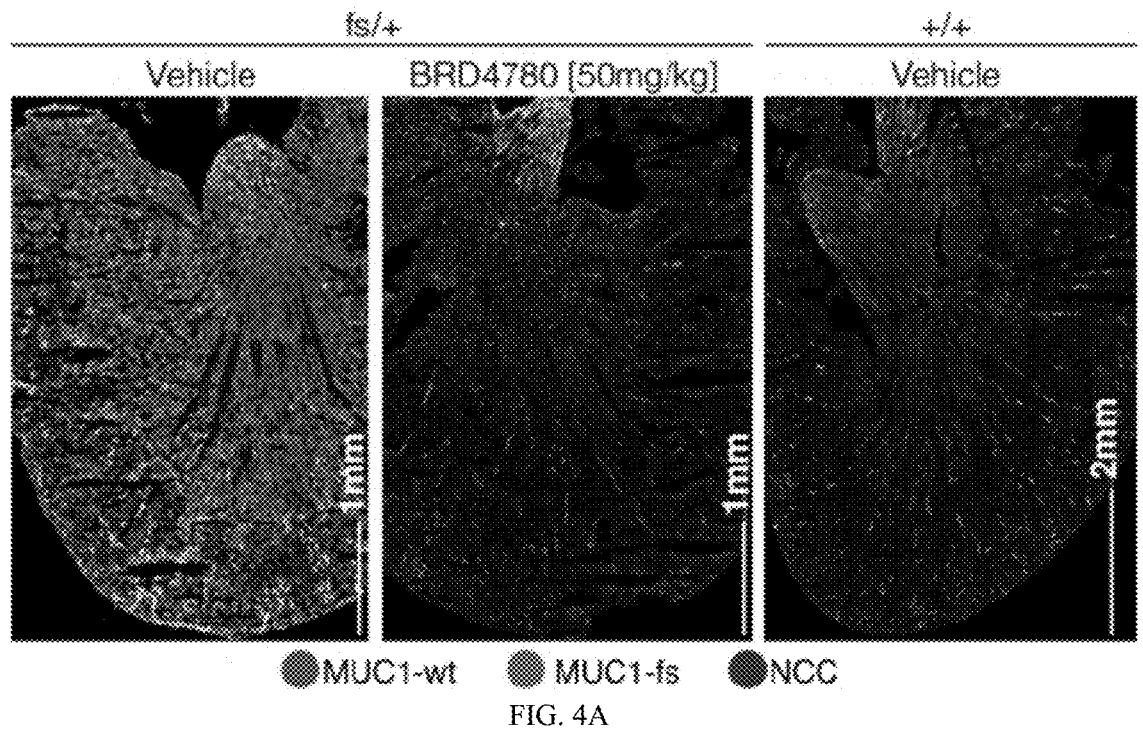
FIGS. 4A to 4G show that BRD-4780 removed mutant MUC1-fs from kidneys of heterozygous knock-in mice and human iPSC-derived kidney organoids.
Figure 4B:
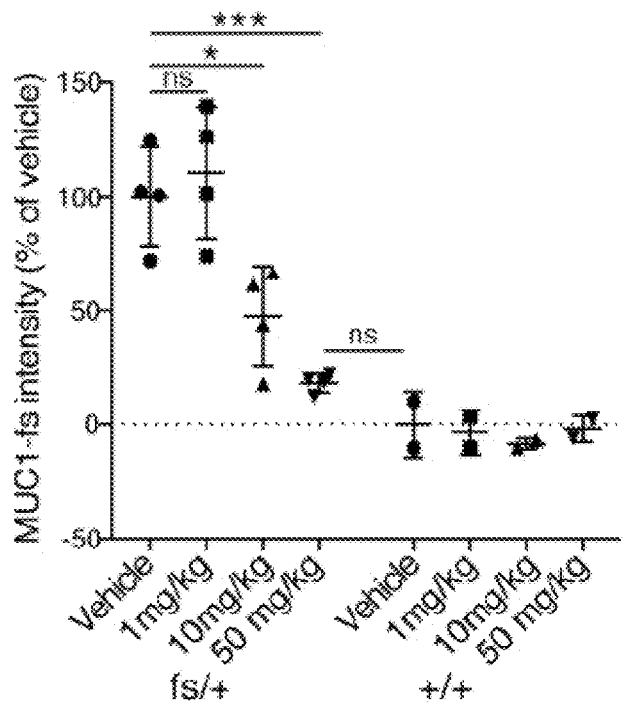
Figure 12A:
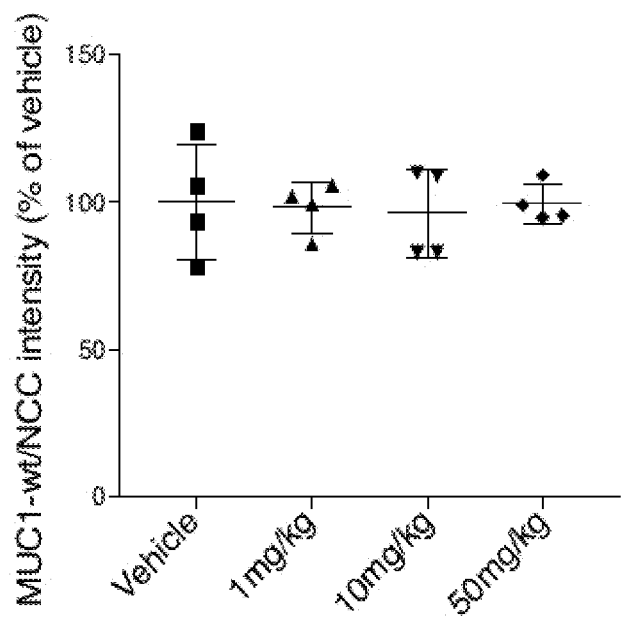
FIGS. 12A and 12B show MUC1 immunofluoresence (IF) staining in kidney sections from fs/+ mice and in iPSC-derived kidney organoids.

MUC1-fs and MUC1-wt mean intensities were calculated in kidney sections of mice treated with either vehicle or BRD-4780 (FIGS. 4A, 4B and 12A). As MUC1-fs and MUC1-wt levels varied in different kidney regions, and as sections might contain different portions of the different kidney regions, the levels of these proteins were analyzed only in NCC-positive distal convoluted tubules. To this end, single cell nuclei were first identified using DAPI channel, followed by cytoplasm detection using all combined channels, excluding the nucleus. Each fluorescent channel intensity was measured and a threshold was set for the identification of NCC positive cells. MUC1-fs and MUC1-wt levels were then calculated only in the NCC positive cells.

Figure 2A:
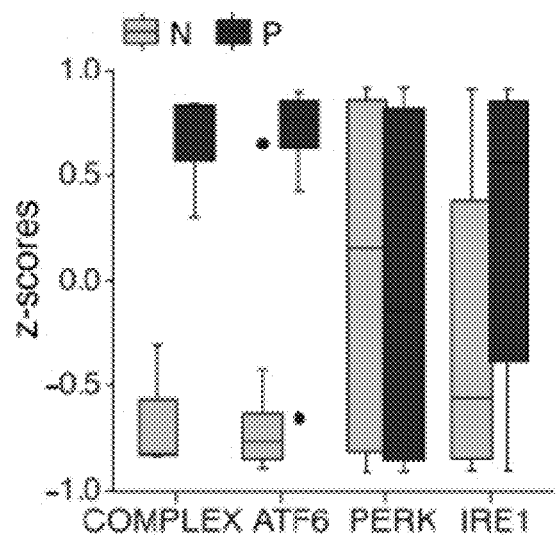
FIGS. 2A to 2H show that MUC1-fs accumulation triggers the ATF6 branch of the UPR.
Figure 2B:
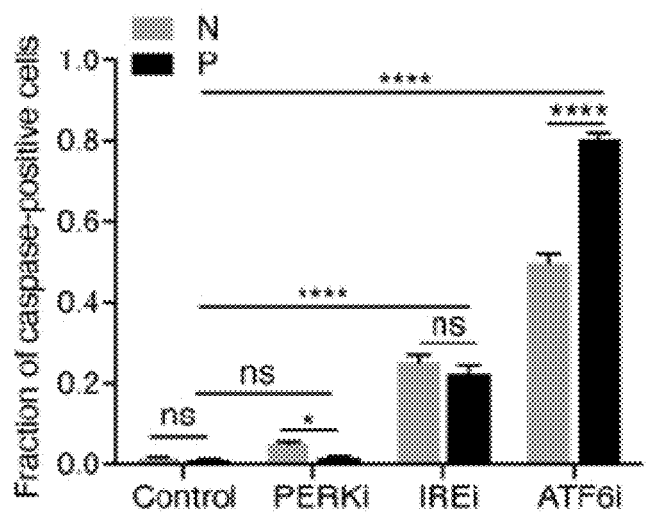
Figure 2C:
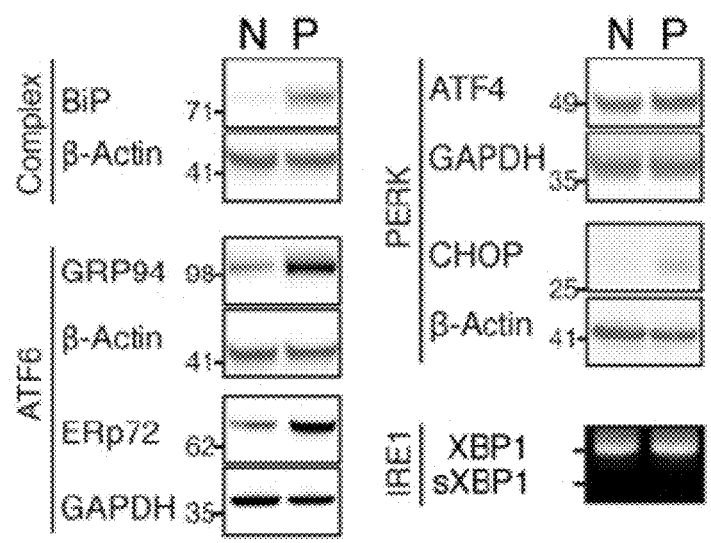
Figure 2D:
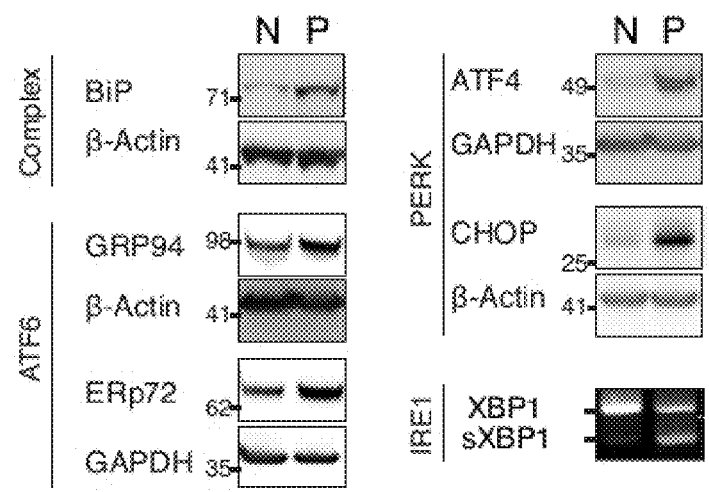
Figure 2E:
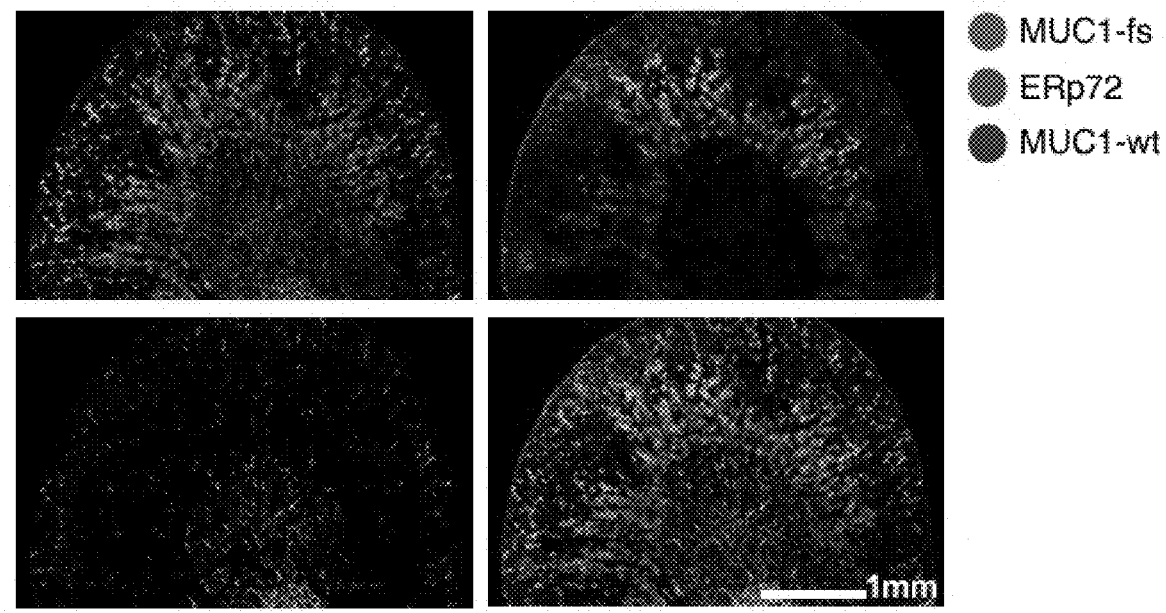
Figure 2F:
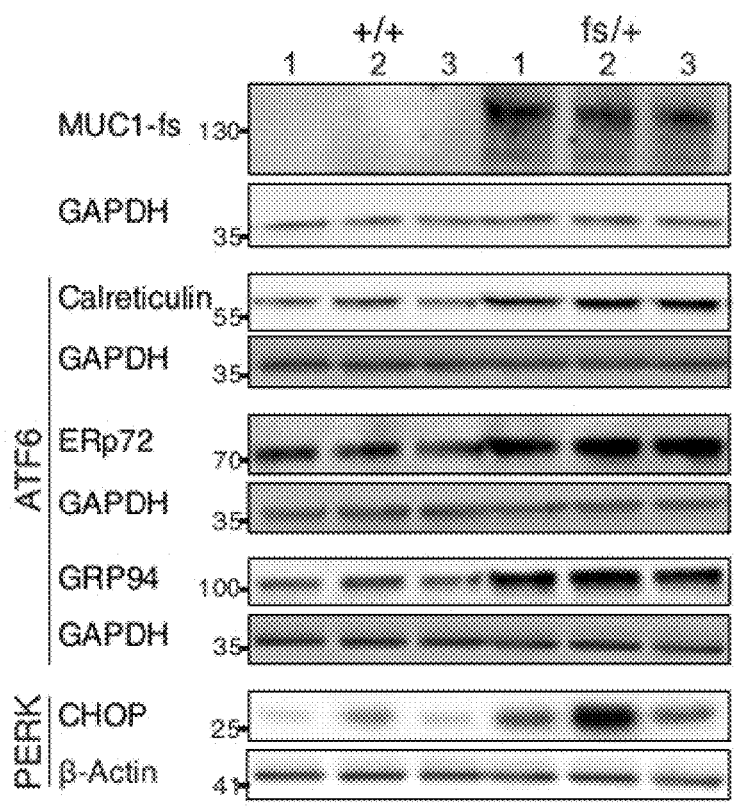
Figure 2G:
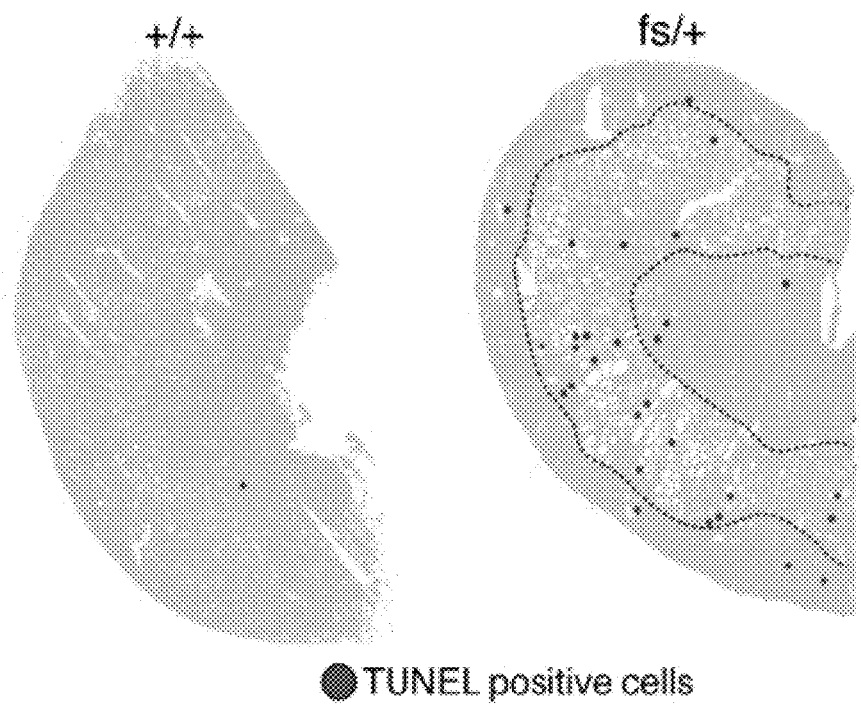
Figure 2H:
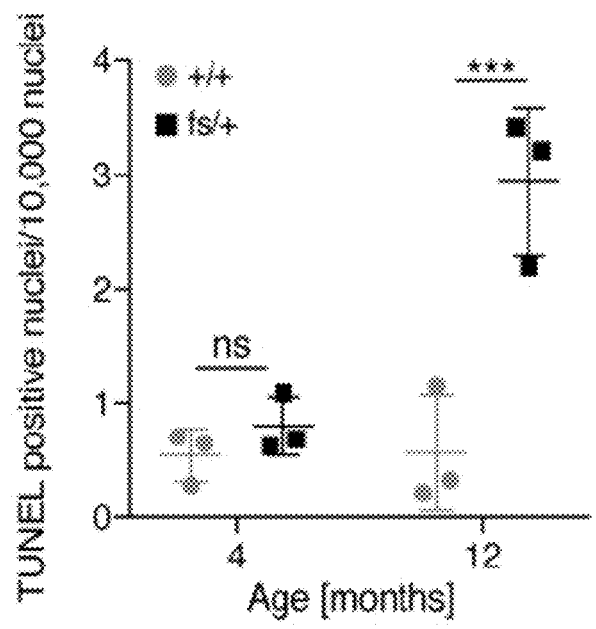

For apoptosis detection using TUNEL staining (FIG. 2G), TUNEL signal was calculated in each nucleus of the section (excluding the tissue periphery) and the threshold for TUNEL-positive cells was established. Total number of apoptotic cells was calculated as the number of nuclei in which TUNEL signal exceeded the threshold level. This number was normalized (divided) to the total number of nuclei in the entire tissue section (FIGS. 2G and 2H). For visualization and validation of tissue image analysis, single cells depicted by the analysis were plotted as a scatter plot according to their position on the slide using Spotfire software allowing thus to observe a tissue architecture and positioning apoptotic cells within their relative location. The identified TUNEL positive cells were highlighted by a red color.

Image Analysis for Mouse Retinal Sections

Rhodopsin intensity was calculated in retinal sections of Rho/+ mice treated with either vehicle or BRD-4780 (FIGS. 21A and 21B), as compared to wild-type mice treated with vehicle alone. In healthy retina, Rhodopsin primarily localized to the outer segment of the photoreceptors (OS, indicated by the arrow in FIG. 21A), instead of localizing around the photoreceptor nuclei in the outer nuclear layer (ONL, indicated by an asterisk in FIG. 21A). Since there is no Rhodopsin-P23H specific antibody, the amount of Rhodopsin staining in the outer nuclear layer was calculated as a measurement of Rhodopsin accumulation in intracellular compartments. The calculated Rhodopsin staining in the ONL was normalized to the nuclear staining, to correct for differences in cell number.

Image Analysis for Organoids

Figure 12B:
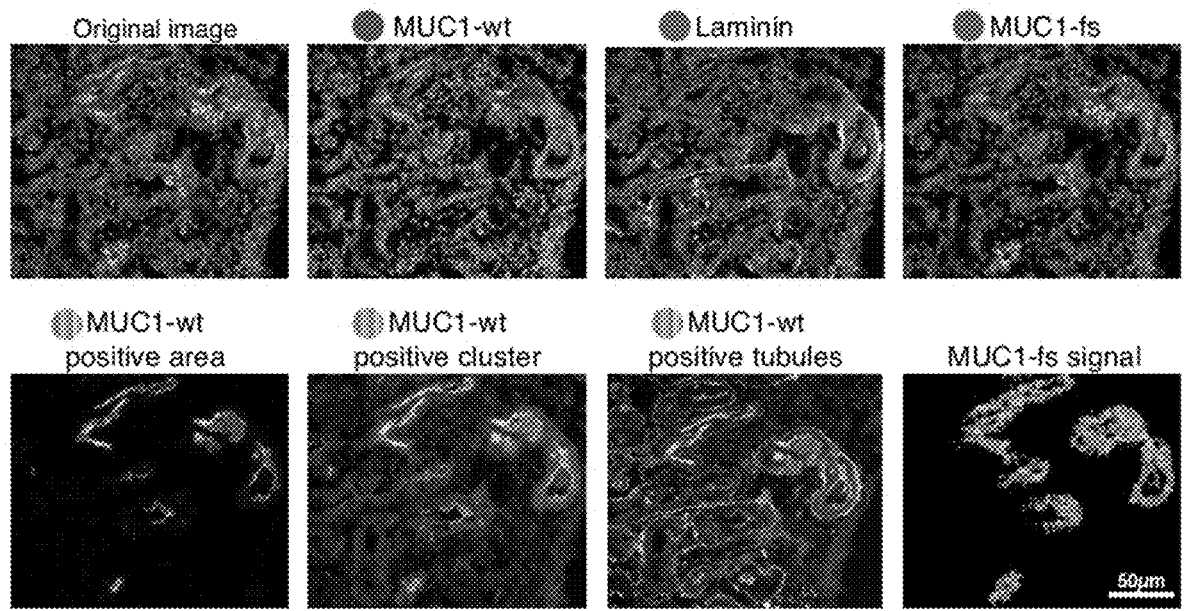

For a sequence analysis illustration, refer to FIG. 12B. Tubular structures expressing MUC1 proteins were identified and selected using MUC1-wt positive staining. First, a reference region was generated according to MUC1-wt positive staining in order to depict the apical part of each tubule. Subsequently, the intratubular region was defined based on the reference region with the addition of 20 µm to expand this region in order to capture the entire tubule. Laminin signal was then used to exclude the extracellular basal space. Finally, MUC1-fs signal was depicted within this intratubular area using the "spot" identification feature, and mean intensity of this signal was averaged for entire organoid section. MUC1-wt signal intensities were calculated within each WT reference region and averaged for entire section.

High Content Screening

For high content screening an automated system was used, consisted of robotic arms; plate stackers; a HighRes Pin Tool; Liconic incubators; Biotek plate washers; dedicated Thermo Fisher Combi Multidrop dispensers for each assay reagent; and PerkinElmer High Content Imaging Instrument Opera Phenix, all choreographed by Cellario software. Cell fixation and immunostaining were all performed in a custom-designed light-protected hood (HighRes Biosolutions). Data analysis and representation was performed using Genedata Screener (Genedata AG.) and Spotfire (TIBCO).

MUC1-fs IF Screen

P cells were seeded 24 hr prior to compound treatment at a density of 12,000 cells/well in 384 well Cell Carrier Ultra plates (6057308, Perkin Elmer), pre-coated with 0.25 mg/mL Synthemax II SC Substrate (3535, Corning). Compounds of the repurposing library set (Corsello et al., 2017) were used at 5 doses (35, 3.5, 0.35, 0.035 and 0.0035 µM) for the primary screen and 10 doses (16, 5.6, 1.8, 0.6, 0.21, 0.07, 0.02, 0.008, 0.002 and 0.0008 µM) for the following screens. The compounds, in two replicates, were transferred from compound source plates to the cell plates using the HighRes Pin Tool. DMSO was used as a negative control and JQ1 (250 nM) (a bromodomain inhibitor) was chosen as a positive control, based on earlier studies showing its potent effect on reducing total MUC1 mRNA levels (data not shown). After 48 hr incubation, cells were fixed for 20 min in 4% PFA (Electron Microscopy Sciences) in PBS, washed twice, then permeabilized (10 min) with 0.5% Triton-X100 (X100-100ML, Sigma-Aldrich) in PBS and washed once more. Cells were blocked for 10 min at RT with Blocking solution (100 mM Tris HCL pH8; 150 mM NaCL; 5 g/L Blocking Reagent [11096176001, Roche]), then incubated 90 min at RT with one of the following primary antibodies in Roche Blocking solution: 1:500, monoclonal Fab-A-VSH anti-MUC1-fs, AbD22655.2, Bio-Rad; 1:2000, monoclonal mouse anti-MUC1 (214D4), 05-652-KC, Millipore; 1:1000, monoclonal, Rabbit anti-GM130 (D6B1) XP, 12480, Cell signaling technology. The primary antibody cocktail was incubated at RT for 1.5 hr, followed by four PBS wash cycles. The secondary antibody cocktail contained four components that were all prepared at a 1:1000 dilution in the Roche blocking solution and consisted of Alexa Fluor® 488-conjugated AffiniPure F(ab')2 Fragment Goat anti-Human IgG, 109-546-097, Jackson Immunoresearch; Alexa Fluor® 647-conjugated Goat anti-Rabbit IgG, A-21246, Thermo Fisher Scientific®; Alexa Fluor® 546 Goat anti-mouse IgG, A-21123, Thermo Fisher Scientific® and Hoechst 33342 stain (62249, Thermo Fisher Scientific®). The secondary antibody cocktail was incubated at RT for 45 min, followed by four PBS wash cycles. Finally, plates were sealed with a Plate Loc plate and stored in Liconic incubator at 10° C. until imaging.

Figure 10A:
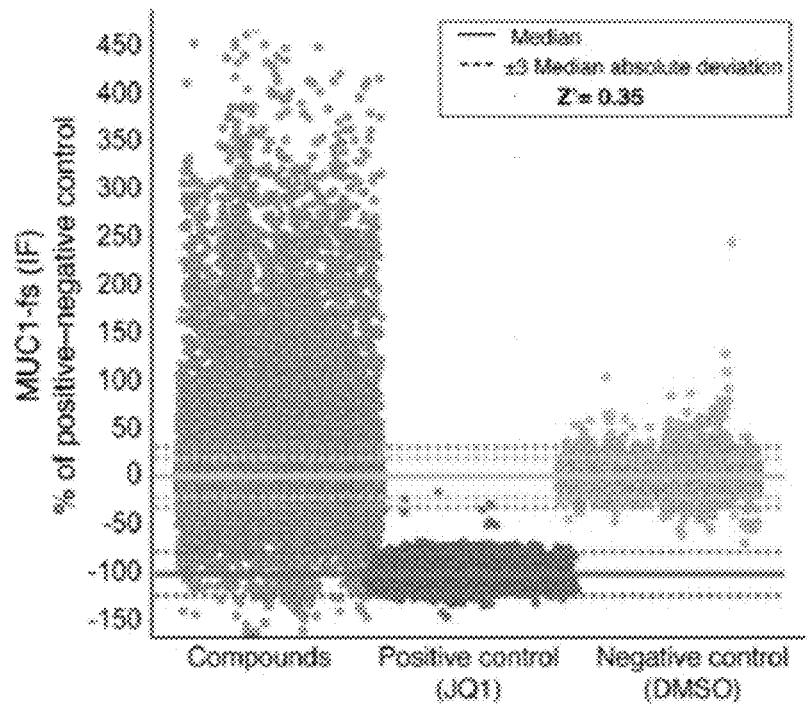
FIGS. 10A and 10B show that BRD-4780 was effective in removing mutant MUC1-fs from MKD patient kidney-derived epithelial cells.

Image acquisition and analysis was done as described elsewhere herein. Following image analysis, three parameters were selected, i) MUC1-fs and ii) MUC1-wt total cytoplasm intensity (averaged per cell) and iii) cell number as was detected by Hoechst 33342 stained nuclei. The levels of MUC1-fs and MUC1-wt found following DMSO and JQ1 were defined as 0 and −100% activity, respectively. The values obtained for all other compounds, including BRD-4780 were normalized accordingly. Cell number was normalized to DMSO control. All compound concentrations showing >−20% reduction in cell number were masked out. Based on ±3 median absolute deviation value (FIG. 10A), hit calling criteria for the primary and secondary screens were chosen as MUC1-fs reduction>30% in two or more consecutive concentrations for both replicates. For the secondary screen, dose response curves were generated for each parameter using Genedata Screener (Genedata AG.), and positive hits for the profiling screens were selected based on the compounds activity for reducing MUC1-fs and lack of toxicity. MUC1-fs specificity (according to MUC1 fs/wt ratio) was used as an additional positive criterion for selection.

RT-PCR Profiling Screen qPCR was performed using a previously described protocol (Bittker, 2012). P cells seeded at 2000 cells/well in 384-well, clear bottom, white wall plates were grown for 24 hr, then treated with profiling compounds transferred by pinning to duplicate plates. JQ1 (250 nM) and DMSO were used for controls as above. After 24 hr, cells were washed and cDNAs were made using ABI Cells-to-Ct kit (Thermo Fisher Scientific®, Waltham, Mass.). MUC1 and HMBS delta Cp values were determined using a Roche LightCycler 480 Instrument and TaqMan probes for MUC1 FAM (4351368 assay ID Hs00159357_m1) and HMBS VIC (4448486-assay ID Hs00609297_m1) (Thermo Fisher Scientific®, Waltham, Mass.), in 5 μL reactions. The fold change effect of the compounds on total MUC1 mRNA was normalized to JQ1 and DMSO controls, as described above.

Viability Profiling Screen

P cells were seeded 12 hr prior to profiling compound treatment at a density of 12,000 cells/well in 384 well Cell Carrier Ultra plates (6057308, Perkin Elmer), pre-coated with 0.25 mg/mL Synthemax II SC Substrate (3535, Corning). After 24 hr, CellEvent Caspase-3/7 Green Detection Reagent (C10423, Thermo Fisher Scientific®) and DRAQ7 (DR71000, Biostatus) were added at 1:5000 final dilution in the presence or absence of thapsigargin (100 nM). Cells were imaged daily during 7 days to monitor viability. Image acquisition and analysis was done as described above and viability was assessed as fraction of live cells at day 5 of thapsigargin treatment, and at the day 6 for DMSO.

Kidney Histology

Formalin-fixed, paraffin-embedded kidney sections of 4 μm thickness were stained with periodic acid-Schiff (PAS) by HMS Pathology Core. Light microscopy PAS images were analyzed in a blinded fashion and classified using standard criteria. Immunoperoxidase staining for MUC1-wt and MUC1-fs was performed by standard protocols using anti-MUC1-wt (ab80952, Abcam) and monoclonal Fab-A-V5H anti-MUC1-fs (AbD22655.2, Bio-Rad). HRP-linked goat anti-Armenian hamster (PA1-32045, Thermo Fisher Scientific®) was used to detect MUC1-wt and Mouse anti V5-HRP (R961-25, Thermo Fisher Scientific®) was used to detect MUC1-fs.

Western Blot and SDS-PAGE Gel Electrophoresis

Cells were lysed in lysing buffer solution (9803, Cell Signaling Technology) containing protease inhibitors (05892791001, Roche) and phosphatase inhibitors (04906837001, Roche). Mouse kidney tissues were lysed by tissue homogenizer (Tissue-Tearor™, BioSpec Products) in lysing buffer solution containing inhibitors as above, followed by 20 min rocking at 4° C. and centrifugation at 16,000 g, 4° C. for 5 min. To normalize protein concentration, proteins in the supernatant of cells or of kidney lysates were quantified using the Pierce BCA Protein Assay Kit (23225, Thermo Fisher Scientific®). Normalized protein lysates were then mixed with NuPAGE LDS sample buffer (NP0008, Thermo Scientific) and NuPAGE reducing agent (NP0004, Thermo Scientific) and heated to 75° C. for 10 min prior to SDS-PAGE gel electrophoresis using NuPAGE Tris-Acetate SDS Running Buffer (LA0041, Thermo Scientific) or NuPAGE MES SDS running buffer (NP0002, Thermo Fisher Scientific®) depending on protein molecular weight of interest. Electrophoretically separated proteins were transferred to a nitrocellulose membrane (1704158, BioRad) using Trans-Blot® Turbo Blotting System (1704155, BioRad) following manufacturer's protocol. Membranes were blocked in 5% Nonfat Dry Milk (9999S, Cell Signaling Technology) in PBS with 0.1% Tween® 20 (PBS-T), and probed with primary antibody overnight at 4° C. Following three washes with PBS-T, the membranes were incubated with secondary antibody for 1 hr at room temperature, washed three more times in PBS-T, and incubated with Super Signal West Dura (34076, Thermo Fisher Scientific®) or Super Signal West Pico (34087, Thermo Fisher Scientific®) and immunoreactive bands were imaged by G:BOX Chemi XT4 (G:BOX-CHEMI-XT4, Syngene).

Cellular Thermal Shift Assay (CETSA)

CETSAs were performed as previously described (Jafari et al., 2014; Reinhard et al., 2015). In brief, P cells were treated in the presence or absence of BRD-4780 for 1 hr, harvested (trypsinized), washed in PBS, resuspended in PBS (containing protease inhibitors) and distributed in 0.2 ml PCR tubes (100 μl; 600,000 cells). Cells were incubated at their designated temperatures for 3 min, then at 25° C. for 3 min and lysed by the addition of 1% NP-40. Immediately thereafter, samples were snap frozen and thawed using thermal cycler set at 25° C. Samples were spun at 20,000×g for 20 min (4° C.) to remove precipitated protein and the supernatant was analyzed by Western blot to examine the TMED9/Nischarin thermal stability.

RNA Extraction from Cells

RNA was extracted from cells seeded onto 12-well plates using the RNeasy kit (74004, Qiagen), following the manufacturer's protocol. RNA was eluted with Nuclease-Free water and total yield and purity of RNA were assessed by NanoDrop™ 2000 (Thermo Fisher Scientific®).

RNA Extraction from Mouse Kidneys

RNA was extracted from a sagittal section of a half-kidney. Kidney tissue was homogenized using tissue homogenizer (Tissue-Tearor™, BioSpec Products) in 1 mL of TRIzol™ Reagent (15596026, Thermo Fisher Scientific®). Following 5 min incubation, 0.2 mL chloroform (C2432-500ML, Sigma-Aldrich) was added, and samples were vigorously mixed for 30 sec, then centrifuged at 12,000×g at 4° C. for 15 min. The upper aqueous phase containing RNA was then vigorously mixed with 0.5 mL of isopropanol for 30 sec. After 10 min incubation at RT, the samples were centrifuged at 12,000×g at 4° C. for 10 min. The pellet was resuspended in 1 mL of 75% ethanol and centrifuged at 12,000×g 4° C. for 5 min. The RNA pellet was then air dried for 15 min, dissolved in 50 μL of Nuclease-Free Water (AM9937, Thermo Fisher Scientific®), treated with DNase I, Amplification Grade (18068015, Thermo Fisher Scientific®) following the manufacturer's protocol and assessed for yield and purity by NanoDrop™ 2000 (Thermo Fisher Scientific®).

RT-PCR Analysis of XBP-1 mRNA Splicing

XBP1 splicing was analyzed by standard RT-PCR. Briefly, RNA was isolated from patient cells using a RNeasy Mini Kit (74106, Qiagen). One μg of RNA was converted to cDNA using the SuperScript First-Strand Synthesis system for RT-PCR (11904-018, Invitrogen). The primer sequences used are as follows: Human XBP1 Forward Primer: 5' TTA CGA GAG AAA ACT CAT GGC C 3' (SEQ ID NO: 12). Human XBP1 Reverse Primer: 5' GGG TCC AAG TTG TCC AGA ATG C 3' (SEQ ID NO: 13). PCR was carried out on 3 µL of the resulting cDNA solution using the OneTaq Hot Start Master Mix (M0484S, NEB). Five µL of PCR product was run on a 2% agarose gel for 90 min at 150 V.

cDNA Library Construction and Illumina® Sequencing cDNA library construction and Illumina® sequencing were performed at the Broad Institute sequencing platform as follows. Concentrations of purified RNA were measured with the Quant-iT™ RiboGreen® RNA Assay Kit (Thermo Scientific #R11490) and normalized to 5 ng/µL. An automated variant of the Illumina® TruSeq™ Stranded mRNA Sample Preparation Kit was used for library preparation from a 200 ng aliquot of RNA. This method preserves strand orientation of the RNA transcript and uses oligo dT beads to select mRNA from the total RNA sample. Following cDNA synthesis and enrichment, cDNA libraries were quantified with qPCR using the KAPA Library Quantification Kit for Illumina® Sequencing Platforms and then pooled equimolarly. For Illumina® sequencing, pooled libraries were normalized to 2 nM and denatured using 0.1 N NaOH prior to sequencing. Flow cell cluster amplification and sequencing were performed according to the manufacturer's protocols using either the HiSeq 2000 or HiSeq 2500. Each run was a 101 bp paired-end with an eight-base index barcode read. Data was analyzed using the Broad Institute Picard Pipeline, which includes de-multiplexing and data aggregation.

UPR Branch Activation

The involvement of the UPR in MUC1-fs induced cytotoxicity was detected in N and P cells using immunoblot or IF. For IF experiments (FIGS. 2B, 9I and 9J), N and P cells were plated at 9,000 and 6,000 cells/well respectively and cultured for 24 hr. Cells were pretreated with either DMSO or 10 µM inhibitors of ATF6 (PF-429242;SML0667, Sigma-Aldrich), PERK (GSK2656157;5046510001, Sigma-Aldrich) and IRE (4g8C;1902, Axon Medchem) for 1 hr, followed by application of different concentrations of THP. Cell viability was determined using caspase activation as described above. For immunoblot experiment (FIGS. 2C and 2D), N and P cells were grown in 6-well plates to high confluence and treated with DMSO or THP (100 nM) for 12 hr. The cells were then processed for immunoblot analysis as described above.

BRD-4780 Treatment in Mice

The effect of BRD-4780 on MUC1-fs levels in mouse kidney was tested in age-matched fs/+ and wt/+ male mice (27-38 weeks old). BRD-4780 (1, 10 and 50 mg/Kg/day) or vehicle (PBS) were administered daily by oral gavage for 7 days. Animal weight was observed daily to monitor toxicity. On day 7, mice anesthetized for 5 min with 3 L/min 3% isoflurane in Oz using the Combi-vet® system (Rothacher Medical, Bern, Switzerland) were sacrificed, and kidneys were removed for further analysis.

BRD-4780 Treatment in Rho-P23H Mice

The effect of BRD-4780 on Rhodopsin accumulation in intracellular compartments of mouse retinae were tested in age-matched Rho-P23H/+ and +/+ male mice. BRD-4780 (50 mg/Kg/day) or vehicle (PBS) were administered daily by oral gavage for 28 days, starting at PND28. Animal weight was observed daily to monitor toxicity. On day 28, mice were sacrificed, and eyes were removed for further analysis.

BRD-4780 Treatment in Kidney Organoids

Day 25 kidney organoids were transferred from Transwell membranes to low-attachment Corning® Costar®) TC-Treated 24-Well Plates (3527, Sigma-Aldrich) in 250 µL STEMdiff™ APEL™2 Medium (05270, Stem cell Technologies), then treated with 10 µM BRD-4780 or DMSO vehicle for 72 hr at 37° C. After 72 hr, organoids were washed twice with PBS and processed for IF detection.

BRD-4780 Treatment in Cells

Figure 13A:
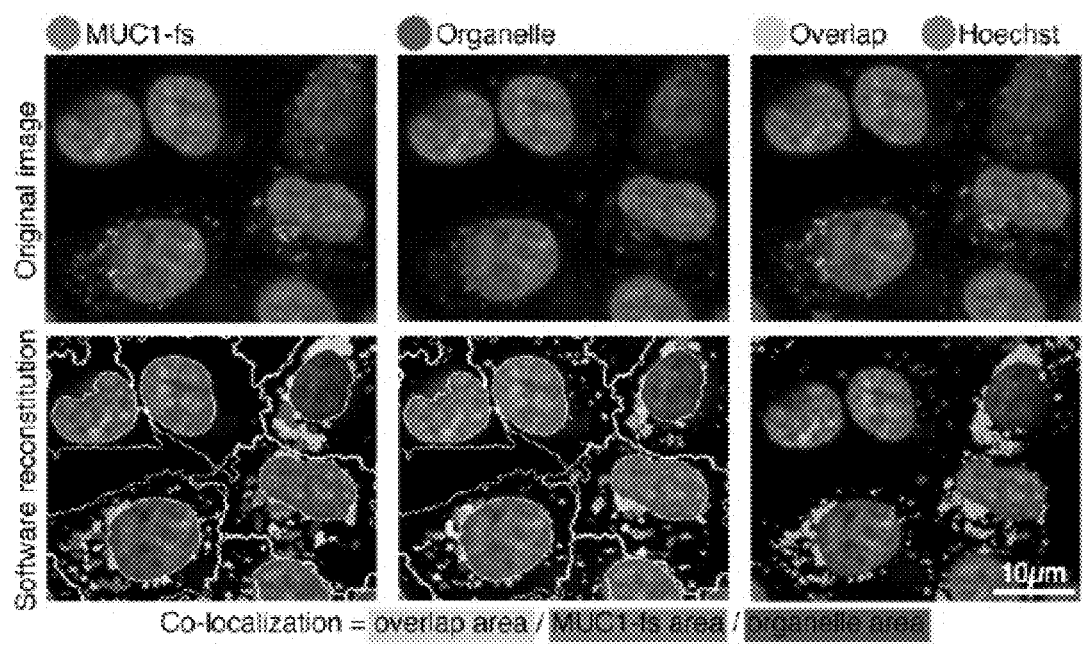
FIGS. 13A to 13D show that MUC1-fs accumulates in the early secretory pathway, in a TMED9 cargo receptor-positive compartment.
Figure 13B:
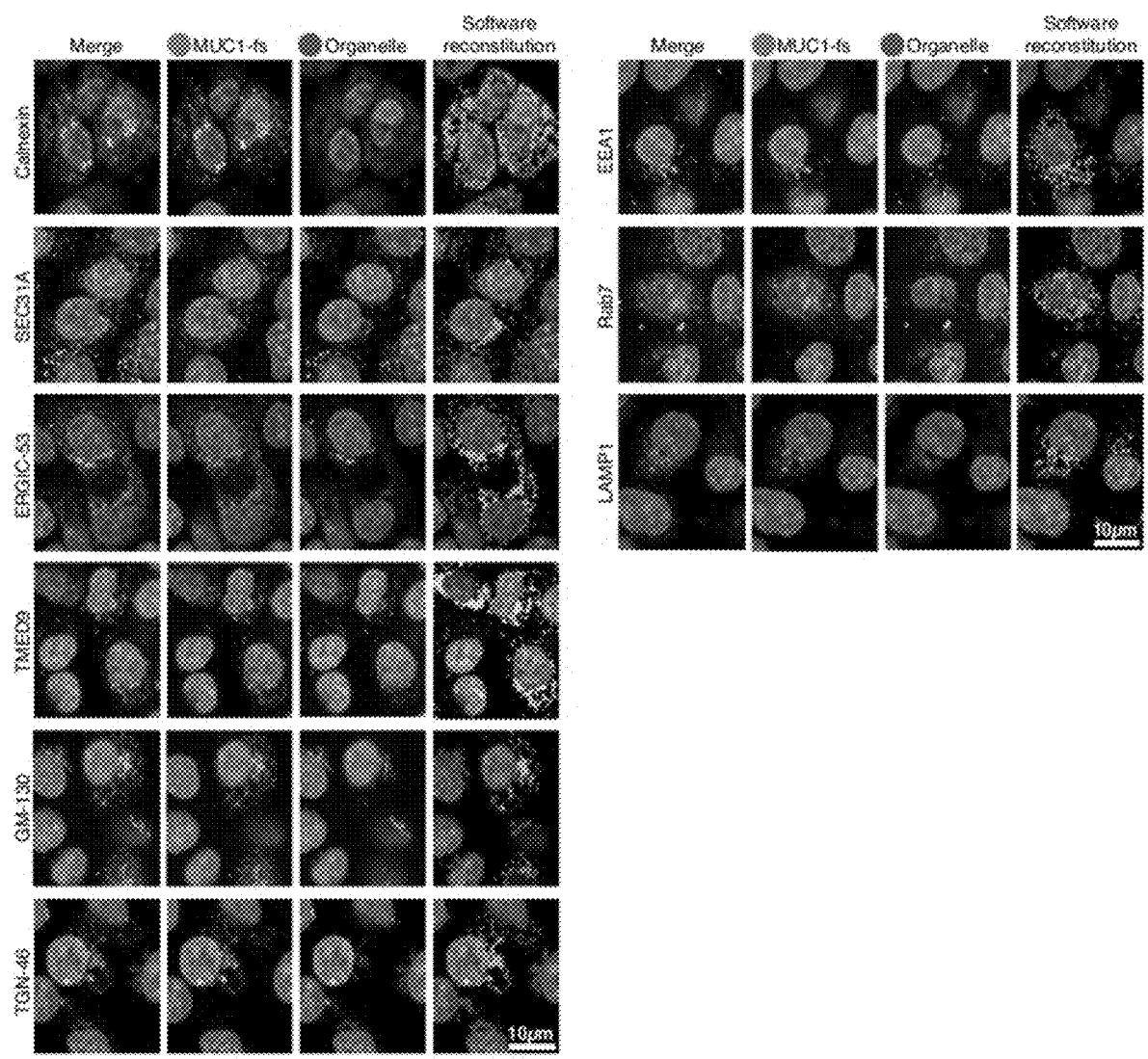
Figure 13C:
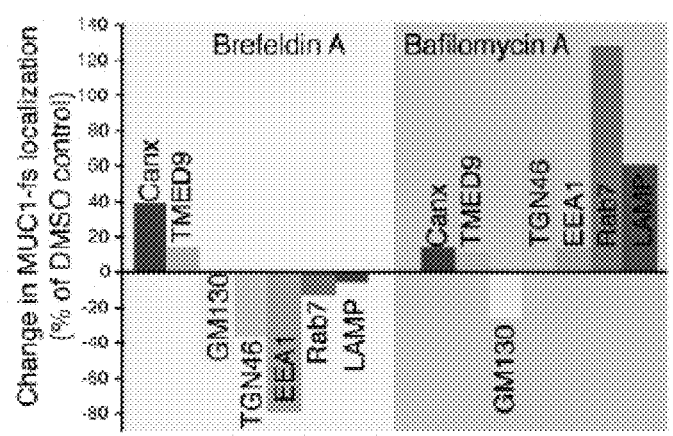
Figure 13D:
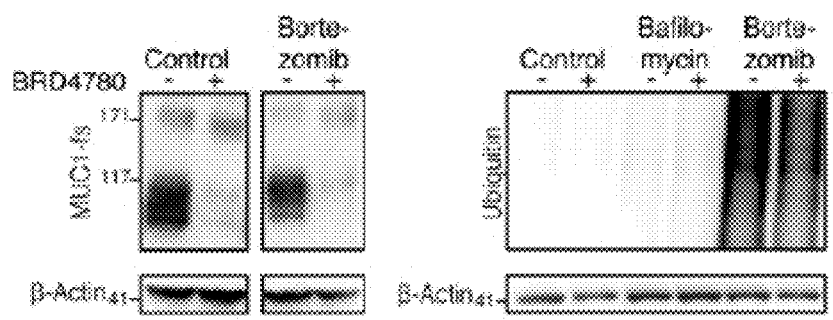
Figure 14A:
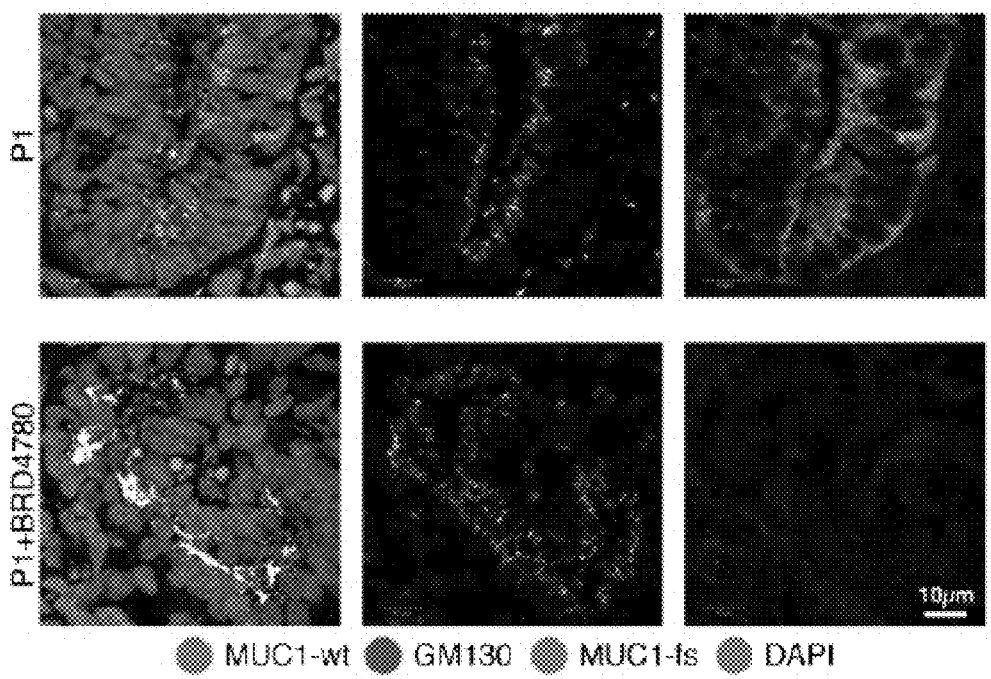
Figure 14B:
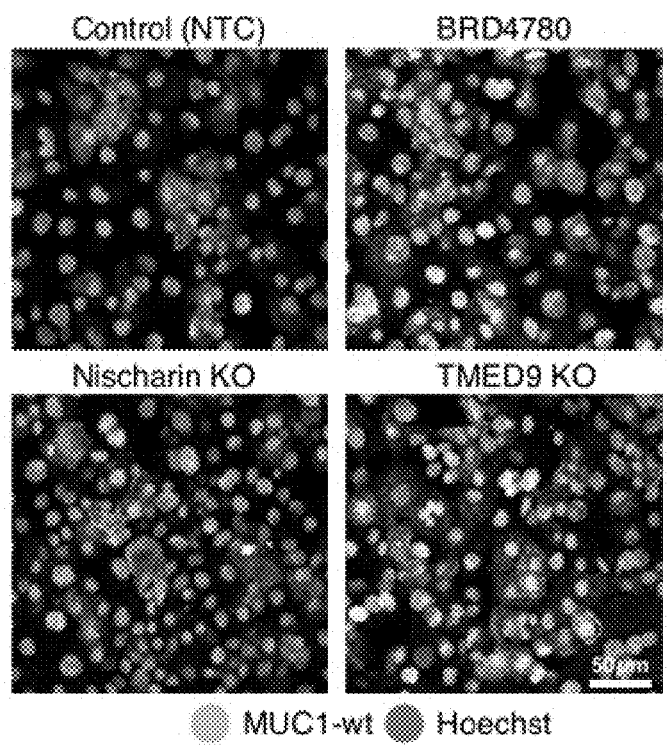
Figure 14C:
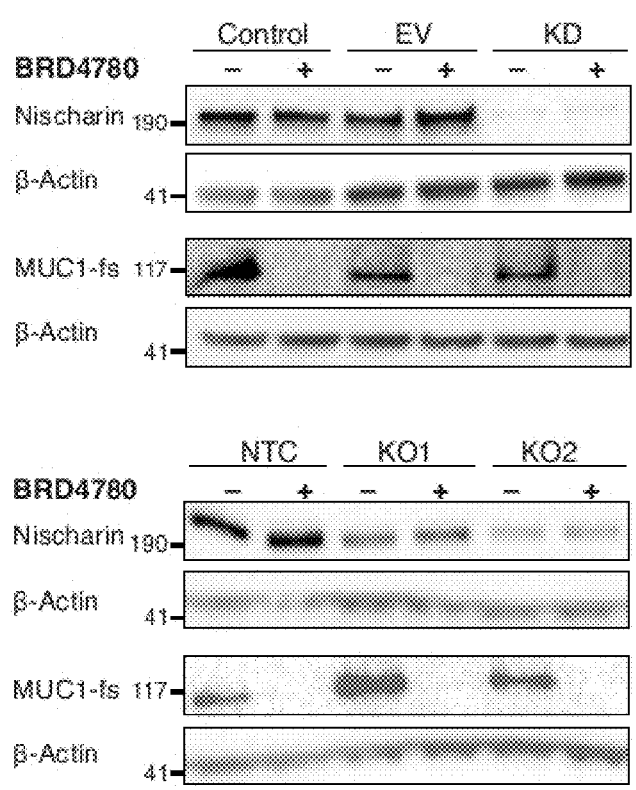
Figure 15A:
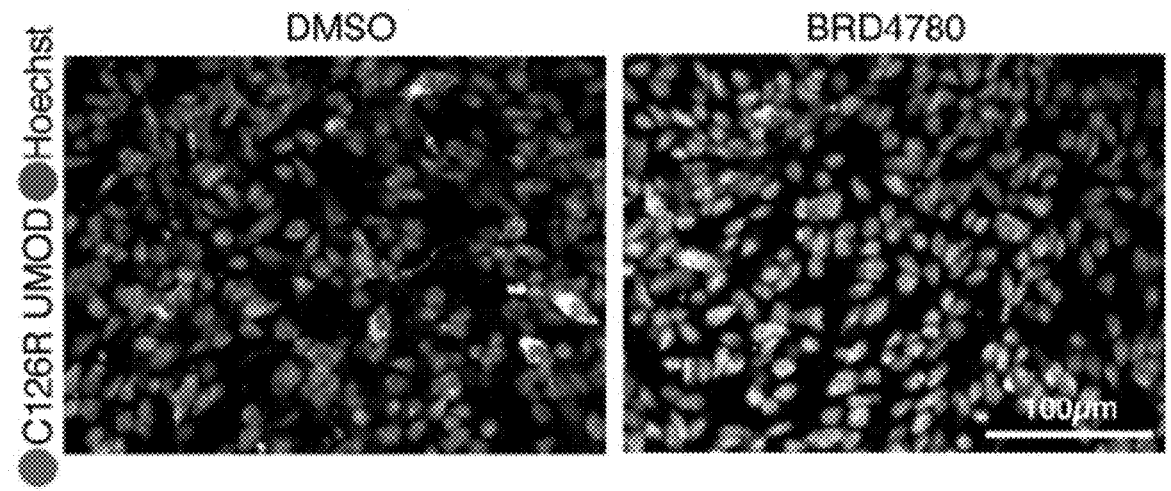
FIGS. 15A to 15H show that BRD-4780 was effective in removing several misfolded proteins.
Figure 15B:
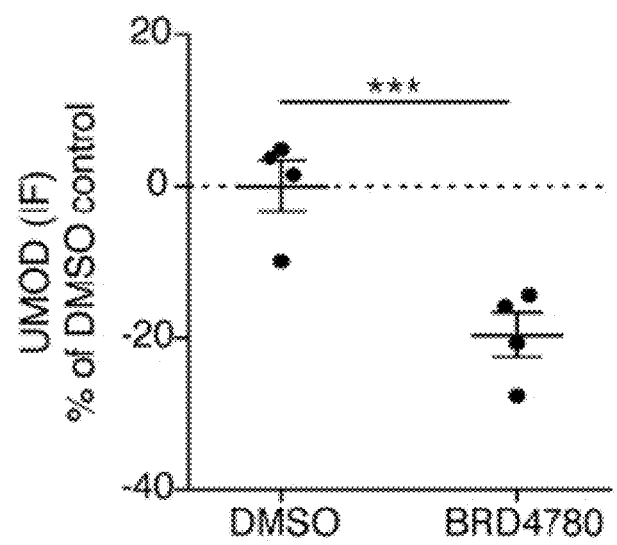

Detection of MUC1-fs in P cells at baseline and following secretory pathway perturbations was performed using immunoblot and IF analyses. For immunoblot experiments (FIGS. 5E and 13D), P cells were grown in 6-well plates to high confluence. For IF experiments (FIGS. 5B-5D and 13A-13C), P cells were plated in 384-well plates at 12,000 cells/well. Following 24 hr, cells were treated with 5 µM BRD-4780 or DMSO alone, or in combination with 100 nM Bafilomycin A (B1793, Sigma-Aldrich), or 200 ng/mL Brefeldin A (B7651, Sigma-Aldrich) for a maximum period of 24 hr as indicated. For TMED9 or Nischarin depletion experiments, transduced/transfected P cells were plated either in 96-well plates at 60,000 cells/well for IF (FIGS. 6C, 6D and 14B), or grown in 6-well plates to high confluence for immunoblot detection (FIGS. 6B and 14C). Cells were then treated with 5 µM BRD-4780 or DMSO for 24 hr (for IF detection) or 72 hr (for immunoblot analysis) and were processed accordingly. AtT-20 cells stably transduced with C126R mutant UMOD plasmid were treated for 72 hr with 10 µM of BRD-4780 or vehicle DMSO. For thapsigargin treatment, AtT-20 cells pretreated 24 hr with 1 or 10 µM of BRD-4780 were exposed to 10 nM of thapsigargin for 48 hr. The cells were either imaged for IF detection of UMOD (FIGS. 15A and 15B) or processed for immunoblot analysis. N cells transiently expressing P23H-GFP mutant rhodopsin were plated in 96-well plates at 20,000 cells/well and grown for 24 hr, then DMSO or 5 µM BRD-4780 were added to the medium as a pre-treatment. Following 48 hr, cells in the presence or absence of BRD-4780, were transfected with P23H mutant rhodopsin-GFP plasmid. Eight hr post-transfection, the cells were washed once and media containing DMSO or 5 µM BRD-4780 was added. Plates were imaged 24 hr following transfection.

HEK293T stably expressing huntingtin 97Q-GFP were treated with 10 µM of BRD-4780 or vehicle DMSO, then monitored for GFP intensity by live cell imaging.

Cell Treatment for RNA-Seq Experiments

For RNA-seq experiments, N and P cells were plated in 12-well plates at 200,000 cells/well. Subsequently, 1 µM of BRD-4780 or DMSO were applied for 24 hr followed by 12 hr exposure to 100 nM of thapsigargin (THP) or DMSO for control. At the end of the experiment, RNA was extracted from treated cells and sequencing was performed as described below.

Absorption, Distribution, Metabolism, and Excretion (ADME) of BRD-4780

PBS Solubility

Compound solubility was determined in PBS at pH 7.4. Each compound was prepared in triplicate at 500 µM in both 100% DMSO and 100% PBS by drying down 10 µL of a 10 mM DMSO compound stock solution and then adding 200 µL of PBS. Compounds were allowed to equilibrate at room temperature with a 750 rpm vortex shake for 18 hr. Prior to equilibration, StirStix were added to each well to aid in the prevention of aggregation. After equilibration, samples were centrifuged (32×G) to remove undissolved particulates and a 20 µL aliquot of supernatant was diluted with 480 µL acetonitrile. The resulting solution was analyzed by UPLC-MS/MS with compounds detected by SIR detection on a single quadrupole mass spectrometer. The peak areas of the 100% DMSO samples were used to create a two-point calibration curve to which the peak area response in PBS was fit. Solubility in PBS was calculated using the following equation: Conc. (PBS)=Conc. (DMSO)×[area (PBS)/area (DMSO)]. (LC System, Waters Acquity H-Class; MS System, Waters Acquity SQ Detector; Column, Waters Acquity UPLC BEH C18, 1.7 µm, 1.0×50 mm; Mobile Phase A, Water with 0.1% Ammonium Hydroxide (or 0.5% trifluoroacetic acid); Mobile Phase B, Acetonitrile with 0.1% Ammonium Hydroxide (or 0.6% trifluoroacetic acid); Flow Rate, 0.45 mL/min; Column Temperature, 60° C.).

Plasma Stability

Plasma stability was determined at 37° C. at 5 hr in plasma. Each compound was prepared in duplicate at 5 µM in plasma diluted 50/50 (v/v) with PBS pH 7.4 (0.95% acetonitrile, 0.05% DMSO). Duplicate plates were prepared. One plate was incubated at 37° C. for 5 hr with a 350 rpm orbital shake, while the other plate was immediately quenched. Each well was quenched by adding acetonitrile to a 3:1 ratio (v/v, ACN/plasma). After quenching, samples were centrifuged (32×G) to pellet precipitated particulates and an aliquot of supernatant was diluted 50/50 (v/v) with water. The resulting solution was analyzed by UPLC-MS/MS with compounds detected by MRM detection on a triple quadrupole mass spectrometer. The compound peak areas at 0 and 5 hr were compared to determine a percent remaining. Percent remaining in plasma was calculated through the following equation: % remaining=[area (5 hr)/area (0 hr)]× 100. (LC System, Waters Acquity I-Class; MS System, AB Sciex Triple Quad 4500; Column, Waters Acquity UPLC BEH C18, 1.7 µm, 2.1×50 mm; Mobile Phase A, Water with 0.1% formic acid; Mobile Phase B, Acetonitrile with 0.1% formic acid; Flow Rate, 0.90 mL/min; Column Temperature, 55° C.).

Plasma Protein Binding

Plasma protein binding was determined by equilibrium dialysis using a Rapid Equilibrium Dialysis (RED) device (Pierce Biotechnology). Each compound was prepared in duplicate at 5 µM in plasma (0.95% acetonitrile, 0.05% DMSO) and added to one side of the membrane with PBS pH 7.4 added to the other side. Compounds were incubated at 37° C. for 5 hr with a 350 rpm orbital shake. After incubation, an aliquot was taken from each side of the membrane and quenched by adding acetontrile to a 3:1 ratio (v/v, ACN:plasma). After quenching, samples were centrifuged (32×G) to pellet precipitated particulates and an aliquot of supernatant was diluted 50/50 (v/v) with water. The resulting solution was analyzed by UPLC-MS/MS with compounds detected by MRM detection on a triple quadrupole mass spectrometer. The compound peak area on the buffer side of the membrane was compared to the peak area on the plasma side of the membrane to determine percent bound. Percent bound in plasma was calculated through the following equations: % free=[area (buffer)/area (plasma)]× 100. % bound=100−% free. (LC System, Waters Acquity I-Class; MS System, AB Sciex Triple Quad 4500; Column, Waters Acquity UPLC BEH 08, 1.7 µm, 2.1×50 mm; Mobile Phase A, Water with 0.1% formic acid; Mobile Phase B, Acetonitrile with 0.1% formic acid; Flow Rate, 0.90 mL/min; Column Temperature, 55° C.).

Liver Microsomes Stability

Stability was determined at 37° C. at 1 hour in liver microsomes. Each compound was prepared in duplicate at 1 µM in liver microsomes diluted 50/50 (v/v) with PBS pH 7.4. After addition of compounds to microsome mixture, the plate was sealed and vortexed and 100 µL of each sample was added to 300 µL acetonitrile (with internal standard). Assay plate was incubated at 37° C. for 1 hr with a 350 rpm orbital shake, and following the hour 100 µL of each sample was added to 300 µL acetonitrile (with internal standard). After quenching, samples were refrigerated for at least 1 hour. The samples were centrifuged (32×G) to pellet precipitated particulates and an aliquot of supernatant was diluted 50/50 (v/v) with water. The resulting solution was analyzed by UPLC-MS/MS with compounds detected by MRM detection on a triple quadrupole mass spectrometer. The compound peak areas in the 0 and 1 hour samples, -NADPH sample, and no compound control sample were compared to determine a percent remaining. Percent remaining in microsomes was calculated through the following equation: % remaining=[area (1 hr)/area (0 hr)]× 100. (LC System, Waters Acquity I-Class; MS System, AB Sciex Triple Quad 4500; Column, Waters Acquity UPLC BEH C18, 1.7 µm, 2.1×50 mm; Mobile Phase A, Water with 0.1% formic acid; Mobile Phase B, Acetonitrile with 0.1% formic acid; Flow Rate, 0.90 mL/min; Column Temperature, 55° C.).

RNA-Seq Analysis

Data processing and statistical analyses for all RNA-seq experiments were performed in RStudio—Version 1.0.153 as follows. First, barn files obtained from the Broad Institute sequencing platform were reverted to FASTQ files followed by alignment of paired end reads to the mm10 mouse or hg19 human reference genome using STAR. Quality control metrics were obtained using RNA-SeQC and expression levels were estimated by running RSEM with default parameters on these alignments. RSEM's gene level expression estimates were normalized according to edgeR for sequencing depth and multiplied by 1,000,000, to obtain counts per million (CPM). Genes with CPM<1 in fewer than three samples (number of replicates) were removed from further analysis. TMM normalization was applied to the data, accounting for gene composition. For further downstream analysis (e.g. boxplots) the data was log 2-transformed. In mouse kidney RNA-seq experiments, two samples were removed from the analysis (fs/+ treated with BRD-4780 replicate 3 and +/+ treated with BRD-4780 replicate 1) due to significantly low library sizes. For statistical testing, generalized linear models obtained in edgeR were applied with the assumption of negative binomial distribution with default parameters using the expected counts from RSEM followed by likelihood ratio test. Genes were considered to be significantly differentially expressed using a significance level of $\alpha=0.05$ following Benjamini Hochberg correction for multiple hypothesis testing.

The Functional Annotation Tool of DAVID was used to detect significant signatures differentially downregulated in fs/+ mice following BRD-4780 treatment. Differentially downregulated genes were analyzed using GO terms of Biological Processes. The reported p-value is a modified Fisher Exact p-value (EASE score) and a gene set was considered enriched if a significance level of $\alpha=0.05$ was reached following Benjamini Hochberg correction.

UPR Specific Transcriptome

UPR branch activation analysis is presented as boxplots. Each box of the boxplot consists of genes comprising an individual UPR branch (Adamson et al., 2016). The expression of each gene in the group is plotted as mean of the scaled expression profiles obtained from three replicates.

Statistical Analysis

Statistical analysis was performed and presented using Graphpad Prism version 7.0 software. All data is presented as means±standard deviation unless otherwise specified.

Statistical comparisons of two groups for a single variable with normal distributions were analyzed by unpaired t-test. Statistical comparisons of two or more groups with one independent variables were analyzed by One-way ANOVA with Tukey post-tests. Statistical comparisons of two or more groups with two independent variables were analyzed by Two-way ANOVA with Tukey post-tests. *p<0.05 p<0.01 *p<0.001 ****p<0.0001.

Figure 1B:
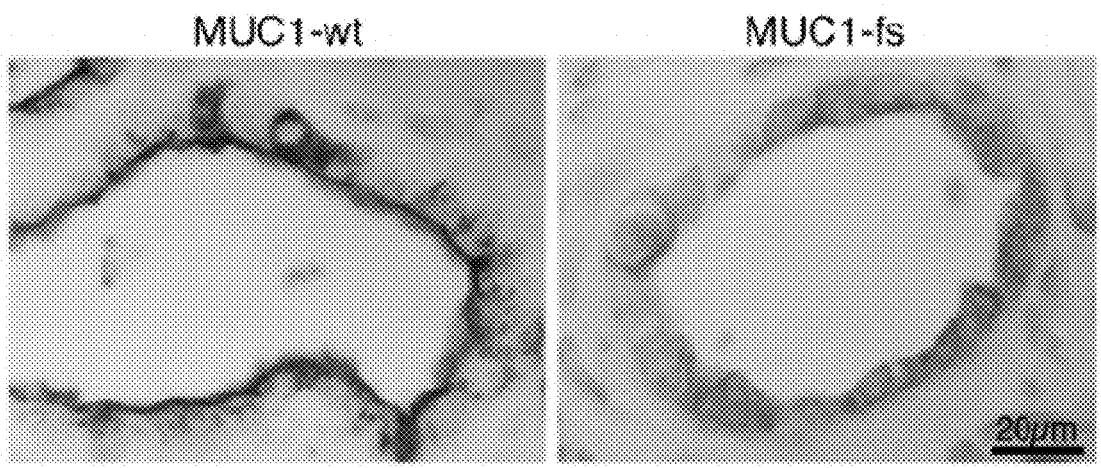

Example 2: Mutant MUC1-fs is Retained Intracellularly in Tubular Epithelial Cells The location of the wild-type (MUC1-wt) and mutant (MUC1-fs) protein in a kidney biopsy from a 50-year-old MKD patient, who was a heterozygous carrier for a C insertion frameshift mutation ($MUC1^{wt}/MUC1^{fs}$) was characterized. As compared to normal kidney (FIG. 1A, left), the patient's tissue showed tubular atrophy, tubular dilation and some interstitial fibrosis (FIG. 1A, right). The MUC1-wt and MUC1-fs protein were visualized by immunoperoxidase staining with wild-type- and mutant-specific antibodies in the same kidney biopsy. MUC1-wt maintained its normal localization at the apical membrane of distal tubules and collecting ducts, whereas MUC1-fs showed intracellular accumulation (FIG. 1B).

Figure 1C:
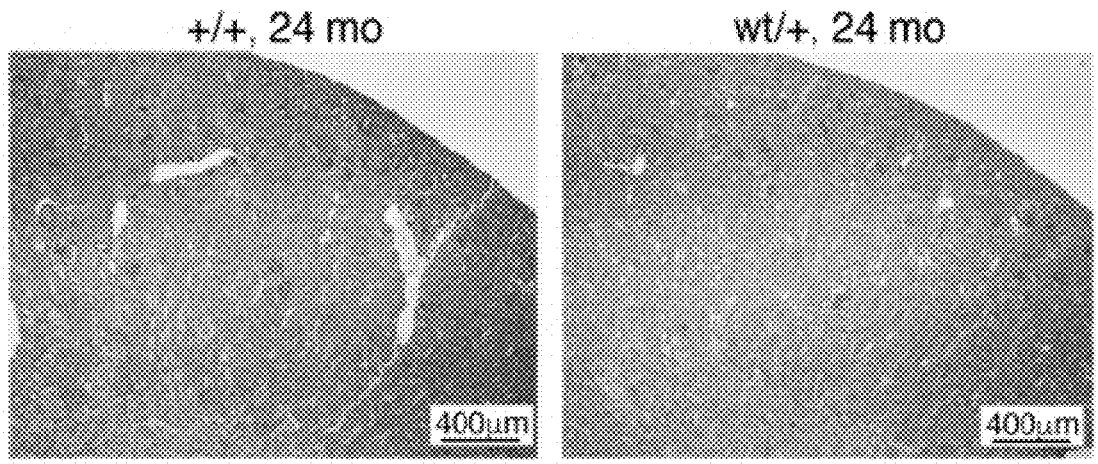
Figure 1D:
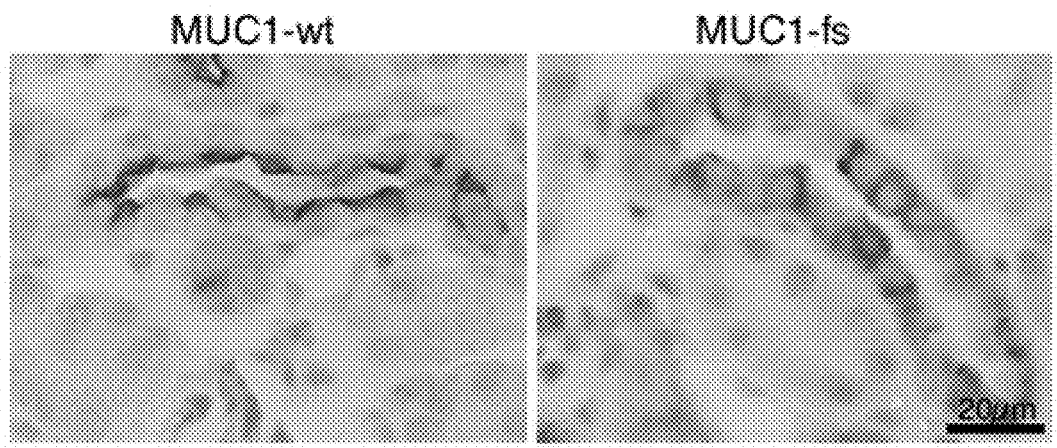
Figure 7C:
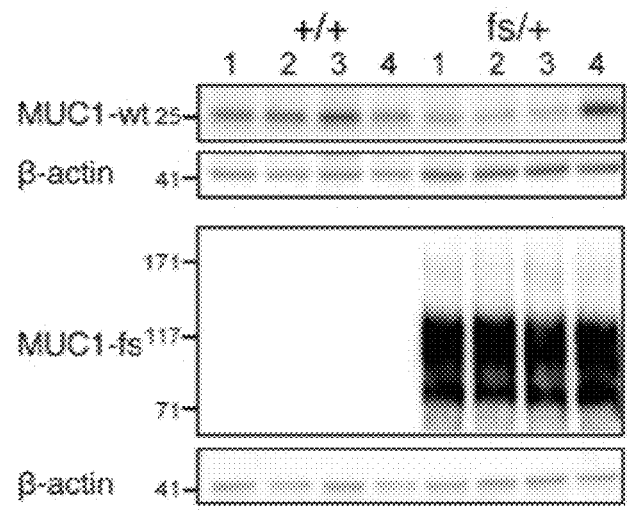
Figure 7D:
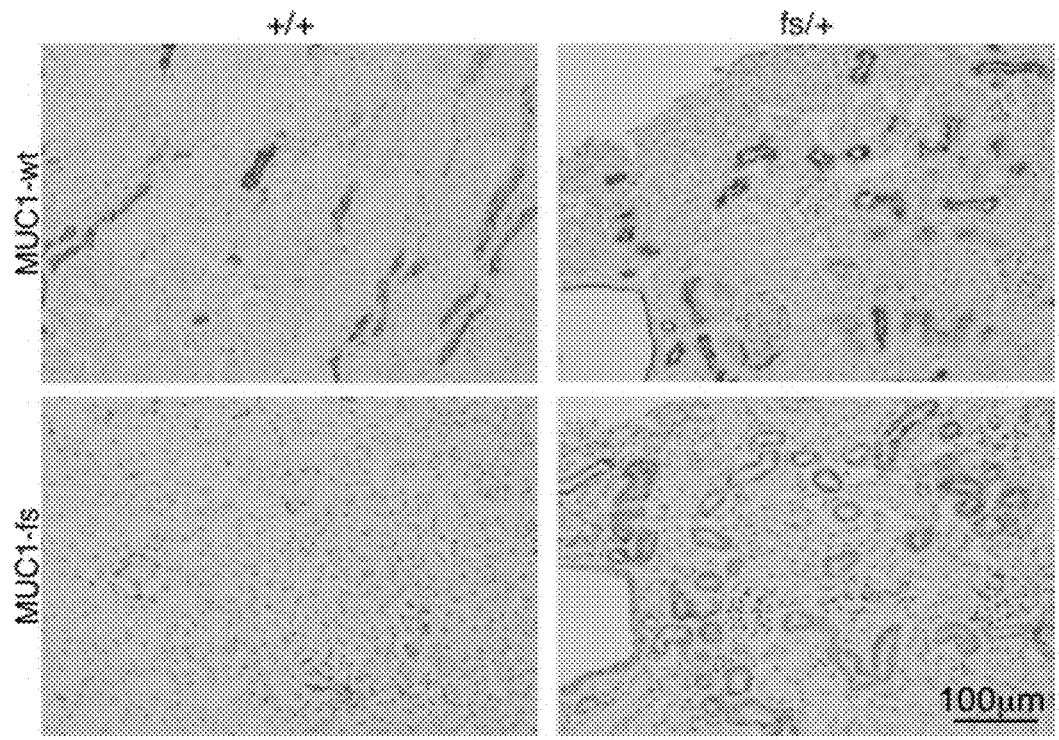

Heterozygous knock-in mice in which one of the normal mouse $mMuc1^{wt}$ (+) alleles was replaced with either a human wild-type ($hMUC1^{wt}$ or wt) or mutant ($hMUC1^{fs}$ or fs) allele (FIGS. 7A and 7B) were generated. The knock-in mice have been indicated as wt/+ or fs/+ as compared to +/+ for the parental wild-type mouse line for clarity. The expression of the corresponding human protein was confirmed using Western blot (FIG. 7C) and immunohistochemistry (IHC) (FIG. 7D). IHC in fs/+ heterozygous mice demonstrated that the distribution of the normal and mutant human MUC1 proteins was consistent with the pattern seen in kidney biopsies from MKD patients (FIG. 1B): normal MUC1-wt protein was found at the plasma membrane of tubular epithelial cells and the mutant MUC1-fs protein was found intracellularly (FIG. 1D).

Figure 1E:
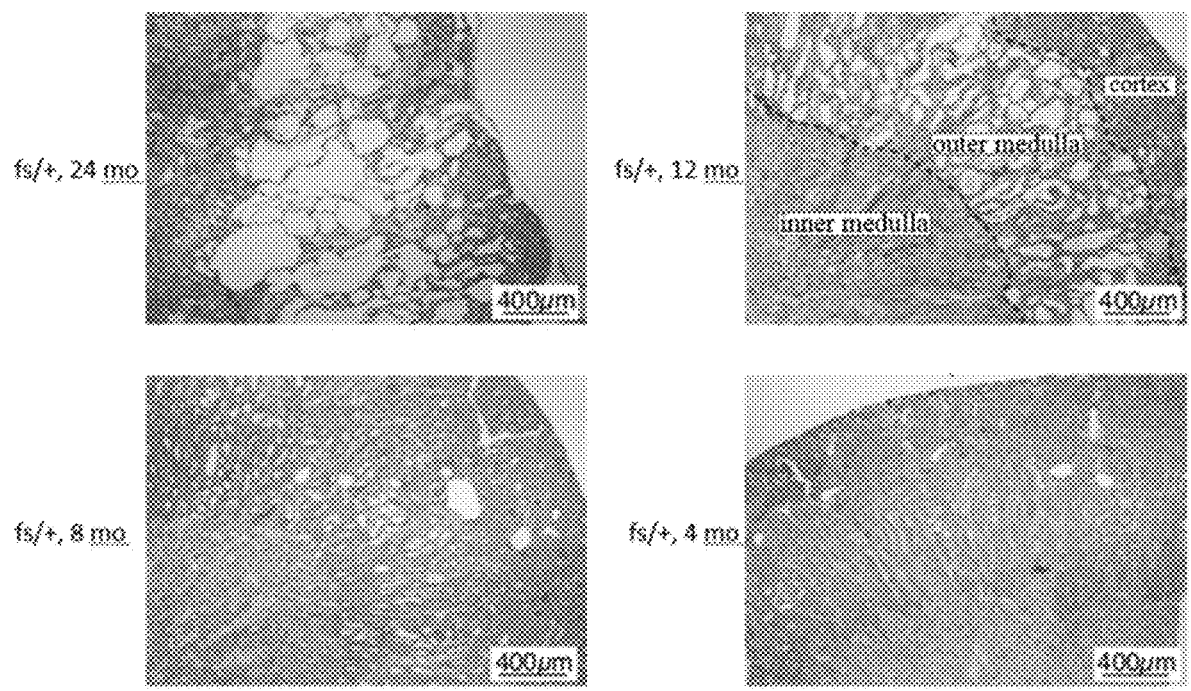
Figure 7E:
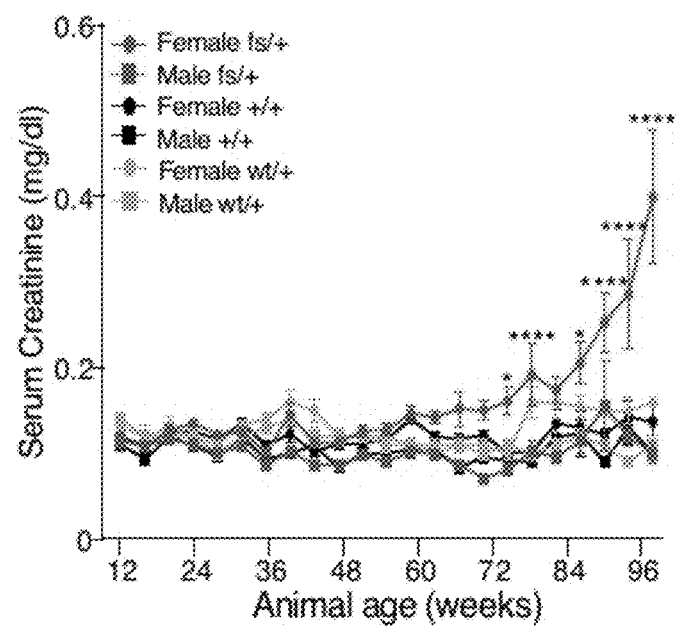
Figure 7F:
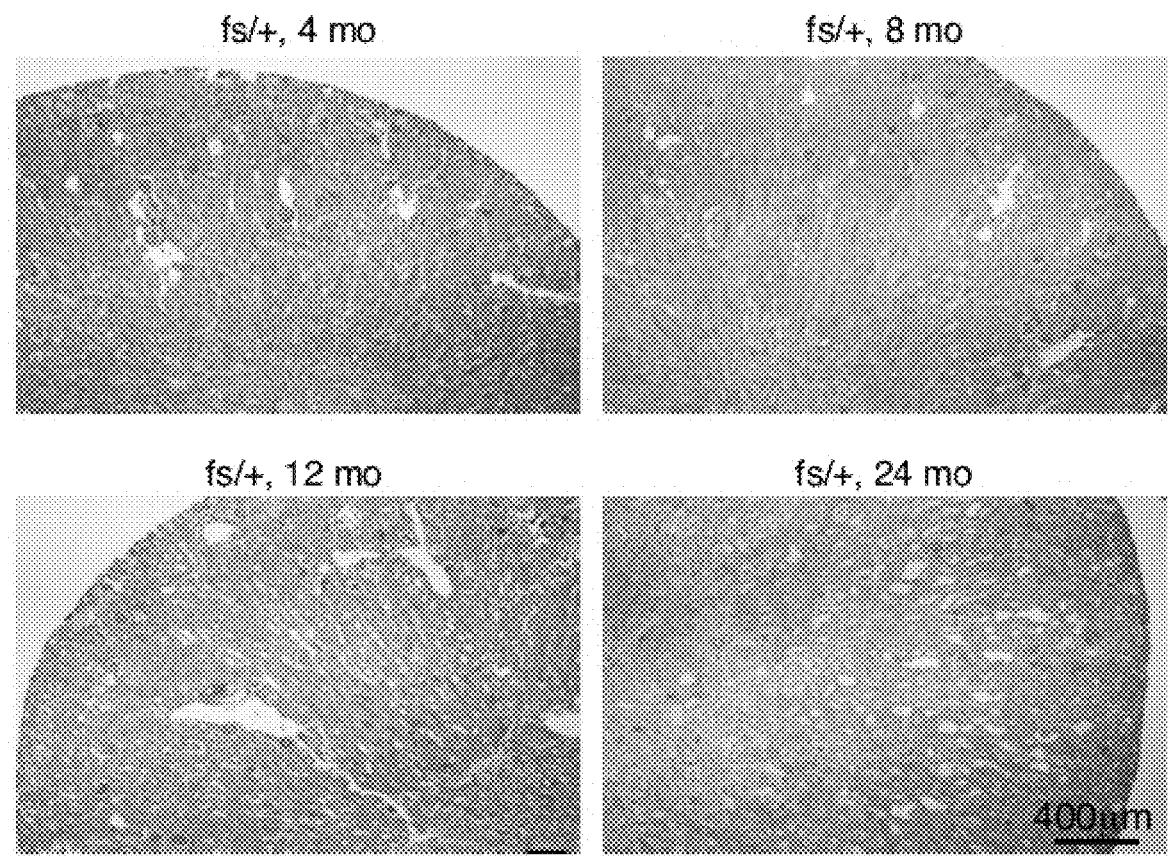
Figure 8A:
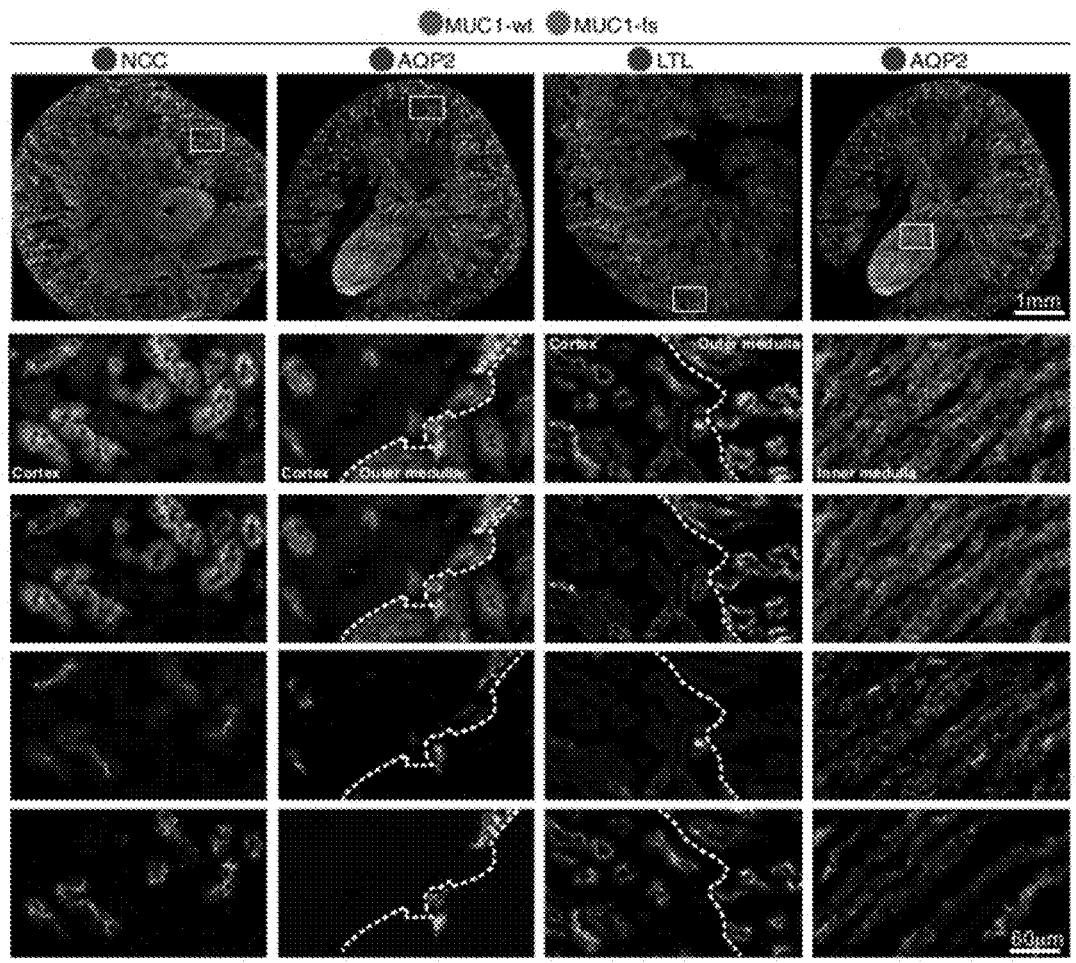
FIGS. 8A and 8B show MUC1-fs and MUC1-wt distribution in different segments of kidneys of fs/+ mouse.
Figure 8B:
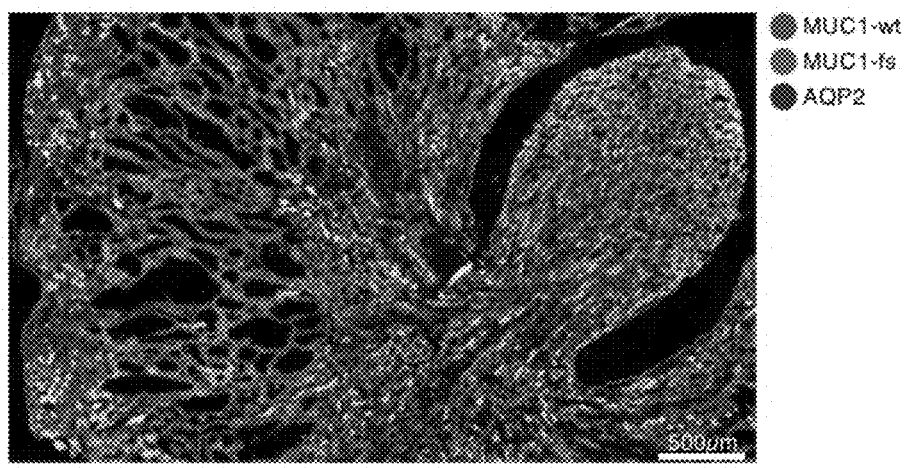
Figures 17, 18:
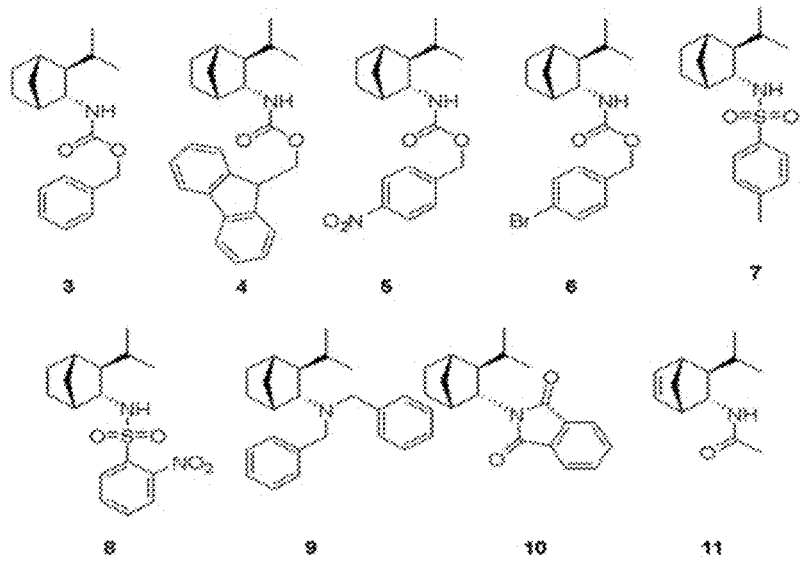
FIG. 17 shows a listing of serum creatinine levels in +/+ and fs/+ mice as a function of age and gender (see FIG. 7E above).
FIG. 18 shows structures of amino functionalized BRD-4780 compounds (identified as compounds 3-11 successively, where all such compounds are racemates), as described in Example 15 below.

While no pathologic changes were detected in kidneys from the parental strain (+/+) or mice carrying the normal human allele (wt/+) (FIG. 1C), mice carrying the mutant allele (fs/+) developed progressive kidney disease (FIG. 1E). The pathological changes detected in fs/+ mice were similar to those observed in MKD patient biopsies, marked by tubular dilations and some interstitial fibrosis (FIG. 1E). This kidney pathology developed as early as 8 months of age in female fs/+ mice (FIG. 1E) compared to male mice in which tubular pathology was noted at 12 months of age (FIG. 7F). Serum creatinine was mildly elevated in female fs/+ mice at 76 weeks of life and beyond, but not in males (FIG. 7E and FIG. 17). The distribution of normal mouse and mutant human MUC1 proteins in different segments of the kidney was characterized by double labeling immunofluorescence (IF) microscopy with segment-specific markers (FIG. 8A). Both MUC1-fs and MUC1-wt were expressed in sodium-chloride symporter (NCC or SLC12A3)-positive distal convoluted tubules and aquaporin 2 (AQP2)-positive collecting ducts in the cortex and inner medulla, whereas Lotus tetragonolobus lectin (LTL)-positive proximal tubules in the outer medulla expressed solely MUC1-fs (FIG. 8A). This finding was of interest because the outer medulla is the kidney region in which the mutant mice exhibited the earliest and ultimately most severe histopathological changes (FIGS. 1E and 8B).

Figure 1F:
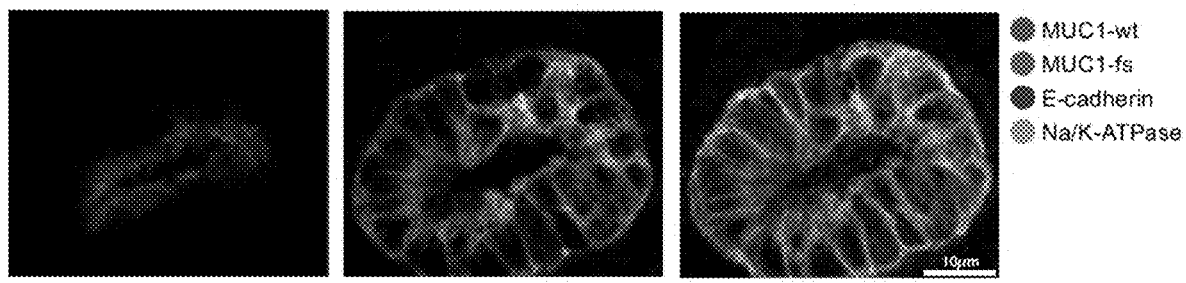
Figure 9A:
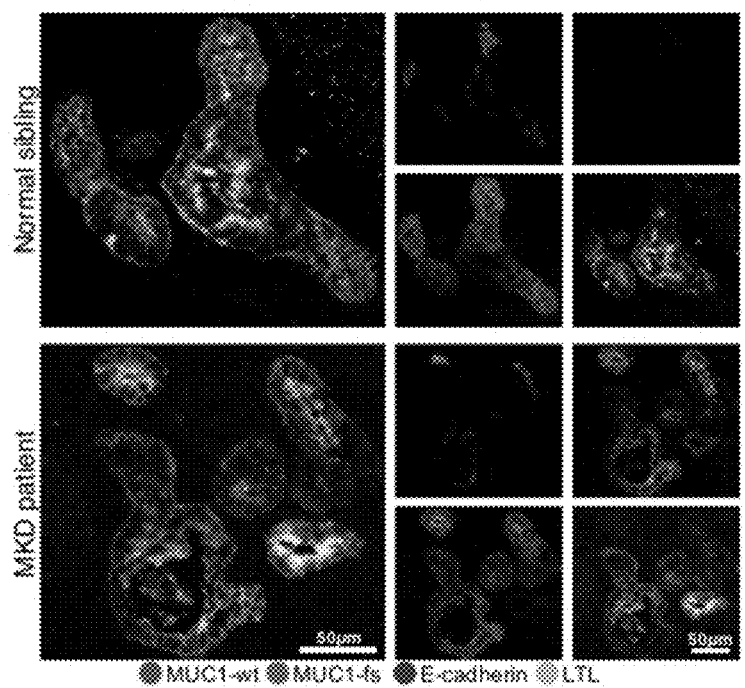
FIGS. 9A to 9J depict the generation and characterization of MKD patient kidney organoids and immortalized tubular epithelial cell lines.

Human kidney organoids were generated (Morizane and Bonventre, 2016; Takasato et al., 2016) from MKD patient iPSCs. The iPSCs were made from erythroblasts obtained from three MKD patients. iPSCs from unaffected siblings served as controls. Mature organoids (29 day, see Example 1 above) developed nephron structures including proximal and distal tubules, which were recently characterized in detail (Subramanian et al., 2019). MUC1-wt was detected in normal, sibling-derived and patient-derived kidney organoids, at highest abundance in distal nephron structures (FIG. 9A). In line with previous observations in MKD patient kidney biopsies (Bleyer et al., 2017; Yu et al., 2018), MUC1-fs was observed exclusively in MKD patient-derived organoids, in E-cadherin and Na/K-ATPase-positive tubules, and to a lesser extent, in LTL-positive tubules (FIGS. 1F and 13A). Notably, MUC1-wt was located at the plasma membrane of these tubules (FIG. 1F), whereas MUC1-fs was localized intracellularly (with basolateral membranes defined by Na/K ATPase staining; FIG. 1F). Thus, human organoids recapitulated the subcellular localization of MUC1-wt and MUC1-fs, as seen in human kidney biopsies.

Figure 1G:
Figure 9B:
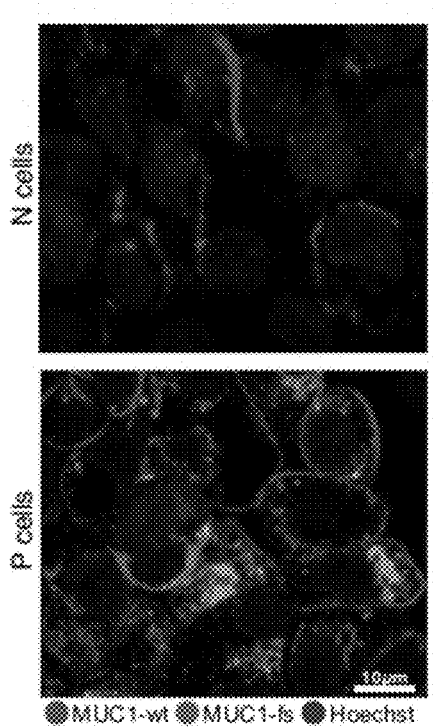
Figure 9C:
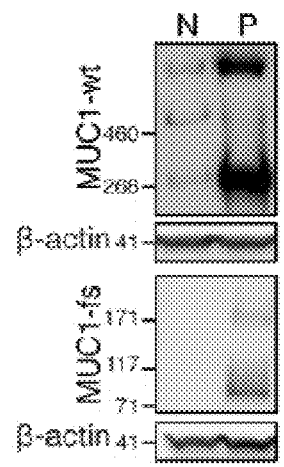

To enable downstream mechanistic studies, an immortalized tubular epithelial cell line was generated from a patient with MKD (P cells) and compared MUC1 expression to a cell line derived from a normal human kidney (N cells; FIGS. 9B and 9C). P cells expressed MUC1-wt on the plasma membrane (FIG. 1G), similar to N cells (FIG. 9B), whereas MUC1-fs was found exclusively in P cells (FIGS. 9B and 9C) in diffuse intracellular, perinuclear pattern similar to that previously seen in patient kidney biopsies, iPSC-derived kidney organoids and knock-in mouse kidneys (FIG. 1G).

Example 3: MUC1-fs Accumulation Triggers the ATF6 Branch of the UPR

To decipher the molecular mechanism by which MUC1-fs accumulation alters epithelial cell function, the involvement of the unfolded protein response (UPR), a prominent mechanism for the regulation of cellular proteostasis (Plate and Wiseman, 2017), was analyzed. First, to address the involvement of IRE1, PERK and ATF6 branches of the UPR (Walter and Ron, 2011) in P cells, the RNA-Seq data from P and N cells using published transcriptional signatures of either general or branch-specific UPR activation (Adamson et al., 2016) was analyzed. This analysis indicated general activation of the UPR (Complex), and clear, significant, upregulation of the ATF6 branch (FIG. 2A). Minimal transcriptional changes were noted in the IRE1 and PERK branches (FIG. 2A).

Figure 9D:
Figure 9E:
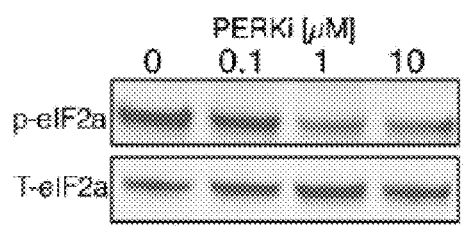
Figure 9F:
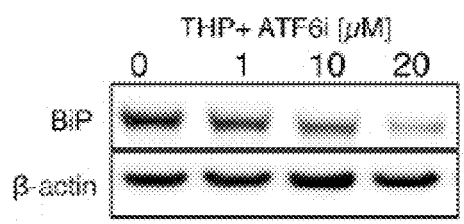
Figure 9G:
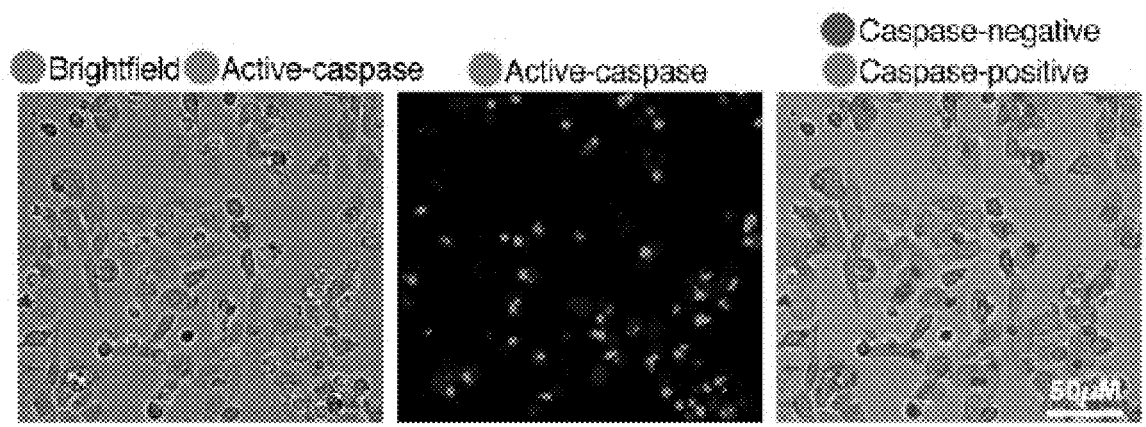
Figure 9H:
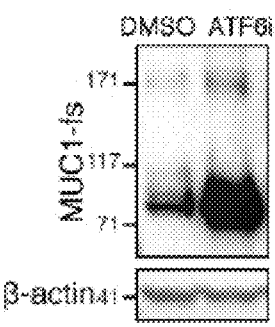

Since the activation of specific UPR branches can promote either cytoprotective or pro-apoptotic outputs (Hetz, 2012), the involvement of UPR branches in P cell viability was tested by inhibiting one branch at a time (FIGS. 9D-9F). MUC1-fs accumulation alone did not induce apoptosis (as measured by caspase 3/7 activity; FIGS. 2B and 9G). However, the inhibition of ATF6 resulted in increased apoptosis in P cells compared to N cells (FIG. 2B), suggesting that the ATF6 UPR branch might be specifically upregulated to protect P cells from MUC1-fs-induced toxicity. Consistent with this, ATF6 inhibition also caused enhanced accumulation of MUC1-fs in P cells (FIG. 9H). IRE1 inhibition induced apoptosis broadly, in line with its general cytoprotective role (Ishikawa et al., 2019; Lin et al., 2007), with no significant difference between P and N cells (FIG. 2B). PERK inhibition had no effect on apoptosis (FIG. 2B). Together, and without wishing to be bound by theory, these results indicate that ATF6 is activated to counteract MUC1-fs accumulation and associated toxicity. These results were validated by measuring the abundance of the main downstream sensor proteins of the three UPR branches. Consistent with the RNA-Seq data (FIG. 2A), upregulation of BiP, a chaperone activated by all three UPR branches (FIG. 2C), was observed. The activation of the ATF6 branch was verified by the increased abundance of ERp72 and GRP94 (FIG. 2C). In keeping with the above results, minimal changes in ATF4, the main transcription factor of the PERK pathway, or CHOP, the proapoptotic target gene of ATF4 (FIG. 2C), were detected. XBP1 mRNA splicing, a key step in the activation of the IRE1 pathway (FIG. 2C), was also not detected.

Figure 9I:
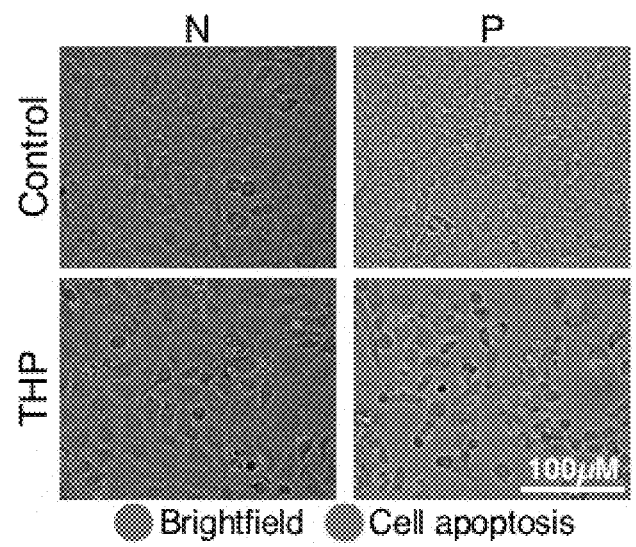
Figure 9J:
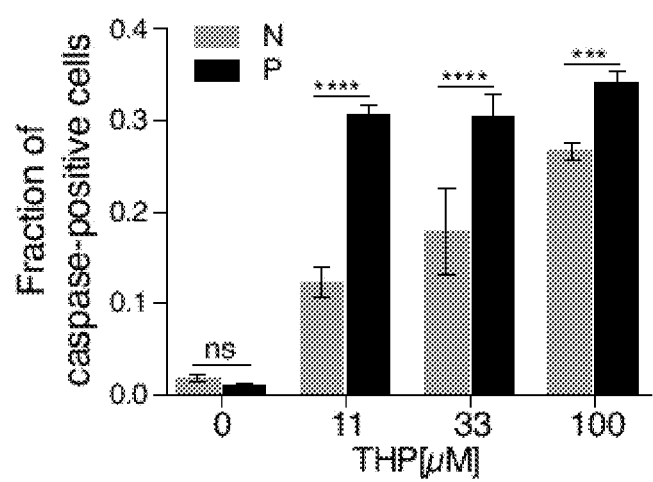

Given the increased vulnerability of P cells to ATF6 inhibition, it was reasoned that increased stress signaling through the activation of the PERK and IRE1 arms of the UPR may further promote tubular cell injury. Therefore, the effect of thapsigargin (THP), a well-known ER stressor, was tested on P cells, and such cells were discovered to exhibit higher susceptibility to apoptosis compared to N cells (FIGS. 9I and 9J). Consistent with this, treatment with THP triggered the pro-apoptotic PERK pathway specifically in P cells, as shown by increased ATF4 and CHOP abundance (FIG. 2D). XBP1 splicing was also noted in P cells after treatment with THP (FIG. 2D). Taken together, these results indicated that THP-induced activation of the UPR drives P cell apoptosis, thereby defining a cell-based assay valuable for downstream drug screening efforts.

The UPR pathways were also relevant in vivo. In kidneys of fs/+ mice, the ATF6 marker ERp72 was most abundant in the same tubular structures as MUC1-fs in the outer medulla (FIG. 2E). Furthermore, increased protein abundance of calreticulin, ERp72, GRP94 and CHOP in tissue lysates from kidneys of 12-month old fs/+ mice (FIG. 2F) were found. The increased abundance of pro-apoptotic CHOP was associated with increased apoptosis in 12-month old mice, as evidenced by positive TUNEL staining primarily in the outer medulla of kidneys from fs/+ mice (FIGS. 2G and 2H).

Example 4: BRD-4780 Selectively Clears Mutant but not Wild-Type MUC1

To identify compounds that can remove MUC1-fs, a high content screen (HCS) using an IF cell-based assay that could simultaneously assess the abundance of MUC1-wt, MUC1-fs and cell number in a 384-well format utilizing a fully automated staining protocol and confocal imaging microscopy system (z' score 0.35, FIG. 10A) was developed. The Broad Repurposing Library, a set of 3713 compounds at different stages of preclinical and clinical development (Corsello et al., 2017) (FIGS. 3A and 10A) was screened. The bromodomain inhibitor JQ1 was used as a positive control because preliminary in vitro experiments in P cells showed that it results in 100% transcriptional suppression of both MUC1-fs and MUC1-wt.

Figure 3A:
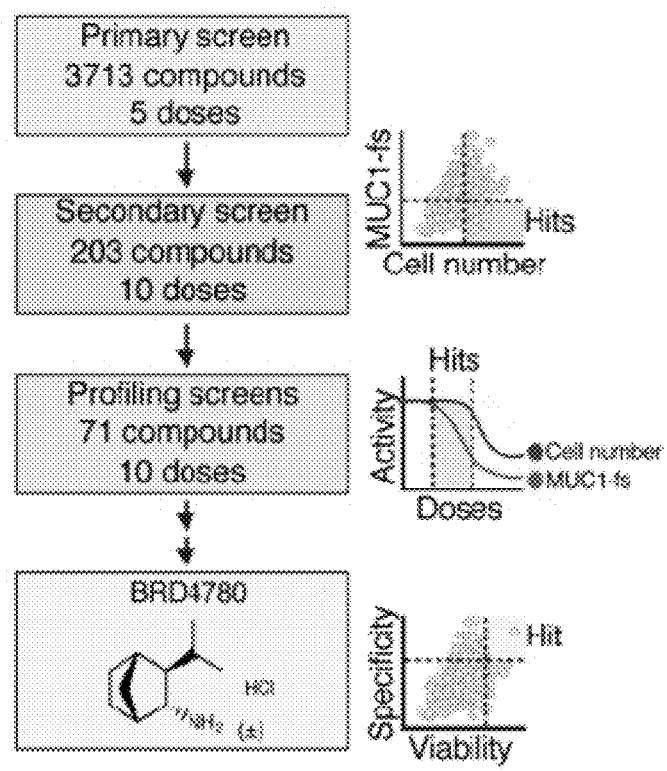
FIGS. 3A to 3J depict that BRD-4780 clears mutant MUC1-fs.
Figure 3B:
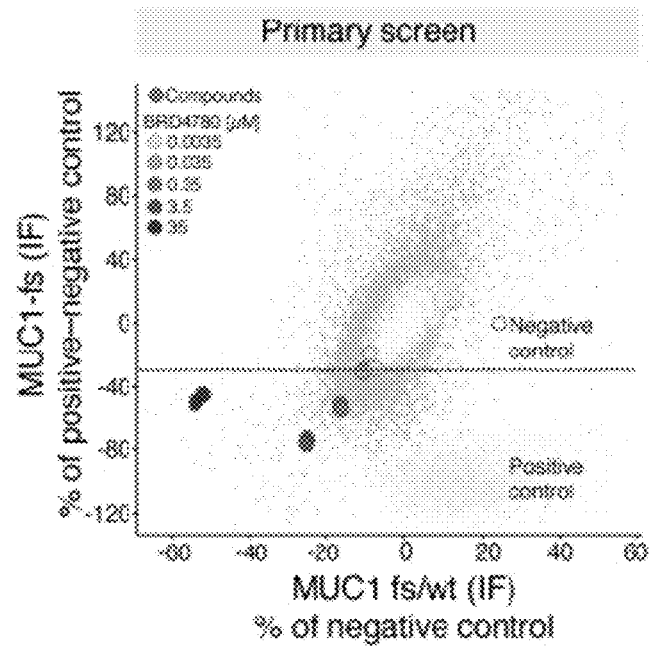
Figure 3C:
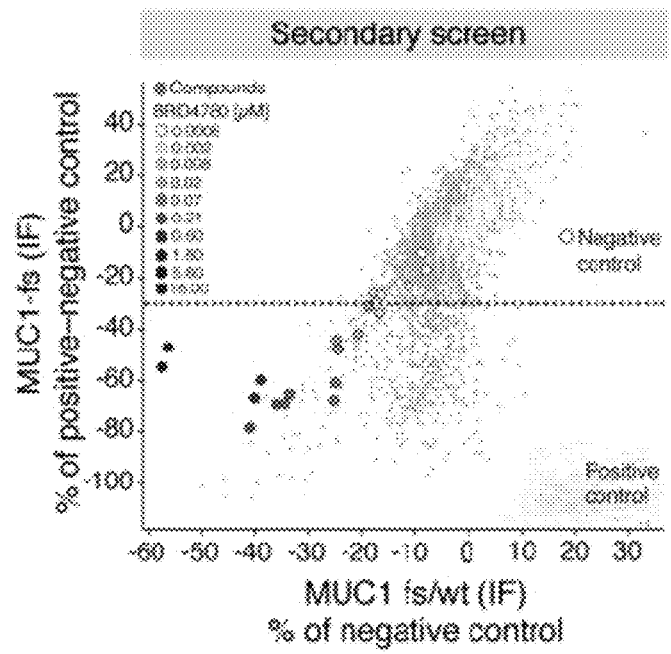
Figure 3D:
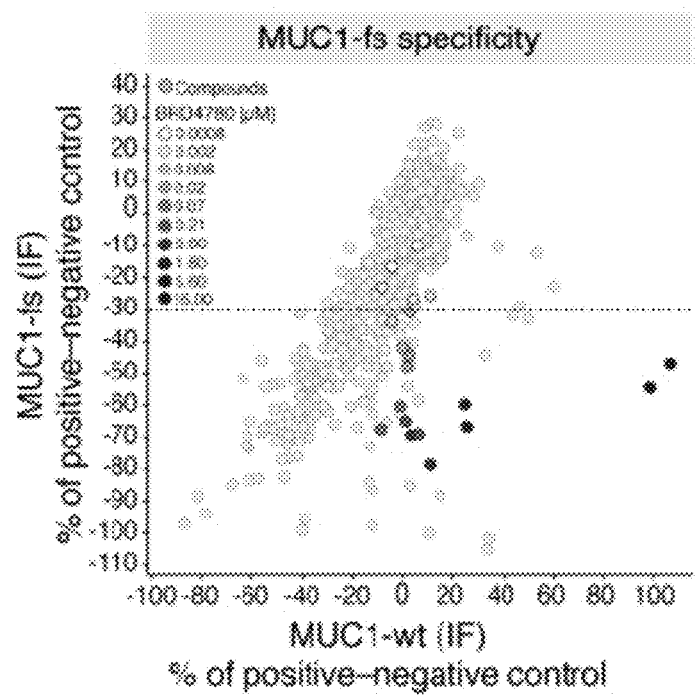
Figure 3E:
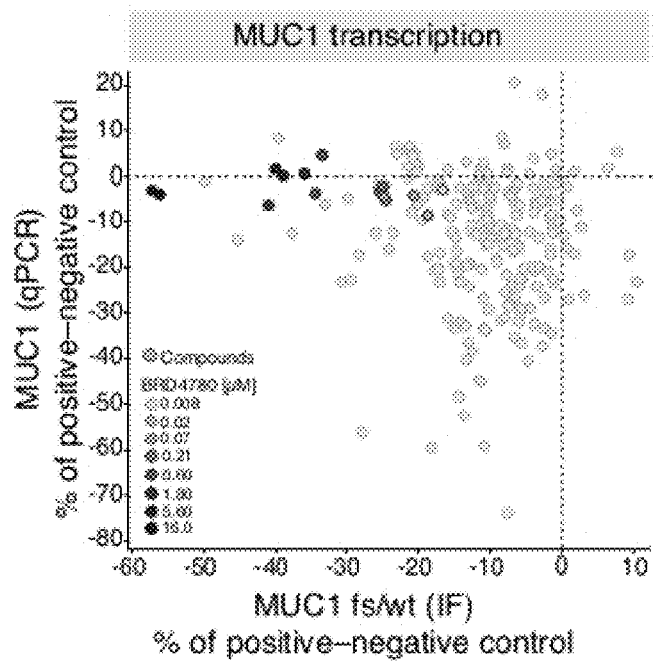
Figure 3F:
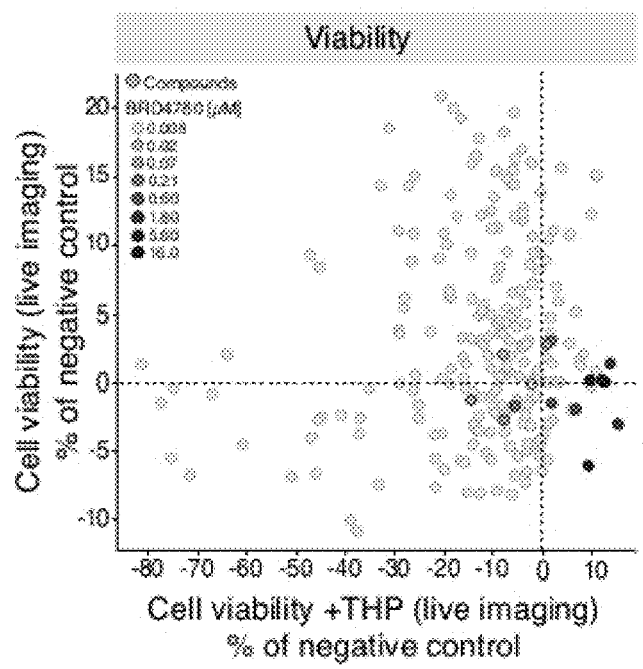

For the primary screen, the Repurposing Library was tested at 5 doses (FIGS. 3A and 3B), with positive hits defined by (i) reduction of MUC1-fs by >30% at a minimum of two consecutive compound doses, and (ii) lack of cell toxicity at these doses (no significant reduction in cell number). A total of 203 compounds (5%) met these criteria (FIG. 3B). These compounds were retested in a secondary screen, generating dose-response curves at 10 doses and defining positive hits based on the same two criteria as for the primary screen. A total of 71 compounds were selected for further evaluation (FIGS. 3A and 3C). While many of the compounds caused comparable reduction of both MUC1-fs and MUC1-wt, it was noticed that some preferentially removed MUC1-fs (FIGS. 3B and 3C). Furthermore, the 71 compounds were characterized utilizing three assays: (i) the 10-point dose-response curve to test for compound specificity for MUC1-fs reduction (FIG. 3D) was re-measured; (ii) MUC1 mRNA levels to eliminate compounds that reduced MUC1 protein abundance through transcriptional suppression were measured (MUC1-wt and MUC1-fs mRNAs are not readily distinguished and are transcribed from the same promoter; FIG. 3E), and (iii) the ability of the compounds to rescue P cells from cell death caused by THP (FIG. 3F) was tested.

Figure 3G:
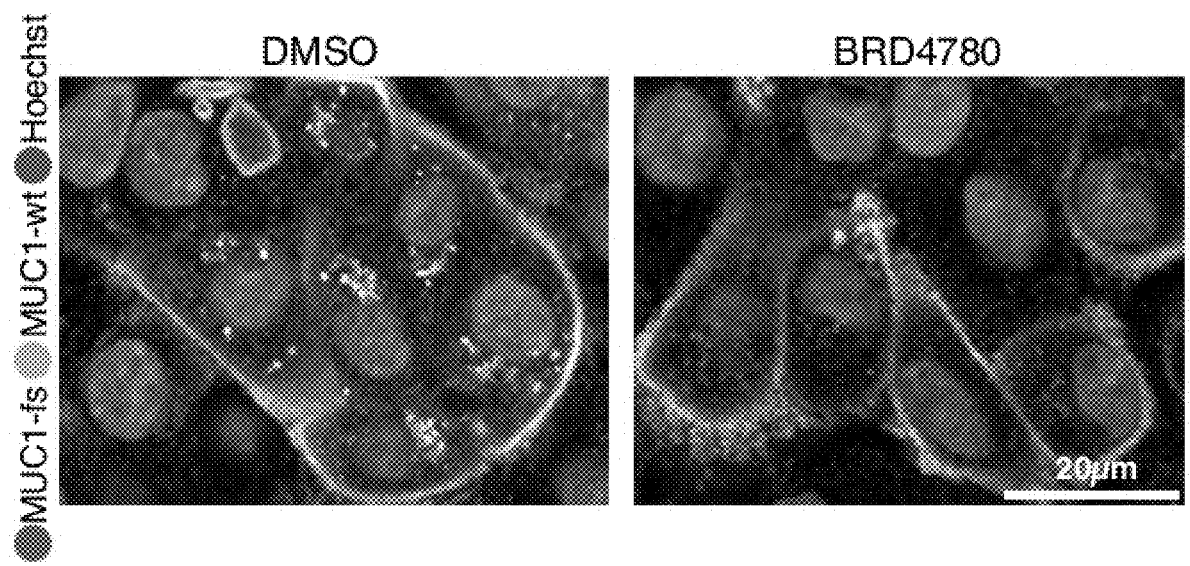
Figure 3H:
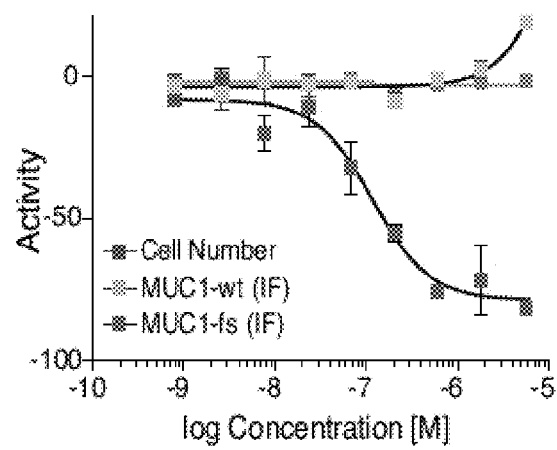
Figure 3I:
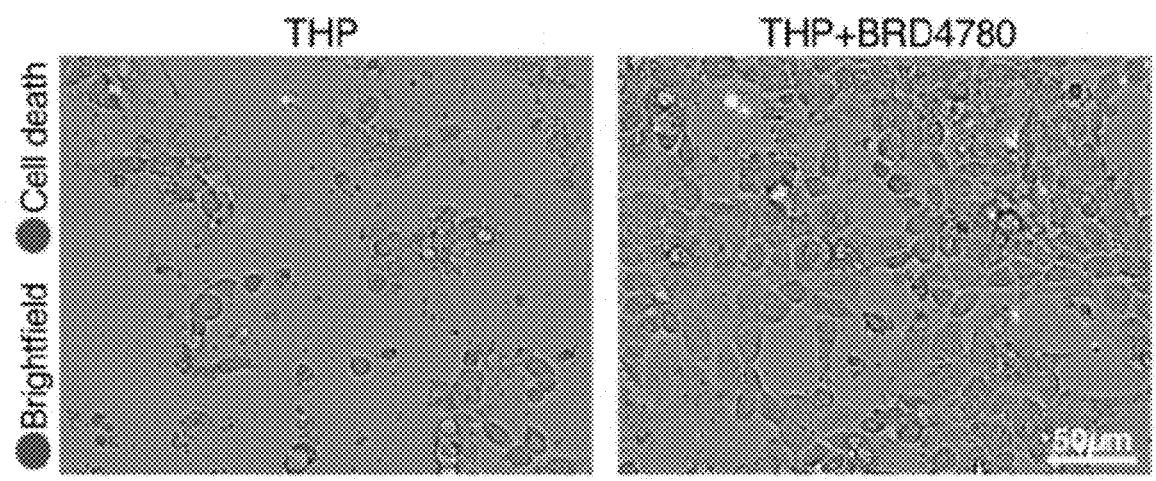
Figure 3J:
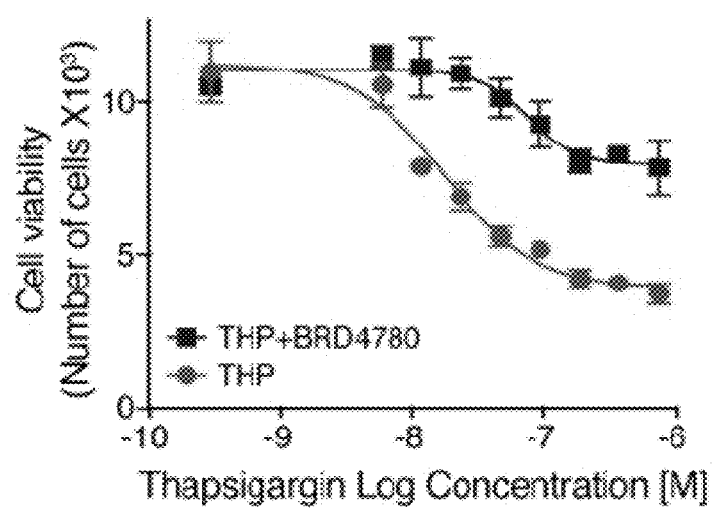
Figure 10B:
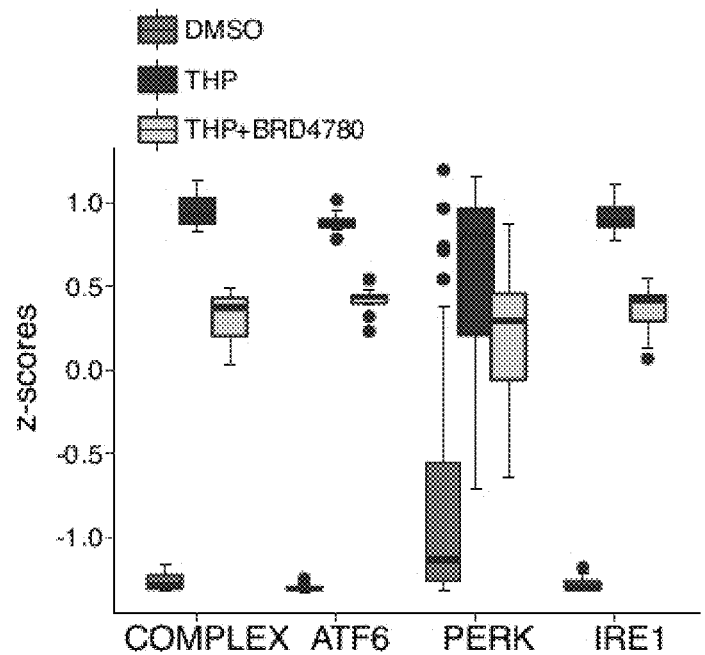

A single compound, BRD-4780, emerged from these three profiling assays (FIG. 3A). First, BRD-4780 resulted in dose-dependent removal (EC50=143 nM) of mutant MUC1-fs without decreasing wild-type MUC1 (FIGS. 3G and 3H). Second, BRD-4780 showed no effect on MUC1 transcriptional regulation while retaining efficacy in specifically removing mutant MUC1-fs protein in a dose responsive manner (FIG. 3E). Third, BRD-4780 rescued P cells from THP-induced cell death (FIGS. 3I and 3J) and significantly reduced UPR activation (FIG. 10B). Taken together, the high-content screening and profiling assays identified BRD-4780 as a compound that selectively reduced mutant but not wild-type MUC1.

Figure 4C:
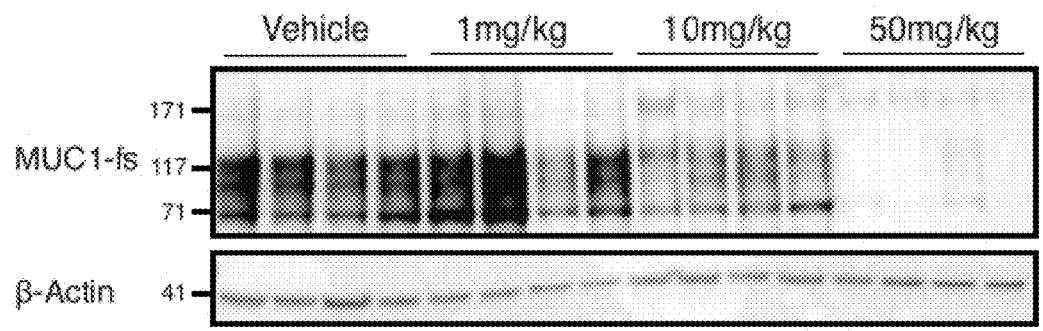
Figure 4D:
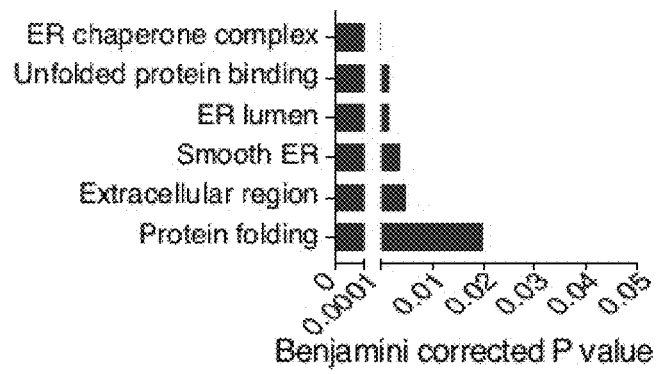

Example 5: BRD-4780 Removes Mutant MUC1-fs from Kidneys of Heterozygous Knock-in Mice The ability of BRD-4780 to reverse the accumulation of MUC1-fs in vivo was then tested. Based on PK studies in 129S2 mice (FIGS. 11A-11F), the compound (1, 10 and 50 mg/kg) or vehicle was administered to 8 month-old male heterozygous knock-in (fs/+) mice by daily oral gavage for 7 days. Following treatment, mice were sacrificed and their kidneys were harvested and processed to assess MUC1-fs protein abundance by IF (FIGS. 4A and 4B) and Western blot (FIG. 4C). BRD-4780 treatment resulted in a dose-dependent removal of mutant MUC1-fs protein from mouse kidneys (FIGS. 4B and 4C). At the highest dose (50 mg/kg), efficient removal of mutant MUC1-fs was noticed such that the tissue appeared nearly indistinguishable from control (+/+) mouse kidneys (FIG. 4A). Consistent with in vitro data, BRD-4780 had no effect on MUC1-wt (FIGS. 4A and 12A). In addition to removing the toxic mutant protein, BRD-4780 treatment downregulated pathways associated with ER stress and the UPR, as shown by pathway analysis of bulk RNA-Seq data (FIG. 4D; see Example 1 above).

Figure 4E:
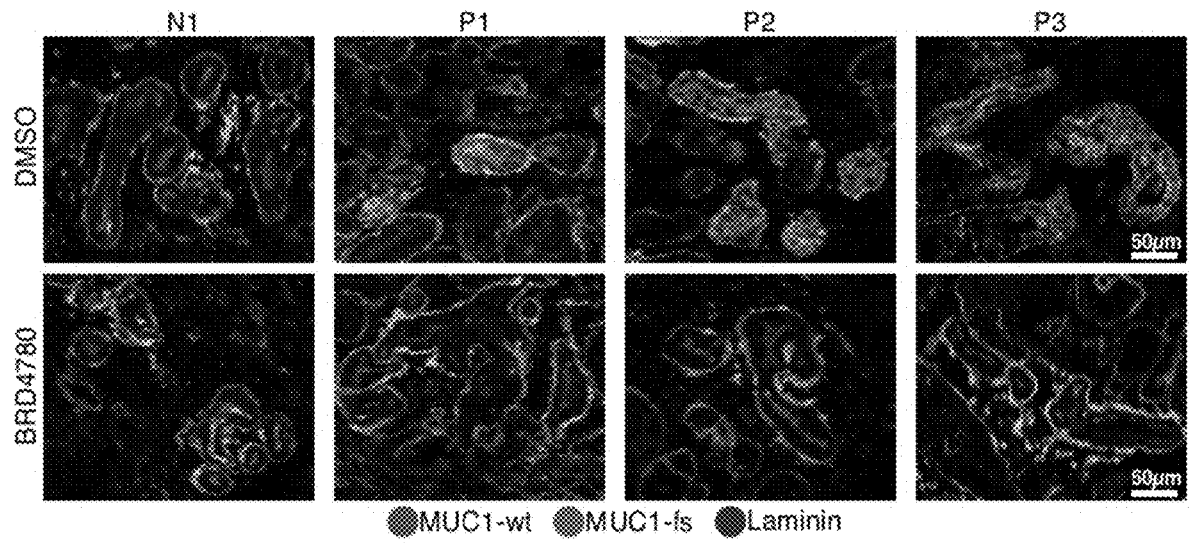
Figure 4F:
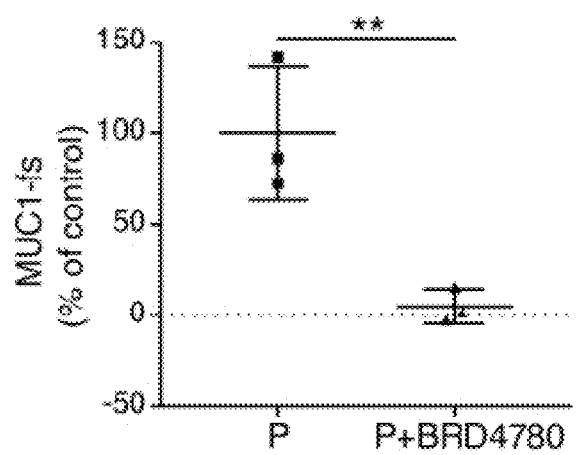
Figure 4G:
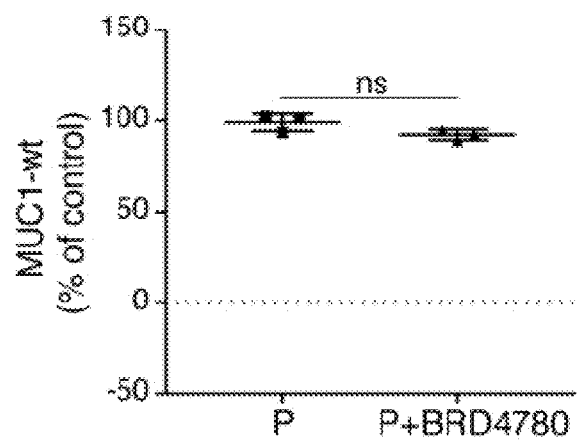

Example 6: BRD-4780 Removes MUC1-fs Protein from Patient iPSC-Derived Kidney Organoids To confirm the human relevance of the above findings, the effect of BRD-4780 on MUC1-fs was evaluated in kidney organoids generated from iPSCs of patients with MKD. Using single cell genomics and IF, a comprehensive characterization of iPSC-derived human kidney organoids was reported, and their reproducibility and potential utility for drug discovery was confirmed (Subramanian et al., 2019). Herein, the effect of BRD-4780 on MUC1-fs protein levels in kidney organoids derived from iPSCs of three patients with MKD (P1-P3) compared to organoids derived from an unaffected control (N1) was tested. BRD-4780 cleared the mutant protein from intracellular compartments in all patient organoids (FIGS. 4E, 4F and 12B), while MUC1-wt protein levels in patient or control organoids remained unchanged (FIGS. 4E and 4G). These results substantiated the human relevance of the above-described findings.

Example 7: MUC1-fs Accumulates in the Early Secretory Pathway, in a TMED9 Cargo Receptor-Positive Compartment MUC1-wt is a transmembrane glycoprotein, with a signal peptide (SP; FIG. 7B) that directs it to the secretory pathway (Nath and Mukherjee, 2014). Newly synthesized MUC1-wt is transported from the ER to the Golgi apparatus for O-glycosylation prior to its delivery to the apical plasma membrane (Apostolopoulos et al., 2015). Like all transmembrane proteins, MUC1-wt is packaged into COPII vesicles and is transported from the ER to the Golgi apparatus (Gomez-Navarro and Miller, 2016). At this point, cells can distinguish between wild-type and mutant proteins, ensuring that only appropriately folded and assembled cargo proteins undergo forward transport through the Golgi apparatus to the endosomal compartment (Gomez-Navarro and Miller, 2016) (FIG. 5A). Retrograde transport from the cis-Golgi to the ER ensures that immature protein cargoes or escaped ER resident proteins are efficiently transported back to the ER by COPI vesicles (Gomez-Navarro and Miller, 2016) (FIG. 5A). However, misfolded proteins can get trapped along the early secretory pathway, between the ER and Golgi compartments (Gomez-Navarro and Miller, 2016). Consistent with this picture, it was identified herein that MUC1-wt localized clearly and specifically to the plasma membrane in P cells (FIG. 1G). In contrast, mutant MUC1-fs was found in a punctate pattern throughout the cytoplasm (FIG. 1G). It was therefore likely that MUC1-fs was being trapped somewhere along the early secretory pathway.

To determine exactly where MUC1-fs was being retained, a comprehensive co-localization study with markers of different compartments of the secretory pathway was performed (illustration, FIGS. 5A, 5B, 13A and 13B). MUC1-fs was substantially more abundant in GM130-positive cis-Golgi compartment and TMED9 cargo receptor-positive vesicles than in other compartments (FIGS. 5A and 5B). TMED9, a member of the p24 cargo receptor family, facilitates packaging and transport between the ER and cis-Golgi compartments (Strating and Martens, 2009), and is thought to play a critical role in COPI retrograde transport from the cis-Golgi back to the ER (Adolf et al., 2019; Beck et al., 2009). It was also verified that MUC1-fs co-localized in a vesicular pattern with TMED9 in P cells, as well as in tubular epithelial cells from fs/+ mouse kidneys, from a kidney biopsy of a patient with MKD and from patient-derived kidney organoids (FIG. 5C). Taken together, these data across four different sources (human cells, kidney organoids, and kidney biopsy as well as mouse kidney) show that MUC1-fs is preferentially co-distributed with the cargo receptor TMED9.

Example 8: BRD-4780 Releases MUC1-fs from the Early Secretory Compartment

Figure 5D:
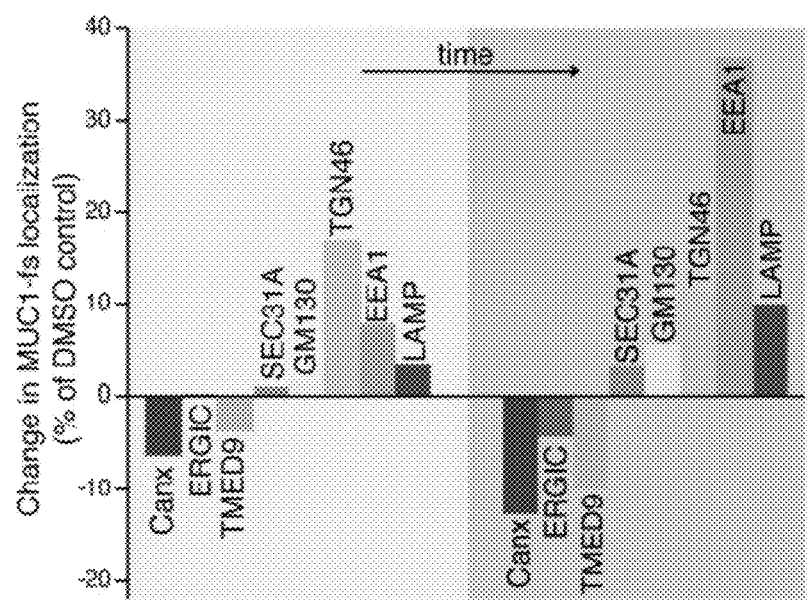

To assess the effect of BRD-4780 treatment on MUC1-fs subcellular distribution over time, the co-localization study was repeated in the presence of BRD-4780 over a 5 hour time course (FIG. 5D). Compared to baseline (FIG. 5B), MUC1-fs was reduced in the early secretory compartment after treatment with BRD-4780, and was instead progressively associated with the TGN46-positive trans-Golgi, the EEA1-positive endosomal and the LAMP1-positive lysosomal compartments (FIG. 5D). These results indicated that BRD-4780 promotes anterograde trafficking and lysosomal degradation of MUC1-fs by releasing it from the early secretory compartment, where it had been trapped in the absence of BRD-4780.

Figure 5E:
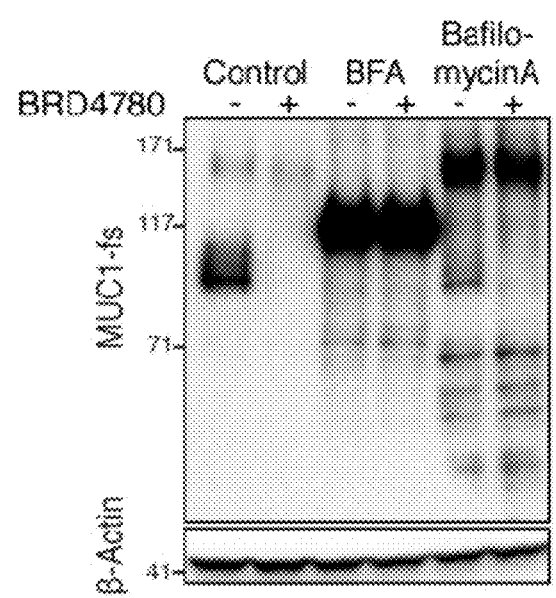

Example 9: An Intact, Functional Secretory Pathway is Required for BRD-4780-Mediated Removal of MUC1-fs To test whether targeting for lysosomal degradation is the mechanism by which BRD-4780 removes mutant MUC1-fs, anterograde trafficking and lysosomal degradation were disrupted before and after treatment with compound. The vesicular transport between the ER and Golgi was first blocked with Brefeldin A (BFA) (Chardin and McCormick, 1999). This resulted in the accumulation of an intermediate glycosylated 117 kD MUC1-fs protein in the ER (as compared to 100 kD MUC1-fs protein at baseline; FIGS. 5E and 13C) (Bosshart et al., 1991). BFA also abrogated the effect of BRD-4780 on MUC1-fs clearance (FIG. 5E). Second, inhibition of lysosomal degradation by Bafilomycin A (Yoshimori et al., 1991) resulted in a 170 kD MUC1-fs protein retained in late secretory compartments (trans-Golgi, late endosomes and lysosomes)(FIGS. 5E and 13C). This 170 kD MUC1-fs protein was present but less abundant in control P cells at baseline, likely representing a fully O-glycosylated version of the protein (Apostolopoulos et al., 2015). Importantly, lysosomal inhibition with Bafilomycin A prevented BRD-4780 from clearing mutant MUC1-fs (FIG. 5E). Given that treatment with BFA or Bafilomycin A alone resulted in accumulation of MUC1-fs, it was concluded that trafficking through the secretory pathway to the lysosome is the fundamental mechanism for MUC1-fs degradation in P cells. In support of this, inhibition of the proteasome had no effect on MUC1-fs accumulation at baseline, or its removal by BRD-4780, reinforcing the conclusion that MUC1-fs is degraded in the lysosome (and not the proteasome)(FIG. 13D). Taken together, these experiments established that the effect of BRD-4780 on clearing MUC1-fs required a functional secretory pathway and lysosomal degradation.

Example 10: TMED9 is Upregulated in Kidney Cells Expressing MUC1-fs

Figure 6A:
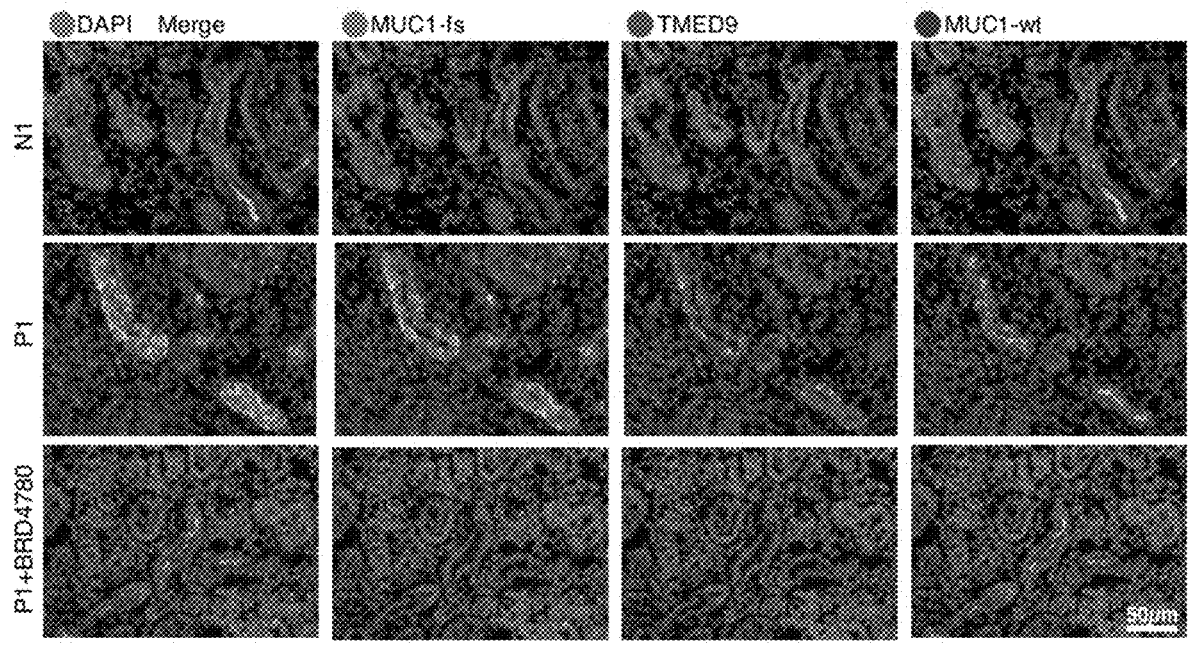
Figure 6B:
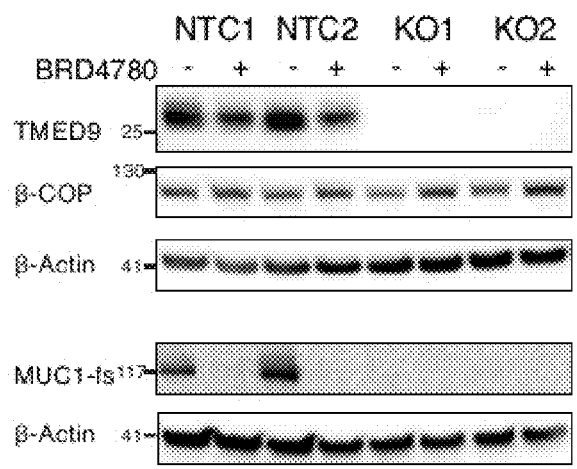

Since MUC1-fs was found at highest abundance in TMED9- and GM130-positive compartments at baseline (FIG. 5B), the abundance of TMED9 and GM130 was explored in tubular epithelial cells. GM130 abundance was comparable between patient iPSC-derived kidney organoids (P1) relative to controls (N1), and was not affected after treatment with BRD-4780 (FIG. 14A). In contrast, TMED9 abundance was higher in patient-derived organoids (P1), specifically in cells expressing MUC1-fs, compared to controls (N1). BRD-4780 treatment not only cleared MUC1-fs, but also reduced TMED9 to levels comparable to cells in N1 organoids (FIG. 6A). This further supported the functional role of TMED9 in the entrapment of mutant MUC1-fs in the early secretory pathway.

Figure 6C:
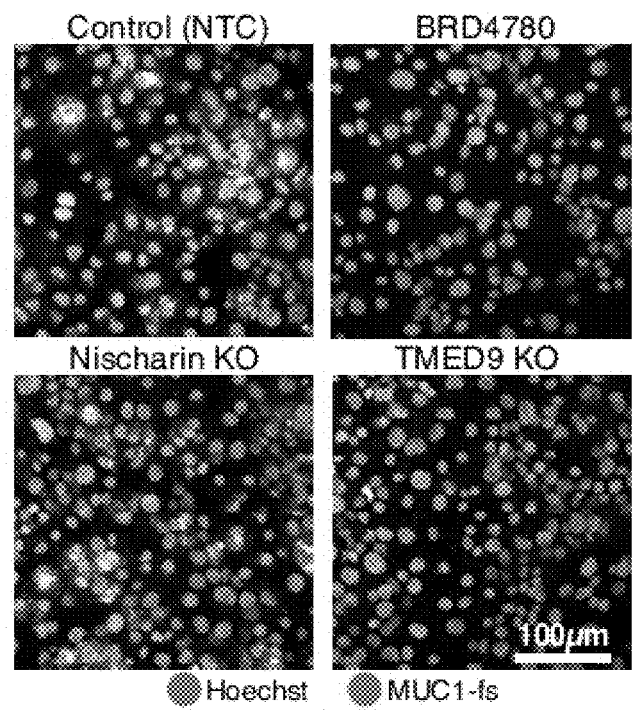
Figure 6D:
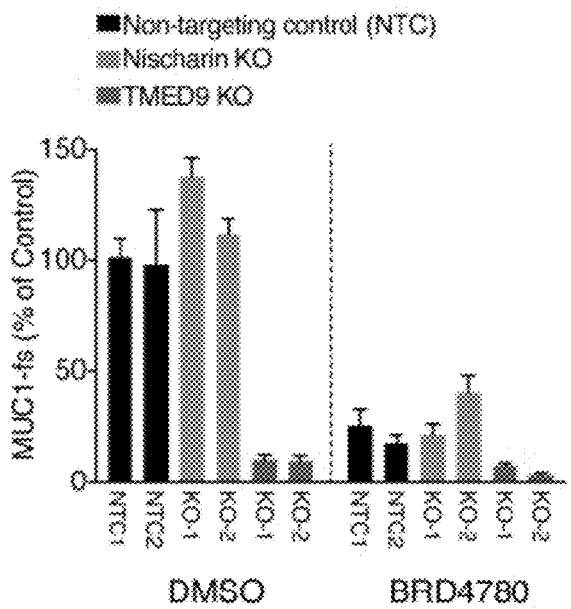

Example 11: TMED9 Deletion Phenocopies the Effect of BRD-4780 on MUC1-fs Removal To confirm the role of TMED9 in the mechanism of action of BRD-4780, CRISPR-Cas9 was used to delete TMED9 from P cells (FIG. 6B). Genetic deletion of TMED9 phenocopied the effect of BRD-4780 and resulted in the removal of MUC1-fs from P cells, as shown by Western blot (FIG. 6B) and IF (FIGS. 6C and 6D). Of note, the abundance of β-COP, an integral component of COPI vesicles (Beck et al., 2009), was not affected either by TMED9 deletion or BRD-4780 treatment (FIG. 6B). Similarly, MUC1-wt abundance and its localization on the plasma membrane were not affected by TMED9 deletion or BRD-4780 treatment (FIG. 14B). Thus, BRD-4780 appears to work in a targeted fashion to remove the mutant protein cargo associated with TMED9 without disrupting the cell's baseline transport machinery.

Example 12: BRD-4780 Directly Binds its Molecular Target, TMED9

BRD-4780 was originally annotated as a selective ligand for the imidazoline-1 receptor (I1R) and studied as a potential central anti-hypertensive therapy. However, due to lack of efficacy as an anti-hypertensive in several animal studies, BRD-4780 was never advanced into the clinic (Munk et al., 1996). The protein nischarin has been previously suggested as a candidate I1R (Nikolic and Agbaba, 2012; Piletz et al., 2000; Zhang and Abdel-Rahman, 2006). Therefore, it was then assessed herein if nischarin is involved in the mechanism of action of BRD-4780 in clearing MUC1-fs. Neither RNAi-mediated depletion nor CRISPR-Cas9-mediated deletion of nischarin in P cells had any effect on MUC1-fs protein abundance or on the efficacy of BRD-4780 (FIGS. 6C, 6D and 14C), ruling out nischarin as a target of the compound. 17 additional small molecules annotated as I1R ligands were tested and it was found that none were active in removing MUC1-fs (FIG. 14D). Collectively, these findings indicated that BRD-4780 works through a molecular mechanism that does not involve nischarin/I1R.

Figure 6F:
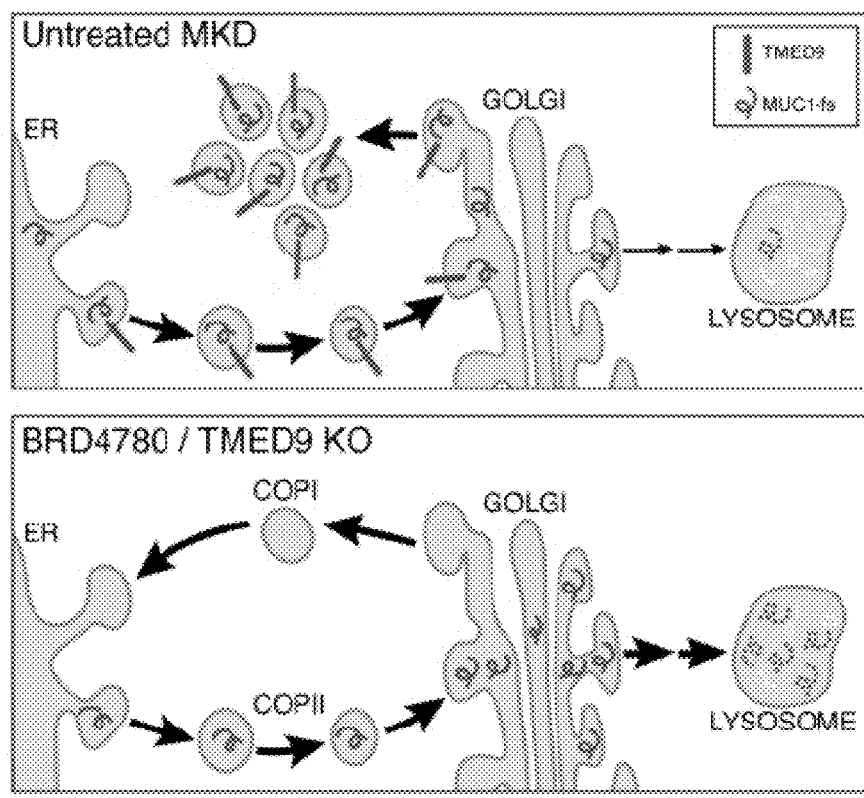

The TMED9 cargo receptor (i) co-localized in the same vesicular compartments as MUC1-fs at baseline, (ii) was upregulated in MUC1-fs expressing kidney cells in patient-derived organoids, (iii) was reduced to baseline levels after BRD-4780 treatment and (iv) its deletion phenocopied the effect of BRD-4780. Suspecting TMED9 as a likely molecular target of BRD-4780, evidence of direct drug-target engagement was sought. A cellular thermal shift assay (CETSA, see Example 1 above) was performed (Jafari et al., 2014; Reinhard et al., 2015), in which unbound proteins denature and precipitate at elevated temperatures, whereas drug-bound proteins remain in solution (Jafari et al., 2014). The CETSA for TMED9 in the presence of BRD-4780 demonstrated two findings consistent with direct binding (FIG. 6E). First, BRD-4780 shifted the TMED9 heat denaturation curve to significantly higher temperatures, and second, BRD-4780 also up-shifted the SDS-PAGE migration of TMED9 at all temperatures, consistent with likely covalent modification of TMED9 or other posttranslational modifications (FIG. 6E). In contrast, the same experiment for nischarin/I1R revealed no evidence indicative of direct engagement with BRD-4780 (FIG. 14E). In aggregate, these findings identified the cargo receptor TMED9 as a molecular target of BRD-4780. Furthermore, these data indicated a heretofore unknown mechanism of action for this compound—namely, that BRD-4780 binding to TMED9 releases MUC1-fs from the early secretory compartment, thereby promoting its anterograde trafficking into endosomes and finally into lysosomes, where it can be degraded (FIG. 6F).

Example 13: BRD-4780 is Effective in Removing Several Misfolded Proteins

Figure 15C:
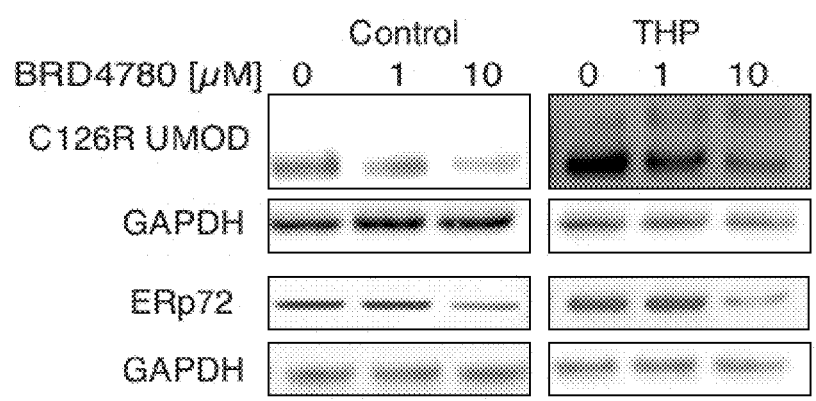

Whether the effect of BRD-4780 was specific to the MUC1-fs protein (as compared to MUC1-wt), or whether it might also facilitate the removal of misfolded proteins in other proteinopathies involving membrane-associated proteins was also examined. The compound was first tested in a cellular model of another autosomal dominant proteinopathy of the kidney, uromodulin (UMOD)-associated kidney disease (Johnson et al., 2017; Schaeffer et al., 2017), a disorder with no available treatment. BRD-4780 was applied to AtT20 cells expressing a mutant C126R UMOD protein that accumulates intracellularly. Remarkably, BRD-4780 reduced the levels of mutant UMOD protein as measured by IF (FIGS. 15A and 15B) and confirmed by Western blot (FIG. 15C).

Figure 15D:
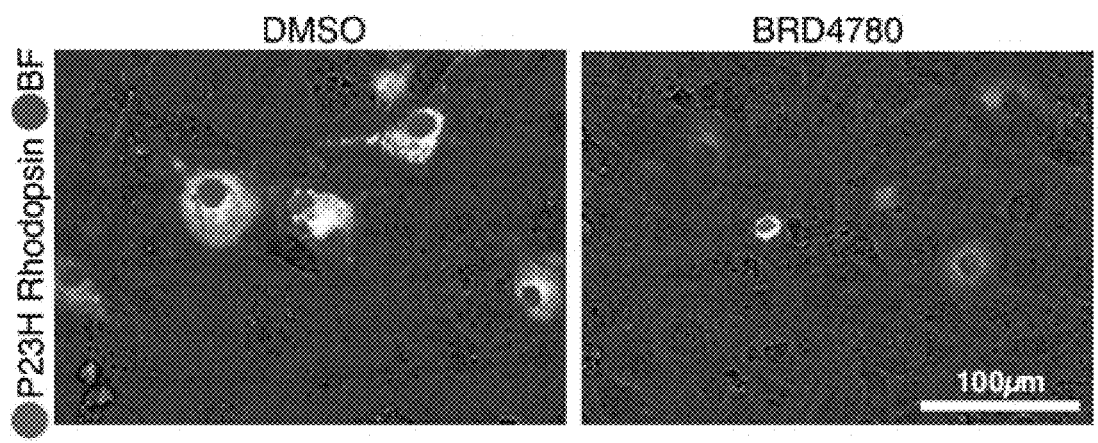
Figure 15E:
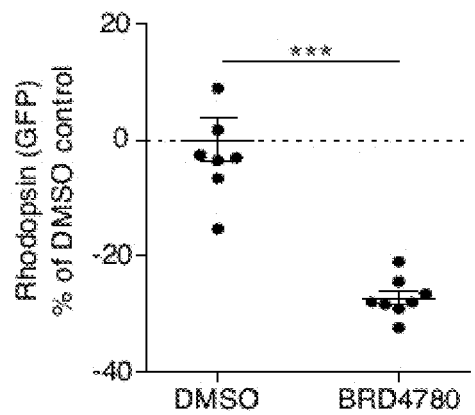
Figure 15F:
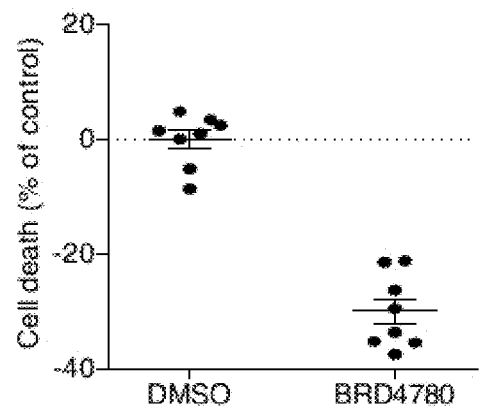

The ability of BRD-4780 to alleviate a proteinopathy outside the kidney was also tested. Retinitis pigmentosa (RP), the most common inherited retinal degenerative disease, is caused by mutations in rhodopsin (Athanasiou et al., 2018; Dryja and Li, 2017). Most rhodopsin mutations, including P23H, result in a misfolded protein that accumulates intracellularly leading to photoreceptor cell death (Athanasiou et al., 2018). BRD-4780 was applied to N cells over-expressing GFP-tagged rhodopsin P23H and the effect of the compound was studied by following GFP fluorescence over 24 hours. BRD-4780 produced significantly decreased GFP fluorescence at 24 hours in GFP-rhodopsin P23H-expressing cells (FIGS. 15D and 15E). The viability of cells expressing P23H mutant significantly improved upon treatment with BRD-4780 (FIG. 15F).

Figure 21A:
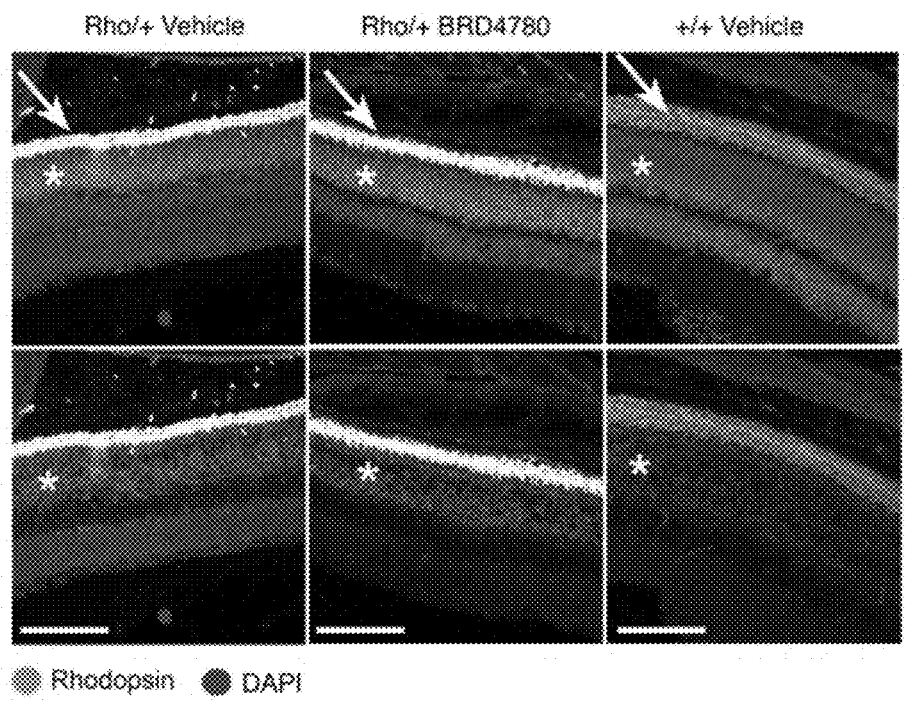
FIGS. 21A and 21B show rhodopsin distribution in mouse retinal sections in response to BRD-4780.
Figure 21B:
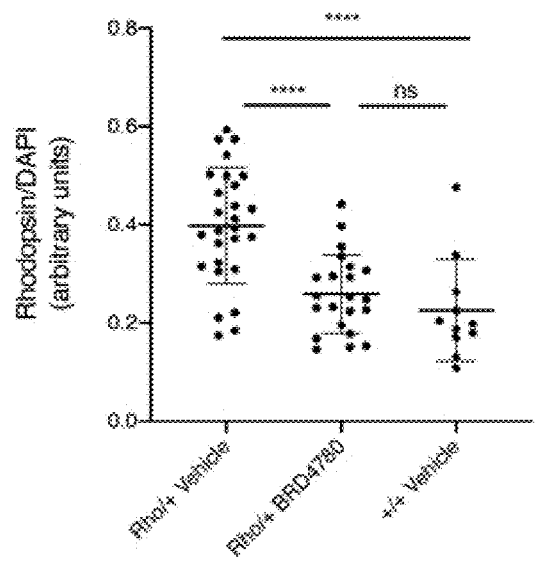

Additional indication of the ability of BRD-4780 to treat RP was obtained via observation of rhodopsin antibody staining of mouse retinal sections in Rho/+ mice treated with either vehicle or BRD-4780. Results of such staining experiments indicated that treatment with BRD-4780 significantly reduced rhodopsin accumulation in intracellular compartments, likely reflective of an alleviation of the rhodopsin proteinopathy present in these mice (FIGS. 21A and 21B).

Figure 15G:
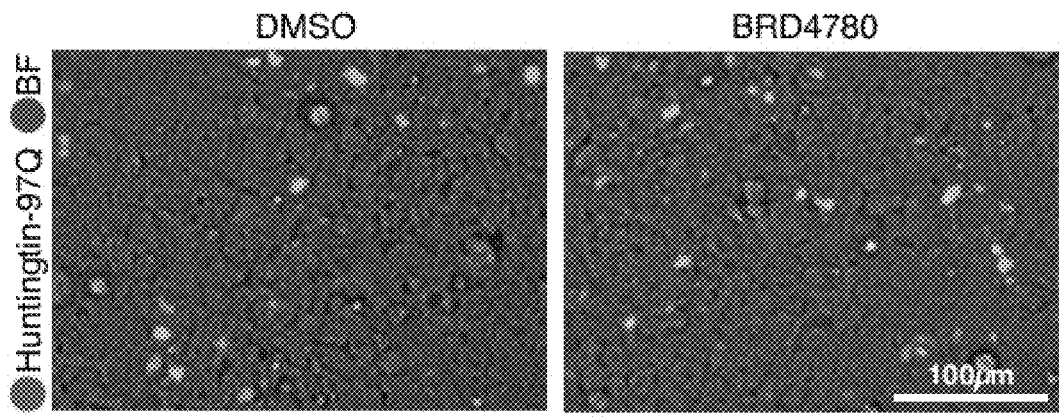
Figure 15H:
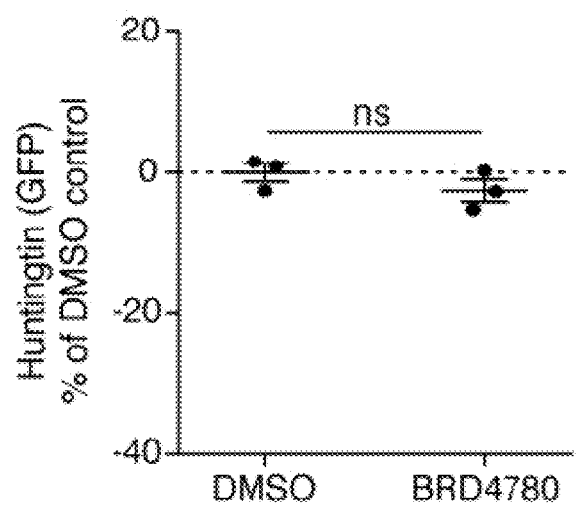

To see if the effect of BRD-4780 was restricted to misfolded proteins whose wild-type versions are membrane-associated (as is the case for MUC1, UMOD and rhodopsin) (Athanasiou et al., 2018; Hilkens and Buijs, 1988; Johnson et al., 2017; Litvinov and Hilkens, 1993; Schaeffer et al., 2017), cells expressing the mutant huntingtin (repeat version) protein, which aggregates in the cytoplasm and the nucleus, and causes neuronal toxicity in Huntington's disease (Zoghbi and On, 2000), were analyzed. It was observed herein that BRD-4780 did not reverse or diminish the intracellular accumulation of a GFP-tagged mutant version of huntingtin (97 polyQ) in HEK cells (FIGS. 15G and 15H). These findings support the therapeutic potential of BRD-4780 for the treatment of toxic proteinopathies caused by mutations in proteins that traffic through the secretory pathway.

Example 14: Pharmacokinetic Studies of BRD-4780, BRD-7709, and BRD-1365

Pharmacokinetic studies were performed to determine the oral bioavailability, plasma and tissue concentrations, and dose response exposures of BRD-4780, BRD-7709, and BRD-1365 in 129S2 mice, 129S-ELITE mice, Sprague Dawley and CD rats (see Example 1 above for methods). In fasted male 129S2/SvPasCrl mice, a single dose of BRD-4780 was administered. The oral bioavailability of BRD-4780 (% F) was determined to be 119%. In plasma protein binding studies, the estimated percent protein bound was 29.7% (FIGS. 11A and 11B). In fed 129S2/SvPasCrl mice, a single dose of BRD-4780 was administered orally. Plasma and tissue drug concentrations of BRD-4780 were obtained for males (FIGS. 11C and 11E) and females (FIGS. 11D and 11F). A comparison of the oral bioavailabilities of BRD-1365, BRD-7709 and BRD-4780 in 129S-ELITE mice was performed, as shown in FIGS. 11G-11J. A single dose of BRD-4780, BRD-1365 or BRD-7709 was administered. Dose response exposures of BRD-4780 (FIGS. 11K and 11N), BRD-1365 (FIGS. 11L and 11O) and BRD-7709 (FIGS. 11M and 11P) in 129S-ELITE mouse plasma, brain, kidney, liver and eye were also determined. All three compounds exhibited a high volume of distribution, with highest exposures in the eye. $C_{max}$ exposures for doses above 10 mg/kg were not dose proportional. AUC exposures for BRD-4780 and BRD-1365 were not dose proportional, but BRD-7709 AUC exposures were nearly dose proportional.

The oral bioavailabilities of BRD-4780, BRD-7709 and BRD-1365 were also determined in Sprague Dawley rats. Plasma concentrations over time for individual rats and the mean of 2 rats per group were plotted for BRD-4780 (FIG. 11Q), BRD-1365 (FIG. 11R) and BRD-7709 (FIG. 11S). Standard pharmacokinetic parameters were calculated (FIG. 11T). The oral bioavailability (% F) was determined to be 40.6%. for BRD-4780, 0.083, 0.5, 1, 3, 6, 10, 24, 32 and 48 hours 32.7% for BRD-1365 and 56.1% for BRD-7709, with BRD-7709 showing the highest oral bioavailability, shown in FIG. 11U.

In addition, the dose-response exposure of BRD-4780, BRD-7709 and BRD-1365 were determined in male and female CD (Sprague Dawley) rats. Plasma concentrations over time for individual rats and the mean of 3 rats per group were plotted for BRD-4780 in male rats (FIG. 11V) and female rats (FIG. 11W), for BRD-7709 in male rats (FIG. 11X) and female rats (FIG. 11Y), and for BRD-1365 in male rats (FIG. 11Z) and female rats (FIG. 11AA). The 24 hour and 48 hour time points for one of three male rats in the BRD-1365 10 mg/kg group were excluded as likely technical outliers. Standard pharmacokinetic parameters were calculated for BRD-4780 (FIG. 11AB), BRD-7709 (FIG. 11AC), and FIG. 11AD). In contrast to mice, in which AUC exposure values were higher in male mice than in female mice, AUC values were 1.4 to 2.3 fold higher in female rats than in male rats.

Example 15: Preparation of Enantiopure Analogs of BRD-4780

BRD-4780 was prepared as a mixture of enantiomers by Diels-Alder reaction of (E)-3-methyl-1-nitrobut-1-ene, 1, and cyclopentadiene followed by catalytic hydrogenation and HCl salt formation (scheme 1; Munk et al. WO 96/01813A1; Munk et al. *J Med Chem.* 39: 1193-1195). An approach was developed herein to prepare the individual stereoisomers, (1R,2R,3R,4S)-3-isopropylbicyclo[2.2.1]heptan-2-amine and (1S,2S,3S,4R)-3-isopropylbicyclo[2.2.1]heptan-2-amine and corresponding salts, based on chiral SFC chromatography. The absolute stereochemistry of the enantiopure fractions can be assigned by formation of the corresponding Mosher amides (Dale and Mosher. *J Am Chem Soc.* 95: 512-519).

Most preparative scale chromatography systems rely on analyte detection by UV-Vis absorbance (PDA detector). On the analytical scale, monitoring of the mobile-phase by mass spectroscopy is available. Potential separation of the (2R, 3R) and (2S, 3S) BRD-4780 was profiled across 5 chiral stationary phases (OJ-H, AD-H, AS-H, IC and OD-H) using four different organic solvent systems (MeOH, MeOH+1% TFA, MeOH+0.05% Et$_3$N and iPrOH) as monitored by MS detection. No separation was observed. Accordingly, a method was pursued in which detection and separation were facilitated by incorporation of an amino protecting group that could be detected by UV absorbance.

During the preparation of BRD-4780, the initial Diels-Alder reaction generated an approximately 2:1 mixture of endo and exo isomers of racemic 5-isopropyl-6-nitrobicyclo [2.2.1]hept-2-ene, 2 (Munk et al. *J Med Chem.* 39: 1193-1195). According to the literature preparation of the compound, separation of the endo and exo isomers could not be achieved at this stage and was performed following subsequent reduction to form the racemic mixture of C2-endo and C2-exo isopropylbicyclo[2.2.1]heptan-2-amine (Id.). The ability to separate the mixture of 5-isopropyl-6-nitrobicyclo [2.2.1]hept-2-ene stereoisomers was profiled using chiral SFC chromatography as monitored by UV-Vis absorbance (PDA detector). Separation of at least four materials was observed using AD-H stationary phase with iPrOH as a mobile phase (Table 2, entry 10). However, this separation was not useful on the preparative scale due to peak overlap. Without wishing to be bound by theory, if an endo selective Diels-Alder reaction were developed, then separation of the (5R, 6R) and (5S, 6S) stereoisomers could likely be effective directly on the racemic (1S,4R,5R,6R)-5-isopropyl-6-nitrobicyclo[2.2.1]hept-2-ene.

To facilitate the detection and separation of BRD-4780, a series of nine amino protected compounds were synthesized and profiled for separation across five chiral stationary phases (OJ-H, AD-H, AS-H, IC and OD-H) using four initial solvent systems (MeOH, MeOH+1% TFA, MeOH+0.05% Et$_3$N and iPrOH) (FIG. 18). The instant study included four carbamate protecting groups (3: Cbz, 4: FMOC, 5: p-NO$_2$-Cbz, and 6: p-Br-Cbz), two sulfonamides (7: tosyl and 8: nosyl), the 9: N-dibenzyl, the 10: phthalimido and an acetamide formed from racemic (1S,2R,3R,4R)-3-isopropylbicyclo[2.2.1]hept-5-en-2-amine, 11, which was prepared by selective reduction of racemic (1S,4R,5R,6R)-5-isopropyl-6-nitrobicyclo[2.2.1]hept-2-ene. Where promising separation was observed using one of the systems, in depth methods of development were pursued.

The results of the instant separation study are summarized in Table 2. For descriptive purposes, "weak separation" has been defined in Table 2 as two observable peaks with apparent Gaussian peak shape that do not approach baseline separation, "moderate separation" as two observable peaks with apparent Gaussian peak shape with near base-line separation and "well separated" as two observable peaks with apparent Gaussian peak shape that reach full baseline separation. All other cases in which there was no observable separation or in which the peak shape was poorly defined have been described as "no separation." For the well separated experiments, the $\Delta_{t_r}$ has been reported as a relative indication of separation efficiency.

Figure 19:
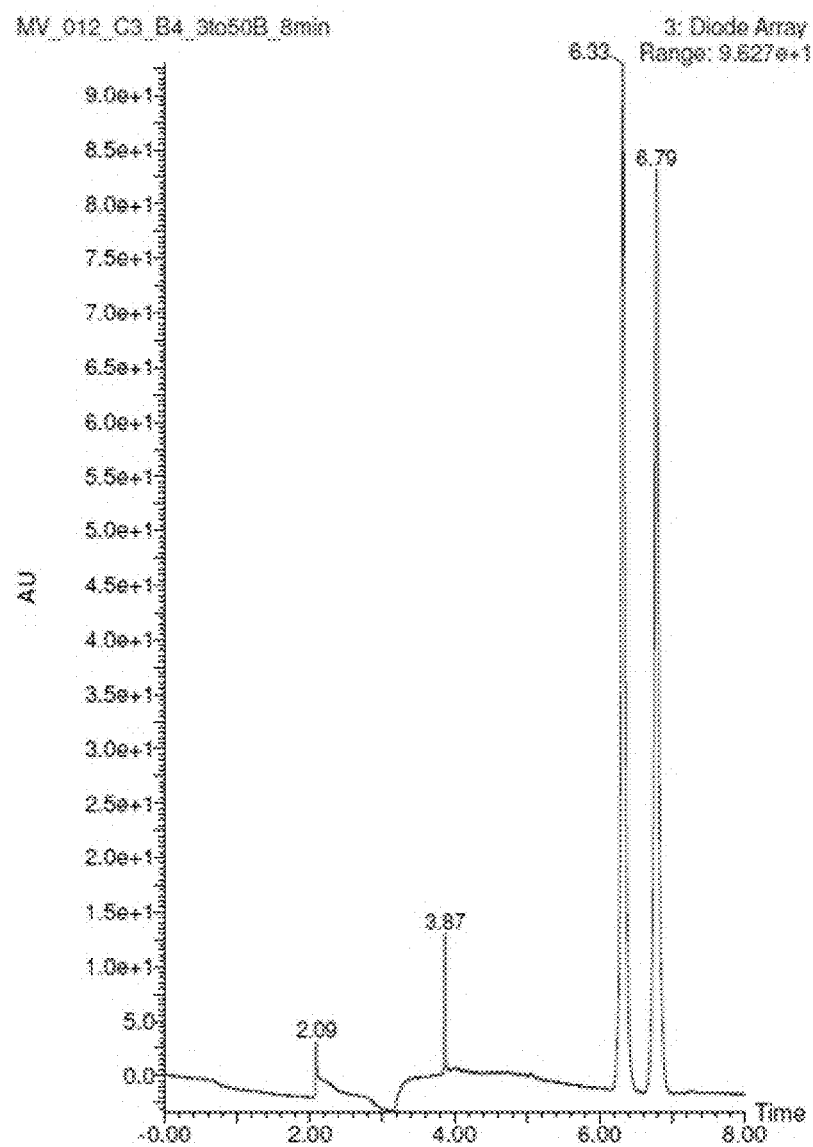
FIG. 19 shows a chromatogram that demonstrates the best separation of p-$NO_2$-Cbz 5 with stationary phase AD-H and mobile phase iPrOH (3-50%).

The tosyl protected amine, 7, and the p-NO$_2$-Cbz compound 5 showed the best separation on column AD-H, thus they were optimized with other solvents systems. As shown in Table 3, analog 7 showed better separation when using either methanol, basic or acidic solvents ($\Delta t_r$=0.78 min). Meanwhile, the p-NO$_2$-Cbz 5 did not show improvement in the enantiomers separation when changing solvents, as iPrOH remained the best mobile phase ($\Delta t_r$=0.46 min) (FIG. 19). Thep-NO$_2$-Cbz 5 was used for the gram scale reaction because it was shown that this could be conveniently removed by catalytic hydrogenation.

Next, 5 was synthesized at gram scale in 90% yield using the corresponding chloroformate with sodium bicarbonate in water and dioxane at room temperature, per scheme 2 below. The enantiomers were cleanly separated during SFC chromatography. Full baseline separation of 25 mg injections was observed on chiralpak AD-H column (250×21 mm, 5 um, 90 mL/min, 9:1 CO$_2$:IPA) and with high recovery (Fraction, 'Fr', 1: 88% of theoretical yield, Fr2: 91% of theoretical yield). Analytical chiral HPLC analysis of the isolated fractions demonstrated a single peak and no absorption at the retention time of the other enantiomer was detected (>99% ee). Deprotection of the p-NO$_2$-Cbz group proceeded well using PdCl$_2$ in ethyl acetate under an atmosphere of H$_2$ giving 51% yield following purification, salt formation and trituration in pentane. Following formation of the HCl salt, the analytical characterization was identical with authentic BRD-4780 other than the specific rotation which showed approximately equal and opposite values: Fr1: $[a]^{25}{}_D$+12.0° (c=0.1, MeOH); Fr2: $[a]^{25}{}_D$−13.0° (c=0.1, MeOH).

Figure 20A:
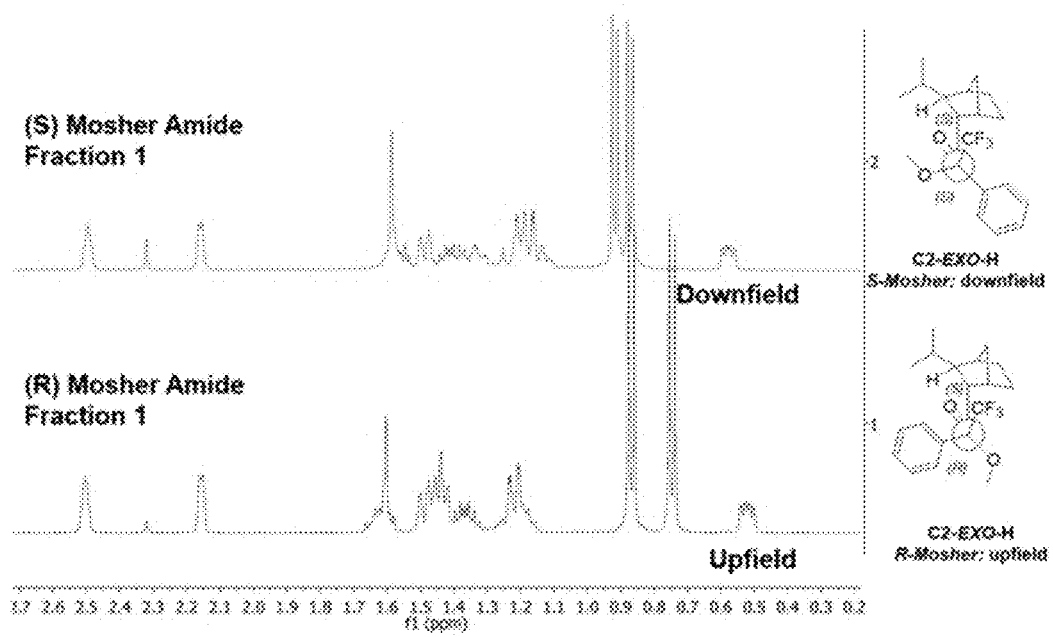
FIGS. 20A and 20B show that $^1$H-NMR spectra of enantiopure Mosher amides presented distinct display diagnostic chemical shift differences.
Figure 20B:
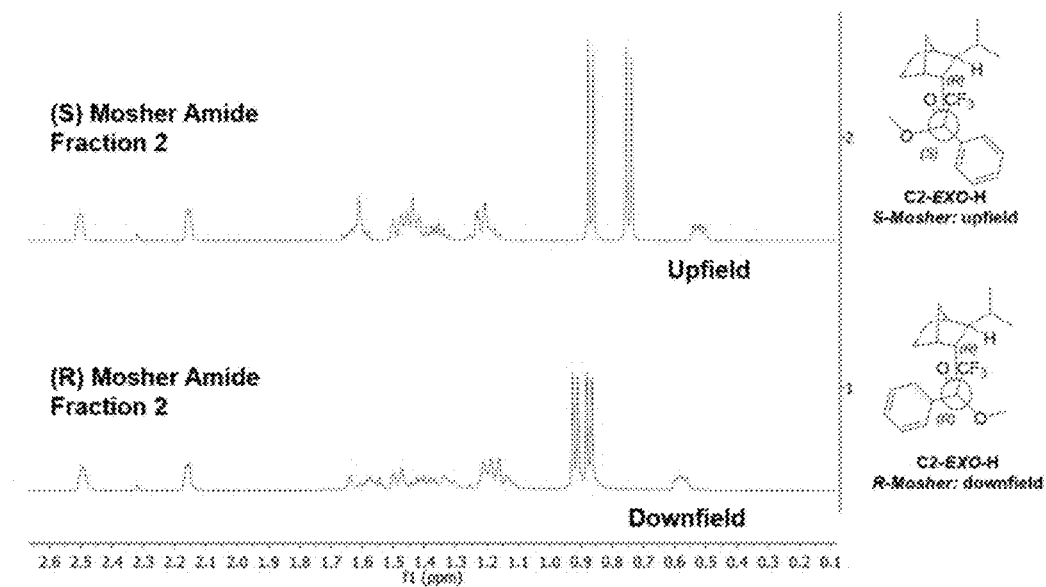

To determine the absolute configuration of BRD-4780 enantiomers, Mosher's model was employed. First, the (+/−) BRD-4780 was derivatized with optically-pure (S)-Mosher's acid chloride. The resulting diastereomeric mixture of (S)-Mosher amides were analyzed by $^1$H NMR spectroscopy and compared to the BRD-4780 $^1$H NMR spectrum. The BRD-4780 C3 proton has a chemical shift of 1.18 ppm while the C3 proton of the mixture of (R)-Mosher amide diastereomers displayed two magnetically inequivalent peaks well resolved and separated with chemical shifts of 0.57 ppm and 0.52 ppm. Then, the (R)- and (S)-Mosher amides were synthesized with both pure BRD-4780 enantiomers. For the BRD-4780 enantiomer with (2R, 3R) configuration, the C3 proton of the R-Mosher diastereoisomer is more downfield than that of the (S)-Mosher diastereoisomer (Fr2). For the enantiomer with the absolute configuration of (2S, 3S), the C3 proton of the (R)-Mosher diastereoisomer is more upfield than the amide formed from the (S)-Mosher acid (FIGS. 20A and 20B).

The pure enantiomers were profiled in the high-content imaging assay for the ability to reduce the amount of FS MUC1 protein in the cytoplasm (Table 1). As was the case for the racemic compound, BRD-4780, there was no observed reduction in wild-type MUC1 levels.

TABLE 1

| Bioactivity of enantiopure BRD-4780 Fr1 and Fr2 | | |
|---|---|---|
| Fraction, Optical rotation | FS MUC1 cytoplasm IC$_{50}$ (uM) | FS MUC1 cytoplasm EMax (%) |
| Fr1, (+) | 0.73 | −39 |
| Fr2, (−) | 0.66 | −39 |

In summary, a method for the preparation of (1R,2R,3R,4S)-3-isopropylbicyclo[2.2.1]heptan-2-amine and (1S,2S,3S,4R)-3-isopropylbicyclo[2.2.1]heptan-2-amine and the corresponding hydrochloride salts in high enantiopurity has been developed, and the absolute stereo-chemistry of the individual enantiomers has been assigned using the Mosher amide method. The instant procedure relies on derivatization of the BRD-4780 amino group, which enabled detection and appeared to be required for efficient separation on the stationary phase identified by methods screening and development. The applicability of this approach has been demonstrated on the hundred milligram scale, and it is projected that the instant process will be applicable to larger scale preparative applications (Caille et al. (2010) *Org Process Res Dev.* 14: 133-141). The ability of these compounds to remove FS MUC1 protein from cells has been profiled in vitro.

Scheme 1. Literature Synthesis of Racemic BRD-4780

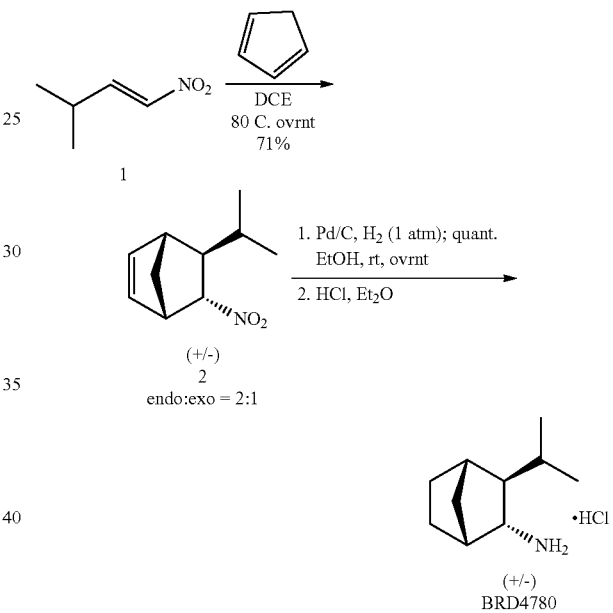

TABLE 2

| | | Summary of Example 15 Compounds | | | | |
|---|---|---|---|---|---|---|
| Entry | Compounds | Col2: OJ—H 3-50% iPrOH | Col3: AD—H 3-50% iPrOH | Col4: AS—H 3-50% iPrOH | Col5: IC 3-50% iPrOH | Col6: OD—H 3-50% iPrOH |
| 1 | (+/−) 3 | Moderate separation Δt$_R$ = 0.14 min | No separation | No separation | No separation | No separation |

TABLE 2-continued

Summary of Example 15 Compounds

| Entry | Compounds | Col2: OJ—H 3-50% iPrOH | Col3: AD—H 3-50% iPrOH | Col4: AS—H 3-50% iPrOH | Col5: IC 3-50% iPrOH | Col6: OD—H 3-50% iPrOH |
|---|---|---|---|---|---|---|
| 2 | 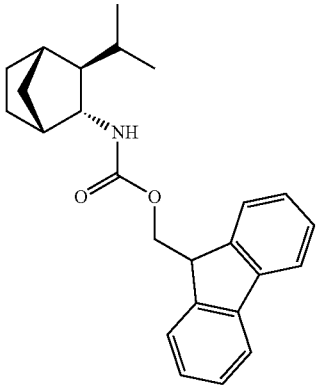<br>(+/−)<br>4 | Weak separation $\Delta t_R = 0.06$ min | Weak separation $\Delta t_R = 0.05$ min | No separation | No separation | No separation |
| 3 | 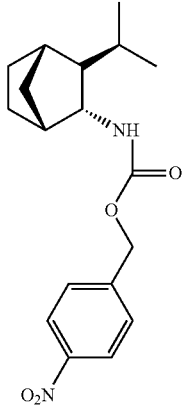<br>(+/−)<br>5 | No separation | Well separated $\Delta t_R = 0.46$ min | No separation | No separation | Weak separation $\Delta t_R = 0.34$ min |
| 4 | 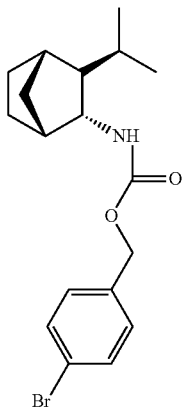<br>(+/−)<br>6 | Moderate separation $\Delta t_R = 0.13$ min | Moderate separation $\Delta t_R = 0.13$ min | No separation | No separation | Moderate separation $\Delta t_R = 0.21$ min |

TABLE 2-continued

Summary of Example 15 Compounds

| Entry | Compounds | Col2: OJ—H 3-50% iPrOH | Col3: AD—H 3-50% iPrOH | Col4: AS—H 3-50% iPrOH | Col5: IC 3-50% iPrOH | Col6: OD—H 3-50% iPrOH |
|---|---|---|---|---|---|---|
| 5 | 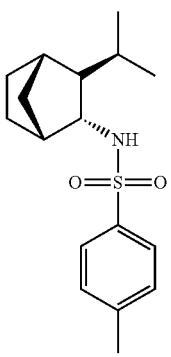 (+/−) 7 | No separation | Well separated $\Delta t_R = 0.27$ min | No separation | No separation | No separation |
| 6 | 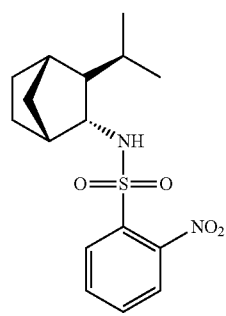 (+/−) 8 | No separation | No separation | Moderate separation $\Delta t_R = 0.15$ min | No separation | No separation |
| 7 | 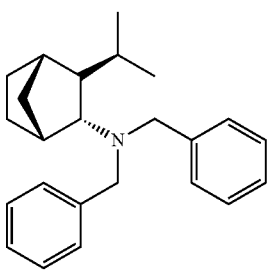 (+/−) 9 | Weak separation $\Delta t_R = 0.08$ min | No separation | No separation | No separation | No separation |
| 8 | 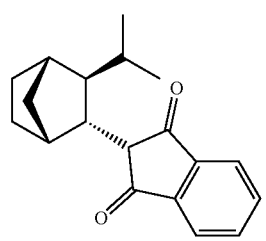 (+/−) 10 | No separation | No separation | No separation | No separation | No separation |

TABLE 2-continued

Summary of Example 15 Compounds

| Entry | Compounds | Col2: OJ—H 3-50% iPrOH | Col3: AD—H 3-50% iPrOH | Col4: AS—H 3-50% iPrOH | Col5: IC 3-50% iPrOH | Col6: OD—H 3-50% iPrOH |
|---|---|---|---|---|---|---|
| 9 | endo (+/−) 11 | No separation | Weak separation $\Delta t_R = 0.1$ min | Weak separation $\Delta t_R = 0.15$ min | Weak separation $\Delta t_R = 0.15$ min | No separation |
| 10 | Endo:exo 2:1 | No separation | Weak separation- multiple peaks from reaction mixture | No separation | No separation | No separation |
| 11 | BRD4780 | No separation | No separation | No separation | No separation | No separation |

TABLE 3

Optimization of Compounds 5 and 7 with Other Solvents Systems

| Entry | Solvents | Chiral Column | B1:MeOH | B2:MeOH + 0.1% TFA | B3:MeOH + 0.05% Et₃N | B4:iPrOH |
|---|---|---|---|---|---|---|
| 1 | (+/−) 5 | Col3: AD—H | Moderate separation $\Delta t_R = 0.14$ min | Moderate separation $\Delta t_R = 0.13$ min | Moderate separation $\Delta t_R = 0.13$ min | Well separated $\Delta t_R = 0.46$ min |

TABLE 3-continued

Optimization of Compounds 5 and 7 with Other Solvents Systems

| Entry | Solvents | Chiral Column | B1:MeOH | B2:MeOH + 0.1% TFA | B3:MeOH + 0.05% Et₃N | B4:iPrOH |
|---|---|---|---|---|---|---|
| 2 | | Col3: AD—H | Well separated $\Delta t_R = 0.76$ min | Well separated $\Delta t_R = 0.78$ min | Well separated $\Delta t_R = 0.78$ min | Moderate separation $\Delta t_R = 0.27$ min |

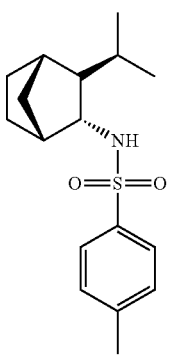

(+/-)
7

Scheme 2. Preparation of Isolated BRD-4780 Enantiomers

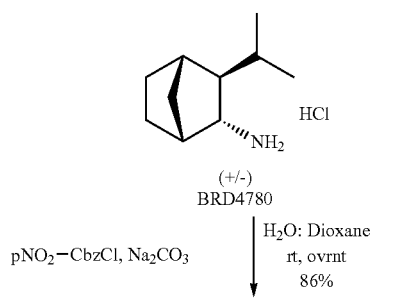

(+/-)
BRD4780 pNO₂—CbzCl, Na₂CO₃ | H₂O: Dioxane
rt, ovrnt
86%

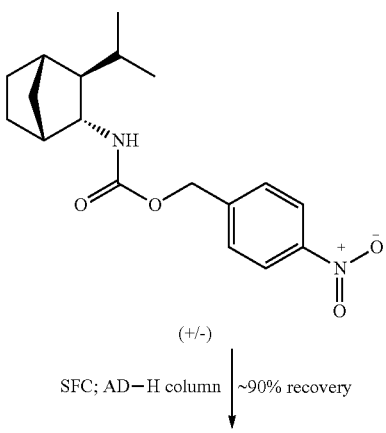

(+/-)

SFC; AD—H column | ~90% recovery

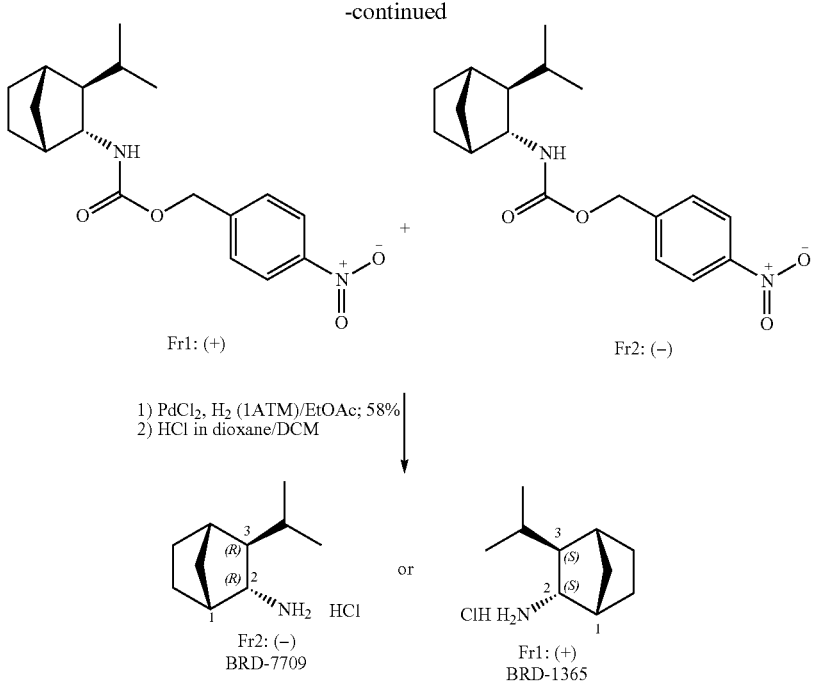

Fr1: (+)

Fr2: (−)

1) PdCl$_2$, H$_2$ (1ATM)/EtOAc; 58%
2) HCl in dioxane/DCM

Fr2: (−)
BRD-7709 or

Fr1: (+)
BRD-1365

Experimental Processes

Analytical scale SFC conditions: columns: CHIRALCEL OJ-H, AD-H, AS-H, IC and OD-H (250×4.6 mm×5 um); Flow rate: 1.5 mL/min; Mobile phases: MeOH, MeOH+1% TFA, MeOH+0.05% Et$_3$N and iPrOH; ABPR: 136 Bar; Column oven temp.: 45° C.

Preparative scale SFC conditions for the separation of 3: Column: CHIRALCEL OX-H (250×21 mm×5 um); Flow rate: 85 mL/min; Mobile phase: Line-A: 93% of Liq. CO$_2$, Line-B: 7% of 0.1% DEA in IPA: Acetonitrile (50:50); Sample injection: 10 mg; ABPR: 100 Bar; Column oven temp.: ambient. Incomplete separation.

Preparative scale SFC conditions for the separation of 5: Column: CHIRALCEL AD-H (250×21 mm×5 um); Flow rate: 90 mL/min; Mobile phase: Line-A: 90% of Liq. CO$_2$, Line-B: 10% IPA; Sample injection: 25 mg; ABPR: 100 Bar; Column oven temp.: ambient. Full Baseline separation.

Procedures rac-benzyl ((1R,2R,3R,4S)-3-isopropylbicyclo[2.2.1]heptan-2-yl)carbamate, 3

To a stirred solution of rac-(1R,2R,3R,4S)-3-isopropyl-norbornan-2-amine hydrochloride (37 mg, 0.196 mmol, 1.00 eq) and disodium carbonate (22 mg, 0.206 mmol, 1.05 eq) in water (1 mL), at 0° C. was added slowly benzyl carbonochloridate (0.028 mL, 0.196 mmol, 1.00 eq). After 20 min of stirring, additional water (0.5 mL) was added and the reaction mixture was stirred for another hour. After complete addition, diethyl ether was added and the product was extracted 3 times with ether. The combined organic layers were washed with HCl (1 M) and NaOH (1 M), dried with MgSO4, filtered and concentrated. The crude residue was purified with flash chromatography on silica gel (Hexane/EtOAc) to afford the desired racemic benzyl ((1R,2R,3R,4S)-3-isopropylbicyclo[2.2.1]heptan-2-yl)carbamate (25 mg, 44% yield) as a solid.

$^1$H NMR (400 MHz, Chloroform-d) δ 7.36 (m, 5H), 5.11 (m, 2H), 4.79 (d, J=7.9 Hz, 1H), 3.62 (m, 1H), 2.43 (m, 1H), 2.12 (d, J=4.2 Hz, 1H), 1.65-1.57 (m, 2H), 1.51 (m, 4H), 1.22 (dd, J=10.1 Hz, 2.1 Hz, 1H), 1.14 (m, 1H), 0.89 (m, 6H), 0.49 (m, 1H).

$^{13}$C NMR (101 MHz, Chloroform-d) δ 155.90, 136.81, 128.66, 128.21, 66.70, 58.52, 58.42, 41.04, 39.43, 35.61, 32.24, 30.87, 21.86, 21.18, 20.23.

MS(ESI): 288.7 [M+H]+ rac-(9H-fluoren-9-yl)methyl ((1R,2R,3R,4S)-3-isopropylbicyclo[2.2.1]heptan-2-yl)carbamate, 4

To a stirred solution of rac-(1R,2R,4S)-3-(1-methylethyl)norbornan-2-amine hydrochloride (37 mg, 0.196 mmol, 1.00 eq) in 1,4-dioxane (1 mL), was added sodium carbonate (1.0 M in water, 0.21 mL, 0.206 mmol, 1.05 eq). At 0° C., a solution of 9H-fluoren-9-ylmethyl carbonochloridate (51 mg, 0.196 mmol, 1.00 eq) in dioxane (0.2 ml) was added. The reaction mixture was allowed to warm up to room temperature and was stirred for overnight. Water was poured into the reaction mixture and the product was extracted with EtOAc. The organic layer was dried with MgSO$_4$, filtered and concentrated. The crude residue was purified with flash chromatography (Hexane/EtOAc 0-30%) to afford the desired rac (9H-fluoren-9-yl)methyl ((1R,2R,3R,4S)-3-isopropylbicyclo[2.2.1]heptan-2-yl)carbamate (30 mg, 41% yield).

$^1$H NMR (400 MHz, Chloroform-d) δ 7.77 (d, J=7.5 Hz, 2H), 7.64-7.56 (m, 2H), 7.45-7.36 (m, 2H), 7.32 (ddd, J=7.4, 7.4, 1.2 Hz, 2H), 4.79 (d, J=7.5 Hz, 1H), 4.44 (m, 2H), 4.23 (m, 1H), 3.59 (m, 1H), 2.42 (s, 1H), 2.13 (m, 1H), 1.68-1.50 (m, 1H), 1.48-1.30 (m, 3H), 1.22 (s, 2H), 0.95-0.83 (m, 6H), 0.50 (ddd, J=9.8, 5.4, 2.0 Hz, 1H).

13C NMR (101 MHz, DMSO-d6) δ 155.61, 143.93, 143.88, 140.72, 127.60, 127.00, 125.25, 125.21, 120.10, 65.03, 58.12, 54.29, 46.84, 40.60, 39.52, 38.78, 36.22, 35.03, 31.74, 29.94, 21.75, 20.79, 19.73.

MS(ESI): 376.5 [M+H]

rac-4-nitrobenzyl ((1R,2R,3R,4S)-3-isopropylbicyclo[2.2.1]heptan-2-yl)carbamate, 5

To a vial containing rac-(1R,2R,3R,4S)-3-isopropylnorbornan-2-amine hydrochloride (1.00 g, 5.27 mmol, 1.00 eq) and (4-nitrophenyl)methyl carbonochloridate (1.19 g, 5.53 mmol, 1.05 eq) were added dioxane (25 mL) and sodium carbonate (1.0 M in water, 5.53 mL, 5.53 mmol, 1.05 eq). The reaction mixture was stirred at room temperature for 18 hours. Water was poured into the reaction mixture and the product was extracted with EtOAc. The organic layer was dried with $MgSO_4$, filtered and concentrated. The crude residue was purified with flash chromatography (silica gel, Hexane/EtOAc 0-40%) to afford the desired product rac-4-nitrobenzyl ((1R,2R,3R,4S)-3-isopropylbicyclo[2.2.1]heptan-2-yl)carbamate (1.57 g, 90% yield).

$^1$H-NMR (400 MHz, Chloroform-d) δ 8.22 (d, J=8.5 Hz, 2H), 7.50 (d, J=8.4 Hz, 2H), 5.18 (m, 2H), 4.83 (d, J=7.9 Hz, 1H), 3.59 (m, 1H), 2.43 (m, 1H), 2.15 (d, J=3.6 Hz, 1H), 1.60-1.52 (m, 2H), 1.49-1.33 (m, 4H), 1.23-1.10 (m, 2H), 0.89 (m, 6H), 0.50 (m, 1H).

MS (ESI): 333.3 [M+H]+ rac-4-bromobenzyl ((1R,2R,3R,4S)-3-isopropylbicyclo[2.2.1]heptan-2-yl)carbamate, 6

To a stirred solution of rac-(2R,3R)-3-isopropylnorbornan-2-amine hydrochloride (30 mg, 0.158 mmol, 1.00 eq) and disodium carbonate (34 mg, 0.316 mmol, 2.00 eq) in 1,4-dioxane (1 mL) was added (4-bromophenyl)methyl carbonochloridate (24 uL, 0.158 mmol, 1.00 eq). The reaction mixture was stirred at room temperature for 24 hours. The reaction mixture was filtered and the filtrate was concentrated. The crude residue was purified with flash chromatography (Hexane/EtOAc 0-25%) to afford the desired rac-4-bromobenzyl ((1R,2R,3R,4S)-3-isopropylbicyclo[2.2.1]heptan-2-yl)carbamate (9 mg, 16%) as a white solid.

$^1$H-NMR (400 MHz, Chloroform-d) δ 7.51 (d, J=8.0 Hz, 2H), 7.24 (d, J=8.0 Hz, 2H), 5.03 (m, 2H), 4.76 (d, J=7.9 Hz, 1H), 3.58 (m, 1H), 2.42 (s, 1H), 2.13 (d, J=3.6 Hz, 1H), 1.64-1.58 (m, 3H), 1.49-1.32 (m, 4H), 1.19 (dd, J=10.3, 2.0 Hz, 1H), 1.16-1.07 (m, 1H), 0.88 (m, 6H), 0.51-0.43 (m, 1H).

$^{13}$C NMR (101 MHz, Chloroform-d) δ 155.69, 145.43, 131.78, 129.84, 65.84, 58.48, 58.45, 41.02, 39.41, 35.60, 35.41, 32.23, 30.82, 21.86, 21.17, 20.21.

MS (ESI): 336.2/368.3 [M+H]+ rac-N-((1R,2R,3R,4S)-3-isopropylbicyclo[2.2.1]heptan-2-yl)-4-methylbenzenesulfonamide, 7

To a stirred solution of rac-(2R,3R)-3-isopropylnorbornan-2-amine hydrochloride (39 mg, 0.254 mmol, 1.00 eq) in dry dichloromethane (1 mL), at 0° C. and under $N_2$ was added triethylamine (0.071 mL, 0.509 mmol, 2.00 eq) and a solution of 4-methylbenzenesulfonyl chloride (53 mg, 0.280 mmol, 1.10 eq) in DCM (0.2 ml). The reaction mixture was allowed to warm up to room temperature and was stirred for 2.5 days. Water was poured into the reaction mixture and the product was extracted with DCM. The organic layer was dried with $MgSO_4$, filtered and concentrated. The crude residue was purified with flash chromatography (silica gel, Hexane/EtOAc 0-15%) to afford the desired rac N-((1R,2R,3R,4S)-3-isopropylbicyclo[2.2.1]heptan-2-yl)-4-methylbenzenesulfonamide (36 mg, 57% yield).

$^1$H NMR (400 MHz, Chloroform-d) δ 7.77 (d, J=8.2 Hz, 2H), 7.28 (d, J=8.2 Hz, 2H), 4.74 (d, J=6.7 Hz, 1H), 3.13 (ddd, J=6.8, 5.3, 3.9 Hz, 1H), 2.42 (s, 3H), 2.11-2.01 (m, 2H), 1.56-1.42 (m, 2H), 1.34-1.17 (m, 3H), 1.10 (m, 2H), 0.82 (d, J=6.5 Hz, 3H), 0.69 (d, J=6.6 Hz, 3H), 0.51 (ddd, J=9.5, 5.1, 2.1 Hz, 1H).

$^{13}$C NMR (101 MHz, Chloroform-d) δ 143.39, 137.88, 129.68, 127.42, 60.42, 58.72, 40.78, 38.88, 35.45, 32.18, 30.59, 21.80, 21.69, 20.90, 20.00.

MS (ESI): 306.1 [M−H]− rac-N-((1R,2R,3R,4S)-3-isopropylbicyclo[2.2.1]heptan-2-yl)-2-nitrobenzenesulfonamide, 8

To a stirred solution of rac-(1R,2R,3R,4S)-3-(1-methylethyl)norbornan-2-amine (30 mg, 0.196 mmol, 1.00 eq) in dry dichloromethane (1 mL), at 0° C. and under $N_2$ was added triethylamine (0.055 mL, 0.391 mmol, 2.00 eq) and a solution of 2-nitrobenzenesulfonyl chloride (48 mg, 0.215 mmol, 1.10 eq) in DCM (0.2 ml). The reaction mixture was allowed to warm up to room temperature and was stirred for 1 hour. Water was poured into the reaction mixture and the product was extracted with DCM. The organic layer was dried with $MgSO_4$, filtered and concentrated to afford the desired rac-N-((1R,2R,3R,4S)-3-isopropylbicyclo[2.2.1]heptan-2-yl)-2-nitrobenzenesulfonamide (37 mg, 56% yield).

$^1$H NMR (400 MHz, Chloroform-d) δ 8.19-8.12 (m, 1H), 7.88-7.81 (m, 1H), 7.79-7.68 (m, 2H), 5.41 (d, J=7.0 Hz, 1H), 3.37 (ddd, J=7.0, 5.4, 4.0 Hz, 1H), 2.25-2.04 (m, 2H), 1.63-1.42 (m, 2H), 1.42-1.07 (m, 6H), 0.85 (d, J=6.6 Hz, 3H), 0.70 (d, J=6.6 Hz, 3H), 0.63 (ddd, J=9.7, 5.2, 2.1 Hz, 1H).

MS (ESI): 337.2 [M−H]− rac-(1R,2R,3R,4S)−N,N-dibenzyl-3-isopropylbicyclo[2.2.1]heptan-2-amine, 9

To stirred a solution of rac-(1R,2R,3R,4S)-3-isopropylbicyclo[2.2.1]heptan-2-amine (0.3 g, 1.960 mmol, 1.0 eq) in N,N-dimethylformamide (3 mL) and potassium carbonate (0.541 g, 3.92 mmol, 2 eq) was added and reaction mass was stirred for 15 min at room temperature. To this, benzyl bromide (0.268 g, 1.568 mmol, 0.8 eq) was added drop wise and reaction mass was stirred at room temperature for 1 h. After completion of reaction, reaction mixture was diluted with water (10 mL) and extracted with dichloromethane (2×10 mL). The combined organic was dried over anhydrous sodium sulfate, filtered and concentrated to get crude material, which was purified using silica gel column chromatography (10% ethyl acetate in hexanes) to get (0.1 g, 0.299 mmol, 15%) of the product.

MS (ESI): 334.2 [M+H]+.

rac-2-((1R,2R,3R,4S)-3-isopropylbicyclo[2.2.1]heptan-2-yl)isoindoline-1,3-dione, 10

To a pressure vessel rac-(2R,3R)-3-isopropylbicyclo[2.2.1]heptan-2-amine (0.150 g, 0.980 mmol, 1 eq.) in N,N-dimethylacetamide (2 mL) was added isobenzofuran-1,3-dione (0.156 g, 1.043 mmol, 1.6 eq) and the reaction mixture was stirred at 180° C. for 3 h. After completion of reaction, reaction mixture was diluted with water and extracted with ethyl acetate (3×20 mL) and the combined organic layer was dried over anhydrous sodium sulphate, filtered and concentrated to get crude, which was purified by silica gel column chromatography (3% ethyl acetate in hexanes) the desired product (160 mg, 0.564 mmol, 58%).

$^1$H NMR (400 MHz, Chloroform-d) δ 7.86 (m, 2H), 7.74 (m, 2H), 4.13 (m, 1H), 2.53-2.48 (m, 2H), 2.41 (m, 1H), 1.78-1.68 (m, 1H), 1.68-1.61 (m, 2H), 1.46-1.40 (m, 2H), 1.30-1.24 (m, 2H), 0.98 (d, J=6.5 Hz, 3H), 0.76 (d, J=6.6 Hz, 3H).

MS (ESI): 284.1 [M−H]$^+$.

N-((3R)-3-isopropylbicyclo[2.2.1]hept-5-en-2-yl) acetamide, 11

To a stirred solution of crude rac-(1S,4R,6R)-5-isopropyl-6-nitro-bicyclo[2.2.1]hept-2-ene (endo:exo NO$_2$ is ~2:1) (5.39 g, 27.6 mmol, 1.00 eq) in (1:1) mixture of methanol (50 mL) and aqueous solution of saturated ammonium formate (50 mL) was added lot wise zinc dust (9.02 g, 138 mmol, 5.00 eq) over a period of 10 minutes at room temperature. The resulting reaction mixture was stirred at room temperature for 12 h. After completion of the reaction, reaction mass was filtered through celite pad and washed with methanol (2×30 mL). The organic layer was basified with saturated ammonium bicarbonate (150-160 mL) till pH=9-10. The resultant aqueous layer was extracted with dichloromethane (2×90 mL), and the combined organic layers were dried over sodium sulphate, filtered through celite, and evaporated in under vacuum at low temperature to get impure product crude rac-(3R)-3-isopropylbicyclo[2.2.1]hept-5-en-2-amine (4 g, 26.45 mmol, 96%) and used in next step with our further purification. MS (ESI): 152.2 [M+H]$^+$ To a stirred solution of the crude rac-(3R)-3-isopropylbicyclo[2.2.1]hept-5-en-2-amine (2.00 g, 13.2 mmol, 1.00 eq) and triethyl amine (4.6 mL, 33.1 mmol, 2.50 eq) in toluene (30 mL) was added acetyl chloride (1.4 mL, 19.8 mmol, 1.50 eq) at 0° C. The reaction mixture was stirred at room temperature for 12 h. After completion of reaction, the reaction was diluted by addition of water (30 mL), and the layers were separated. The aqueous layer was extracted with dichloromethane (2×50 mL) and the combined organics were dried over anhydrous sodium sulphate, filtered through celite and evaporated to provide crude material, which was purified by silica gel chromatography (25% ethyl acetate in hexanes) to provide N-[rac-(2R,3R)-3-isopropyl-2-bicyclo[2.2.1]hept-5-enyl]acetamide, 11 (endo isomer, 0.65 g, 3.36 mmol, 25%). The N-[rac-(2S,3S)-3-isopropyl-2-bicyclo[2.2.1]hept-5-enyl]acetamide eluted after the endo isomer was also isolated (exo isomer, 0.55 g, 2.85 mmol, 22%).

$^1$H NMR (400 MHz, Chloroform-d) δ 6.42 (dd, J=5.8, 3.2 Hz, 1H), 6.06 (dd, J=5.7, 2.8 Hz, 1H), 5.15 (bs, 1H), 4.16 (m, 1H), 3.00 (m, 1H), 2.73 (m, 1H), 1.93 (s, 3H), 1.68 (s, 2H), 1.59-1.41 (m, 1H), 1.33-1.25 (m, 1H), 0.98 (m, 6H).

MS (ESI): 194.2 [M+H]+

Representative deprotection of enantiomerically pure 5. (+) and (−) BRD-4780

To a stirred solution of PdCl$_2$ (250 mg, w/w) in ethyl acetate (2.5 mL) was added a solution of enantiopure 4-nitrobenzyl ((1R,2R,3R,4S)-3-isopropylbicyclo[2.2.1]heptan-2-yl)carbamate (250 mg, 0.752 mmol) in ethyl acetate (2.5 mL)) under nitrogen atmosphere. The reaction mass was stirred at room temperature for 2 h under hydrogen purging. The reaction mixture was filtered through celite bed and washed with ethyl acetate (2×15 mL). The filtrate was concentrated, dissolved in 2 mL of dichloromethane and cooled to 0° C. 4M hydrochloric acid in 1,4-dioxane (0.2 mL) was added drop wise and reaction mixture was stirred at room temperature for 15 min, concentrated and triturated with n-pentane to get (1R,2R,3R,4S)-3-isopropylbicyclo[2.2.1]heptan-2-amine hydrochloride (73 mg, 0.385 mmol, 51%). NMR and MS characterization were identical to authentic racemic AGN192403. Fraction 1: [a]$^{25}_D$+12.0° (c=0.1, MeOH); Fraction 2: [a]$^{25}_D$−13.0° (c=0.1, MeOH).

BRD-4780 (R) Mosher amide, Fr1. (R)-3,3,3-trifluoro-N-((1S,2S,3S,4R)-3-isopropylbicyclo[2.2.1]heptan-2-yl)-2-methoxy-2-phenylpropanamide To a stirred solution of (1S,2S,3S,4R)-3-isopropylbicyclo[2.2.1]heptan-2-amine hydrochloride (10 mg, 0.053 mmol, 1.00 eq) and N,N-diethylethanamine (22 uL, 0.158 mmol, 3.00 eq) in dichloromethane (0.50 mL) was added (2S)-3,3,3-trifluoro-2-methoxy-2-phenyl-propanoyl chloride (15 mg, 0.0580 mmol, 1.10 eq). The reaction mixture was stirred at room temperature for 1 hour. Then, the reaction mixture was concentrated and purified with flash chromatography (silica gel, Hexane/EtOAC 0-30%) to afford the desired (R)-3,3,3-trifluoro-N-((1S,2S,3S,4R)-3-isopropylbicyclo[2.2.1]heptan-2-yl)-2-methoxy-2-phenylpropanamide (10 mg, 51% yield).

$^1$H NMR (400 MHz, Chloroform-d) δ 7.55-7.49 (m, 2H), 7.40-7.35 (m, 3H), 6.64 (d, J=8.0 Hz, 1H), 3.83 (m, 1H), 3.45 (q, J=1.6 Hz, 3H), 2.50 (m, 1H), 2.16 (d, 3.6 Hz, 1H), 1.61 (m, 1H), 1.46 (m, 3H), 1.37 (m, 1H), 1.24-1.19 (m, 2H), 0.87 (d, J=6.6 Hz, 3H), 0.75 (d, J=6.6 Hz, 3H), 0.52 (ddd, J=9.9, 5.2, 2.0 Hz, 1H).

13C NMR (101 MHz, Chloroform-d) δ 165.68, 132.90, 129.53, 128.53, 127.75, 125.35, 122.47 58.24, 56.79, 55.26, 41.10, 39.54, 35.81, 32.09, 30.74, 21.90, 21.31, 20.06.

BRD-4780-(S) Mosher amide, Fr1. (S)-3,3,3-trifluoro-N-((1S,2S,3S,4R)-3-isopropylbicyclo[2.2.1]heptan-2-yl)-2-methoxy-2-phenylpropanamide To a stirred solution of (1S,2S,3S,4R)-3-isopropylbicyclo[2.2.1]heptan-2-amine hydrochloride (10 mg, 0.0527 mmol, 1.00 eq) and N,N-diethylethanamine (22 uL, 0.158 mmol, 3.00 eq) in dichloromethane (0.50 mL) was added (2R)-3,3,3-trifluoro-2-methoxy-2-phenyl-propanoyl chloride (15 mg, 0.0580 mmol, 1.10 eq). The reaction mixture was stirred at room temperature for 1 hour. Then, the reaction mixture was concentrated and purified with flash chromatography (silica gel, Hexane/EtOAC 0-30%) to afford the desired (R)-3,3,3-trifluoro-N-((1S,2S,3S,4R)-3-isopropylbicyclo[2.2.1]heptan-2-yl)-2-methoxy-2-phenylpropanamide (8 mg, 31% yield).

$^1$H NMR (400 MHz, Chloroform-d) δ 7.55-7.49 (m, 2H), 7.43-7.35 (m, 3H), 6.63 (d, J=7.7 Hz, 1H), 3.83 (m, 1H), 3.44 (q, J=1.6 Hz, 3H), 2.50 (m, 1H), 2.16 (d, 3.6 Hz, 1H), 1.59 (m, 2H), 1.51-1.45 (m, 1H), 1.45-1.36 (m, 1H), 1.24-1.11 (m, 3H), 0.92 (d, J=6.5 Hz, 3H), 0.87 (d, J=6.6 Hz, 3H), 0.58 (ddd, J=10.0, 5.3, 2.0 Hz, 1H).

$^{13}$C NMR (101 MHz, Chloroform-d) δ 165.90, 133.10, 129.55, 128.60, 127.81, 125.35, 122.47, 58.22, 56.93, 55.21, 40.71, 39.52, 35.75, 32.24, 30.78, 21.94, 21.23, 20.08.

BRD-4780-(R) Mosher amide, Fr2. (R)-3,3,3-trifluoro-N-((1R,2R,3R,4S)-3-isopropylbicyclo[2.2.1]heptan-2-yl)-2-methoxy-2-phenylpropanamide To a stirred solution of (1R,2R,3R,4S)-3-isopropylbicyclo[2.2.1]heptan-2-amine hydrochloride (12 mg, 0.0527 mmol, 1.00 eq) and N,N-diethylethanamine (22 uL, 0.158 mmol, 3.00 eq) in dichloromethane (0.50 mL) was added (2S)-3,3,3-trifluoro-2-methoxy-2-phenyl-propanoyl chloride (15 mg, 0.0580 mmol, 1.10 eq). The reaction mixture was stirred at room temperature for 2 hours. Then, the reaction mixture was concentrated and purified with flash chromatography (silica gel, Hexane/EtOAC 0-30%) to afford the desired (R)-3,3,3-trifluoro-N-((1S,2S,3S,4R)-3-isopropylbicyclo[2.2.1]heptan-2-yl)-2-methoxy-2-phenylpropanamide (14 mg, 60% yield).

$^1$H NMR (400 MHz, Chloroform-d) δ 7.56-7.47 (m, 2H), 7.42-7.33 (m, 3H), 6.63 (d, J=7.9 Hz, 1H), 3.87-3.80 (m, 1H), 3.44 (d, J=1.6 Hz, 3H), 2.49 (m, 1H), 2.16 (d, J=4.2 Hz, 1H), 1.65-1.52 (m, 2H), 1.49 (m, 1H), 1.44-1.29 (m, 1H), 1.23-1.12 (m, 3H), 0.92 (d, J=6.5 Hz, 3H), 0.87 (d, J=6.6 Hz, 3H), 0.58 (ddd, J=10.0, 5.3, 1.9 Hz, 1H).

$^{13}$C NMR (101 MHz, Chloroform-d) δ 165.89, 133.11, 129.53, 128.58, 127.82, 125.36, 122.48, 58.23, 56.93, 55.20, 40.72, 39.53, 35.75, 32.24, 30.78, 21.92, 21.23, 20.07.

BRD-4780-(S) Mosher amide, Fr2. (S)-3,3,3-trifluoro-N-((1R,2R,3R,4S)-3-isopropylbicyclo[2.2.1]heptan-2-yl)-2-methoxy-2-phenylpropanamide To a stirred solution of (1R,2R,3R,4S)-3-isopropylbicyclo[2.2.1]heptan-2-amine hydrochloride (12 mg, 0.0527 mmol, 1.00 eq) and N,N-diethylethanamine (22 uL, 0.158 mmol, 3.00 eq) in dichloromethane (0.50 mL) was added (2R)-3,3,3-trifluoro-2-methoxy-2-phenyl-propanoyl chloride (15 mg, 0.0580 mmol, 1.10 eq). The reaction mixture was stirred at room temperature for 2 hours. Then, the reaction mixture was concentrated and purified with flash chromatography (silica gel, Hexane/EtOAC 0-30%) to afford the desired (R)-3,3,3-trifluoro-N-((1S,2S,3S,4R)-3-isopropylbicyclo[2.2.1]heptan-2-yl)-2-methoxy-2-phenylpropanamide (14 mg, 60% yield).

$^1$H NMR (400 MHz, Chloroform-d) δ 7.55-7.49 (m, 2H), 7.41-7.35 (m, 3H), 6.64 (d, J=8.2 Hz, 1H), 3.83 (m, 1H), 3.45 (q, J=1.6 Hz, 3H), 2.50 (m, 1H), 2.16 (d, J=3.8 Hz, 1H), 1.61 (m, 2H), 1.52-1.41 (m, 2H), 1.36 (m, 1H), 1.22 (m, 2H), 0.87 (d, J=6.5 Hz, 3H), 0.75 (d, J=6.6 Hz, 3H), 0.52 (ddd, J=9.9, 5.2, 2.0 Hz, 1H).

$^{13}$C NMR (101 MHz, Chloroform-d) δ 165.68, 132.91, 129.52, 128.53, 127.75, 125.36, 122.48, 58.25, 56.80, 55.24, 41.10, 39.55, 35.81, 32.09, 30.74, 21.89, 21.31, 20.06.

Example 16: Identification of Additional TMED9-Binding Agents

A further screen for TMED9-binding agents is performed upon cells harboring a misfolded protein of the secretory pathway (e.g., a MUC1 mutant protein (e.g., a MUC1 frameshift mutant protein), a UMOD pathogenic variant protein (e.g., a C126R UMOD mutant protein) and/or a rhodopsin mutant protein (e.g., a P23H rhodopsin mutant protein)). Cells harboring the misfolded protein of the secretory pathway are contacted with a library of test compounds (e.g., small molecule library, nucleic acid library and/or other macromolecule library), and immunofluorescence (or other appropriate means of detection) is employed to identify a preferential diminishment in misfolded protein levels in the cells, relative to a corresponding wild-type form of the misfolded protein. Additional TMED9-binding agents are thereby identified.

Treatments are currently lacking for toxic proteinopathies, which affect a wide range of cell types from neurons to photoreceptors to kidney cells, and result in debilitating and often fatal diseases (Bayer, 2015). New drug development to prevent or halt disease progression has been challenging, due in large part to the dearth of mechanism-based approaches (Dubnikov et al., 2017; Dugger and Dickson, 2017). Here, the molecular mechanism underlying a rare and poorly understood autosomal dominant kidney condition, MKD, has been elucidated, initially showing that MKD is a toxic proteinopathy. Using several models, it was demonstrated that MKD is caused by TMED9 cargo receptor-dependent retention of mutant MUC1-fs in the early secretory compartment. A lead molecule, BRD-4780, and its target, TMED9, were also identified. The molecule and the target demonstrated a heretofore unknown mechanism of action for the removal of mutant protein, based on binding to TMED9. Herein, answers to several important questions have been provided about both MKD and, more generally, mechanisms for clearance of misfolded secretory proteins. The instant findings also have important implications for future therapeutic efforts against toxic proteinopathies.

First, certain discoveries of the instant disclosure have elucidated the cellular mechanism by which the toxic proteinopathy MKD begins, with the accumulation of a mutant neo-protein. The results obtained show that accumulation of the protein alone is not immediately toxic, owing to the activation of the cytoprotective ATF6 branch of the UPR, and that additional stress signaling likely activates the pro-apoptotic branches of the UPR, ultimately leading to epithelial cell injury. This may explain the late onset of kidney failure in MKD patients (Bleyer et al., 2017), which is mirrored by the late onset of histologic changes in the kidneys of heterozygous knock-in mice. Without wishing to be bound by theory, it is speculated that while MKD patients accumulate MUC1-fs in kidney tubular epithelial cells throughout life, additional insults (such as exposure to nephrotoxins, inflammation or infections) and the general decline in UPR homeostasis that accompanies normal aging (Klaips et al., 2017) may ultimately lead to kidney failure.

In addition to revealing the molecular mechanism of MKD, the instant disclosure has identified a lead compound, BRD-4780, that is likely capable of clearing not only MUC1-fs, but also other misfolded proteins such as UMOD (C126R) and rhodopsin (P23H). In contrast, BRD-4780 had no effect on mutant huntingtin, which accumulates in the cytoplasm and nucleus. This underscores the specificity of BRD-4780 for misfolded proteins retained in the early secretory pathway. It is estimated that more than 20 known proteinopathies are associated with misfolded proteins trapped in compartments between the ER and Golgi apparatus (Dubnikov et al., 2017; Dugger and Dickson, 2017). Thus, BRD-4780 likely provides a therapeutic lead for multiple proteinopathies associated with mutant protein accumulation.

In addition to identifying a lead compound, the cargo receptor TMED9 (also known as p25 and p24α2; (Gomez-Navarro and Miller, 2016)) was discovered to be a molecular target for BRD-4780, thereby uncovering a previously unknown cell biological mechanism for misfolded protein cargo entrapment. Cargo receptors are proteins that span the membrane and physically link cargo with vesicle coat subunits to efficiently and selectively recruit soluble proteins to the emerging vesicles (Barlowe and Helenius, 2016; Geva and Schuldiner, 2014). MUC1-fs, trapped in TMED9 cargo receptor-enriched vesicles between the cis-Golgi and the ER, was identified herein as released by the action of BRD-4780, and was thus allowed to traffic through the secretory pathway into endosomes and finally into lysosomes, where it could be degraded. Precisely how BRD-4780 binding to TMED9 results in the re-routing of MUC1-fs into the lysosome remains unclear. Without wishing to be bound by theory, if TMED9 receptors directly bind MUC1-fs cargo, BRD-4780 (and potentially other TMED9-binding agents) may work by blocking (either competitively or non-competitively) MUC1-fs binding to its TMED9 receptor. Alternatively, BRD-4780 (and potentially other TMED9-binding agents) may block TMED9 interactions with other coatomer or integral vesicular proteins, thereby indirectly promoting MUC1-fs anterograde trafficking. The detailed molecular interactions between BRD-4780 (and potentially other TMED9-binding agents), TMED9 and MUC1-fs (or other misfolded protein cargoes) in the early secretory pathway are currently being examined.

The instant disclosure has revealed a new strategy of identifying cargo receptors that retain misfolded secretory proteins and producing compounds that promote their release and anterograde trafficking to the lysosome as a therapeutic approach to toxic proteinopathies.

BRD-4780 is a promising therapeutic lead. While careful toxicology studies are needed, there are several pieces of evidence that are reassuring about the safety of the compound: (i) in in vitro studies, BRD-4780 showed no overt toxicity at any concentration tested, and in fact, it rescued cells from THP-induced cell death, and (ii) in in vivo experiments, BRD-4780 was well tolerated at several doses up to 50 mg/kg with no overt toxicity. Additionally, BRD-4780 has excellent drug-like properties including excellent solubility, good microsomal and plasma stability, low protein binding and excellent oral bioavailability (FIG. 16). Therefore, this lead compound holds significant potential for its successful development into a therapy.

In summary, the molecular mechanism underlying MKD has been identified herein, and a small molecule possessing exciting and promising potential as a therapeutic lead for a class of difficult-to-treat diseases with no available treatments has also been discovered.

REFERENCES

Adamson, B., Norman, T. M., Jost, M., Cho, M. Y., Nunez, J. K., Chen, Y., Villalta, J. E., Gilbert, L. A., Horlbeck, M. A., Hein, M. Y., et al. (2016). A Multiplexed Single-Cell CRISPR Screening Platform Enables Systematic Dissection of the Unfolded Protein Response. Cell 167, 1867-1882 e21.

Adolf, F., Rhiel, M., Hessling, B., Gao, Q., Hellwig, A., Bé, J., and Wieland, F. T. (2019). Proteomic Profiling of Mammalian COPII and COPI Vesicles Correspondence. Cell Rep. 26, 250-265.

Al-bataineh, M. M., Kinlough, C. L., Poland, P. A., Pastor-Soler, N. M., Sutton, T. A., Mang, H. E., Bastacky, S. I., Gendler, S. J., Madsen, C. S., Singh, S., et al. (2016). Muc1 enhances the β-catenin protective pathway during ischemia-reperfusion injury. Am. J. Physiol. Physiol. 310, F569-F579.

Apostolopoulos, V., Stojanovska, L., and Gargosky, S. E. (2015). MUC1 (CD227): a multi-tasked molecule. Cell. Mol. Life Sci. 72, 4475-4500.

Athanasiou, D., Aguila, M., Bellingham, J., Li, W., McCulley, C., Reeves, P. J., and Cheetham, M. E. (2018). The molecular and cellular basis of rhodopsin retinitis pigmentosa reveals potential strategies for therapy. Prog Retin Eye Res 62, 1-23.

Barlowe, C., and Helenius, A. (2016). Cargo Capture and Bulk Flow in the Early Secretory Pathway. Annu. Rev. Cell Dev. Biol. 32, 197-222.

Bayer, T. A. (2015). Proteinopathies, a core concept for understanding and ultimately treating degenerative disorders? Eur. Neuropsychopharmacol. 25, 713-724.

Beck, R., Ravet, M., Wieland, F. T., Cassel, D., and Cassel, D. (2009). The COPI system: Molecular mechanisms and function. FEBS Lett. 583, 2701-2709.

Bittker, J. A. (2012). High-Throughput RT-PCR for Small-Molecule Screening Assays. In Current Protocols in Chemical Biology, (Hoboken, N.J., USA: John Wiley & Sons, Inc.), pp. 49-63.

Bleyer, A. J., Kidd, K., ivná, M., and Kmoch, S. (2017). Autosomal Dominant Tubulointerstitial Kidney Disease. Adv. Chronic Kidney Dis. 24, 86-93.

Bosshart, H., Straehl, P., Berger, B., and Berger, E. G. (1991). Brefeldin A induces endoplasmic reticulum-associated O-glycosylation of galactosyltransferase. J. Cell. Physiol. 147, 149-156.

Brandizzi, F., and Barlowe, C. (2013). Organization of the ER-Golgi interface for membrane traffic control. Nat Rev Mol Cell Biol 14, 382-392.

Caille et al. (2010) *Org Process Res Dev.* 14: 133-141.

Chardin, P., and McCormick, F. (1999). Brefeldin A. Cell 97, 153-155.

Corsello, S. M., Bittker, J. A., Liu, Z., Gould, J., McCarren, P., Hirschman, J. E., Johnston, S. E., Vrcic, A., Wong, B., Khan, M., et al. (2017). The Drug Repurposing Hub: a next-generation drug library and information resource. Nat Med 23, 405-408.

Dale and Mosher. (1973) J Am Chem Soc. 95: 512-519.

Dryja, T., and Li, T. (2017). Molecular genetics of retinitis pigmentosa. Hum. Mol. Genet.

Dubnikov, T., Ben-Gedalya, T., and Cohen, E. (2017). Protein quality control in health and disease. Cold Spring Harb. Perspect. Biol.

Dugger, B. N., and Dickson, D. W. (2017). Pathology of neurodegenerative diseases. Cold Spring Harb. Perspect. Biol.

Geva, Y., and Schuldiner, M. (2014). The Back and Forth of Cargo Exit from the Endoplasmic Reticulum. Curr. Biol. 24, R130-R136.

Gibier, J.-B., Hémon, B., Fanchon, M., Gaudelot, K., Pottier, N., Ringot, B., Van Seuningen, I., Glowacki, F., Cauffiez, C., Blum, D., et al. (2017). Dual role of MUC1 mucin in kidney ischemia-reperfusion injury: Nephroprotector in early phase, but pro-fibrotic in late phase. Biochim. Biophys. Acta—Mol. Basis Dis. 1863, 1336-1349.

Godiska, R., Mead, D., Dhodda, V., Wu, C., Hochstein, R., Karsi, A., Usdin, K, Entezam, A., and Ravin, N. (2010). Linear plasmid vector for cloning of repetitive or unstable sequences in *Escherichia coli.* Nucleic Acids Res. 38, e88.

Gomez-Navarro, N., and Miller, E. (2016). Protein sorting at the ER-Golgi interface. J. Cell Biol.

Hattrup, C. L., and Gendler, S. J. (2008). Structure and Function of the Cell Surface (Tethered) Mucins. Annu. Rev. Physiol. 70, 431-457.

Hetz, C. (2012). The unfolded protein response: controlling cell fate decisions under ER stress and beyond. Nat Rev Mol Cell Biol 13, 89-102.

Hetz, C., Chevet, E., and Oakes, S. A. (2015). Proteostasis control by the unfolded protein response. Nat. Cell Biol. 17, 829-838.

Hilkens, J., and Buijs, F. (1988). Biosynthesis of MAM-6, an epithelial sialomucin. Evidence for involvement of a rare proteolytic cleavage step in the endoplasmic reticulum. J. Biol. Chem. 263, 4215-4222.

Ishikawa, Y., Fedeles, S., Marlier, A., Zhang, C., Gallagher, A.-R., Lee, A.-H., and Somlo, S. (2019). Spliced XBP1

Rescues Renal Interstitial Inflammation Due to Loss of Sec63 in Collecting Ducts. J. Am. Soc. Nephrol. 30, 443-459.

Jafari, R., Almqvist, H., Axelsson, H., Ignatushchenko, M., Lundback, T., Nordlund, P., and Molina, D. M. (2014). The cellular thermal shift assay for evaluating drug target interactions in cells. Nat. Protoc. 9, 2100-2122.

Johnson, B. G., Dang, L. T., Marsh, G., Roach, A. M., Levine, Z. G., Monti, A., Reyon, D., Feigenbaum, L., and Duffield, J. S. (2017). Uromodulin p.Cys147Trp mutation drives kidney disease by activating ER stress and apoptosis. J. Clin. Invest. 127, 3954-3969.

Kirby, A., Gnirke, A., Jaffe, D. B., Barešová, V., Pochet, N., Blumenstiel, B., Ye, C., Aird, D., Stevens, C., Robinson, J. T., et al. (2013). Mutations causing medullary cystic kidney disease type 1 lie in a large VNTR in MUC1 missed by massively parallel sequencing. Nat. Genet. 45, 299-303.

Klaips, C. L., Jayaraj, G. G., and Hartl, F. U. (2017). Pathways of cellular proteostasis in aging and disease. J Cell Biol 217, jcb.201709072.

Leroy, X., Copin, M. C., Devisme, L., Buisine, M. P., Aubert, J. P., Gosselin, B., and Porchet, N. (2002). Expression of human mucin genes in normal kidney and renal cell carcinoma. Histopathology.

Lin, J. H., Li, H., Yasumura, D., Cohen, H. R., Zhang, C., Panning, B., Shokat, K. M., Lavail, M. M., and Walter, P. (2007). IRE1 signaling affects cell fate during the unfolded protein response. Science (80-.). 318, 944-949.

Litvinov, S. V, and Hilkens, J. (1993). The epithelial sialomucin, episialin, is sialylated during recycling. J. Biol. Chem. 268, 21364-21371.

Mitrovic, S., Ben-Tekaya, H., Koegler, E., Gruenberg, J., and Hauri, H.-P. (2008). The cargo receptors Surf4, endoplasmic reticulum-Golgi intermediate compartment (ERGIC)-53, and p25 are required to maintain the architecture of ERGIC and Golgi. Mol. Biol. Cell 19, 1976-1990.

Morizane, R., and Bonventre, J. V (2016). Generation of nephron progenitor cells and kidney organoids from human pluripotent stem cells. Nat. Protoc. 12, 195-207.

Munk, S. A., Lai, R. K., Burke, J. E., Arasasingham, P. N., Kharlamb, A. B., Manlapaz, C. A., Padillo, E. U., Wijono, M. K., Hasson, D. W., Wheeler, L. A., et al. (1996). Synthesis and pharmacologic evaluation of 2-endo-amino-3-exo-isopropylbicyclo[2.2.1]heptane: a potent imidazoline1 receptor specific agent. J Med Chem 39, 1193-1195.

Munk et al. (1996) WO 96/01813A1.

Nath, S., and Mukherjee, P. (2014). MUC1: A multifaceted oncoprotein with a key role in cancer progression. Trends Mol. Med.

Nikolic, K., and Agbaba, D. (2012). Imidazoline Antihypertensive Drugs: Selective I 1-Imidazoline Receptors Activation. Cardiovasc. Ther.

Piletz, J. E., Ivanov, T. R., Sharp, J. D., Ernsberger, P., Chang, C. H., Pickard, R. T., Gold, G., Roth, B., Zhu, H., Jones, J. C., et al. (2000). Imidazoline receptor antisera-selected (IRAS) cDNA: cloning and characterization. DNA Cell Biol 19, 319-329.

Plate, L., and Wiseman, R. L. (2017). Regulating Secretory Proteostasis through the Unfolded Protein Response: From Function to Therapy. Trends Cell Biol. 27, 722-737.

Reinhard, F. B. M., Eberhard, D., Werner, T., Franken, H., Childs, D., Doce, C., Savitski, M. F., Huber, W., Bantscheff, M., Savitski, M. M., et al. (2015). Thermal proteome profiling monitors ligand interactions with cellular membrane proteins. Nat. Methods 12, 1129-1131.

Remondelli, P., and Renna, M. (2017). The Endoplasmic Reticulum Unfolded Protein Response in Neurodegenerative Disorders and Its Potential Therapeutic Significance. Front. Mol. Neurosci. 10, 187.

Schaeffer, C., Merella, S., Pasqualetto, E., Lazarevic, D., and Rampoldi, L. (2017). Mutant uromodulin expression leads to altered homeostasis of the endoplasmic reticulum and activates the unfolded protein response. PLoS One 12, e0175970.

Strating, J. R. P. M., and Martens, G. J. M. (2009). The p24 family and selective transport processes at the ER-Golgi interface. Biol. Cell 101, 495-509.

Subramanian, A., Sidhom, E.-H., Emani, M., Sahakian, N., Vernon, K., Zhou, Y., Kost-Alimova, M., Weins, A., Slyper, M., Waldman, J., et al. (2019). Kidney organoid reproducibility across multiple human iPSC lines and diminished off target cells after transplantation revealed by single cell transcriptomics. BioRxiv 516807.

Takasato, M., Er, P. X., Chiu, H. S., and Little, M. H. (2016). Generation of kidney organoids from human pluripotent stem cells. Nat. Protoc. 11, 1681-1692.

Walker, B. J., Abeel, T., Shea, T., Priest, M., Abouelliel, A., Sakthikumar, S., Cuomo, C. A., Zeng, Q., Wortman, J., Young, S. K., et al. (2014). Pilon: An Integrated Tool for Comprehensive Microbial Variant Detection and Genome Assembly Improvement. PLoS One 9, el12963.

Walter, P., and Ron, D. (2011). The unfolded protein response: from stress pathway to homeostatic regulation. Science 334, 1081-1086.

Wenzel, A., Altmueller, J., Ekici, A. B., Popp, B., Stueber, K., Thiele, H., Pannes, A., Staubach, S., Salido, E., Nuemberg, P., et al. (2018). Single molecule real time sequencing in ADTKD-MUC1 allows complete assembly of the VNTR and exact positioning of causative mutations. Sci. Rep. 8, 4170.

Witkos, T. M., and Lowe, M. (2017). Recognition and tethering of transport vesicles at the Golgi apparatus. Curr. Opin. Cell Biol. 47, 16-23.

Yamamoto, S., Kaimori, J.-Y., Yoshimura, T., Namba, T., Imai, A., Kobayashi, K., Imamura, R., Ichimaru, N., Kato, K., Nakaya, A., et al. (2017). Analysis of an ADTKD family with a novel frameshift mutation in MUC1 reveals characteristic features of mutant MUC1 protein. Nephrol. Dial. Transplant. 32, 2010-2017.

Yoshimori, T., Yamamoto, A., Moriyamas, Y., Futais, M., and Tashiroq, Y. (1991). THE JOURNAL OF BIOLOGICAL CHEMISTRY Bafilomycin AI, a Specific Inhibitor of Vacuolar-type H+-ATPase, Inhibits Acidification and Protein Degradation in Lysosomes of Cultured Cells*.

Yu, S. M.-W., Bleyer, A. J., Anis, K., Herlitz, L., ivná, M., Hůlková, H., Markowitz, G. S., and Jim, B. (2018). Autosomal Dominant Tubulointerstitial Kidney Disease Due to MUC1 Mutation. Am. J. Kidney Dis. 71, 495-500.

Zhang, J., and Abdel-Rahman, A. A. (2006). Nischarin as a functional imidazoline (I1) receptor. FEBS Lett 580, 3070-3074.

ivná, M., Kidd, K., Přistoupilová, A., Barešová, V., DeFelice, M., Blumenstiel, B., Harden, M., Conlon, P., Lavin, P., Connaughton, D. M., et al. (2018). Noninvasive Immunohistochemical Diagnosis and Novel MUC1 Mutations Causing Autosomal Dominant Tubulointerstitial Kidney Disease. J. Am. Soc. Nephrol.

Zoghbi, H. Y., and Orr, H. T. (2000). Glutamine Repeats and Neurodegeneration. Annu. Rev. Neurosci. 23, 217-247.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better Illumina®te the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method of treating MUC1-associated kidney disease in a subject, the method comprising administering to the subject 2-endo-amino-3-exo-isopropylbicyclo[2.2.1]heptane or a pharmaceutically acceptable salt thereof in an amount effective to treat MUC1-associated kidney disease, thereby treating MUC1-associated kidney disease in the subject.

2. The method of claim 1, wherein the 2-endo-amino-3-exo-isopropylbicyclo[2.2.1]heptane is racemic (±) 2-endo-amino-3-exo-isopropylbicyclo[2.2.1]heptane.

3. The method of claim 1, wherein the 2-endo-amino-3-exo-isopropylbicyclo[2.2.1]heptane is (+) 2-endo-amino-3-exo-isopropylbicyclo[2.2.1]heptane.

4. The method of claim 1, wherein the 2-endo-amino-3-exo-isopropylbicyclo[2.2.1]heptane is (−) 2-endo-amino-3-exo-isopropylbicyclo[2.2.1]heptane.

5. The method of claim 1, wherein the 2-endo-amino-3-exo-isopropylbicyclo[2.2.1]heptane is a hydrochloride salt of 2-endo-amino-3-exo-isopropylbicyclo[2.2.1]heptane.

6. A method for selecting a composition comprising 2-endo-amino-3-exo-isopropylbicyclo[2.2.1]heptane for administration to a subject for treating MUC1-associated kidney disease in the subject, the method comprising:
   (a) identifying the subject as having MUC1-associated kidney disease; and
   (b) selecting a composition comprising 2-endo-amino-3-exo-isopropylbicyclo[2.2.1]heptane for administration to the subject in an amount effective to treat MUC1-associated kidney disease,
   thereby selecting the composition comprising 2-endo-amino-3-exo-isopropylbicyclo[2.2.1]heptane for administration to the subject for treating MUC1-associated kidney disease in the subject.

7. The method of claim 6, wherein step (a) comprises identifying the presence in the subject of a mutation in MUC1.

8. The method of claim 6, wherein the subject has one or more of the following: end-stage renal disease, urinalysis revealing minimal protein and no blood, slowly progressive kidney failure, hyperglycemia and/or gout.

9. The method of claim 6, wherein the subject has been identified to be in need of dialysis or kidney transplantation.

10. The method of claim 6, wherein step (a) comprises identifying the presence in the subject of a MUC1 frameshift mutation.

11. The method of claim 6, further comprising: (c) administering the selected 2-endo-amino-3-exo-isopropylbicyclo[2.2.1]heptane to the subject.

12. The method of claim 6, wherein identifying step (a) comprises use of a kit consisting essentially of (i) an oligonucleotide for detection of a MUC1 frameshift mutant or (ii) an antibody capable of binding a MUC1 frameshift mutant protein, and instructions for its use.

13. The method of claim 6, wherein the subject is human.

14. A method for treating MUC1-associated kidney disease in a subject, the method comprising:
   identifying a subject as having MUC1-associated kidney disease; and
   administering 2-endo-amino-3-exo-isopropylbicyclo[2.2.1]heptane or a pharmaceutically acceptable salt thereof, to the subject in an amount effective to cause reduction or improvement of a symptom of MUC1-associated kidney disease in the subject,
   thereby treating MUC1-associated kidney disease in the subject.

15. The method of claim 14, wherein said compound causes release of MUC1, from an early secretory compartment.

16. The method of claim 14, wherein the subject has a mutation in MUC1.

17. The method of claim 14, wherein the symptom of MUC1-associated kidney disease is selected from the group consisting of slowly progressive tubulointerstitial disease, end-stage renal disease, and a need for dialysis or kidney transplantation.

18. The method of claim 14, wherein the subject has a MUC1 frameshift mutation.

19. The method of claim 14, wherein the 2 endo-amino-3-exo-isopropylbicyclo[2.2.1]heptane or a pharmaceutically acceptable salt thereof is administered to the subject via the oral route.

20. The method of claim 14, wherein the 2-endo-amino-3-exo-isopropylbicyclo[2.2.1]heptane or pharmaceutically acceptable salt thereof comprises a pharmaceutically-acceptable carrier or excipient.

* * * * *